US006797718B2

(12) United States Patent
Dellaria et al.

(10) Patent No.: US 6,797,718 B2
(45) Date of Patent: Sep. 28, 2004

(54) ETHER SUBSTITUTED IMIDAZOPYRIDINES

(75) Inventors: Joseph F. Dellaria, Woodbury, MN (US); Kyle J. Lindstrom, Houlton, WI (US); Luke T. Dressel, Somerset, WI (US); Philip D. Heppner, Forest Lake, MN (US); John R. Jacobsen, Woodbury, MN (US); Matthew R. Radmer, Robbinsdale, MN (US); Doris Stoermer, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/456,308

(22) Filed: Jun. 6, 2003

(65) Prior Publication Data

US 2004/0010007 A1 Jan. 15, 2004

Related U.S. Application Data

(60) Provisional application No. 60/387,268, filed on Jun. 7, 2002.

(51) Int. Cl.[7] ..................... A61K 31/437; C07D 471/04

(52) U.S. Cl. ..................... 514/303; 546/118; 544/127; 544/333; 514/234.2; 514/256

(58) Field of Search ................... 514/303, 234.2, 514/333; 546/118; 544/127, 333

(56) References Cited

U.S. PATENT DOCUMENTS

| | | | |
|---|---|---|---|
| 3,314,941 | A | 4/1967 | Littell et al. |
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,238,944 | A | 8/1993 | Wick et al. |
| 5,266,575 | A | 11/1993 | Gerster |
| 5,268,376 | A | 12/1993 | Gester |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,446,153 | A | 8/1995 | Lindstrom et al. |
| 5,482,936 | A | 1/1996 | Lindstrom |
| 5,693,811 | A | 12/1997 | Lindstrom |
| 5,741,908 | A | 4/1998 | Gerster et al. |
| 5,756,747 | A | 5/1998 | Gerster |
| 5,939,090 | A | 8/1999 | Beaurline et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,194,425 | B1 | 2/2001 | Gerster et al. |
| 6,245,776 | B1 | 6/2001 | Skwierczynski et al. |
| 6,331,539 | B1 | 12/2001 | Crooks et al. |
| 6,376,669 | B1 | 4/2002 | Rice et al. |
| 6,451,810 | B1 | 9/2002 | Coleman et al. |
| 6,518,265 | B1 | 2/2003 | Kato et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 2002/0055517 | A1 | 5/2002 | Smith |
| 2002/0058674 | A1 | 5/2002 | Hedenstrom et al. |

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46191 | 6/2002 |
| WO | WO 02/46192 | 6/2002 |
| WO | WO 02/46193 | 6/2002 |
| WO | WO 02/46749 | 6/2002 |
| WO | WO 02/102377 | 12/2002 |
| WO | WO 03/020889 | 3/2003 |
| WO | WO 03/043572 | 5/2003 |
| WO | WO 03/045391 | 6/2003 |

OTHER PUBLICATIONS

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society*, 102, pp 511–513, Dec. 12, 1983.

Brennan, et al, "Automated Bioassay of Interferons in Micro–test Plates", *Biotechniques*, Jun./Jul., 78, 1983.

Testerman, et al., "Cytokine Induction by the Immunomodulators Imiquimod and S–27609", *Journal of Leukocyte Biology*, vol. 58, pp. 365–372, Sep. 1995.

Bachman, et al, "Synthesis of Substituted Quinolylamines. Derivatives of 4–Amino–7–Chloroquinoline", *J. Org. Chem.*, 15, pp 1278–1284 (1950).

(List continued on next page.)

*Primary Examiner*—Charanjit S. Aulakh
(74) *Attorney, Agent, or Firm*—Dean A. Ersfeld

(57) ABSTRACT

Imidazopyridine compounds that contain an ether or thioether functionality at the 1-position are useful as immune response modifiers. The compounds and compositions of the invention can induce the biosynthesis of various cytokines and are useful in the treatment of a variety of conditions including viral diseases and neoplastic diseases. Methods of preparing the compounds and intermediates useful in the preparation of the compounds are also disclosed.

22 Claims, No Drawings

OTHER PUBLICATIONS

Jain, et al, "Chemical and Pharmacological Investigations of Some ω–Substituted Alkylamino–3–aminopyridines", *J. Med. Chem.*., 11, pp 87–92 (1968).

Baranov, et al., *Chem. Abs.* 85, 94362, (1976).

Berényi, et al, "Ring Transformation of Condensed Dihydro–as–triazines", *J. Heterocyclic Chem.*, 18, pp 1537–1540 (1981).

Chollet, et al, "Development of a Topically Active Imiquimod Formulation", *Pharmaceutical Development and Technology*, 4(1), pp 35–43 (1999).

Izumi, et al., "1H–Imidazo[4,5–c]quinoline Derivatives as Novel Potent TNF–α Suppressors: Synthesis and Structure–Activity Relationship of 1–, 2– and 4–Substituted 1H–imidazo[4,5–c]pyridines", *Bioorganic & Medicinal Chemistry*, 11, pp 2541–2550 (2003).

ETHER SUBSTITUTED IMIDAZOPYRIDINES

CROSS REFERENCE TO RELATED APPLICATION

This application claims the benefit of U.S. Provisional Application No. 60/387,268, filed Jun. 7, 2002.

FIELD

This invention relates to imidazopyridine compounds that have ether or thioether substitution at the 1-position, and that may contain additional functionality. The invention also provides pharmaceutical compositions containing these compounds and methods of inducing cytokine biosynthesis by administration of the compounds.

BACKGROUND

The first reliable report on the 1H-imidazo[4,5-c]quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c] quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

Substituted 1H-imidazopyridine-4-amine compounds useful as immune response modifiers are described in U.S. Pat. Nos. 5,446,153; 5,494,916; 5,644,063; 6,525,064; 6,545,016; and 6,545,017. The compounds described in these patents do not have ether substitution at the 1-position. Certain 1H-imidazo[4,5-c]quinolin-4-amines that have amide, sulfonamide, and urea functionality at the 1-position are described in U.S. Pat. Nos. 6,331,539; 6451,810; and 6,541,485.

Despite these recent discoveries of compounds that are useful as immune response modifiers, there is a continuing need for compounds that have the ability to modulate the immune response, by induction of cytokine biosynthesis or other mechanisms.

SUMMARY

In one aspect, the invention provides imidazopyridine compounds that have ether substitution at the 1-position. These compounds have the general formula (Ia):

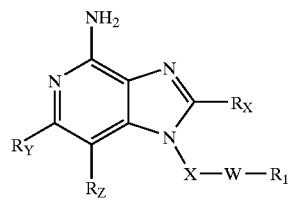

(Ia)

wherein X, W, and the various R variables are as defined herein. In other aspects, the invention provides pharmaceutical compositions containing the compounds and methods of using the compounds to achieve a therapeutic effect. Such effects include the induction of cytokine biosynthesis, the induction of interferon biosynthesis, treatment of viral conditions and treatment of neoplastic conditions. In other aspects, the invention additionally provides methods of making the compounds and intermediate compounds useful in their synthesis.

Many of the compounds of the invention have an ether linkage at the 1-position of the compounds. The compounds may include additional substitution that occurs after the initial ether linkage, such as aryl, heteroaryl, heterocyclyl, amido, sulfonamido, urea, and the like. An additional set of compounds provided by the invention contain a thioether linkage at the 1-position; these thioether compounds may also have additional substitution after the initial thioether linkage, including alkyl, aryl, heteroaryl, and heterocyclyl.

DETAILED DESCRIPTION

Several classes of ether and thioether substituted imidazopyridine compounds are disclosed herein. Although each has a different type of substitution at the 1-position of the compound, many of the substituents at the other positions of the imidazopyridine core can be independently selected from the same group of radicals. Therefore, the following system is used to describe some embodiments of the invention: different classes of compounds are each described by a different general structure of Formula Ia, such as Ib, I-1, I-2, and so on. Corresponding different $R_1$ substituents for those compounds will be similarly identified as $R_{1-1}$, $R_{1-2}$, and so on. The other substituents, which have the same definitions for each class of compounds, will have common designations such as X, Y, Z, $R_2$, $R_3$, $R_4$, $R_5$, and so on. If the same variable appears twice in a particular substituent or compound, such as in "—N($R_5$)$_2$", then each instance of the variable can be independently selected from the permitted values for the variable.

In one aspect, compounds of the invention are repesented by Formula Ia:

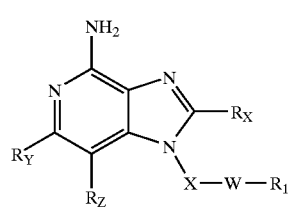

(Ia)

wherein:
X is —CH($R_5$)—, —CH($R_5$)-alkylene-, —CH($R_5$)-alkenylene-, or CH($R_5$)-alkylene-Y-alkylene-;
Y is —O—, or —S(O)$_{0-2}$—;
—W—R, is selected from —O—$R_{1-1-5}$ and —S(O)$_{0-2}$—$R_{1-6}$;

$R_{1\text{-}1\text{-}5}$ is selected from
—$R_6$—C($R_7$)—Z—$R_8$-alkyl;
—$R_6$—C($R_7$)—Z—$R_8$-alkenyl;
—$R_6$—C($R_7$)—Z—$R_8$-aryl;
—$R_6$—C($R_7$)—Z—$R_8$-heteroaryl;
—$R_6$—C($R_7$)—Z—$R_8$-heterocyclyl;
—$R_6$—C($R_7$)—Z—H;
—$R_6$—N($R_9$)—C($R_7$)—$R_8$-alkyl;
—$R_6$—N($R_9$)—C($R_7$)—$R_8$-alkenyl;
—$R_6$—N($R_9$)—C($R_7$)—$R_8$-aryl;
—$R_6$—N($R_9$)—C($R_7$)—$R_8$-heteroaryl;
—$R_6$—N($R_9$)—C($R_7$)—$R_8$-heterocyclyl;
—$R_6$—N($R_9$)—C($R_7$)—$R_{10}$;
—$R_6$—N($R_9$)—SO$_2$—$R_8$-alkyl;
—$R_6$—N($R_9$)—SO$_2$—$R_8$-alkenyl;
—$R_6$—N($R_9$)—SO$_2$—$R_8$-aryl;
—$R_6$—N($R_9$)—SO$_2$—$R_8$-heteroaryl;
—$R_6$—N($R_9$)—SO$_2$—$R_8$-heterocyclyl;
—$R_6$—N($R_9$)—SO$_2$—$R_{10}$;
—$R_6$—N($R_9$)—SO$_2$—N($R_5$)—$R_8$-alkyl;
—$R_6$—N($R_9$)—SO$_2$—N($R_5$)—$R_8$-alkenyl;
—$R_6$—N($R_9$)—SO$_2$—N($R_5$)—$R_8$-aryl;
—$R_6$—N($R_9$)—SO$_2$—N($R_5$)—$R_8$-heteroaryl;
—$R_6$—N($R_9$)—SO$_2$—N($R_5$)—$R_8$-heterocyclyl;
—$R_6$—N($R_9$)—SO$_2$—NH$_2$;
—$R_6$—N($R_9$)—C($R_7$)—N($R_5$)—Q—$R_8$-alkyl;
—$R_6$—N($R_9$)—C($R_7$)—N($R_5$)—Q—$R_8$-alkenyl;
—$R_6$—N($R_9$)—C($R_7$)—N($R_5$)—Q—$R_8$-aryl;
—$R_6$—N($R_9$)—C($R_7$)—N($R_5$)—Q—$R_8$-heteroaryl;
—$R_6$—N($R_9$)—C($R_7$)—N($R_5$)—Q—$R_8$-heterocyclyl;
—$R_6$—N($R_9$)—C($R_7$)—N($R_5$)$_2$;

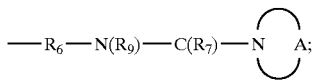

—$R_6$—N($R_9$)—C($R_7$)—N($R_{11}$)—Q—$R_8$-alkyl;
—$R_6$—N($R_9$)—C($R_7$)—N($R_{11}$)—Q—$R_8$-alkenyl;
—$R_6$—N($R_9$)—C($R_7$)—N($R_{11}$)—Q—$R_8$-aryl;
—$R_6$—N($R_9$)—C($R_7$)—N($R_{11}$)—Q—$R_8$-heteroaryl;
—$R_6$—N($R_9$)—C($R_7$)—N($R_{11}$)—Q—$R_8$-heterocyclyl;
—$R_6$—N($R_9$)—C($R_7$)—N($R_{11}$)H;
-alkenyl;
-aryl;
—$R_6$-aryl;
-heteroaryl;
-heterocyclyl;
—$R_6$-heteroaryl; and
—$R_6$-heterocyclyl;
Z is —N($R_5$)—, —O—, or —S—;
Q is a bond, —CO—, or —SO$_2$—;
A represents the atoms necessary to provide a 5- or 6-membered heterocyclic or heteroaromatic ring that contains up to three heteroatoms;
$R_{1\text{-}6}$ is selected from:
-alkyl;
-aryl;
-heteroaryl;
-heterocyclyl;
-alkenyl;
—$R_6$-aryl;
—$R_6$-heteroaryl; and
—$R_6$-heterocyclyl;

each $R_5$ is independently hydrogen, $C_{1\text{-}10}$alkyl, or $C_{2\text{-}10}$alkenyl;

$R_6$ is alkylene, alkenylene, or alkynylene, which may be interrupted by one or more —O— groups;

$R_7$ is =O or =S;

$R_8$ is a bond, alkylene, alkenylene, or alkynylene, which may be interrupted by one or more —O— groups;

$R_9$ is hydrogen, $C_{1\text{-}10}$alkyl, or arylalkyl; or $R_9$ can join together with any carbon atom of $R_6$ to form a ring of the formula

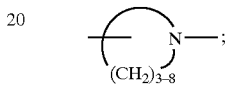

$R_{10}$ is hydrogen or $C_{1\text{-}10}$ alkyl; or $R_9$ and $R_{10}$ can join together to form a ring selected from

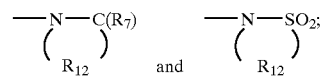

$R_{11}$ is $C_{1\text{-}10}$ alkyl; or $R_9$ and $R_{11}$ can join together to form a ring having the structure

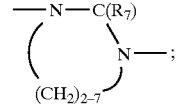

$R_{12}$ is $C_{2\text{-}7}$ alkylene which is straight chain or branched, wherein the branching does not prevent formation of the ring; and $R_X$, $R_Y$ and $R_Z$ are independently selected from hydrogen and non-interfering substituents;

or a pharmaceutically acceptable salt thereof, wherein the compound or salt of Formula Ia induces the biosynthesis of one or more cytokines.

Compounds of Formula Ib

In one embodiment, compounds of the invention are represented by Formula Ib:

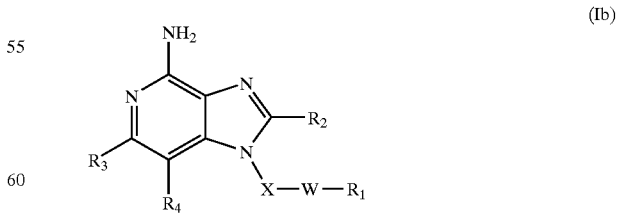

wherein:

X is —CH($R_5$)—, —CH($R_5$)-alkylene-, —CH($R_5$)-alkenylene-, or CH($R_5$)-alkylene-Y-alkylene-;

—W—$R_1$ is selected from —O—$R_{1\text{-}1\text{-}5}$ and —S(O)$_{0\text{-}2}$—

$R_{1-6}$;

$R_{1-1-5}$ is selected from
- —$R_6$—C($R_7$)—Z—$R_8$-alkyl;
- —$R_6$—C($R_7$)—Z—$R_8$-alkenyl;
- —$R_6$—C($R_7$)—Z—$R_8$-aryl;
- —$R_6$—C($R_7$)—Z—$R_8$-heteroaryl;
- —$R_6$—C($R_7$)—Z—$R_8$-heterocyclyl;
- —$R_6$—C($R_7$)—Z—H;
- —$R_6$—N($R_9$)—C($R_7$)—$R_8$-alkyl;
- —$R_6$—N($R_9$)—C($R_7$)—$R_8$-alkenyl;
- —$R_6$—N($R_9$)—C($R_7$)—$R_8$-aryl;
- —$R_6$—N($R_9$)—C($R_7$)—$R_8$-heteroaryl;
- —$R_6$—N($R_9$)—C($R_7$)—$R_8$-heterocyclyl;
- —$R_6$—N($R_9$)—C($R_7$)—$R_{10}$;
- —$R_6$—N($R_9$)—SO$_2$—$R_8$-alkyl;
- —$R_6$—N($R_9$)—SO$_2$—$R_8$-alkenyl;
- —$R_6$—N($R_9$)—SO$_2$—$R_8$-aryl;
- —$R_6$—N($R_9$)—SO$_2$—$R_8$-heteroaryl;
- —$R_6$—N($R_9$)—SO$_2$—$R_8$-heterocyclyl;
- —$R_6$—N($R_9$)—SO$_2$—$R_{10}$;
- —$R_6$—N($R_9$)—SO$_2$—N($R_5$)—$R_8$-alkyl;
- —$R_6$—N($R_9$)—SO$_2$—N($R_5$)—$R_8$-alkenyl;
- —$R_6$—N($R_9$)—SO$_2$—N($R_5$)—$R_8$-aryl;
- —$R_6$—N($R_9$)—SO$_2$—N($R_5$)—$R_8$-heteroaryl;
- —$R_6$—N($R_9$)—SO$_2$—N($R_5$)—$R_8$-heterocyclyl;
- —$R_6$—N($R_9$)—SO$_2$—NH$_2$;
- —$R_6$—N($R_9$)—C($R_7$)—N($R_5$)—Q—$R_8$-alkyl;
- —$R_6$—N($R_9$)—C($R_7$)—N($R_5$)—Q—$R_8$-alkenyl;
- —$R_6$—N($R_9$)—C($R_7$)—N($R_5$)—Q—$R_8$-aryl;
- —$R_6$—N($R_9$)—C($R_7$)—N($R_5$)—Q—$R_8$-heteroaryl;
- —$R_6$—N($R_9$)—C($R_7$)—N($R_5$)—Q—$R_8$-heterocyclyl;
- —$R_6$—N($R_9$)—C($R_7$)—N($R_5$)$_2$;

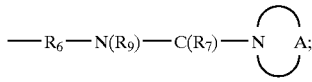

- —$R_6$—N($R_9$)—C($R_7$)—N($R_{11}$)—Q—$R_8$-alkyl;
- —$R_6$—N($R_9$)—C($R_7$)—N($R_{11}$)—Q—$R_8$-alkenyl;
- —$R_6$—N($R_9$)—C($R_7$)—N($R_{11}$)—Q—$R_8$-aryl;
- —$R_6$—N($R_9$)—C($R_7$)—N($R_{11}$)—Q—$R_8$-heteroaryl;
- —$R_6$—N($R_9$)—C($R_7$)—N($R_{11}$)—Q—$R_8$-heterocyclyl;
- —$R_6$—N($R_9$)—C($R_7$)—N($R_{11}$)H;
- -alkenyl;
- -aryl;
- —$R_6$-aryl;
- -heteroaryl;
- -heterocyclyl;
- —$R_6$-heteroaryl; and
- —$R_6$-heterocyclyl;

$R_{1-6}$ is selected from:
- -alkyl;
- -aryl;
- -heteroaryl;
- -heterocyclyl;
- -alkenyl;
- —$R_6$-aryl;
- —$R_6$-heteroaryl; and
- —$R_6$-heterocyclyl;

$R_2$ is selected from the group consisting of:
- -hydrogen;
- -alkyl;
- -alkenyl;
- -aryl;
- -heteroaryl;
- -heterocyclyl;
- -alkylene-Y-alkyl;
- -alkylene-Y-alkenyl;
- -alkylene-Y-aryl; and
- -alkyl or alkenyl substituted by one or more substituents selected from the group consisting of:
  - —OH;
  - -halogen;
  - —N($R_5$)$_2$;
  - —C(O)—C$_{1-10}$alkyl;
  - —C(O)—O—C$_{1-10}$alkyl;
  - —N$_3$;
  - -aryl;
  - -heteroaryl;
  - -heterocyclyl;
  - —C(O)-aryl; and
  - —C(O)-heteroaryl;

Y is —O— or —S(O)$_{0-2}$—;

Z is —N($R_5$)—, —O—, or —S—;

Q is a bond, —C(O)—, or —SO$_2$—;

A represents the atoms necessary to provide a 5- or 6-membered heterocyclic or heteroaromatic ring that contains up to three heteroatoms;

$R_3$ and $R_4$ are independently selected from the group consisting of hydrogen, C$_{1-10}$ alkyl, C$_{2-10}$ alkenyl, C$_{2-10}$ alkynyl, C$_{1-10}$ alkoxy, C$_{1-10}$ alkylthio, amino, alkylamino, dialkylamino, halogen, and nitro;

each $R_5$ is independently hydrogen, C$_{1-10}$alkyl, or C$_{2-10}$ alkenyl;

$R_6$ is alkylene, alkenylene, or alkynylene, which may be interrupted by one or more —O— groups;

$R_7$ is =O or =S;

$R_8$ is a bond, alkylene, alkenylene, or alkynylene, which may be interrupted by one or more —O— groups;

$R_9$ is hydrogen, C$_{1-10}$ alkyl, or arylalkyl; or $R_9$ can join together with any carbon atom of $R_6$ to form a ring of the formula

$R_{10}$ is hydrogen or C$_{1-10}$ alkyl; or $R_9$ and $R_{10}$ can join together to form a ring selected from

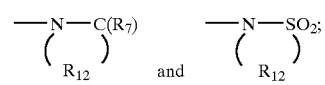

$R_{11}$ is C$_{1-10}$ alkyl; or $R_9$ and $R_{11}$ can join together to form a ring having the structure

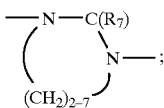

and

R$_{12}$ is C$_{2-7}$ alkylene which is straight chain or branched, wherein the branching does not prevent formation of the ring;

or a pharmaceutically acceptable salt thereof.

Compounds of Formula I-1

One embodiment includes a class of compounds represented by Formula (I-1):

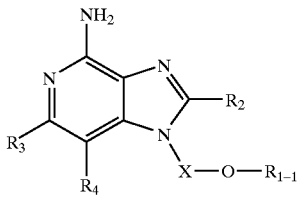

(I-1)

wherein:

X is —CH(R$_5$)—, —CH(R$_5$)-alkylene-, —CH(R$_5$)-alkenylene-, or CH(R$_5$)-alkylene-Y-alkylene-;

R$_{1-1}$ is selected from the group consisting of:
—R$_6$—C(R$_7$)—Z—R$_8$-alkyl;
—R$_6$—C(R$_7$)—Z—R$_8$-alkenyl;
—R$_6$—C(R$_7$)—Z—R$_8$-aryl;
—R$_6$—C(R$_7$)—Z—R$_8$-heteroaryl;
—R$_6$—C(R$_7$)—Z—R$_8$-heterocyclyl;
—R$_6$—C(R$_7$)—Z—H;
—R$_6$—N(R$_9$)—C(R$_7$)—R$_8$-alkyl;
—R$_6$—N(R$_9$)—C(R$_7$)—R$_8$-alkenyl;
—R$_6$—N(R$_9$)—C(R$_7$)—R$_8$-aryl;
—R$_6$—N(R$_9$)—C(R$_7$)—R$_8$-heteroaryl;
—R$_6$—N(R$_9$)—C(R$_7$)—R$_8$-heterocyclyl; and
—R$_6$—N(R$_9$)—C(R$_7$)—R$_{10}$;

Z is —N(R$_5$)—, —O—, or —S—;

R$_2$ is selected from the group consisting of:
-hydrogen;
-alkyl;
-alkenyl;
-aryl;
-heteroaryl;
-heterocyclyl;
-alkylene-Y-alkyl;
-alkylene-Y- alkenyl;
-alkylene-Y-aryl; and
-alkyl or alkenyl substituted by one or more substituents selected from the group consisting of:
—OH;
-halogen;
—N(R$_5$)$_2$;
—C(O)—C$_{1-10}$ alkyl;
—C(O)—O—C$_{1-10}$ alkyl;
—N$_3$;
-aryl;
-heteroaryl;
-heterocyclyl;

—C(O)-aryl; and
—C(O)-heteroaryl;

Y is —O— or —S(O)$_{0-2}$—;

R$_3$ and R$_4$ are independently selected from the group consisting of hydrogen, C$_{1-10}$ alkyl, C$_{2-10}$ alkenyl, C$_{2-10}$ alkynyl, C$_{1-10}$ alkoxy, C$_{1-10}$ alkylthio, amino, alkylamino, dialkylamino, halogen, and nitro;

each R$_5$ is independently hydrogen, C$_{1-10}$ alkyl, or C$_{2-10}$ alkenyl;

R$_6$ is alkylene, alkenylene, or alkynylene, which may be interrupted by one or more —O— groups;

R$_7$ is =O or =S;

R$_8$ is a bond, alkylene, alkenylene, or alkynylene, which may be interrupted by one or more —O— groups;

R$_9$ is hydrogen, C$_{1-10}$ alkyl, or arylalkyl; or R$_9$ can join together with any carbon atom of R$_6$ to form a ring of the formula

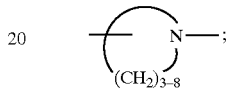

R$_{10}$ is hydrogen or C$_{1-10}$ alkyl; or R$_9$ and R$_{10}$ can join together to form a ring selected from $$\begin{pmatrix} -\text{N} - \text{C}(\text{R}_7) \\ \text{R}_{12} \end{pmatrix};$$

and

R$_{12}$ is C$_{2-7}$ alkylene which is straight chain or branched, wherein the branching does not prevent formation of the ring;

or a pharmaceutically acceptable salt thereof.

Compounds of Formula I-2

Another embodiment includes a class of compounds represented by Formula (I-2):

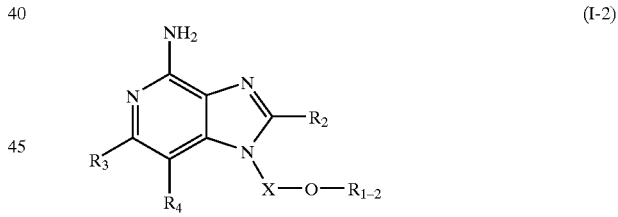

(I-2)

wherein:

X is —CH(R$_5$)—, —CH(R$_5$)-alkylene-, —CH(R$_5$)-alkenylene-, or CH(R$_5$)-alkylene-Y-alkylene-;

R$_{1-2}$ is selected from the group consisting of:
—R$_6$—N(R$_9$)—SO$_2$—R$_8$-alkyl;
—R$_6$—N(R$_9$)—SO$_2$—R$_8$-alkenyl;
—R$_6$—N(R$_9$)—SO$_2$—R$_8$-aryl;
—R$_6$—N(R$_9$)—SO$_2$—R$_8$-heteroaryl;
—R$_6$—N(R$_9$)—SO$_2$—R$_8$-heterocyclyl;
—R$_6$—N(R$_9$)—SO$_2$—R$_{10}$;
—R$_6$—N(R$_9$)—SO$_2$—N(R$_5$)—R$_8$-alkyl;
—R$_6$—N(R$_9$)—SO$_2$—N(R$_5$)—R$_8$-alkenyl;
—R$_6$—N(R$_9$)—SO$_2$—N(R$_5$)—R$_8$-aryl;
—R$_6$—N(R$_9$)—SO$_2$—N(R$_5$)—R$_8$-heteroaryl;
—R$_6$—N(R$_9$)—SO$_2$—N(R$_5$)—R$_8$-heterocyclyl; and
—R$_6$—N(R$_9$)—SO$_2$—NH$_2$;

$R_2$ is selected from the group consisting of:
- -hydrogen;
- -alkyl;
- -alkenyl;
- -aryl;
- -heteroaryl;
- -heterocyclyl;
- -alkylene-Y-alkyl;
- -alkylene-Y-alkenyl;
- -alkylene-Y-aryl; and
- -alkyl or alkenyl substituted by one or more substituents selected from the group consisting of:
  - —OH;
  - -halogen;
  - —N(R$_5$)$_2$;
  - —C(O)—C$_{1-10}$ alkyl;
  - —C(O)—O—C$_{1-10}$ alkyl;
  - —N$_3$;
  - -aryl;
  - -heteroaryl;
  - -heterocyclyl;
  - —C(O)-aryl; and
  - —C(O)-heteroaryl;

Y is —O— or —S(O)$_{0-2}$—;

$R_3$ and $R_4$ are independently selected from the group consisting of hydrogen, C$_{1-10}$ alkyl, C$_{2-10}$ alkenyl, C$_{2-10}$ alkynyl, C$_{1-10}$ alkoxy, C$_{1-10}$ alkylthio, amino, alkylamino, dialkylamino, halogen, and nitro;

each $R_5$ is independently hydrogen, C$_{1-10}$ alkyl, or C$_{2-10}$ alkenyl;

$R_6$ is alkylene, alkenylene, or alkynylene, which may be interrupted by one or more —O— groups;

$R_8$ is a bond, alkylene, alkenylene, or alkynylene, which may be interrupted by one or more —O— groups;

$R_9$ is hydrogen, C$_{1-10}$ alkyl, or arylalkyl; or $R_9$ can join together with any carbon atom of $R_6$ to form a ring of the formula

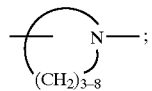

$R_{10}$ is hydrogen or C$_{1-10}$ alkyl; or $R_9$ and $R_{10}$ can join together to form a ring having the structure

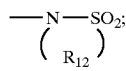

and $R_{12}$ is C$_{2-7}$ alkylene which is straight chain or branched, wherein the branching does not prevent formation of the ring;

or a pharmaceutically acceptable salt thereof.

Compounds of Formula I-3

Another embodiment includes a class of compounds represented by Formula (I-3):

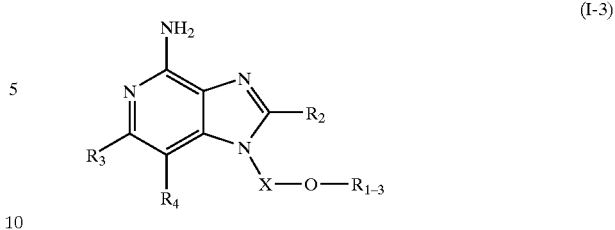

(I-3)

wherein:

X is —CH(R$_5$)—, —CH(R$_5$)-alkylene-, —CH(R$_5$)-alkenylene-, or CH(R$_5$)-alkylene-Y-alkylene-;

$R_{1-3}$ is selected from the group consisting of:
- —R$_6$—N(R$_9$)—C(R$_7$)—N(R$_5$)—Q—R$_8$-alkyl;
- —R$_6$—N(R$_9$)—C(R$_7$)—N(R$_5$)—Q—R$_8$-alkenyl;
- —R$_6$—N(R$_9$)—C(R$_7$)—N(R$_5$)—Q—R$_8$-aryl;
- —R$_6$—N(R$_9$)—C(R$_7$)—N(R$_5$)—Q—R$_8$-heteroaryl;
- —R$_6$—N(R$_9$)—C(R$_7$)—N(R$_5$)—Q—R$_8$-heterocyclyl;
- —R$_6$—N(R$_9$)—C(R$_7$)—N(R$_5$)$_2$;

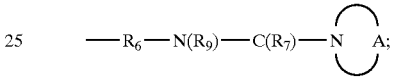

- —R$_6$—N(R$_9$)—C(R$_7$)—N(R$_{11}$)—Q—R$_8$-alkyl;
- —R$_6$—N(R$_9$)—C(R$_7$)—N(R$_{11}$)—Q—R$_8$-alkenyl;
- —R$_6$—N(R$_9$)—C(R$_7$)—N(R$_{11}$)—Q—R$_8$-aryl;
- —R$_6$—N(R$_9$)—C(R$_7$)—N(R$_{11}$)—Q—R$_8$-heteroaryl;
- —R$_6$—N(R$_9$)—C(R$_7$)—N(R$_{11}$)—Q—R$_8$-heterocyclyl; and
- —R$_6$—N(R$_9$)—C(R$_7$)—N(R$_{11}$)H;

$R_2$ is selected from the group consisting of:
- -hydrogen;
- -alkyl;
- -alkenyl;
- -aryl;
- -heteroaryl;
- -heterocyclyl;
- -alkylene-Y-alkyl;
- -alkylene-Y-alkenyl;
- -alkylene-Y-aryl; and
- -alkyl or alkenyl substituted by one or more substituents selected from the group consisting of:
  - —OH;
  - -halogen;
  - —N(R$_5$)$_2$;
  - —C(O)—C$_{1-10}$ alkyl;
  - —C(O)—O—C$_{1-10}$ alkyl;
  - —N$_3$;
  - -aryl;
  - -heteroaryl;
  - -heterocyclyl;
  - —C(O)-aryl; and
  - —C(O)-heteroaryl;

Y is —O— or —S(O)$_{0-2}$—;

Q is a bond, —C(O)—, or —SO$_2$—;

A represents the atoms necessary to provide a 5- or 6-membered heterocyclic or heteroaromatic ring that contains up to three heteroatoms;

$R_3$ and $R_4$ are independently selected from the group consisting of hydrogen, C$_{1-10}$ alkyl, C$_{2-10}$ alkenyl, C$_{2-10}$ alkynyl, $C_{1-10}$ alkoxy, $C_{1-10}$ alkylthio, amino, alkylamino, dialkylamino, halogen, and nitro;

each $R_5$ is independently hydrogen, $C_{1-10}$ alkyl, or $C_{2-10}$ alkenyl;

$R_6$ is alkylene, alkenylene, or alkynylene, which may be interrupted by one or more —O— groups;

each $R_7$ is =O or =S;

$R_8$ is a bond, alkylene, alkenylene, or alkynylene, which may be interrupted by one or more —O— groups;

$R_9$ is hydrogen, $C_{1-10}$ alkyl, or arylalkyl; or $R_9$ can join together with any carbon atom of $R_6$ to form a ring of the formula

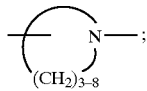

and $R_{11}$ is $C_{1-10}$ alkyl; or $R_9$ and $R_{11}$ can join together to form a ring having the structure

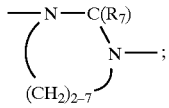

or a pharmaceutically acceptable salt thereof.

Compounds of Formula I-4

Another embodiment includes a class of compounds represented by Formula (I-4):

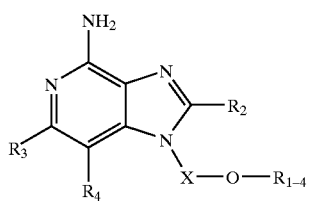

(I-4)

wherein:

X is —CH($R_5$)—, —CH($R_5$)-alkylene-, —CH($R_5$)-alkenylene-, or CH($R_5$)-alkylene-Y-alkylene-;

$R_{1-4}$ is selected from the group consisting of:
-alkenyl;
-aryl; and
—$R_6$-aryl;

$R_2$ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
—OH;
-halogen;
—N($R_5$)$_2$;
—C(O)—$C_{1-10}$ alkyl;
—C(O)—O—$C_{1-10}$ alkyl;
—N$_3$;
-aryl;
-heteroaryl;
-heterocyclyl;
—C(O)-aryl; and
—C(O)-heteroaryl;

Y is —O— or —S(O)$_{0-2}$—;

$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;

each $R_5$ is independently hydrogen, $C_{1-10}$ alkyl, or $C_{2-10}$ alkenyl; and $R_6$ is alkylene, alkenylene, or alkynylene, which may be interrupted by one or more —O— groups;

or a pharmaceutically acceptable salt thereof

Compounds of Formula I-5

Another embodiment includes a class of compounds represented by Formula (I-5):

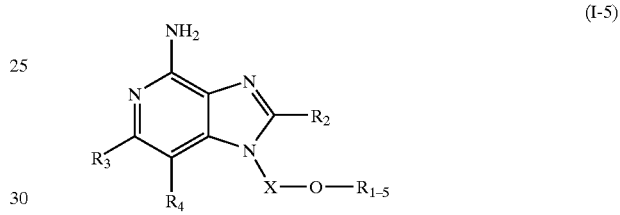

(I-5)

wherein:

X is —CH($R_5$)—, —CH($R_5$)-alkylene-, —CH($R_5$)-alkenylene-, or CH($R_5$)-alkylene-Y-alkylene-;

$R_{1-5}$ is selected from the group consisting of:
-heteroaryl;
-heterocyclyl;
—$R_6$-heteroaryl; and
—$R_6$-heterocyclyl;

$R_2$ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
—OH;
-halogen;
—N($R_5$)$_2$;
—C(O)—$C_{1-10}$ alkyl;
—C(O)—O—$C_{1-10}$ alkyl;
—N$_3$;
-aryl;
-heteroaryl;
-heterocyclyl;
—C(O)-aryl; and
—C(O)-heteroaryl;

Y is —O— or —S(O)$_{0-2}$—;

$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;

each $R_5$ is independently hydrogen, $C_{1-10}$ alkyl, or $C_{2-10}$ alkenyl; and $R_6$ is alkylene, alkenylene, or alkynylene, which may be interrupted by one or more —O— groups;
or a pharmaceutically acceptable salt thereof.

Compounds of Formula I-6

Another embodiment includes thioether compounds represented by Formula (I-6):

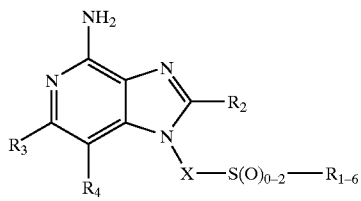

(I-6)

wherein:

X is —CH($R_5$)—, —CH($R_5$)-alkylene-, —CH($R_5$)-alkenylene-, or CH($R_5$)-alkylene-Y-alkylene-;

$R_{1-6}$ is selected from the group consisting of:
-alkyl;
-aryl;
-heteroaryl;
-heterocyclyl;
-alkenyl;
—$R_6$-aryl;
—$R_6$-heteroaryl;
—$R_6$-heterocyclyl;

$R_2$ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
 —OH;
 -halogen;
 —N($R_5$)$_2$;
 —C(O)—$C_{1-10}$ alkyl;
 —C(O)—O—$C_{1-10}$ alkyl;
 —$N_3$;
 -aryl;
 -heteroaryl;
 -heterocyclyl;
 —C(O)-aryl; and
 —C(O)-heteroaryl;

Y is —O— or —S(O)$_{0-2}$—;

$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;

each $R_5$ is independently hydrogen, $C_{1-10}$ alkyl, or $C_{2-10}$ alkenyl; and $R_6$ is alkylene, alkenylene, or alkynylene, which may be interrupted by one or more —O— atoms;

or a pharmaceutically acceptable salt thereof.

Intermediate Compounds

Another aspect of the invention includes intermediate compounds of Formulas II, IV, V, LVIII, LIX-1, LIX-2, LIX-3, LIX-4, LIX-5, LXXVIII, LXXIX, LXXX-4, and LXXX-5.

In one embodiment, a class of intermediate compounds is represented by Formula II:

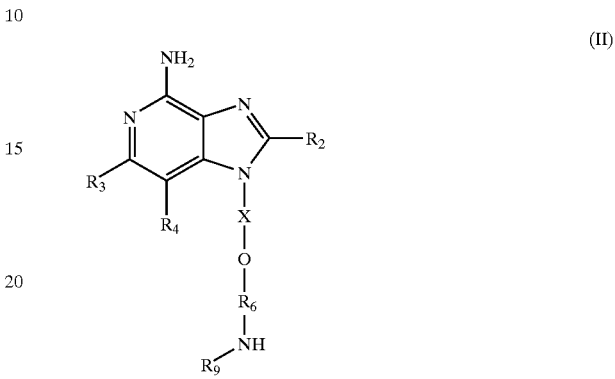

(II)

wherein

X is —CH($R_5$)—, —CH($R_5$)-alkylene-, —CH($R_5$)-alkenylene-, or CH($R_5$)-alkylene-Y-alkylene;

$R_2$ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
 —OH;
 -halogen;
 —N($R_5$)$_2$;
 —C(O)—$C_{1-10}$ alkyl;
 —C(O)—O—$C_{1-10}$ alkyl;
 —$N_3$;
 -aryl;
 -heteroaryl;
 -heterocyclyl;
 —C(O)-aryl; and
 —C(O)-heteroaryl;

Y is —O— or —S(O)$_{0-2}$—;

$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;

each $R_5$ is independently hydrogen, $C_{1-10}$ alkyl, or $C_{2-10}$ alkenyl;

$R_6$ is alkylene, alkenylene, or alkynylene, which may be interrupted by one or more —O— atoms; and $R_9$ is hydrogen, $C_{1-10}$ alkyl, or arylalkyl; or $R_9$ can join together with any carbon atom of $R_6$ to form a ring of the formula

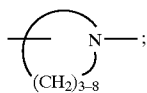

or a pharmaceutically acceptable salt thereof.

In another embodiment, a class of intermediate compounds is represented by Formula IV:

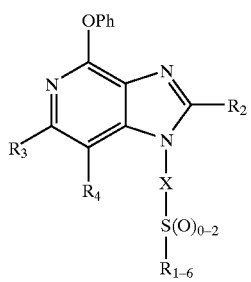

(IV)

wherein:
X is —CH($R_5$)—, —CH($R_5$)-alkylene-, —CH($R_5$)-alkenylene-, or CH($R_5$)-alkylene-Y-alkylene-;
$R_{1-6}$ is selected from the group consisting of:
-alkyl;
-aryl;
-heteroaryl;
-heterocyclyl;
-alkenyl;
—$R_6$-aryl;
—$R_6$-heteroaryl;
—$R_6$-heterocyclyl;
$R_2$ is selected from the group consisting of:
-hydrogen;
-alkyl;
-alkenyl;
-aryl;
-heteroaryl;
-heterocyclyl;
-alkylene-Y-alkyl;
-alkyene-Y-alkenyl;
-alkylene-Y-aryl; and
-alkyl or alkenyl substituted by one or more substituents selected from the group consisting of:
—OH;
-halogen;
—N($R_5$)$_2$;
—C(O)—$C_{1-10}$ alkyl;
—C(O)—O—$C_{1-10}$ alkyl;
—$N_3$;
-aryl;
-heteroaryl;
-heterocyclyl;
—C(O)-aryl; and
—C(O)-heteroaryl;
Y is —O— or —S(O)$_{0-2}$—;
$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;
each $R_5$ is independently hydrogen, $C_{1-10}$ alkyl, or $C_{2-10}$ alkenyl; and $R_6$ is alkylene, alkenylene, or alkynylene, which may be interrupted by one or more —O— atoms;
or a pharmaceutically acceptable salt thereof.

In another embodiment, a class of intermediate compounds is represented by Formula V:

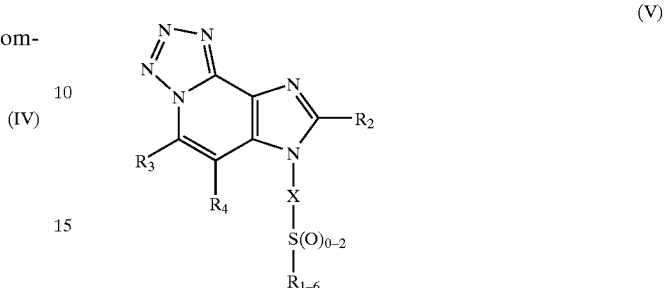

(V)

wherein:
X is —CH($R_5$)—, —CH($R_5$)-alkylene-, —CH($R_5$)-alkenylene-, or CH($R_5$)-alkylene-Y-alkylene-;
$R_{1-6}$ is selected from the group consisting of:
-alkyl;
-aryl;
-heteroaryl;
-heterocyclyl;
-alkenyl;
—$R_6$-aryl;
—$R_6$-heteroaryl;
—$R_6$-heterocyclyl;
$R_2$ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
—OH;
-halogen;
—N($R_5$)$_2$;
—C(O)—$C_{1-10}$ alkyl;
—C(O)—O—$C_{1-10}$ alkyl;
—$N_3$;
-aryl;
-heteroaryl;
-heterocyclyl;
—C(O)-aryl; and
—C(O)-heteroaryl;
Y is —O— or —S(O)$_{0-2}$—;
$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;
each $R_5$ is independently hydrogen, $C_{1-10}$ alkyl, or $C_{2-10}$ alkenyl; and
$R_6$ is alkylene, alkenylene, or alkynylene, which may be interrupted by one or more —O— atoms;
or a pharmaceutically acceptable salt thereof.

In another embodiment, a class of intermediate compounds is represented by Formula LVIII:

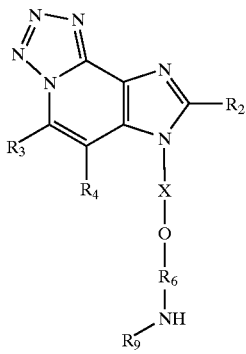

(LVIII)

wherein
X is —CH(R$_5$)—, —CH(R$_5$)-alkylene-, —CH(R$_5$)-alkenylene-, or CH(R$_5$)-alkylene-Y-alkylene-;
R$_2$ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
 —OH;
 -halogen;
 —N(R$_5$)$_2$;
 —C(O)—C$_{1-10}$ alkyl;
 —C(O)—O—C$_{1-10}$ alkyl;
 —N$_3$;
 -aryl;
 -heteroaryl;
 -heterocyclyl;
 —C(O)-aryl; and
 —C(O)-heteroaryl;
Y is —O— or —S(O)$_{0-2}$—;
R$_3$ and R$_4$ are independently selected from the group consisting of hydrogen, C$_{1-10}$ alkyl, C$_{2-10}$ alkenyl, C$_{2-10}$ alkynyl, C$_{1-10}$ alkoxy, C$_{1-10}$ alkylthio, amino, alkylamino, dialkylamino, halogen, and nitro;
each R$_5$ is independently hydrogen, C$_{1-10}$ alkyl, or C$_{2-10}$ alkenyl;
R$_6$ is alkylene, alkenylene, or alkynylene, which may be interrupted by one or more —O— atoms; and
R$_9$ is hydrogen, C$_{1-10}$ alkyl, or arylalkyl; or R$_9$ can join together with any carbon atom of R$_6$ to form a ring of the formula

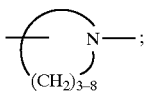

or a pharmaceutically acceptable salt thereof.
In another embodiment, a class of intermediate compounds is represented by Formulas LIX-1, LIX-2, and LIX-3:

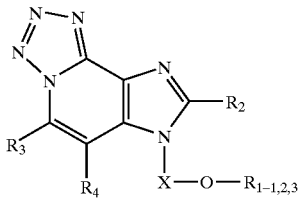

(LIX-1 LIX-2 LIX-3)

wherein:
R$_{1-1,2,3}$ is R$_{1-1}$ in LIX-1, R$_{1-2}$ in LIX-2, and R$_{1-3}$ in LIX-3;
X is —CH(R$_5$)—, —CH(R$_5$)-alkylene-, —CH(R$_5$)-alkenylene-, or CH(R$_5$)-alkylene-Y-alkylene-;
R$_{1-1}$ is selected from the group consisting of:
—R$_6$—C(R$_7$)—Z—R$_8$-alkyl;
—R$_6$—C(R$_7$)—Z—R$_8$-alkenyl;
—R$_6$—C(R$_7$)—Z—R$_8$-aryl;
—R$_6$—C(R$_7$)—Z—R$_8$-heteroaryl;
—R$_6$—C(R$_7$)—Z—R$_8$-heterocyclyl;
—R$_6$—C(R$_7$)—Z—H;
—R$_6$—N(R$_9$)—C(R$_7$)—R$_8$-alkyl;
—R$_6$—N(R$_9$)—C(R$_7$)—R$_8$-alkenyl;
—R$_6$—N(R$_9$)—C(R$_7$)—R$_8$-aryl;
—R$_6$—N(R$_9$)—C(R$_7$)—R$_8$-heteroaryl;
—R$_6$—N(R$_9$)—C(R$_7$)—R$_8$-heterocyclyl; and
—R$_6$—N(R$_9$)—C(R$_7$)—R$_{10}$;
R$_{1-2}$ is selected from the group consisting of:
—R$_6$—N(R$_9$)—SO$_2$—R$_8$-alkyl;
—R$_6$—N(R$_9$)—SO$_2$—R$_8$-alkenyl;
—R$_6$—N(R$_9$)—SO$_2$—R$_8$-aryl;
—R$_6$—N(R$_9$)—SO$_2$—R$_8$-heteroaryl;
—R$_6$—N(R$_9$)—SO$_2$—R$_8$-heterocyclyl;
—R$_6$—N(R$_9$)—SO$_2$—R$_{10}$;
—R$_6$—N(R$_9$)—SO$_2$—N(R$_5$)—R$_8$-alkyl;
—R$_6$—N(R$_9$)—SO$_2$—N(R$_5$)—R$_8$-alkenyl;
—R$_6$—N(R$_9$)—SO$_2$—N(R$_5$)—R$_8$-aryl;
—R$_6$—N(R$_9$)—SO$_2$—N(R$_5$)—R$_8$-heteroaryl;
—R$_6$—N(R$_9$)—SO$_2$—N(R$_5$)—R$_8$-heterocyclyl; and
—R$_6$—N(R$_9$)—SO$_2$—NH$_2$;
R$_{1-3}$ is selected from the group consisting of:
—R$_6$—N(R$_9$)—C(R$_7$)—N(R$_5$)—Q—R$_8$-alkyl;
—R$_6$—N(R$_9$)—C(R$_7$)—N(R$_5$)—Q—R$_8$-alkenyl;
—R$_6$—N(R$_9$)—C(R$_7$)—N(R$_5$)—Q—R$_8$-aryl;
—R$_6$—N(R$_9$)—C(R$_7$)—N(R$_5$)—Q—R$_8$-heteroaryl;
—R$_6$—N(R$_9$)—C(R$_7$)—N(R$_5$)—Q—R$_8$-heterocyclyl;
—R$_6$—N(R$_9$)—C(R$_7$)—N(R$_5$)$_2$;

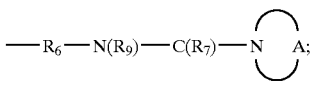

—R$_6$—N(R$_9$)—C(R$_7$)—N(R$_{11}$)—Q—R$_8$-alkyl;
—R$_6$—N(R$_9$)—C(R$_7$)—N(R$_{11}$)—Q—R$_8$-alkenyl;
—R$_6$—N(R$_9$)—C(R$_7$)—N(R$_{11}$)—Q—R$_8$-aryl;
—R$_6$—N(R$_9$)—C(R$_7$)—N(R$_{11}$)—Q—R$_8$-heteroaryl;

—R₆—N(R₉)—C(R₇)—N(R₁₁)—Q—R₈-heterocyclyl; and

—R₆—N(R₉)—C(R₇)—N(R₁₁)H;

R₂ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
—OH;
-halogen;
—N(R₅)₂;
—C(O)—C₁₋₁₀ alkyl;
—C(O)—O—C₁₋₁₀ alkyl;
—N₃;
-aryl;
-heteroaryl;
-heterocyclyl;
—C(O)-aryl; and
—C(O)-heteroaryl;

Y is —O— or —S(O)₀₋₂—;
Z is —N(R₅)—, —O—, or —S—;
Q is a bond, —CO—, or —SO₂—;

A represents the atoms necessary to provide a 5- or 6-membered heterocyclic or heteroaromatic ring that contains up to three heteroatoms;

R₃ and R₄ are independently selected from the group consisting of hydrogen, C₁₋₁₀ alkyl, C₂₋₁₀ alkenyl, C₂₋₁₀ alkynyl, C₁₋₁₀ alkoxy, C₁₋₁₀ alkylthio, amino, alkylamino, dialkylamino, halogen, and nitro;

each R₅ is independently hydrogen, C₁₋₁₀ alkyl, or C₂₋₁₀ alkenyl;

R₆ is alkylene, alkenylene, or alkynylene, which may be interrupted by one or more —O— groups;

R₇ is =O or =S;

R₈ is a bond, alkylene, alkenylene, or alkynylene, which may be interrupted by one or more —O— groups;

R₉ is hydrogen, C₁₋₁₀ alkyl, or arylalkyl; or R₉ can join together with any carbon atom of R₆ to form a ring of the formula

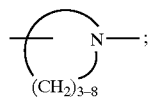

R₁₀ is hydrogen or C₁₋₁₀ alkyl; or R₉ and R₁₀ can join together to form a ring selected from

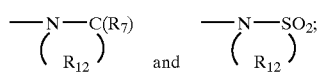

R₁₁ is C₁₋₁₀ alkyl; or R₉ and R₁₁ can join together to form a ring having the structure

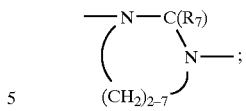

and

R₁₂ is C₂₋₇ alkylene which is straight chain or branched, wherein the branching does not prevent formation of the ring;

or a pharmaceutically acceptable salt thereof.

In another embodiment, a class of intermediate compounds is represented by Formulas LIX-4, and LIX-5:

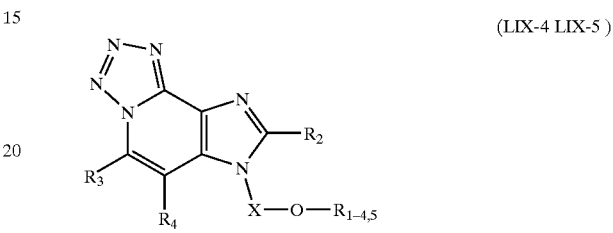

(LIX-4 LIX-5)

wherein:
R₁₋₄,₅ is R₁₋₄ in LIX-4, and R₁₋₅ in LIX-5;
X is —CH(R₅)—, —CH(R₅)-alkylene-, —CH(R₅)-alkenylene-, or CH(R₅)-alkylene-Y-alkylene-;
R₁₋₄ is selected from the group consisting of:
-alkenyl;
-aryl; and
—R₆-aryl;
R₁₋₅ is selected from the group consisting of:
-heteroaryl;
-heterocyclyl;
—R₆- heteroaryl; and
—R₆-heterocyclyl;
R₂ is selected from the group consisting of:
-hydrogen;
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
—OH;
-halogen;
—N(R₅)₂;
—C(O)—C₁₋₁₀ alkyl;
—C(O)—O—C₁₋₁₀ alkyl;
—N₃;
-aryl;
-heteroaryl;
-heterocyclyl;
—C(O)-aryl; and
—C(O)-heteroaryl;
Y is —O— or —S(O)₀₋₂—;
R₃ and R₄ are independently selected from the group consisting of hydrogen, C₁₋₁₀ alkyl, C₂₋₁₀ alkenyl, C₂₋₁₀ alkynyl, C₁₋₁₀ alkoxy, C₁₋₁₀ alkylthio, amino, alkylamino, dialkylamino, halogen, and nitro;

each $R_5$ is independently hydrogen, $C_{1-10}$ alkyl, or $C_{2-10}$ alkenyl; and
$R_6$ is alkylene, alkenylene, or alkynylene, which may be interrupted by one or more —O— groups;
or a pharmaceutically acceptable salt thereof.

In another embodiment, a class of intermediate compounds is represented by Formula LXXVIII:

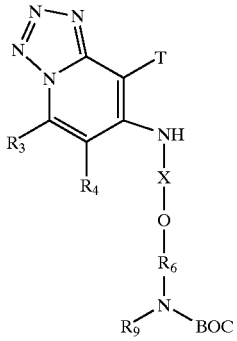

(LXXVIII)

wherein
X is —CH($R_5$)—, —CH($R_5$)-alkylene-, —CH($R_5$)-alkenylene-, or CH($R_5$)-alkylene-Y-alkylene-;
Y is —O— or —S(O)$_{0-2}$—;
BOC is tert-butoxycarbonyl;
each $R_5$ is independently hydrogen, $C_{1-10}$ alkyl, or $C_{2-10}$ alkenyl;
$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;
$R_6$ is alkylene, alkenylene, or alkynylene, which may be interrupted by one or more —O— atoms;
$R_9$ is hydrogen, $C_{1-10}$ alkyl, or arylalkyl; or $R_9$ can join together with any carbon atom of $R_6$ to form a ring of the formula

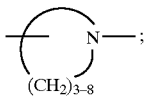

and
T is selected from nitro and amino;
or a pharmaceutically acceptable salt thereof.

In another embodiment, a class of intermediate compounds is represented by Formula LXXIX:

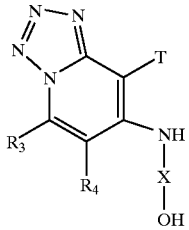

(LXXIX)

wherein
X is —CH($R_5$)—, —CH($R_5$)-alkylene-, —CH($R_5$)-alkenylene-, or CH($R_5$)-alkylene-Y-alkylene-;
Y is —O— or —S(O)$_{0-2}$—;
$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;
each $R_5$ is independently hydrogen, $C_{1-10}$ alkyl, or $C_{2-10}$ alkenyl;
T is selected from nitro and amino;
or a pharmaceutically acceptable salt thereof.

In another embodiment, a class of intermediate compounds is represented by Formulas LXXX-4 and LXXX-5:

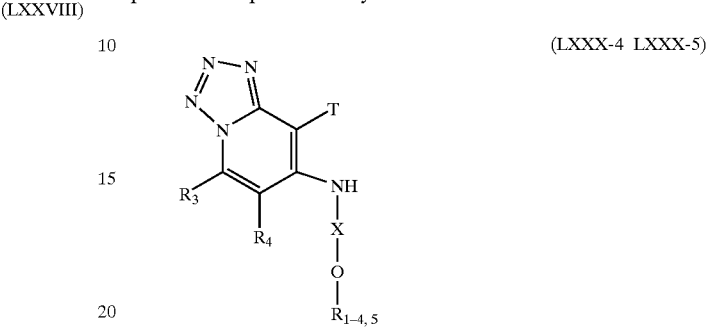

(LXXX-4 LXXX-5)

wherein
$R_{1-4,5}$ is $R_{1-4}$ in LXXX-4, and $R_{1-5}$ in LXXX-5;
X is —CH($R_5$)—, —CH($R_5$)-alkylene-, —CH($R_5$)-alkenylene-, or CH($R_5$)-alkylene-Y-alkylene-;
Y is —O— or —S(O)$_{0-2}$—;
$R_{1-5}$ is selected from the group consisting of:
-heteroaryl;
-heterocyclyl;
—$R_6$-heteroaryl; and
—$R_6$-heterocyclyl;
$R_{1-4}$ is selected from the group consisting of:
-alkenyl;
-aryl; and
—$R_6$-aryl;
$R_3$ and $R_4$ are independently selected from the group consisting of hydrogen, $C_{1-10}$ alkyl, $C_{2-10}$ alkenyl, $C_{2-10}$ alkynyl, $C_{1-10}$ alkoxy, $C_{1-10}$ alkylthio, amino, alkylamino, dialkylamino, halogen, and nitro;
each $R_5$ is independently hydrogen, $C_{1-10}$ alkyl, or $C_{2-10}$ alkenyl;
$R_6$ is alkylene, alkenylene, or alkynylene, which may be interrupted by one or more —O— groups; and
T is selected from nitro and amino;
or a pharmaceutically acceptable salt thereof.

Preparation of the Compounds

Some embodiments of the invention including compounds Formula I-6 and intermediate compounds can be prepared according to Reaction Scheme I where $R_{1-6}$, $R_2$, $R_3$, $R_4$, and X are as defined above and Ph is phenyl.

In step (1) of Reaction Scheme I, a 2,4-dihydroxy-3-nitropyridine of Formula X is chlorinated using conventional chlorinating agents to provide a 2,4-dichloro-3-nitropyridine of Formula XI. Preferably, a compound of Formula X is combined with phosphorous oxychloride and heated. Many 2,4-dihydroxy-3-nitropyridines are known and others can be readily prepared using known synthetic methods, see for example, Lindstrom et al., U.S. Pat. No. 5,446,153 and the references cited therein.

In step (2) of Reaction Scheme I, a 2,4-dichloro-3-nitropyridine of Formula XI is reacted with an amine of formula HO—X—NH$_2$ to provide a 2-chloro-3-nitropyridine of Formula XII. The reaction can be carried out by adding the amine to a solution of a compound of Formula XI in a suitable solvent such as N,N- dimethylformamide in the presence of triethylamine. Many amines of the formula HO—X—$NH_2$ are commercially available; others can be readily prepared using known synthetic methods.

In step (3) of Reaction Scheme I, a 2-chloro-3-nitropyridine of Formula XII is reacted with sodium phenoxide to provide a 3-nitro-2-phenoxypyridine of Formula XIII. Phenol is reacted with sodium hydride in a suitable solvent such as tetrahydrofuran to form the phenoxide. The phenoxide is then reacted at an elevated temperature with a compound of Formula XII.

In step (4) of Reaction Scheme I, a 3-nitro-2-phenoxypyridine of Formula XIII is chlorinated using conventional chlorinating agents to provide a 3-nitro-2-phenoxypyridine of Formula XIV. Preferably, the reaction is carried out by combining a compound of Formula XIII with thionyl chloride in a suitable solvent such as dichloromethane and heating.

In step (5) of Reaction Scheme I, a 3-nitro-2-phenoxypyridine of Formula XIV is reduced to provide a 2-phenoxypyridine-3,4-diamine of Formula XV. Preferably, the reduction is carried out using a conventional heterogeneous catalyst such as platinum on carbon. The reaction can be conveniently carried out on a Parr apparatus in a suitable solvent such as toluene or acetonitrile.

Alternatively in step (5), $Ni_2B$ can be generated in situ from sodium borohydride and $NiCl_2$ in the presence of methanol. A compound of Formula XIV can be added to the resulting reducing agent solution to effect reduction of the nitro group. When a compound of Formula XIV contains an alkenyl, alkynyl, alkenylene or alkynylene moiety, the $Ni_2B$ reducing agent can be used without reducing these moieties. The product can be isolated from the reaction mixture using conventional methods.

In step (6) of Reaction Scheme I, a 2-phenoxypyridine-3,4-diamine of Formula XV is reacted with a carboxylic acid or an equivalent thereof to provide a 4-phenoxy-1H-imidazo[4,5-c]pyridine of Formula XVI. Suitable equivalents to a carboxylic acid include orthoesters, and 1,1-dialkoxyalkyl alkanoates. The carboxylic acid or equivalent is selected such that it will provide the desired $R_2$ substituent in a compound of Formula XVI. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally, a catalyst such as pyridine hydrochloride can be included.

Alternatively, step (6) can be carried out by (i) reacting the diamine of Formula XV with an acyl halide of Formula $R_2C(O)Cl$ or $R_2C(O)Br$ and then (ii) cyclizing. In part (i), the acyl halide is added to a solution of the diamine in a suitable solvent such as pyridine. The reaction can be carried out at ambient temperature. In part (ii), the product of part (i) is heated in pyridine in the presence of pyridine hydrochloride.

In step (7) of Reaction Scheme I, a 4-phenoxy-1H-imidazo[4,5-c]pyridine of Formula XVI is reacted with a compound of Formula $R_{1-6}SNa$ to provide a 2-phenoxy-1H-imidazo[4,5-c]pyridine of Formula III. Preferably, a thiol of the Formula $R_{1-6}SH$ is reacted with sodium hydride in a suitable solvent such as N,N-dimethylformamide to generate the anion, which is then reacted with a compound of Formula XVI.

In step (8) of Reaction Scheme I, a 4-phenoxy-1H-imidazo[4,5-c]pyridine of Formula III is aminated to provide a 1H-imidazo[4,5-c]pyridin-4-amine of Formula XVII which is a subgenus of Formula I-6. The reaction can be carried out by combining a compound of Formula III with ammonium acetate and heating (140–160° C.). Optionally, the reaction can be carried out in a pressure vessel. The product or a pharmaceutically acceptable salt thereof can be isolated using conventional methods.

In step (9) of Reaction Scheme I, a 1H-imidazo[4,5-c]pyridin-4-amine of Formula XVII is oxidized to provide a 1H-imidazo[4,5-c]pyridin-4-amine of Formula XVIII which is a subgenus of Formula I-6. Preferably, a solution of a compound of Formula XVII in a suitable solvent such as chloroform or dichloromethane is treated with 3-chloroperoxybenzoic acid. The degree of oxidation is controlled by adjusting the amount of 3-chloroperoxybenxzoic acid used in the reaction; i.e., using approximately one equivalent will provide the sulfoxide whereas using two equivalents will provide the sulfone. The product or a pharmaceutically acceptable salt thereof can be isolated using conventional methods.

Alternatively, steps (8) and (9) of Reaction Scheme I can be reversed as shown in steps (10) and (11). In step (10) of Reaction Scheme I, a 4-phenoxy-1H-imidazo[4,5-c]pyridine of Formula III is oxidized as in step (9) to provide a 4-phenoxy-1H-imidazo[4,5-c]pyridin-4-amine of Formula XLIII. Preferably, the oxidation reaction is carried out at a reduced temperature, for example, about 0° C. The product or a pharmaceutically acceptable salt thereof can be isolated using conventional methods.

In step (11) of Reaction Scheme I, a 4-phenoxy-1H-imidazo[4,5-c]pyridin-4-amine of Formula XLIII is aminated as in step (8) to provide a 1H-imidazo[4,5-c]pyridin-4-amine of Formula XVIII which is a subgenus of Formula I-6. The product or a pharmaceutically acceptable salt thereof can be isolated using conventional methods.

Reaction Scheme I

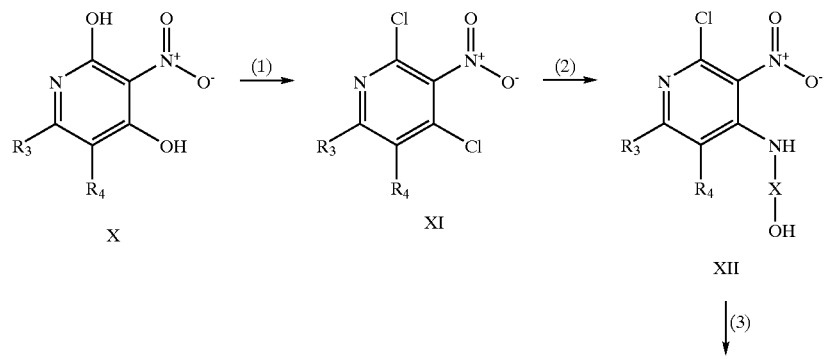

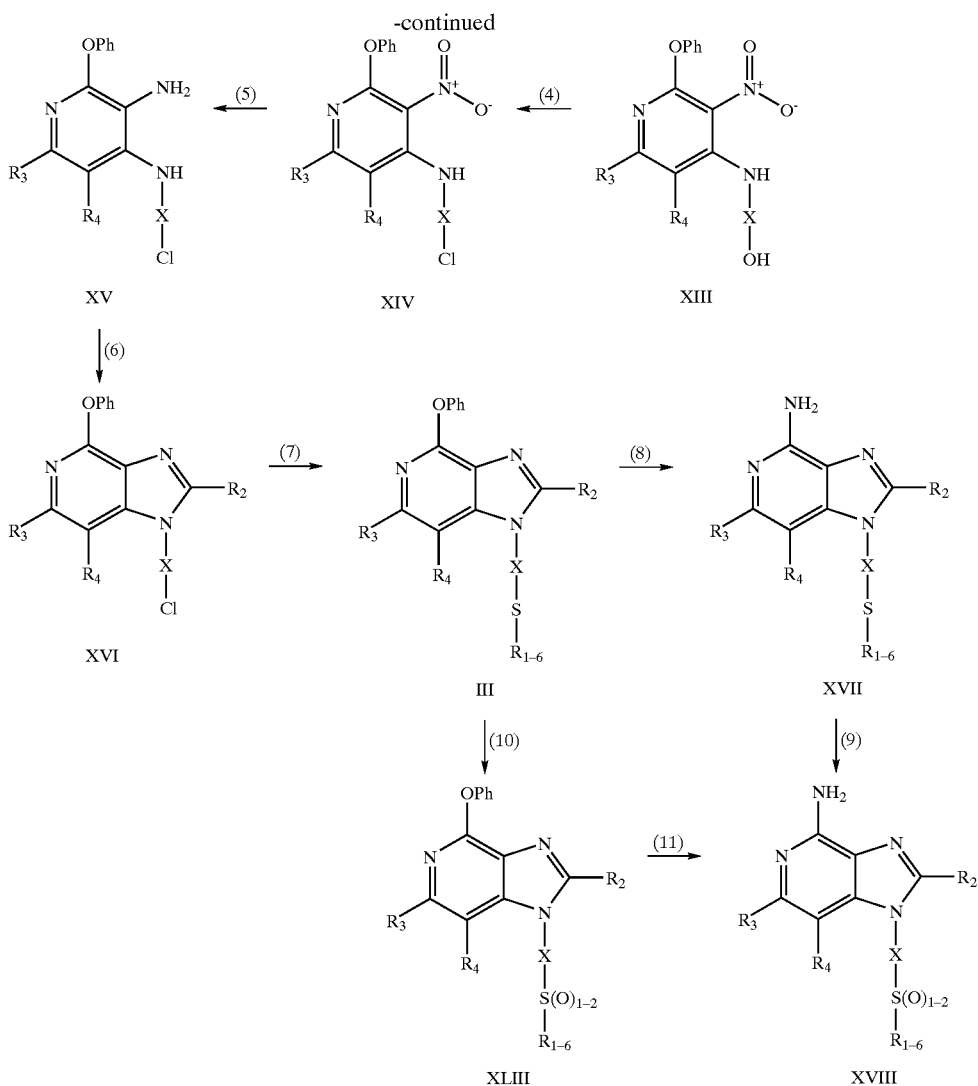

Some embodiments of the invention including compounds of Formula I-1, I-2, I-3, and intermediate compounds can be prepared according to Reaction Scheme II where $R_{1-1, 2, 3}$ ($R_{1-1}$, $R_{1-2}$, and $R_{1-3}$), $R_2$, $R_3$, $R_4$, $R_6$, $R_9$ and X are as defined above and BOC is tert-butoxycarbonyl.

In step (1) of Reaction Scheme II, the amino group of an aminoalcohol of Formula XIX is protected with a tert-butoxycarbonyl group to provide a compound of Formula XX. A solution of the aminoalcohol in tetrahydrofuran is treated with di-tert-butyl dicarbonate in the presence of a base such as sodium hydroxide. Many aminoalcohols of Formula XIX are commercially available; others can be prepared using known synthetic methods.

In step (2) of Reaction Scheme II, a protected amino alcohol of Formula XX is converted to a methanesulfonate of Formula XXI. A solution of a compound of Formula XX in a suitable solvent such as dichloromethane is treated with methanesulfonyl chloride in the presence of a base such as triethylamine. The reaction can be carried out at a reduced temperature (0° C.).

In step (3a) of Reaction Scheme II, a methanesulfonate of Formula XXI is converted to an azide of Formula XXII. Sodium azide is added to a solution of a compound of Formula XXI in a suitable solvent such as N,N-dimethylformamide. The reaction can be carried out at an elevated temperature (80–100° C.).

In step (3b) of Reaction Scheme II, a compound of Formula XXII is alkylated with a halide of Formula Hal-$R_9$ to provide a compound of Formula XXIII. In compounds where $R_9$ is hydrogen, this step is omitted. The compound of Formula XXII is reacted with sodium hydride in a suitable solvent such as N,N-dimethylformamide to form the anion and then combined with the halide. The reaction can be carried out at ambient temperature.

In step (4) of Reaction Scheme II, an azide of Formula XXIII is reduced to provide an amine of Formula XXIV. Preferably, the reduction is carried out using a conventional heterogeneous hydrogenation catalyst such as palladium on carbon. The reaction can conveniently be carried out on a Parr apparatus in a suitable solvent such as toluene.

In step (5) of Reaction Scheme II, a 2,4-dichloro-3-nitropyridine of Formula XI (see Reaction Scheme I) is reacted with an amine of Formula XXIV to provide a 2-chloro-3-nitropyridine of Formula XXV. The reaction can be carried out by adding an amine of Formula XXIV to a solution of a compound of Formula XI in a suitable solvent such as N,N-dimethylformamide in the presence of a base such as triethylamine.

In step (6) of Reaction Scheme II, a 2-chloro-3-nitropyridine of Formula XXV is reacted with sodium phenoxide to provide a 3-nitro-2-phenoxypyridine of Formula XXVI. Phenol is reacted with sodium hydride in a suitable solvent such as tetrahydrofuran to form the phenoxide. The phenoxide is then reacted at an elevated temperature with a compound of Formula XXV.

In step (7) of Reaction Scheme II, a 3-nitro-2-phenoxypyridine of Formula XXVI is reduced to provide a 2-phenoxypyridine-3,4-diamine of Formula XXVII. Preferably, the reduction is carried out using a conventional heterogeneous catalyst such as platinum on carbon. The reaction can be conveniently carried out on a Parr apparatus in a suitable solvent such as, for example, toluene, 2-propanol, ethanol, and mixtures thereof.

Alternatively in step (7), $Ni_2B$ can be generated in situ from sodium borohydride and $NiCl_2$ in the presence of methanol. A compound of Formula XXVI can be added to the resulting reducing agent solution to effect reduction of the nitro group. When a compound of Formula XXVI contains an alkenyl, alkynyl, alkenylene or alkynylene moiety, the $Ni_2B$ reducing agent can be used without reducing these moieties. The product can be isolated from the reaction mixture using conventional methods.

In step (8) of Reaction Scheme II, a 2-phenoxypyridine-3,4-diamine of Formula XXVII is reacted with a carboxylic acid or an equivalent thereof to provide a 4-phenoxy-1H-imidazo[4,5-c]pyridine of Formula XXVIII. Suitable equivalents to a carboxylic acid include orthoesters, and 1,1-dialkoxyalkyl alkanoates. The carboxylic acid or equivalent is selected such that it will provide the desired $R_2$ substituent in a compound of Formula XXVIII. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally, a catalyst such as pyridine hydrochloride can be included.

Alternatively, step (8) can be carried out by (i) reacting the diamine of Formula XXVII with an acyl halide of Formula $R_2C(O)Cl$ or $R_2C(O)Br$ and then (ii) cyclizing. In part (i), the acyl halide is added to a solution of the diamine in a suitable solvent such as pyridine. The reaction can be carried out at ambient temperature. In part (ii), the product of part (i) is heated in pyridine in the presence of pyridine hydrochloride.

In step (9) of Reaction Scheme II, a 4-phenoxy-1H-imidazo[4,5-c]pyridine of Formula XXVIII is aminated to, provide a (4-amino-1H-imidazo[4,5-c]pyridinyl)acetamide of Formula VI. The reaction can be carried out by combining a compound of Formula XXVIII with ammonium acetate and heating (140–160° C.). Optionally, the reaction can be carried out in a pressure vessel.

In step (10) of Reaction Scheme II, (4-amino-1H-imidazo[4,5-c]pyridinyl)acetamide of Formula VI is hydrolyzed under acidic conditions to provide a 1H-imidazo[4,5-c]pyridin-4-amine of Formula II. Preferably, a compound of Formula VI is treated with hydrochloric acid/ethanol at an elevated temperature.

In step (11) of Reaction Scheme II, a 1H-imidazo[4,5-c]pyridin-4-amine of Formula II is converted to a 1H-imidazo[4,5-c]pyridin-4-amine of Formula I-2 using conventional methods. For example, sulfonamides of Formula I-2 can be prepared by reacting a compound of Formula II with a sulfonyl chloride of Formula $R_aS(O_2)Cl$, where $R_a$ is $R_8$-alkyl, $R_8$-alkenyl, $R_8$-aryl, $R_8$-heteroaryl or $R_8$-heterocyclyl. The reaction can be carried out by adding the sulfonyl chloride to a solution of a compound of Formula II in a suitable solvent such as chloroform at ambient temperature. Sulfamides of Formula I-2 can be prepared by reacting a compound of Formula II with sulfuryl chloride to generate a sulfamoyl chloride in situ and then reacting the sulfamoyl chloride with an amine of Formula $HNR_5R_a$. The product or a pharmaceutically acceptable salt thereof can be isolated using conventional methods.

Amides of Formula I-1 can be prepared from 1H-imidazo[4,5-c]pyridin-4-amines of Formula II using conventional methods. For example, a compound of Formula II can be reacted with an acid chloride of Formula $R_aC(O)Cl$. The reaction can be carried out by adding the acid chloride to a solution of a compound of Formula II in a suitable solvent such as chloroform, optionally in the presence of a base such as triethylamine, at ambient temperature. The product or a pharmaceutically acceptable salt thereof can be isolated using conventional methods.

Ureas and thioureas of Formula I-3 can be prepared from 1H-imidazo[4,5-c]pyridin-4-amines of Formula II using conventional methods. For example, a compound of Formula II can be reacted with an isocyanate of Formula $R_aN=C=O$. The reaction can be carried out by adding the isocyanate to a solution of a compound of Formula II in a suitable solvent such as chloroform, optionally in the presence of a base such as triethylamine, at ambient temperature. Alternatively, a compound of Formula II can be reacted with a thioisocyanate of Formula $R_aN=C=S$, a sulfonyl isocyanate of Formula $R_aS(O_2)N=C=O$ or a carbamoyl chloride of Formula $R_aNC(O)Cl$. The product or a pharmaceutically acceptable salt thereof can be isolated using conventional methods.

Reaction Scheme II

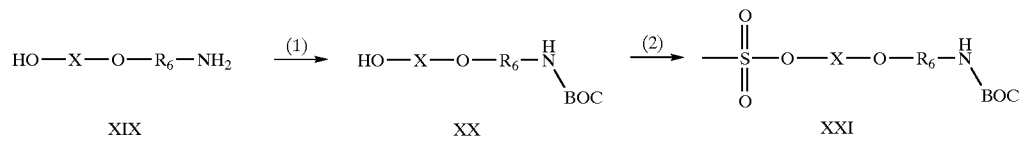

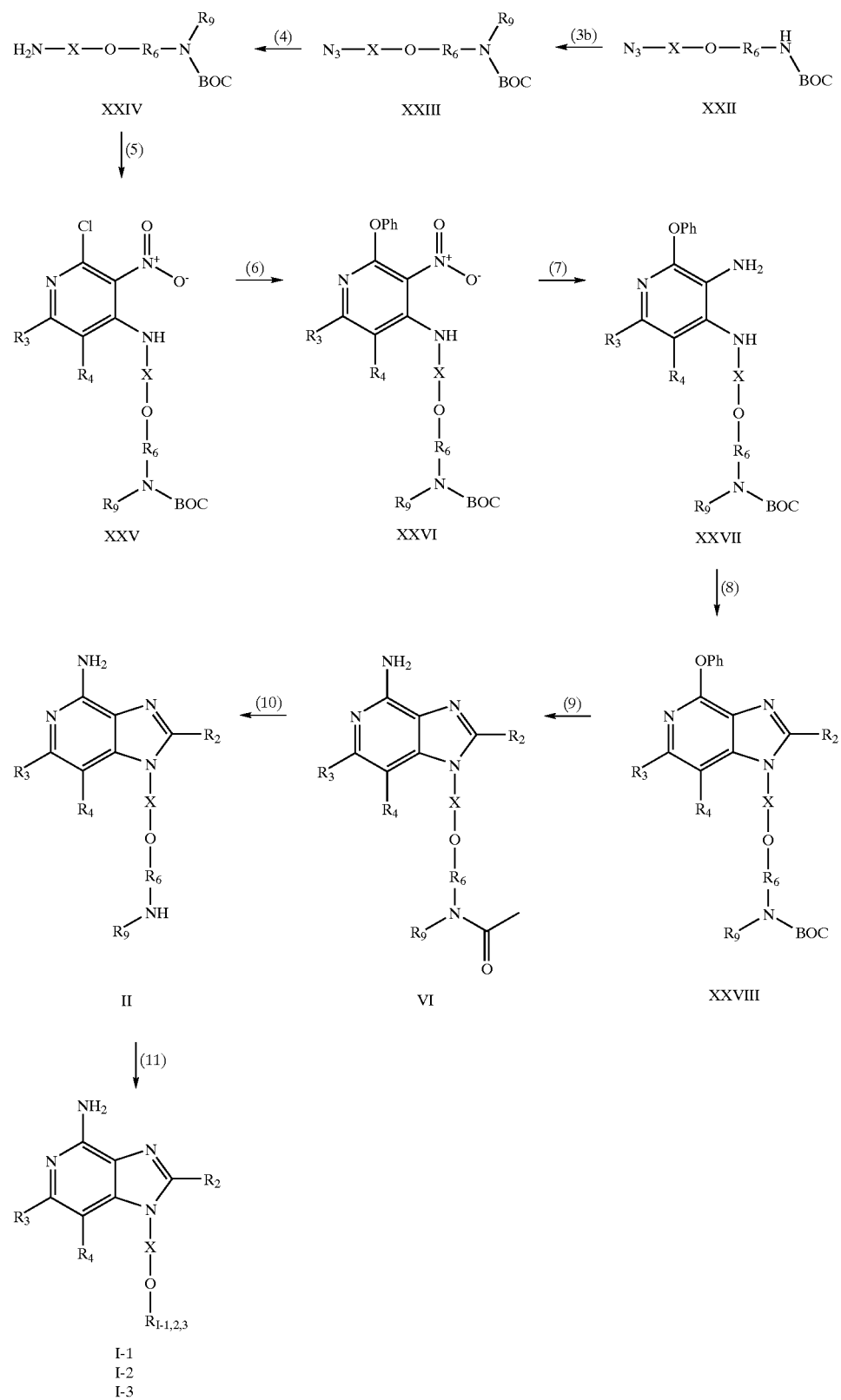

Some embodiments of the invention including compounds of Formulas I-4, I-5, and intermediate compounds can be prepared according to Reaction Scheme III where $R_{1-4,5}$ ($R_{1-4}$ and $R_{1-5}$), $R_2$, $R_3$, $R_4$, X, and Ph are as defined above.

In step (1) of Reaction Scheme III, a 2,4-dichloro-3-nitropyridine of Formula XI is reacted with an amine of formula $R_{1-4}$—O—X—$NH_2$ or $R_{1-5}$—O—X—$NH_2$ to provide a 2-chloro-3-nitropyridine of Formula XXIX-4 or XXIX-5. The reaction can be carried out by adding the amine to a solution of compound of Formula XI in a suitable solvent such as N, N-dimethylformamide in the presence of triethylamine. The product of the reaction can be isolated from the reaction mixture using conventional methods. Many amines of the formula $R_{1-4}$—O—X—$NH_2$ or $R_{1-5}$—O—X—$NH_2$ are commercially available; others can be readily prepared using known synthetic methods. For example, benzyloxyethylamine hydrochloride can be prepared by reacting tert-butyl 2-(hydroxy)ethylcarbamate with benzyl bromide in the presence of sodium hydroxide and benzyltrimethylammonium chloride, and then converting the resulting tert-butyl 2-(benzyloxy)ethylcarbamate to benzyloxyethylamine hydrochloride in the presence of hydrochloric acid, ethanol, and water.

In other examples, 2-(3-pyridin-3-yl-propoxy)ethylamine and 2-[3-(1,3-thiazol-2-yl)propoxy]ethylamine can be prepared by reacting tert-butyl 2-(hydroxy)ethylcarbamate with 3-bromopropyne under the phase transfer conditions described above. The resulting tert-butyl 2-(prop-2-ynyloxy) ethylcarbamate can be coupled with heteroaryl bromides such as 3-bromopyridine and 2-bromothiazole by means of a palladium complex generated from a palladium catalyst such as dichlorobis(triphenylphosphine)palladium (II) in the presence of copper (I) iodide and a base such as triethylamine. The reaction is conveniently carried out in a suitable solvent such as acetonitrile and can be heated at an elevated temperature. The products from the coupling reaction can be hydrogenated in the presence of a conventional heterogeneous catalyst such as 10% palladium on carbon. The hydrogenation reaction is conveniently carried out in a Parr vessel in a solvent such as methanol. Finally, the resulting tert-butyl 2-(heteroarylpropoxy)ethylcarbamates can be deprotected to provide 2-(heteroarylpropoxy)ethylamines under conditions described above.

In step (2) of Reaction Scheme III, a 2-chloro-3-nitropyridine of Formula XXIX-4 or XXIX-5 is reacted with sodium phenoxide to provide a 3-nitro-2-phenoxypyridine of Formula XXX-4 or XXX-5. Phenol is reacted with sodium hydride in a suitable solvent such as diglyme (bis (2-methoxyethyl) ether) to form the phenoxide. The phenoxide is then reacted at an elevated temperature with a compound of Formula XXIX-4 or XXIX-5. The product can be isolated from the reaction mixture using conventional methods.

In step (3) of Reaction Scheme III, a 3-nitro-2-phenoxypyridine of Formula XXX-4 or XXX-5 is reduced to provide a 2-phenoxypyridine-3,4-diamine of Formula XXXI-4 or XXXI-5. Preferably, the reduction is carried out using a conventional heterogeneous catalyst such as platinum on carbon. The reaction can be conveniently carried out on a Parr apparatus in a suitable solvent such as toluene.

Alternatively in step (3), $Ni_2B$ can be generated in situ from sodium borohydride and $NiCl_2$ in the presence of methanol. A compound of Formula XXX-4 or XXX-5 can be added to the resulting reducing agent solution to effect reduction of the nitro group. When a compound of Formula XXX-4 or XXX-5 contains an alkenyl, alkynyl, alkenylene or alkynylene moiety, the $Ni_2B$ reducing agent can be used without reducing these moieties. The product can be isolated from the reaction mixture using conventional methods.

In step (4) of Reaction Scheme III, a 2-phenoxypyridine-3,4-diamine of Formula XXXI-4 or XXXI-5 is reacted with a carboxylic acid or an equivalent thereof to provide a 4-phenoxy-1H-imidazo[4,5-c]pyridine of Formula XXXII-4 or XXXII-5. Suitable equivalents to a carboxylic acid include orthoesters, 1,1-dialkoxyalkyl alkanoates, corresponding acyl halides, and mixtures thereof. The carboxylic acid or equivalent is selected such that it will provide the desired $R_2$ substituent in a compound of Formula XXXII-4 or XXXII-5. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally, a catalyst such as pyridine hydrochloride can be included.

Alternatively, step (4) can be carried out by (i) reacting the diamine of Formula XXXI-4 or XXXI-5 with an acyl halide of Formula $R_2C(O)Cl$ or $R_2C(O)Br$ and then (ii) cyclizing. In part (i), the acyl halide is added to a solution of the diamine in a suitable solvent such as pyridine. The reaction can be carried out at ambient temperature. In part (ii), the product of part (i) is heated in pyridine in the presence of pyridine hydrochloride. The product can be isolated from the reaction mixture using conventional methods.

In step (5) of Reaction Scheme III, a 4-phenoxy-1H-imidazo[4,5-c]pyridine of Formula XXXII-4 or XXXII-5 is aminated to provide a 1H-imidazo[4,5-c]pyridin-4-amine of Formula I-4 or I-5. The reaction can be carried out by combining a compound of Formula XXXII-4 or XXXII-5 with ammonium acetate and heating (140–160° C.). Optionally, the reaction can be carried out in a pressure vessel. The product or a pharmaceutically acceptable salt thereof can be isolated using conventional methods.

In Reaction Scheme III, when $R_{1-4,5}$ is $R_{1-4}$ the products of steps (1)-(5) are of the Formulas XXIX-4, XXX-4, XXXI-4, XXXII-4, and 1–4, respectively. Likewise, when $R_{1-4,5}$ is $R_{1-5}$ the products of steps (1)-(5) are of the Formulas XXIX-5, XXX-5, XXXI-5, XXXII-5, and I-5.

Reaction Scheme III

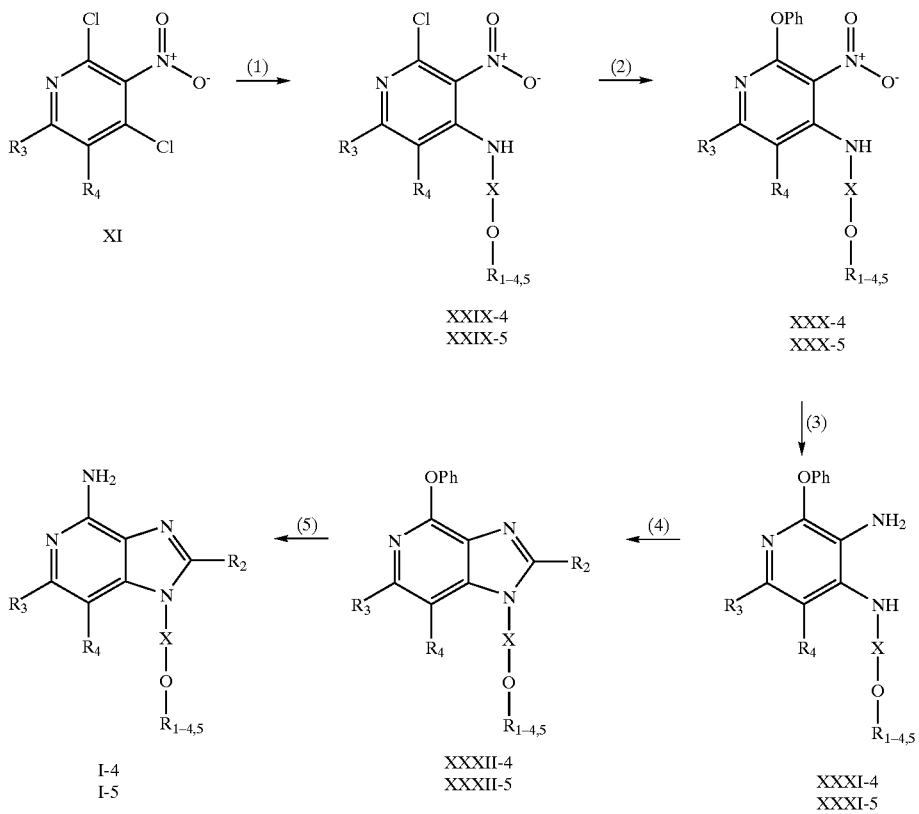

Some embodiments of the invention including compounds of Formula I-1 and intermediate compounds can be prepared according to Reaction Scheme IV where $R_{1-4}$, $R_2$, $R_3$, $R_4$, X, and Ph are as defined above, and Ac is acetyl.

In step (1) of Reaction Scheme IV, a 3-nitro-2-phenoxypyridine of Formula XIII is esterified to provide a 3-nitro-2-phenoxypyridine acetate of Formula XXXIII. Preferably, the esterification is carried out using acetic anhydride in suitable solvents such as anhydrous dichloromethane and pyridine. The product can be isolated from the reaction mixture using conventional methods.

In step (2) of Reaction Scheme IV, 3-nitro-2-phenoxypyridine acetate of Formula XXXIII is reduced to provide a 2-phenoxypyridine-3,4-diamine Formula XXXIV. Preferably, the reduction is carried out using a conventional heterogeneous catalyst such as platinum on carbon. The reaction can be conveniently carried out on a Parr apparatus in a suitable solvent such as toluene.

Alternatively in step (2), $Ni_2B$ can be generated in situ from sodium borohydride and $NiCl_2$ in the presence of methanol. A compound of Formula XXXIII can be added to the resulting reducing agent solution to effect reduction of the nitro group. When a compound of Formula XXXIII contains an alkenyl, alkynyl, alkenylene or alkynylene moiety, the $Ni_2B$ reducing agent can be used without reducing these moieties. The product can be isolated from the reaction mixture using conventional methods.

In step (3) of Reaction Scheme IV, a 2-phenoxypyridine-3,4-diamine of Formula XXXIV is reacted with a carboxylic acid or an equivalent thereof to provide a 4-phenoxy-1H-imidazo[4,5-c]pyridine of Formula XXXV. Suitable equivalents to a carboxylic acid include orthoesters, 1,1-dialkoxyalkyl alkanoates, corresponding acyl halides, and mixtures thereof. The carboxylic acid or equivalent is selected such that it will provide the desired $R_2$ substituent in a compound of Formula XXXV. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally, a catalyst such as pyridine hydrochloride can be included.

Alternatively, step (3) can be carried out by (i) reacting the diamine of Formula XXXIV with an acyl halide of Formula $R_2C(O)Cl$ or $R_2C(O)Br$ and then (ii) cyclizing. In part (i), the acyl halide is added to a solution of the diamine in a suitable solvent such as pyridine. The reaction can be carried out at ambient temperature. In part (ii), the product of part (i) is heated in pyridine in the presence of pyridine hydrochloride. The product can be isolated from the reaction mixture using conventional methods.

In step (4) of Reaction Scheme IV, a 4-phenoxy-1H-imidazo[4,5-c]pyridine acetate of Formula XXXV is hydrolyzed to provide a 4-phenoxy-1H-imidazo[4,5-c]pyridine alcohol of Formula XXXVI. The reaction is preferably carried out in methanol in the presence of potassium carbonate at an elevated temperature. The product can be isolated from the reaction mixture using conventional methods.

In step (5) of Reaction Scheme IV, a 4-phenoxy-1H-imidazo[4,5-c]pyridine alcohol of Formula XXXVI is reacted with a compound of formula Halo-$R_{1-4}$ to provide a 4-phenoxy-1H-imidazo[4,5-c]pyridine of Formula XXXII- 4. The reaction can be carried out by first reacting the alcohol of Formula XXXVI with sodium hydride in a suitable solvent such as N,N-dimethylformamide to form the corresponding anion and then reacting the anion with a compound of formula Halo-$R_{1-4}$. The product can be isolated from the reaction mixture using conventional methods.

In step (6) of Reaction Scheme IV, a 4-phenoxy-1H-imidazo[4,5-c]pyridine of Formula XXXII-4 is aminated to provide a 1H-imidazo[4,5-c]pyridin-4-amine of Formula I-4. The reaction can be carried out by combining a compound of Formula XXXII-4 with ammonium acetate and heating (140–160° C.). Optionally, the reaction can be carried out in a pressure vessel. The product or a pharmaceutically acceptable salt thereof can be isolated using conventional methods.

In step (1) of Reaction Scheme V, the alkyne bond of a 4-phenoxy-1H-imidazo[4,5-c]pyridine of Formula XXXVII, which is a subgenus of Formula XXXII-4 or XXXII-5, is reduced to form a 4-phenoxy-1H-imidazo[4,5-c]pyridine of Formula XXXVIII, which is also a subgenus of Formula XXXII-4 or XXXII-5. Preferably, the reduction is carried out using a conventional heterogeneous catalyst such as platinum oxide, platinum on carbon, or palladium on carbon. The reaction can conveniently be carried out on a Parr apparatus in a suitable solvent such as methanol. The product can be isolated from the reaction mixture using conventional methods.

In step (2) of Reaction Scheme V, a 4-phenoxy-1H-imidazo[4,5-c]pyridine of Formula XXXVIII is aminated to

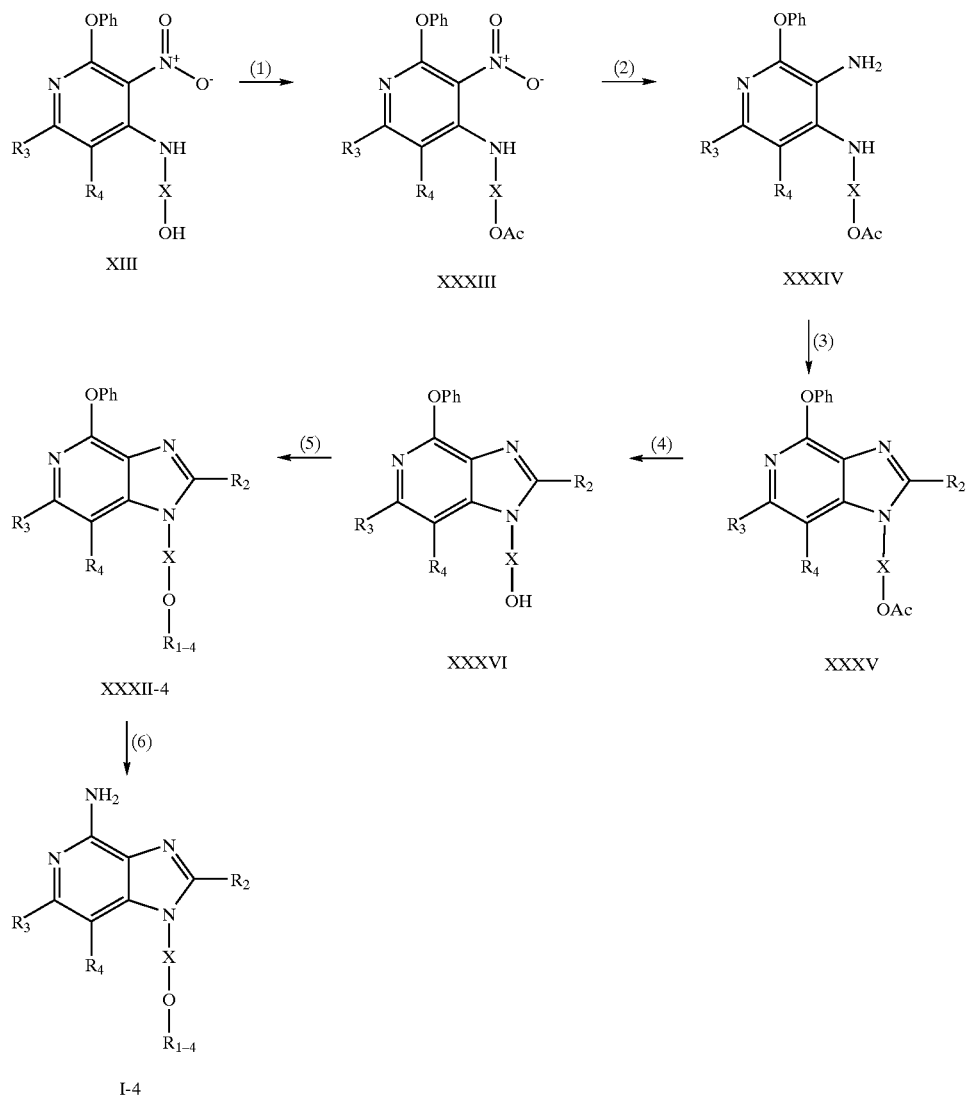

Some embodiments of the invention including compounds of Formula XXXIX and intermediate compounds can be prepared according to Reaction Scheme V where $R_2$, $R_3$, $R_4$, X, and Ph are as defined above, and $R_{13}$ is aryl, substituted aryl, heteroaryl, or substituted heteroaryl.

provide a 1H-imidazo[4,5-c]pyridin-4-amine of Formula XXXIX, which a subgenus of Formula I-4 or I-5. The reaction can be carried out by combining a compound of Formula XXXVIII with ammonium acetate and heating (140–160° C.). Optionally, the reaction can be carried out in a pressure vessel. The product or a pharmaceutically acceptable salt thereof can be isolated using conventional methods.

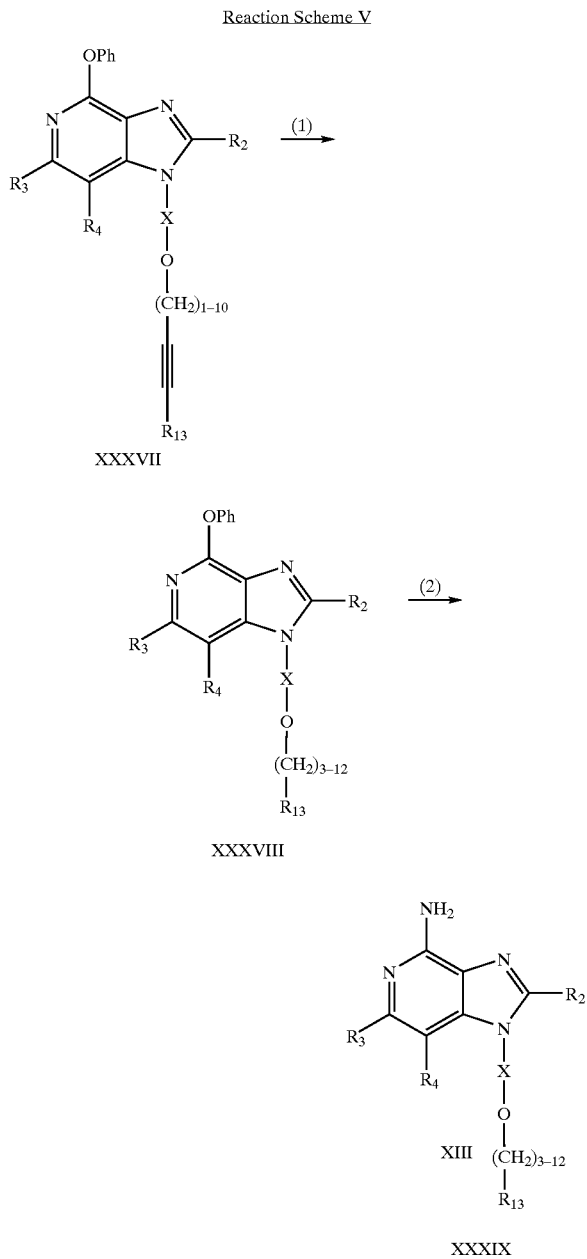

Reaction Scheme V

Some embodiments of the invention including compounds of Formula I-4 and intermediate compounds can be prepared according to Reaction Scheme VI where $R_{1-4}$, $R_2$, $R_3$, $R_4$, X, and Ph are as defined above.

In step (1) of Reaction Scheme VI, a 2-chloro-3-nitropyridine of Formula XXIX-4, prepared as described in Reaction Scheme III, is reduced to provide a 2-chloropyridine-3,4-diamine of Formula XL. Preferably, the reduction is carried out using a conventional heterogeneous catalyst such as platinum on carbon or palladium on carbon. The reaction can be conveniently carried out on a Parr apparatus in a suitable solvent such as toluene.

Alternatively in step (1), $Ni_2B$ can be generated in situ from sodium borohydride and $NiCl_2$ in the presence of methanol. A compound of Formula XXIX-4 can be added to the resulting reducing agent solution to effect reduction of the nitro group. When a compound of Formula XXIX-4 contains an alkenyl, alkynyl, alkenylene or alkynylene moiety, the $Ni_2B$ reducing agent can be used without reducing these moieties. The product can be isolated from the reaction mixture using conventional methods.

In step (2) of Reaction Scheme VI, a 2-chloropyridine-3,4-diamine of Formula XL is reacted with a carboxylic acid or an equivalent thereof to provide a 4-chloro-1H-imidazo[4,5-c]pyridine of Formula XLII. Suitable equivalents to a carboxylic acid include orthoesters, 1,1-dialkoxyalkyl alkanoates, corresponding acyl halides, and mixtures thereof. The carboxylic acid or equivalent is selected such that it will provide the desired $R_2$ substituent in a compound of Formula XLII. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally, a catalyst such as pyridine hydrochloride can be included.

Alternatively, step (2) can be carried out by (2a) reacting the diamine of Formula XL with an acyl halide of Formula $R_2C(O)Cl$ or $R_2C(O)Br$ and then (2b) cyclizing. For example, in part (2a), the acyl halide is added to a solution of the diamine of Formula XL in an inert solvent such as dichloromethane or acetonitrile. The reaction can be carried out at ambient temperature. Optionally, a tertiary amine, for example triethylamine, is included. In part (2b), the product of part (2a), a compound of Formula XLI, is heated at reflux in a suitable solvent such as ethanol in the presence of triethylamine. The product can be isolated from the reaction mixture using conventional methods.

In step (3) of Reaction Scheme VI, a 4-chloro-1H-imidazo[4,5-c]pyridine of Formula XLII is reacted with sodium phenoxide to provide a 4-phenoxy-1H-imidazo[4,5-c]pyridine of Formula XXXII-4. Phenol is reacted with sodium hydride in a suitable solvent such as diglyme (bis(2-methoxyethyl) ether) to form the phenoxide. The phenoxide is then reacted at an elevated temperature with a compound of Formula XLII. The product can be isolated from the reaction mixture using conventional methods.

In step (4) of Reaction Scheme VI, a 4-phenoxy-1H-imidazo[4,5-c]pyridine of Formula XXXII-4 is aminated to provide a 1H-imidazo[4,5-c]pyridin-4-amine of Formula I-4. The reaction can be carried out by combining a compound of Formula XXXII-4 with ammonium acetate and heating (140–160° C.). Optionally, the reaction can be carried out in a pressure vessel. The product or a pharmaceutically acceptable salt thereof can be isolated using conventional methods.

Reaction Scheme VI

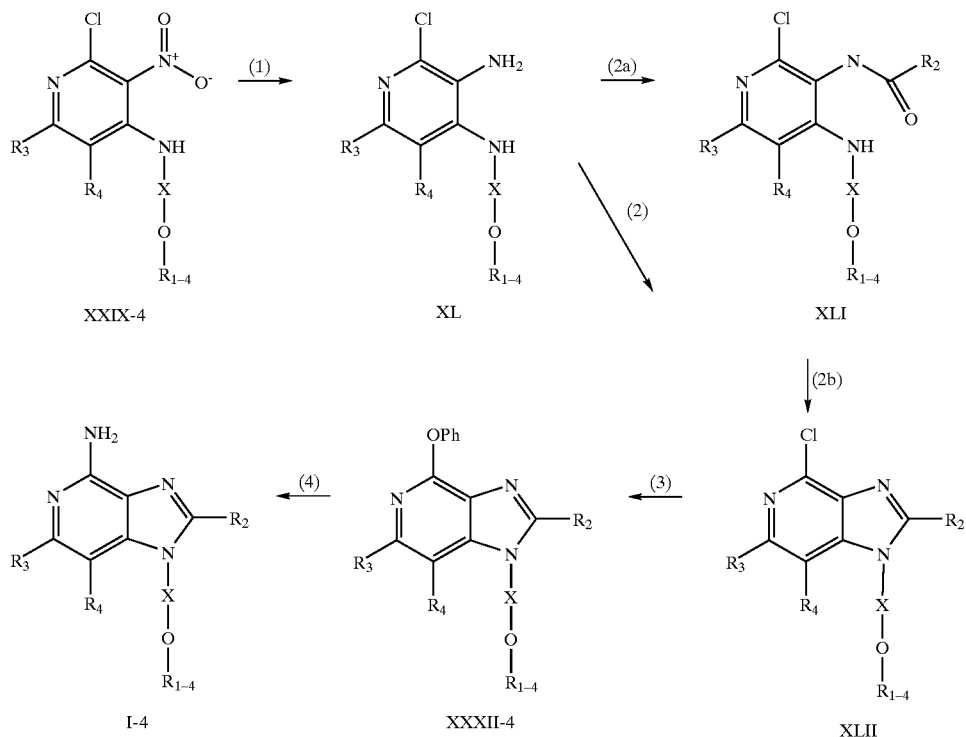

Some embodiments of the invention including compounds of Formulas XLV-1, XLV-2, XLV-3, XLVI-1, XLVI-2, XLVI-3, and intermediate compounds can be prepared according to Reaction Scheme VII where $R_{1-1, 2, 3}$ ($R_{1-1}$, $R_{1-2}$, $R_{1-3}$), $R_2$, $R_6$, $R_9$, and X defined above, $R_{4a}$ is —Br or —NO$_2$, and $R_{4b}$ is $C_{2-10}$ alkynyl and $C_{1-10}$ alkyl.

In step (1) of Reaction Scheme VII, bromination or nitration of a (4-amino-1H-imidazo[4,5-c]pyridinyl) acetamide of Formula VIa provides a (7-substituted)-(4-amino-1H-imidazo[4,5-c]pyridinyl)acetamide of Formula XLIV. The bromination reaction can be carried out by treating the acetamide of Formula VIa in a solution of acetic acid with bromine and potassium acetate at ambient temperature. The direct nitration reaction can be carried out by treating the acetamide of Formula VIa with one equivalent of nitric acid in the presence of excess acetic acid and heating the reaction, optionally, at reflux. The product can be isolated using conventional methods.

In step (2) of Reaction Scheme VII, a (7-substituted)-(4-amino-1H-imidazo[4,5-c]pyridinyl)acetamide of Formula XLIV is hydrolyzed under acidic conditions to provide a (7-substituted)-1H-imidazo[4,5-c]pyridin-4-amine of Formula IIa, which is a subgenus of compounds of Formula II. Preferably, a compound of Formula XLIV is treated with hydrochloric acid/ethanol at an elevated temperature, for example, at reflux. The product can be isolated using conventional methods.

In step (3) of Reaction Scheme VII, a 1H-imidazo[4,5-c] pyridin-4-amine of Formula IIa is converted to a 1H-imidazo[4,5-c]pyridin-4-amine of Formula XLV-1, XLV-2, or XLV-3 using conventional methods. Formulas XLV-1, XLV-2, and XLV-3 are subgenera of Formulas I-1, I-2, and I-3, respectively. For example, sulfonamides of Formula XLV-2 can be prepared by reacting a compound of Formula IIa with a sulfonyl chloride of Formula $R_aS(O_2)Cl$, where $R_a$ is $R_8$-alkyl, $R_8$-alkenyl, $R_8$-aryl, $R_8$-heteroaryl or $R_8$-heterocyclyl. The reaction can be carried out by adding the sulfonyl chloride to a solution of a compound of Formula Ia in a suitable solvent such as chloroform at ambient temperature. Sulfamides of Formula XLV-2 can be prepared by reacting a compound of Formula IIa with sulfuryl chloride to generate a sulfamoyl chloride in situ, and then reacting the sulfamoyl chloride with an amine of Formula HNR$_5$R$_a$. The product or a pharmaceutically acceptable salt thereof can be isolated using conventional methods.

Amides of Formula XLV-1 can be prepared from 1H-imidazo[4,5-c]pyridin-4-amines of Formula IIa using conventional methods. For example, a compound of Formula IIa can be reacted with an acid chloride of Formula $R_aC(O)Cl$, where $R_a$ is $R_8$-alkyl, $R_8$-alkenyl, $R_8$-aryl, $R_8$-heteroaryl or $R_8$-heterocyclyl. The reaction can be carried out by adding the acid chloride to a solution of a compound of Formula IIa in a suitable solvent such as chloroform, optionally in the presence of a base such as triethylamine, at ambient temperature. The product or a pharmaceutically acceptable salt thereof can be isolated using conventional methods.

Ureas and thioureas of Formula XLV-3 can be prepared from 1H-imidazo[4,5-c]pyridin-4-amines of Formula IIa using conventional methods. For example, a compound of Formula IIa can be reacted with an isocyanate of Formula $R_aN=C=O$, where $R_a$ is $R_8$-alkyl, $R_8$-alkenyl, $R_8$-aryl, $R_8$-heteroaryl or $R_8$-heterocyclyl. The reaction can be carried out by adding the isocyanate to a solution of a compound of Formula IIa in a suitable solvent such as chloroform, optionally in the presence of a base such as triethylamine, at ambient temperature. Alternatively, a compound of Formula IIa can be reacted with a thioisocyanate of Formula $R_aN=C=S$, a sulfonyl isocyanate of Formula $R_aS(O_2)N=C=O$ or a carbamoyl chloride of Formula $R_a$NC(O)Cl. The product or a pharmaceutically acceptable salt thereof can be isolated using conventional methods.

In step (4) of Reaction Scheme VII, a 1H-imidazo[4,5-c]pyridin-4-amine of Formula XLV-1, XLV-2, or XLV-3 undergoes a coupling reaction with a $C_{2-10}$ alkyne, conveniently by means of a palladium complex to provide a 1H-imidazo[4,5-c]pyridin-4-amine of Formula XLVI-1, XLVI-2, or XLVI-3, which are subgenera of Formulas I-1, I-2, and I-3, respectively. The alkyne is added to a solution of a compound of Formula XLV-1, XLV-2, or XLV-3 in a suitable solvent such as acetonitrile in the presence of a palladium catalyst, for example, dichlorobis(triphenylphosphine)palladium (II), copper (I) iodide, and a base such as triethylamine. The reaction can be heated at an elevated temperature. When $R_{4b}$ is $C_{2-10}$ alkynyl, reduction as described in step (1) of Reaction Scheme V can be used to convert $R_{4b}$ to $C_{2-10}$ alkyl. The product or a pharmaceutically acceptable salt thereof can be isolated using conventional methods.

ride. Alternatively, the reaction can be carried out by combining the compound of Formula XII with an alkali metal azide, for example, sodium azide, in a suitable solvent such as 90/10 acetonitrile/$H_2O$ in the presence of cerium III chloride, preferably cerium III chloride heptahydrate, optionally with heating, for example, at reflux. The product can be isolated from the reaction mixture using conventional methods.

In step (2) of Reaction Scheme VIII, an 8-nitrotetrazolo[1,5-a]pyridine of Formula XLVII is chlorinated using conventional chlorinating agents to provide an 8-nitrotetrazolo[1,5-a]pyridine of Formula XLVIII. Preferably, the reaction is carried out by combining a compound of Formula XLVII with thionyl chloride in a suitable solvent such as dichloromethane and heating.

In step (3) of Reaction Scheme VIII, an 8-nitrotetrazolo[1,5-a]pyridine of Formula XLVIII is reduced to provide a tetrazolo[1,5-a]pyridine-7,8-diamine of Formula XLIX. Preferably, the reduction is carried out using a conventional

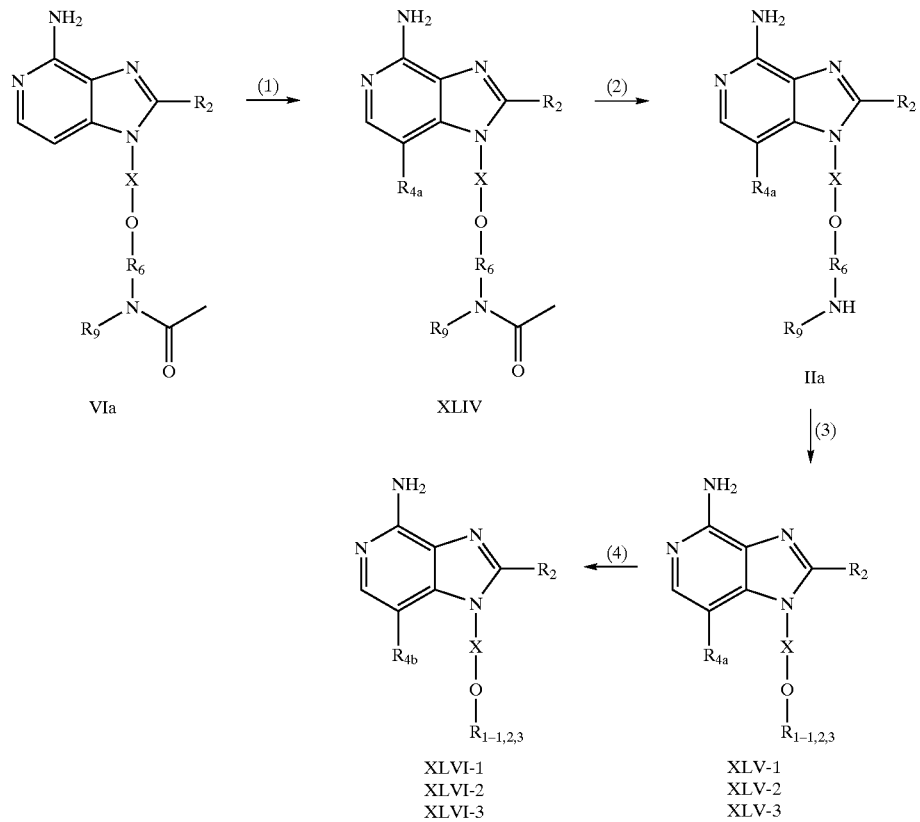

Reaction Scheme VII

Some embodiments of the invention including compounds of Formula XVIII and intermediate compounds can be prepared according to Reaction Scheme VIII where $R_{1-6}$, $R_2$, $R_3$, $R_4$, and X are as defined above.

In step (1) of Reaction Scheme VIII, a 2-chloro-3-nitropyridine of Formula XII is reacted with an alkali metal azide to provide an 8-nitrotetrazolo[1,5-a]pyridine of Formula XLVII. The reaction can be carried out by combining the compound of Formula XII with an alkali metal azide, for example, sodium azide, in a suitable solvent such as anhydrous N,N-dimethylformamide, and heating to about 50–100° C., optionally in the presence of ammonium chloheterogeneous catalyst such as platinum on carbon. The reaction can be conveniently carried out on a Parr apparatus in a suitable solvent such as toluene.

Alternatively in step (3), $Ni_2B$ can be generated in situ from sodium borohydride and $NiCl_2$ in the presence of methanol. A compound of Formula XLVIII can be added to the resulting reducing agent solution to effect reduction of the nitro group. When a compound of Formula XLVIII contains an alkenyl, alkynyl, alkenylene or alkynylene moiety, the $Ni_2B$ reducing agent can be used without reducing these moieties. The product can be isolated from the reaction mixture using conventional methods.

In step (4) of Reaction Scheme VIII, a tetrazolo[1,5-a]pyridine-7,8-diamine of Formula XLIX is reacted with a carboxylic acid or an equivalent thereof to provide a 7H-imidazo[4,5-c]tetrazolo[1,5-a]pyridine of Formula L. Suitable equivalents to a carboxylic acid include, for example, orthoesters, and 1,1-dialkoxyalkyl alkanoates. The carboxylic acid or equivalent is selected such that it will provide the desired $R_2$ substituent in a compound of Formula L. For example, triethyl orthoformate will provide a compound where $R_2$ is hydrogen, and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally, a catalyst such as pyridine hydrochloride can be included.

Alternatively, step (4) can be carried out by (i) reacting the diamine of Formula XLIX with an acyl halide of Formula $R_2C(O)Cl$ or $R_2C(O)Br$ and then (ii) cyclizing. In part (i), the acyl halide is added to a solution of the diamine in a suitable solvent such as pyridine. The reaction can be carried out at ambient temperature. In part (ii), the product of part (i) is heated in pyridine in the presence of pyridine hydrochloride.

In step (5) of Reaction Scheme VIII, a 7H-imidazo[4,5-c]tetrazolo[1,5-a]pyridine of Formula L is reacted with a compound of Formula $R_{1-6}SNa$ to provide a 7H-imidazo[4,5-c]tetrazolo[1,5-a]pyridine of Formula LI. Preferably, a thiol of the Formula $R_{1-6}SH$ is reacted with sodium hydride in a suitable solvent such as N,N-dimethylformamide to generate the anion, which is then reacted with a compound of Formula L.

In step (6) of Reaction Scheme VIII, a 7H-imidazo[4,5-c]tetrazolo[1,5-a]pyridine of Formula LI is oxidized to provide a 7H-imidazo[4,5-c]tetrazolo[1,5-a]pyridine of Formula LII. Preferably, a solution of a compound of Formula LI in a suitable solvent such as chloroform or dichloromethane is treated with 3-chloroperoxybenzoic acid. The degree of oxidation is controlled by adjusting the amount of 3-chloroperoxybenxzoic acid used in the reaction; i.e., using approximately one equivalent will provide the sulfoxide whereas using two equivalents will provide the sulfone. The product can be isolated using conventional methods.

In step (7) of Reaction Scheme VIII a 7H-imidazo[4,5-c]tetrazolo[1,5-a]pyridine of Formula LII is reacted with triphenylphosphine to form an N-triphenylphosphinyl compound of Formula LIII. The reaction with triphenylphosphine can be run in a suitable solvent such as toluene or 1,2-dichlorobenzene under an atmosphere of nitrogen with heating, for example at the reflux temperature.

In step (8) of Reaction Scheme VIII an N-triphenylphosphinyl compound of Formula LIII is hydrolyzed to provide a 1H-imidazo[4,5-c]pyridin-4-amine of Formula XVIII, which is a subgenus of Formula 1–6. The hydrolysis can be carried out by general methods well known to those skilled in the art, for example, by heating in a lower alkanol in the presence of an inorganic acid, such as hydrochloric acid. The product can be isolated from the reaction mixture using conventional methods as the compound of Formula XVIII or as a pharmaceutically acceptable salt thereof.

Alternatively, steps (7) and (8) of Reaction Scheme VIII can be omitted, and the tetrazolo ring can be reductively removed from a 7H-imidazo[4,5-c]tetrazolo[1,5-a]pyridine of Formula LII to provide a 1H-imidazo[4,5-c]pyridin-4-amine of Formula XVIII. The reaction can be carried out by reacting the 7H-imidazo[4,5-c]tetrazolo[1,5-a]pyridine of Formula LII with hydrogen in the presence of an catalyst and an acid. The reaction can be conveniently run in a Parr apparatus with a suitable catalyst, such as platinum IV oxide, and a suitable acid, such as trifluoroacetic acid or concentrated hydrochloric acid. The product can be isolated from the reaction mixture using conventional methods.

Reaction Scheme VIII

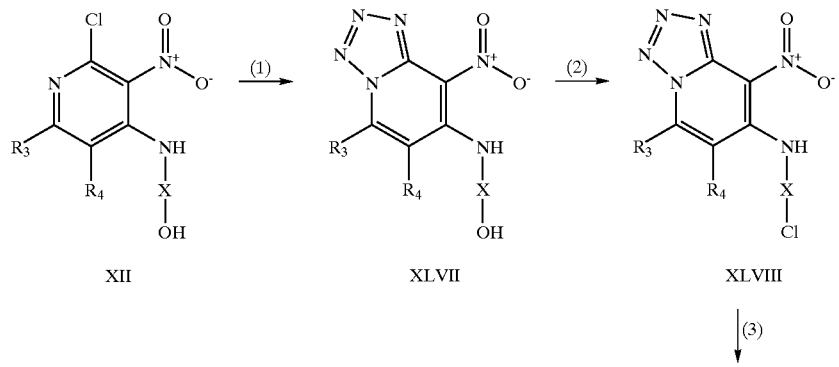

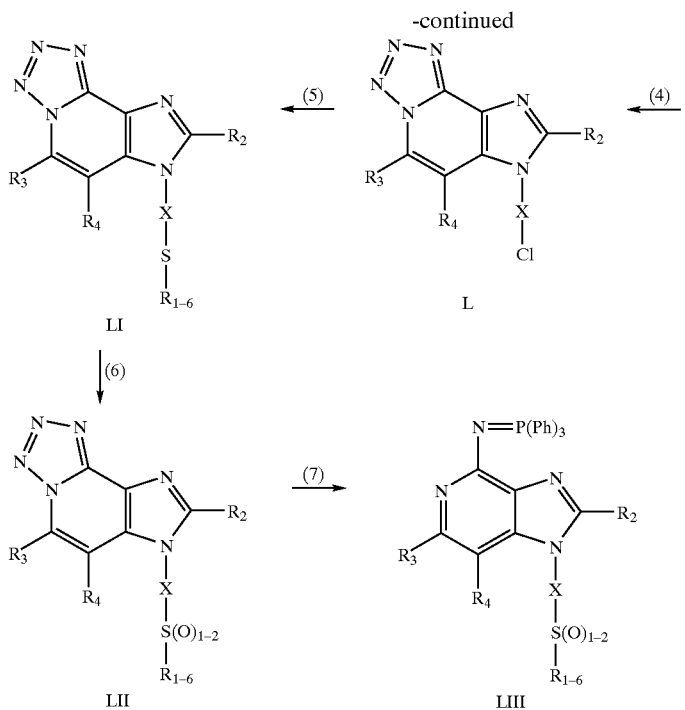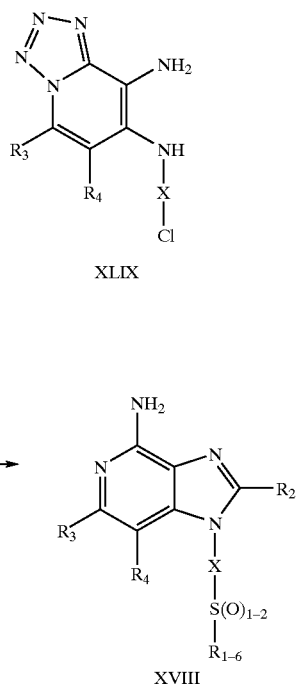

Some embodiments of the invention including compounds of Formula XVIIIa and intermediate compounds can be prepared according to Reaction Scheme IX where $R_2$, $R_3$, $R_4$, and X are as defined above, R' and R" are independently hydrogen or $C_{1-10}$ alkyl, and Et is ethyl.

In step (1) of Reaction Scheme IX a 7H-imidazo[4,5-c]tetrazolo[1,5-a]pyridine of Formula LIIa, which is a subgenus of Formula LII, is hydrolyzed to provide a 7H-imidazo[4,5-c]tetrazolo[1,5-a]pyridine of Formula LIIb. The reaction can be carried out under conventional saponification conditions by treating the ester with aqueous sodium hydroxide in a suitable solvent or solvent mixture such as tetrahydrofuran/methanol. The reaction can be optionally carried out with heating. The reaction mixture is acidified in a subsequent step by stirring with, for example, hydrochloric acid to provide the carboxylic acid.

In step (2) of Reaction Scheme IX a 7H-imidazo[4,5-c]tetrazolo[1,5-a]pyridine of Formula LIIb, which is a subgenus of Formula LII, is converted to a 7H-imidazo[4,5-c]tetrazolo[1,5-a]pyridine acid chloride of Formula LIV. The reaction can be carried out by combining a compound of Formula LIIb with oxalyl chloride or thionyl chloride in a suitable solvent such as dichloromethane and, optionally, heating.

In step (3) of Reaction Scheme IX a 7H-imidazo[4,5-c]tetrazolo[1,5-a]pyridine acid chloride of Formula LIV is converted to a 7H-imidazo[4,5-c]tetrazolo[1,5-a]pyridine amide of Formula LIIc, which is a subgenus of Formula LII. The reaction can be carried out by combining a compound of Formula LIV with an amine in a suitable solvent such as dichloromethane and stirring at ambient temperature.

In step (4) of Reaction Scheme IX a 7H-imidazo[4,5-c]tetrazolo[1,5-a]pyridine amide of Formula LIIc is reacted with triphenylphosphine to form an N-triphenylphosphinyl compound of Formula LIIa, which is a subgenus of Formula LIII. The reaction with triphenylphosphine can be run in a suitable solvent such as toluene or 1,2-dichlorobenzene under an atmosphere of nitrogen with heating, for example at the reflux temperature.

In step (5) of Reaction Scheme IX an N-triphenylphosphinyl compound of Formula LIIIa is hydrolyzed to provide a 1H-imidazo[4,5-c]pyridin-4-amine of Formula XVIIIa, which is a subgenus of Formula XVIII, which in turn is a subgenus of Formula I-6. The hydrolysis can be carried out by general methods well known to those skilled in the art, for example, by heating in a lower alkanol in the presence of an inorganic acid, such as hydrochloric acid. The product can be isolated from the reaction mixture using conventional methods as the compound of Formula XVIIIa or as a pharmaceutically acceptable salt thereof.

Alternatively, steps (4) and (5) of Reaction Scheme IX can be omitted, and the tetrazolo ring can be reductively removed from a 7H-imidazo[4,5-c]tetrazolo[1,5-a]pyridine amide of Formula LIIc to provide a 1H-imidazo[4,5-c]pyridin-4-amine of Formula XVIIIa. The reaction can be carried out by reacting the 7H-imidazo[4,5-c]tetrazolo[1,5-a]pyridine amide of Formula LIIc with hydrogen in the presence of an catalyst and an acid. The reaction can be conveniently run in a Parr apparatus with a suitable catalyst, such as platinum IV oxide, and a suitable acid, such as trifluoroacetic acid or concentrated hydrochloric acid. The product can be isolated from the reaction mixture using conventional methods.

Reaction Scheme IX

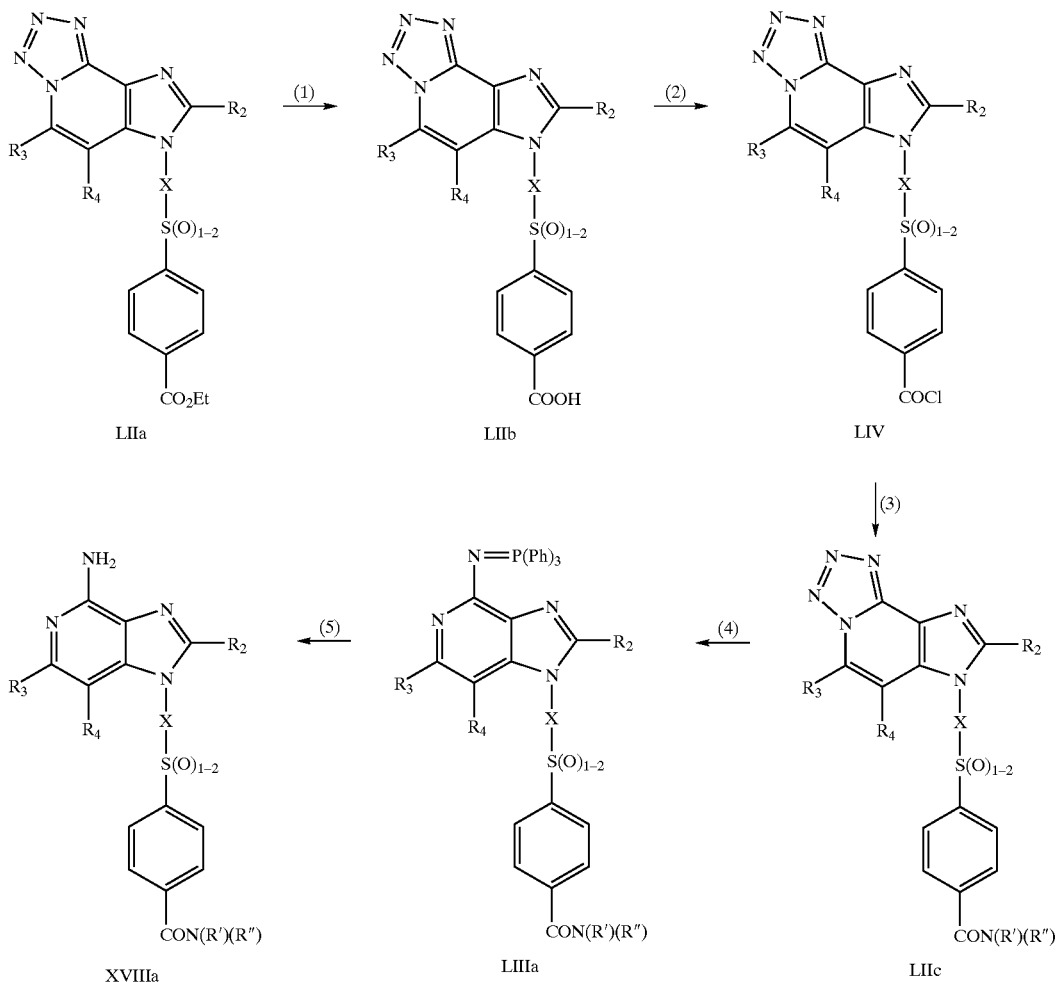

Some embodiments of the invention including compounds of Formulas I-1, I-2, I-3, and intermediate compounds can be prepared according to Reaction Scheme X where $R_{1-1, 2, 3}$ ($R_{1-1}$, $R_{1-2}$, and $R_{1-3}$), $R_2$, $R_3$, $R_4$, $R_6$, $R_9$, $R_{10}$, $R_{12}$ and X are as defined above, and BOC is tert-butoxycarbonyl.

In step (1) of Reaction Scheme X a 2-chloro-3-nitropyridine of Formula XXV is reacted with an alkali metal azide to provide an 8-nitrotetrazolo[1,5-a]pyridine of Formula LV. The reaction can be carried out as described in step (1) of Reaction Scheme VIII. The product can be isolated from the reaction mixture using conventional methods.

In step (2) of Reaction Scheme X, an 8-nitrotetrazolo[1,5-a]pyridine of Formula LV is reduced to provide a tetrazolo[1,5-a]pyridine-7,8-diamine of Formula LVI. The reduction can be carried out as described in step (3) of Reaction Scheme VIII.

In step (3) of Reaction Scheme X, a tetrazolo[1,5-a]pyridine-7,8-diamine of Formula LVI is reacted with a carboxylic acid or an equivalent thereof to provide a 7H-imidazo[4,5-c]tetrazolo[1,5-a]pyridine of Formula LVII. The reaction can be carried out as described in step (4) of Reaction Scheme VIII.

In step (4) of Reaction Scheme X, the BOC group of a 7H-imidazo[4,5-c]tetrazolo[1,5-a]pyridine of Formula LVII is removed to provide a 7H-imidazo[4,5-c]tetrazolo[1,5-a]pyridine of Formula LVIII. The reaction can be carried out by treating a solution of a 7H-imidazo[4,5-c]tetrazolo[1,5-a]pyridine of Formula LVII in a suitable solvent such as, for example, dichloromethane with an acid, preferably trifluoroacetic acid, at ambient temperature. The product can be isolated from the reaction mixture using conventional methods.

In step (5) of Reaction Scheme X a 7H-imidazo[4,5-c]tetrazolo[1,5-a]pyridine of Formula LVIII is converted to a 7H-imidazo[4,5-c]tetrazolo[1,5-a]pyridine of Formula LIX-1, LIX-2, or LIX-3 using conventional methods. For example, sulfonamides of Formula LIX-2 can be prepared by reacting a compound of Formula LVIII with a sulfonyl chloride of Formula $R_aS(O_2)Cl$, where $R_a$ is $R_8$-alkyl, $R_8$-alkenyl, $R_8$-aryl, $R_8$-heteroaryl or $R_8$-heterocyclyl. The reaction can be carried out by adding the sulfonyl chloride to a solution of a compound of Formula LVIII in a suitable solvent such as chloroform at ambient temperature. Sulfamides of Formula LIX-2 can be prepared by reacting a compound of Formula LVIII with sulfuryl chloride to generate a sulfamoyl chloride in situ, and then reacting the sulfamoyl chloride with an amine of Formula $HNR_5R_a$. The product or a pharmaceutically acceptable salt thereof can be isolated using conventional methods.

In another example, a 7H-imidazo[4,5-c]tetrazolo[1,5-a]pyridine of Formula LVIII is reacted with a chloroalkanesulfonyl chloride of formula $Cl$—$R_{12}$—$S(O)_2Cl$ to provide a subgenus of compounds of Formula LIX-2 wherein $R_9$ and $R_{10}$ join to form a ring having the structure

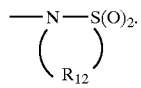

The reaction is preferably carried out by adding the chloroalkanesulfonyl chloride to a solution of a compound of Formula LVIII in a suitable solvent such as dichloromethane in the presence of a base such as triethylamine. The intermediate chloroalkanesulfonamide may optionally be isolated before treatment with a stronger base such as 1,8-diazabicyclo[5.4.0]undecene-7 (DBU) at ambient temperature. If the intermediate chloroalkanesulfonamide is isolated, the reaction with DBU can be carried out in a suitable solvent such as N,N-dimethylformamide. The product or a pharmaceutically acceptable salt thereof can be isolated using conventional methods.

Amides of Formula LIX-1 can be prepared from 7H-imidazo[4,5-c]tetrazolo[1,5-a]pyridine of Formula LVIII using conventional methods. For example, a compound of Formula LVIII can be reacted with an acid chloride of Formula $R_aC(O)Cl$ where $R_a$ is $R_8$-alkyl, $R_8$-alkenyl, $R_8$-aryl, $R_8$-heteroaryl or $R_8$-heterocyclyl. The reaction can be carried out by adding the acid chloride to a solution of a compound of Formula LVIII in a suitable solvent such as chloroform, optionally in the presence of a base such as triethylamine, at ambient temperature. The product can be isolated using conventional methods.

In another example, a 7H-imidazo[4,5-c]tetrazolo[1,5-a]pyridine of Formula LVIII is reacted with a chloroalkanoyl chloride compound of formula $Cl$—$R_{12}$—$C(O)Cl$ to provide a subgenus of compounds of Formula LIX-1 wherein $R_9$ and $R_{10}$ join to form a ring having the structure

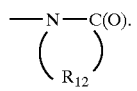

The reaction is preferably carried out by adding the chloroalkanoyl chloride compound to a solution of a compound of Formula LVIII in a suitable solvent such as dichloromethane in the presence of a base such as triethylamine. The intermediate chloroalkanamide may optionally be isolated before treatment with a stronger base such as 1,8-diazabicyclo[5.4.0]undecene-7 (DBU) at ambient temperature. If the intermediate chloroalkanamide is isolated, the reaction with DBU can be carried out in a suitable solvent such as N,N-dimethylformamide. The product can be isolated using conventional methods.

Ureas and thioureas of Formula LIX-3 can be prepared from 7H-imidazo[4,5-c]tetrazolo[1,5-a]pyridine of Formula LVIII using conventional methods. For example, a compound of Formula LVIII can be reacted with an isocyanate of Formula $R_aN=C=O$ where $R_a$ is $R_8$-alkyl, $R_8$-alkenyl, $R_8$-aryl, $R_8$-heteroaryl or $R_8$-heterocyclyl. The reaction can be carried out by adding the isocyanate to a solution of a compound of Formula LVIII in a suitable solvent such as chloroform, optionally in the presence of a base such as triethylamine, at ambient temperature. Alternatively, a compound of Formula LVIII can be reacted with a thioisocyanate of Formula $R_aN=C=S$, a sulfonyl isocyanate of Formula $R_aS(O_2)N=C=O$ or a carbamoyl chloride of Formula $R_aNC(O)Cl$. The product can be isolated using conventional methods.

In step (6) of Reaction Scheme X a 7H-imidazo[4,5-c]tetrazolo[1,5-a]pyridine of Formula LIX-1, LIX-2, or LIX-3 is reacted with triphenylphosphine to form an N-triphenylphosphinyl compound of Formula LX-1, LX-2, or LX-3. The reaction with triphenylphosphine can be run in a suitable solvent such as toluene or 1,2-dichlorobenzene under an atmosphere of nitrogen with heating, for example at the reflux temperature.

In step (7) of Reaction Scheme X an N-triphenylphosphinyl compound of Formula LX-1, LX-2, or LX-3 is hydrolyzed to provide a 1H-imidazo[4,5-c]pyridin-4-amine of Formula I-1, I-2, or I-3. The hydrolysis can be carried out by general methods well known to those skilled in the art, for example, by heating in a lower alkanol in the presence of an inorganic acid such as hydrochloric acid. The product can be isolated from the reaction mixture using conventional methods as the compound of Formula I-1, I-2, or I-3 or as a pharmaceutically acceptable salt thereof.

Alternatively, steps (6) and (7) of Reaction Scheme X can be omitted, and the tetrazolo ring can be reductively removed from a 7H-imidazo[4,5-c]tetrazolo[1,5-a]pyridine of Formula LIX-1, LIX-2, or LIX-3 to provide a 1H-imidazo[4,5-c]pyridin-4-amine of Formula I-1, I-2, or I-3. The reaction can be carried out by reacting the 7H-imidazo[4,5-c]tetrazolo[1,5-a]pyridine of Formula LIX-1, LIX-2, or LIX-3 with hydrogen in the presence of an catalyst and an acid. The reaction can be conveniently run in a Parr apparatus with a suitable catalyst, such as platinum IV oxide, and a suitable acid, such as trifluoroacetic acid or concentrated hydrochloric acid. The product can be isolated from the reaction mixture using conventional methods.

Reaction Scheme X

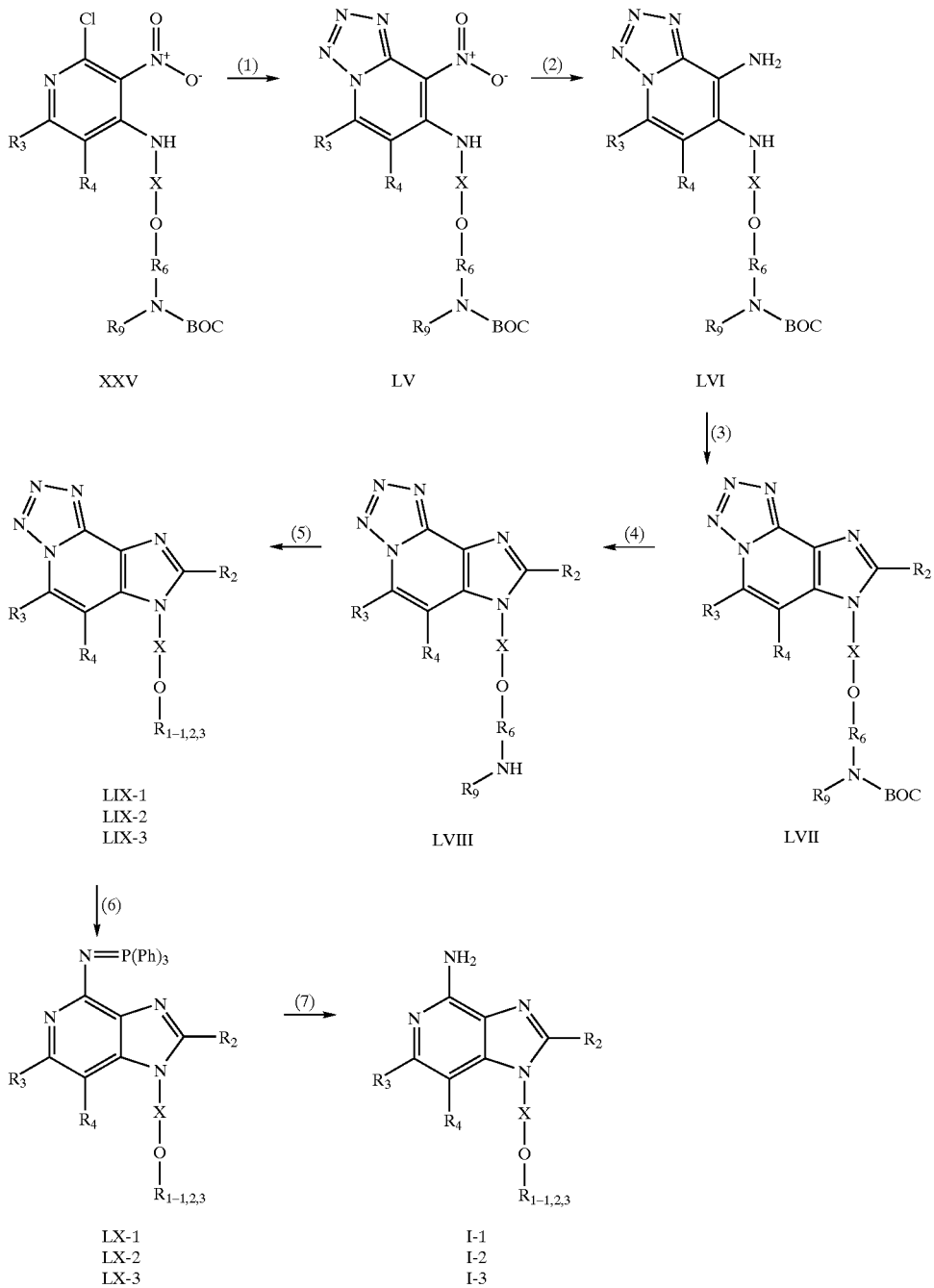

Some embodiments of the invention including compounds of Formula I-4, I-5, and intermediate compounds can be prepared according to Reaction Scheme XI where $R_{1-4,\,5}$ ($R_{1-4}$ and $R_{1-5}$), $R_2$, $R_3$, $R_4$, and X are as defined above.

In step (1) of Reaction Scheme XI, a 2-chloro-3-nitropyridine of Formula XXIX-4 or XXIX-5 is reacted with an alkali metal azide to provide an 8-nitrotetrazolo[1,5-a]pyridine of Formula LXII-4 or LXII-5. The reaction can be carried out as described in step (1) of Reaction Scheme VIII. The product can be isolated from the reaction mixture using conventional methods.

In step (2) of Reaction Scheme XI, an 8-nitrotetrazolo[1,5-a]pyridine of Formula LXII-4 or LXII-5 is reduced to provide tetrazolo[1,5-a]pyridine-7,8-diamine of Formula LXIII-4 or LXIII-5. The reduction can be carried out as described in step (3) of Reaction Scheme VIII.

The product can be isolated from the reaction mixture using conventional methods.

In step (3) of Reaction Scheme XI, a tetrazolo[1,5-a]pyridine-7,8-diamine of Formula LXIII-4 or LXIII-5 is reacted with a carboxylic acid or an equivalent thereof to provide a 7H-imidazo[4,5-c]tetrazolo[1,5-a]pyridine of Formula LIX-4 or LIX-5. The reaction can be carried out as described in step (4) of Reaction Scheme VIII. The product can be isolated from the reaction mixture using conventional methods.

In step (4) of Reaction Scheme XI, a 7H-imidazo[4,5-c]tetrazolo[1,5-a]pyridine of Formula LIX-4 or LIX-5 is reacted with triphenylphosphine to form an N-triphenylphosphinyl compound of Formula LX-4, or LX-5. The reaction can be carried out as described in step (6) of Reaction Scheme X. The product can be isolated from the reaction mixture using conventional methods.

In step (5) of Reaction Scheme XI an N-triphenylphosphinyl compound of Formula LX-4, or LX-5 is hydrolyzed to provide a 1H-imidazo[4,5-c]pyridin-4-amine of Formula I-4 or I-5. The hydrolysis can be carried out as described in step (7) of Reaction Scheme X. The product can be isolated from the reaction mixture using conventional methods as the compound of Formula I-4, or I-5 or as a pharmaceutically acceptable salt thereof.

Alternatively, steps (4) and (5) of Reaction Scheme XI can be omitted, and the tetrazolo ring can be reductively removed from a 7H-imidazo[4,5-c]tetrazolo[1,5-a]pyridine of Formula LIX-4 or LIX-5 to provide a 1H-imidazo[4,5-c]pyridin-4-amine of Formula I-4 or I-5. The reaction can be carried out by reacting the 7H-imidazo[4,5-c]tetrazolo[1,5-a]pyridine of Formula LIX-4 or LIX-5 with hydrogen in the presence of an catalyst and an acid. The reaction can be conveniently run in a Parr apparatus with a suitable catalyst, such as platinum TV oxide, and a suitable acid, such as trifluoroacetic acid or concentrated hydrochloric acid. The product can be isolated from the reaction mixture using conventional methods.

In step (1) of Reaction Scheme XII, a 2-chloro-3-nitropyridine of Formula XII is esterified to provide a 2-chloro-3-nitropyridine acetate of Formula LXVI. Preferably, the esterification is carried out using acetic anhydride in a suitable solvent such as anhydrous dichloromethane in the presence of pyridine and catalytic 4-dimethylaminopyridine (DMAP). The product can be isolated from the reaction mixture using conventional methods.

In step (2) of Reaction Scheme XII, a 2-chloro-3-nitropyridine of Formula LXVI is reacted with an alkali metal azide to provide an 8-nitrotetrazolo[1,5-a]pyridine of Formula LXVII. The reaction can be carried out as described in step (1) of Reaction Scheme VIII. The product can be isolated from the reaction mixture using conventional methods.

In step (3) of Reaction Scheme XII, an 8-nitrotetrazolo[1,5-a]pyridine of Formula LXVII is reduced to provide tetrazolo[1,5-a]pyridine-7,8-diamine of Formula LXVIII. The reduction can be carried out as described in step (3) of Reaction Scheme VIII. The product can be isolated from the reaction mixture using conventional methods.

In step (4) of Reaction Scheme XII, a tetrazolo[1,5-a]pyridine-7,8-diamine of Formula LXVIII is reacted with a carboxylic acid or an equivalent thereof to provide a 7H-imidazo[4,5-c]tetrazolo[1,5-a]pyridine of Formula LXIX. The reaction can be carried out as described in step (4) of Reaction Scheme VIII. The product can be isolated from the reaction mixture using conventional methods.

Reaction Scheme XI

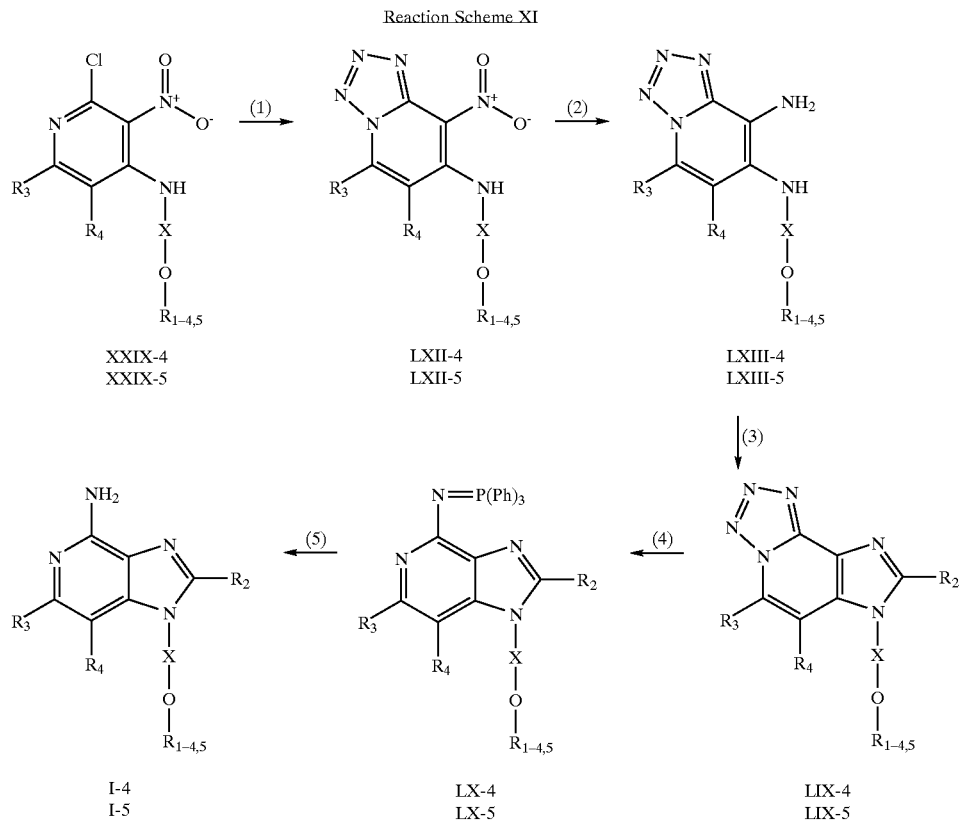

Some embodiments of the invention including compounds of Formula I-5 and intermediate compounds can be prepared according to Reaction Scheme XII where $R_{1-5}$, $R_2$, $R_3$, $R_4$, X, and Ac are as defined above.

In step (5) of Reaction Scheme XII, a 7H-imidazo[4,5-c]tetrazolo[1,5-a]pyridine of Formula LXIX is hydrolyzed using conventional methods to provide a 7H-imidazo[4,5-c]tetrazolo[1,5-a]pyridine of Formula LXX. For example, the reaction can be conveniently carried out by adding potassium carbonate to a 7H-imidazo[4,5-c]tetrazolo[1,5-a]pyridine of Formula LXIX dissolved in methanol at an elevated temperature. The product can be isolated from the reaction mixture using conventional methods.

In step (6) of Reaction Scheme XII, a 7H-imidazo[4,5-c]tetrazolo[1,5-a]pyridine of Formula LXX is reacted with 3-bromopropyne to provide a 7H-imidazo[4,5-c]tetrazolo[1,5-a]pyridine of Formula LXXI. The reaction can be carried out by adding 3-bromopropyne to 7H-imidazo[4,5-c]tetrazolo[1,5-a]pyridine of Formula LXX under phase transfer conditions with catalytic benzyltrimethylammonium chloride in a mixture of a a suitable solvent such as dichloromethane and 50% aqueous sodium hydroxide. The product can be isolated from the reaction mixture using conventional methods.

In step (7) of Reaction Scheme XII, 7H-imidazo[4,5-c]tetrazolo[1,5-a]pyridine of Formula LXXI is reacted with a heteroarylbromide or heterocyclylbromide to provide a 7H-imidazo[4,5-c]tetrazolo[1,5-a]pyridine of Formula LIX-5. The reaction can be carried out by coupling a heteroarylbromide, for example, 5-bromopyrimidine, or heterocyclylbromide with the alkyne group of a 7H-imidazo[4,5-c]tetrazolo[1,5-a]pyridine of Formula LXXI. The coupling reaction can proceed through a palladium complex, generated from a palladium catalyst, for example dichlorobis(triphenylphosphine)palladium (II), in the presence of copper (I) iodide and a base such as triethylamine. The reaction is carried out in a suitable solvent such as N,N-dimethylformamide and can be heated at an elevated temperature. The product can be isolated from the reaction mixture using conventional methods.

In step (8) of Reaction Scheme XII, a 7H-imidazo[4,5-c]tetrazolo[1,5-a]pyridine of Formula LIX-5 is reacted with triphenylphosphine to form an N-triphenylphosphinyl compound of Formula LX-5. The reaction can be carried out as described in step (6) of Reaction Scheme X. The product can be isolated from the reaction mixture using conventional methods.

In step (9) of Reaction Scheme XII, an N-triphenylphosphinyl compound of Formula LX-5 is hydrolyzed to provide a 1H-imidazo[4,5-c]pyridin-4-amine of Formula I-5. The hydrolysis can be carried out as described in step (7) of Reaction Scheme X. The product can be isolated from the reaction mixture using conventional methods as the compound of Formula I-5 or as a pharmaceutically acceptable salt thereof.

Alternatively, steps (8) and (9) of Reaction Scheme XII can be omitted, and the tetrazolo ring can be reductively removed from a 7H-imidazo[4,5-c]tetrazolo[1,5-a]pyridine of Formula LIX-5 to provide a 1H-imidazo[4,5-c]pyridin-4-amine of Formula I-5. The reaction can be carried out by reacting the 7H-imidazo[4,5-c]tetrazolo[1,5-a]pyridine of Formula LIX-5 with hydrogen in the presence of an catalyst and an acid. The reaction can be conveniently run in a Parr apparatus with a suitable catalyst, such as platinum IV oxide, and a suitable acid, such as trifluoroacetic acid or concentrated hydrochloric acid. The product can be isolated from the reaction mixture using conventional methods.

Reaction Scheme XII

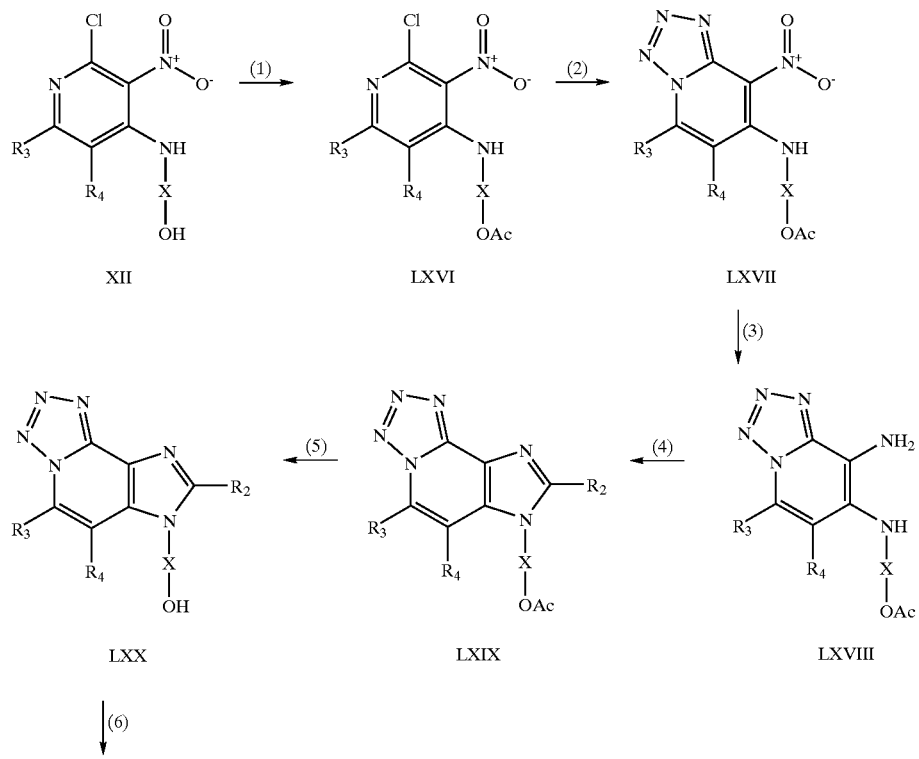

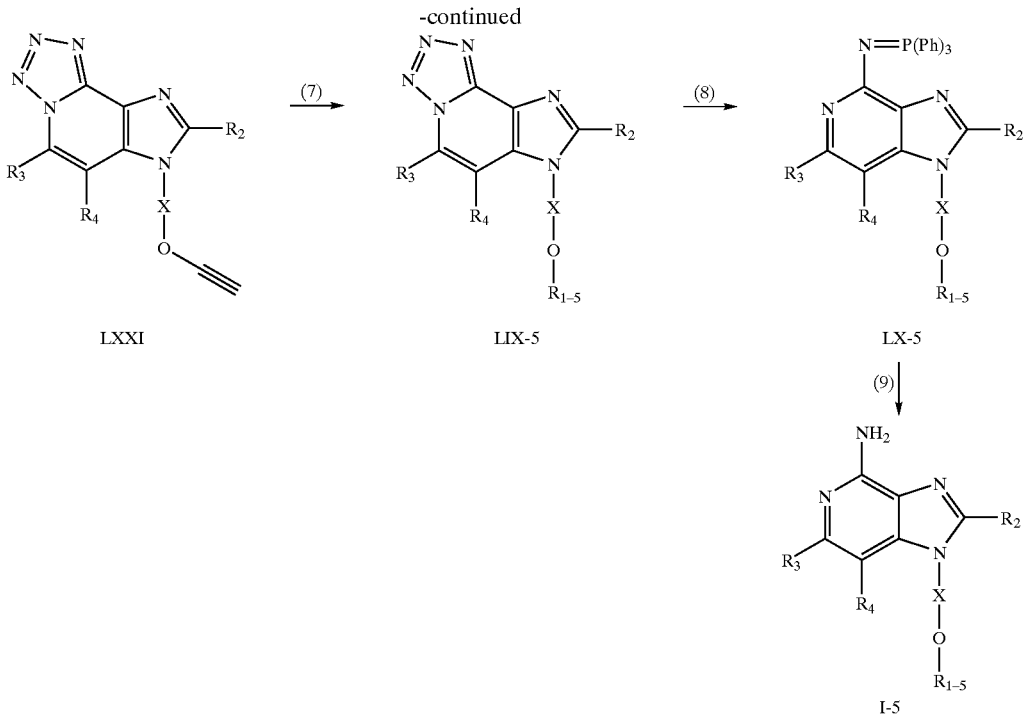

Some embodiments of the invention including compounds of Formulas LXXVII-1, LXXVII-2, LXXVII-3, and intermediate compounds can be prepared according to Reaction Scheme XIII where $R_{1-1,2,3}$ ($R_{1-1}$, $R_{1-2}$, and $R_{1-3}$), $R_2$, $R_6$, $R_9$, X, and BOC are as defined above, Tf is trifluoromethylsulfonyl, and PMB is 4-methoxybenzyl.

In step (1) of Reaction Scheme XIII malonyl dichloride is stirred with propanenitrile at ambient temperature to provide 6-chloro-4-hydroxy-5-methylpyridin-2(1H)-one hydrochloride hydrate, which precipitates from the solution.

In step (2) of Reaction Scheme XIII, direct nitration of 6-chloro-4-hydroxy-5-methylpyridin-2(1H)-one hydrochloride hydrate is carried out in excess sulfuric acid and one equivalent of nitric acid to provide 6-chloro-4-hydroxy-5-methyl-3-nitropyridin-2(1H)-one. The reaction is run at a reduced temperature. The product conveniently can be precipitated from the solution by the addition of ice water.

In step (3) of Reaction Scheme XIII, 6-chloro-4-hydroxy-5-methyl-3-nitropyridin-2(1H)-one is converted to the triflate of Formula LXXII. The reaction can be carried out by adding trifluoromethanesulfonic anhydride to a solution of 6-chloro-4-hydroxy-5-methyl-3-nitropyridin-2(1H)-one in a suitable solvent such as dichloromethane in the presence of a base such as triethylamine. The reaction can be carried out at sub-ambient temperatures. An amine of Formula XXIV is then added to the reaction at ambient temperature to provide a pyridine of Formula LXXII. The product can be isolated from the reaction mixture using conventional methods.

In step (4) of Reaction Scheme XIII, the triflate group of a compound of Formula LXXII is displaced with bis(4-methoxybenzyl)amine to provide a pyridine of Formula LXXIII. The reaction can be carried out in the presence of a base such as triethylamine and in a suitable solvent such as toluene. The reaction is conveniently carried out at elevated temperatures. The product can be isolated from the reaction mixture using conventional methods.

In step (5) of Reaction Scheme XIII, the nitro group of a compound of Formula LXXIII is reduced to provide a pyridine-7,8-diamine of Formula LXXIV. The reaction can be carried out by the addition of sodium borohydride and nickel chloride to a solution of a compound of Formula LXXIII in a suitable solvent or solvent mixture such as methanol/dichloromethane at ambient temperature. The product can be isolated from the reaction mixture using conventional methods.

In step (6) of Reaction Scheme XIII, a pyridine-7,8-diamine of Formula LXXIV reacts with a carboxylic acid or an equivalent thereof to provide an imidazo[4,5-c]pyridine of Formula LXXV. The reaction can be carried out as described in step (4) of Reaction Scheme VIII.

In step (7) of Reaction Scheme XIII, an imidazo[4,5-c]pyridine of Formula LXXV is deprotected under acidic conditions to provide a 1H-imidazo[4,5-c]pyridin-4-amine of Formula LXXVI. The reaction can be carried out by dissolving an imidazo[4,5-c]pyridine of Formula LXXV in trifluoroacetic acid and stirring at ambient temperature. Optionally, the reaction can be carried out in a suitable solvent such as dichloromethane.

In step (8) of Reaction Scheme XIII, a 1H-imidazo[4,5-c]pyridin-4-amine of Formula LXXVI is converted to a 1H-imidazo[4,5-c]pyridin-4-amine of Formula LXXVII-1, 2,3, which is a subgenus of Formula I-1, I-2, and I-2, using conventional methods. The reaction can be carried out as described in step (11) of Reaction Scheme II.

Reaction Scheme XIII

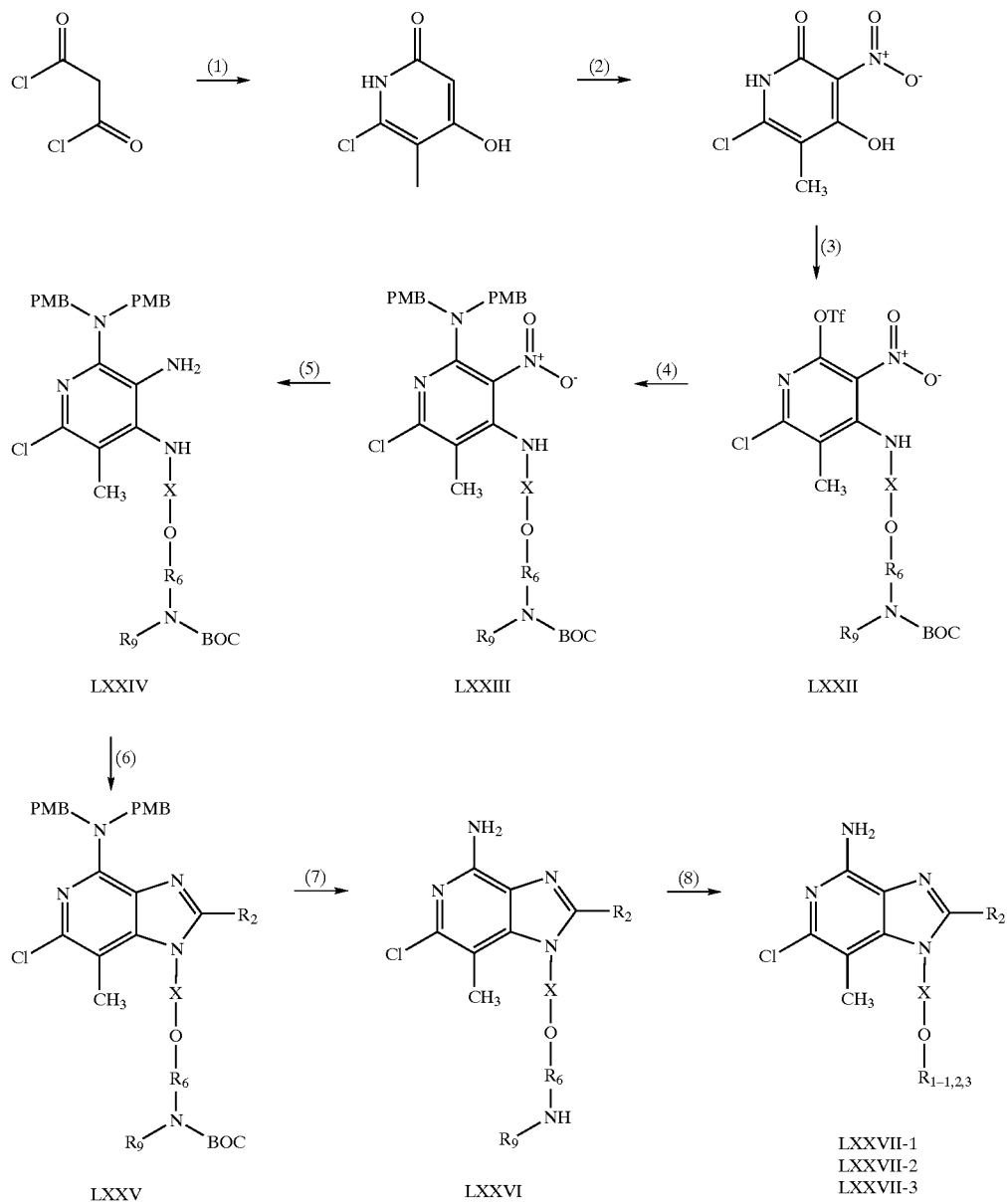

It is understood that one skilled in the art will select the appropriate reaction schemes and steps therein to prepare a compound described in the various aspects and embodiments of the invention to avoid or minimize undesired or conflicting reactions. For example, when $R_3$ is chloro a reaction scheme which does not involve a tetrazolo intermediate can be selected. Reduction of a nitro group at $R_3$ or $R_4$ can be avoided by placement on the pyridine ring after reduction of the nitro group at the 3-position of the pyridine ring. When an alkenyl, alkynyl, alkenylene, or alkynylene group is present, reduction of the nitro group at the 3-position of the pyridine ring can be carried out by using the $Ni_2B$ reduction without reducing the alkenyl, alkynyl, alkenylene, or alkynylene group. When removing a tetrazolo ring in the presence of a readily reducible group such as an alkenyl or heteroaryl group, the formation of an N-triphenylphosphinyl compound followed by hydrolysis can be used in place of the reductive removal to preserve, for example, the alkenyl or heteroaryl group.

The term "non-interfering substituents" refers to $R_X$, $R_Y$, and $R_Z$ groups which do not prevent a compound of Formula Ia from inducing the biosynthesis of one or more cytokines. Illustrative non-interfering $R_X$ groups include those described above for $R_2$. Illustrative non-interfering $R_Y$ and $R_Z$ groups include those described above for $R_3$ and $R_4$.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. Preferred groups have a total of up to 10 carbon atoms, for example, up to 8 carbon atoms, up to 6 carbon atoms, and up to 4 carbon atoms.

Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted norbornyl and norbornenyl.

Unless otherwise specified, "alkylene", "alkenylene", and "alkynylene" are the divalent forms of "alkyl", "alkenyl", and "alkynyl" defined above.

The term "haloalkyl" is inclusive of groups that are substituted by one or more halogen atoms, including perfluorinated groups. This is also true of groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, and the like.

The aryl, heteroaryl, and heterocyclyl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, heterocyclylcarbonyl, aryloxycarbonyl, heteroaryloxycarbonyl, arylthiocarbonyl, heteroarylthiocarbonyl, alkanoyloxy, alkanoylthio, alkanoylamino, aroyloxy, aroylthio, aroylamino, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonyl, dialkylaminocarbonyl, arylaminocarbonyl, arylalkylaminocarbonyl, alkenylaminocarbonyl, heteroarylaminocarbonyl, heteroarylalkylaminocarbonyl, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If any other groups are identified as being "substituted" or "optionally substituted", then those groups can also be substituted by one or more of the above enumerated substituents.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers.

Preferred compounds of the invention include:

N-(2-{2-[4-amino-2-(cyclopropylmethyl)-6,7-dimethyl-1H-imidazo[4,5-c]pyridin-1-yl]ethoxy}ethyl)-2-methylpropanamide;

N-(2-{2-[4-amino-2-(cyclopropylmethyl)-6,7-dimethyl-1H-imidazo[4,5-c]pyridin-1-yl]ethoxy}ethyl)cyclopentanecarboxamide;

N-(2-{2-[4-amino-2-(cyclopropylmethyl)-6,7-dimethyl-1H-imidazo[4,5-c]pyridin-1-yl]ethoxy}ethyl)nicotinamide;

N-(2-{2-[4-amino-2-(cyclopropylmethyl)-6,7-dimethyl-1H-imidazo[4,5-c]pyridin-1-yl]ethoxy}ethyl)-N,2-dimethylpropanamide;

N-(2-{2-[4-amino-2-(cyclopropylmethyl)-6,7-dimethyl-1H-imidazo[4,5-c]pyridin-1-yl]ethoxy}ethyl)-N-methylcyclopentanecarboxamide;

N-(2-{2-[4-amino-2-(cyclopropylmethyl)-6,7-dimethyl-1H-imidazo[4,5-c]pyridin-1-yl]ethoxy}ethyl)-N-methylnicotinamide;

N-(2-{2-[4-amino-2-(cyclopropylethyl)-6,7-dimethyl-1H-imidazo[4,5-c]pyridin-1-yl]ethoxy}ethyl)-2-methylpropanamide;

N-(2-{2-[4-amino-2-(cyclopropylethyl)-6,7-dimethyl-1H-imidazo[4,5-c]pyridin-1-yl]ethoxy}ethyl)cyclopentanecarboxamide;

N-(2-{2-[4-amino-2-(cyclopropylethyl)-6,7-dimethyl-1H-imidazo[4,5-c]pyridin-1-yl]ethoxy}ethyl)nicotinamide;

N-(2-{2-[4-amino-2-(methoxyethyl)-6,7-dimethyl-1H-imidazo[4,5-c]pyridin-1-yl]ethoxy}ethyl)-N,2-dimethylpropanamide;

N-(2-{2-[4-amino-2-(methoxyethyl)-6,7-dimethyl-1H-imidazo[4,5-c]pyridin-1-yl]ethoxy}ethyl)-N-methylcyclopentanecarboxamide;

N-(2-{2-[4-amino-2-(methoxyethyl)-6,7-dimethyl-1H-imidazo[4,5-c]pyridin-1-yl]ethoxy}ethyl)-N-methylnicotinamide;

N-(2-{2-[4-amino-2-(cyclopropylmethyl)-6-methyl-1H-imidazo[4,5-c]pyridin-1-yl]ethoxy}ethyl)-2-methylpropanamide;

N-(2-{2-[4-amino-2-(cyclopropylmethyl)-6-methyl-1H-imidazo[4,5-c]pyridin-1-yl]ethoxy}ethyl)cyclopentanecarboxamide;

N-(2-{2-[4-amino-2-(cyclopropylmethyl)-6-methyl-1H-imidazo[4,5-c]pyridin-1-yl]ethoxy}ethyl)nicotinamide;

N-(2-{2-[4-amino-2-(cyclopropylmethyl)-6-methyl-1H-imidazo[4,5-c]pyridin-1-yl]ethoxy}ethyl)-N,2-dimethylpropanamide;

N-(2-{2-[4-amino-2-(cyclopropylmethyl)-6-methyl-1H-imidazo[4,5-c]pyridin-1-yl]ethoxy}ethyl)-N-methylcyclopentanecarboxamide;

N-(2-{2-[4-amino-2-(cyclopropylmethyl)-6-methyl-1H-imidazo[4,5-c]pyridin-1-yl]ethoxy}ethyl)-N-methylnicotinamide;

N-(2-{2-[4-amino-2-propyl-6,7-dimethyl-1H-imidazo[4,5-c]pyridin-1-yl]ethoxy}ethyl)-2-methylpropanamide;

N-(2-{2-[4-amino-2-propyl-6,7-dimethyl-1H-imidazo[4,5-c]pyridin-1-yl]ethoxy}ethyl)cyclopentanecarboxamide;

N-(2-{2-[4-amino-2-propyl-6,7-dimethyl-1H-imidazo[4,5-c]pyridin-1-yl]ethoxy}ethyl)nicotinamide;

N-(2-{2-[4-amino-2-propyl-6,7-dimethyl-1H-imidazo[4,5-c]pyridin-1-yl]ethoxy}ethyl)-N,2-dimethylpropanamide;

N-(2-{2-[4-amino-2-propyl-6,7-dimethyl-1H-imidazo[4,5-c]pyridin-1-yl]ethoxy}ethyl)-N-methylcyclopentanecarboxamide;

N-(2-{2-[4-amino-2-propyl-6,7-dimethyl-1H-imidazo[4,5-c]pyridin-1-yl]ethoxy}ethyl)-N-methylnicotinamide;

N-(2-{2-[4-amino-2-propyl-6-methyl-1H-imidazo[4,5-c]pyridin-1-yl]ethoxy}ethyl)-2-methylpropanamide;

N-(2-{2-[4-amino-2-propyl-6-methyl-1H-imidazo[4,5-c]pyridin-1-yl]ethoxy}ethyl)cyclopentanecarboxamide;

N-(2-{2-[4-amino-2-propyl-6-methyl-1H-imidazo[4,5-c]pyridin-1-yl]ethoxy}ethyl)nicotinamide;

N-(2-{2-[4-amino-2-propyl-6-methyl-1H-imidazo[4,5-c]pyridin-1-yl]ethoxy}ethyl)-N,2-dimethylpropanamide;

N-(2-{2-[4-amino-2-propyl-6-methyl-1H-imidazo[4,5-c]pyridin-1-yl]ethoxy}ethyl)-N-methylcyclopentanecarboxamide;

N-(2-{2-[4-amino-2-propyl-6-methyl-1H-imidazo[4,5-c]pyridin-1-yl]ethoxy}ethyl)-N-methylnicotinamide;

N-(2-{2-[4-amino-2-(cyclopropylmethyl)-6,7-dimethyl-1H-imidazo[4,5-c]pyridin-1-yl]ethoxy}ethyl)morpholine-4-carboxamide;

N-(2-{2-[4-amino-2-(cyclopropylmethyl)-6,7-dimethyl-1H-imidazo[4,5-c]pyridin-1-yl]ethoxy}ethyl)-N'-cyclohexylurea;

N-(2-{2-[4-amino-2-(cyclopropylmethyl)-6,7-dimethyl-1H-imidazo[4,5-c]pyridin-1-yl]ethoxy}ethyl)-N'-pyridin-3-ylurea;

N-(2-{2-[4-amino-2-(cyclopropylethyl)-6,7-dimethyl-1H-imidazo[4,5-c]pyridin-1-yl]ethoxy}ethyl)morpholine-4-carboxamide;

N-(2-{2-[4-amino-2-(cyclopropylethyl)-6,7-dimethyl-1H-imidazo[4,5-c]pyridin-1-yl]ethoxy}ethyl)-N'-cyclohexylurea;

N-(2-{2-[4-amino-2-(cyclopropylethyl)-6,7-dimethyl-1H-imidazo[4,5-c]pyridin-1-yl]ethoxy}ethyl)-N-pyridin-3-ylurea;

N-(2-{2-[4-amino-2-(methoxyethyl)-6,7-dimethyl-1H-imidazo[4,5-c]pyridin-1-yl]ethoxy}ethyl)morpholine-4-carboxamide;

N-(2-{2-[4-amino-2-(methoxyethyl)-6,7-dimethyl-1H-imidazo[4,5-c]pyridin-1-yl]ethoxy}ethyl)-N'-cyclohexylurea;

N-(2-{2-[4-amino-2-(methoxyethyl)-6,7-dimethyl-1H-imidazo[4,5-c]pyridin-1-yl]ethoxy}ethyl)-N'-pyridin-3-ylurea;

N-(2-{2-[4-amino-2-(cyclopropylmethyl)-6-methyl-1H-imidazo[4,5-c]pyridin-1-yl]ethoxy}ethyl)morpholine-4-carboxamide;

N-(2-{2-[4-amino-2-(cyclopropylmethyl)-6-methyl-1H-imidazo[4,5-c]pyridin-1-yl]ethoxy}ethyl)-N'-cyclohexylurea;

N-(2-{2-[4-amino-2-(cyclopropylmethyl)-6-methyl-1H-imidazo[4,5-c]pyridin-1-yl]ethoxy}ethyl)-N'-pyridin-3-ylurea;

N-(2-{2-[4-amino-2-(cyclopropylethyl)-6-methyl-1H-imidazo[4,5-c]pyridin-1-yl]ethoxy}ethyl)morpholine-4-carboxamide;

N-(2-{2-[4-amino-2-(cyclopropylethyl)-6-methyl-1H-imidazo[4,5-c]pyridin-1-yl]ethoxy}ethyl)-N'-cyclohexylurea;

N-(2-{2-[4-amino-2-(cyclopropylethyl)-6-methyl-1H-imidazo[4,5-c]pyridin-1-yl]ethoxy}ethyl)-N'-pyridin-3-ylurea;

N-(2-{2-[4-amino-2-(methoxyethyl)-6-methyl-1H-imidazo[4,5-c]pyridin-1-yl]ethoxy}ethyl)morpholine-4-carboxamide;

N-(2-{2-[4-amino-2-(methoxyethyl)-6-methyl-1H-imidazo[4,5-c]pyridin-1-yl]ethoxy}ethyl)-N'-cyclohexylurea;

N-(2-{2-[4-amino-2-(methoxyethyl)-6-methyl-1H-imidazo[4,5-c]pyridin-1-yl]ethoxy}ethyl)-N'-pyridin-3-ylurea;

N-(2-{2-[4-amino-2-propyl-6,7-dimethyl-1H-imidazo[4,5-c]pyridin-1-yl]ethoxy}ethyl)morpholine-4-carboxamide;

N-(2-{2-[4-amino-2-propyl-6,7-dimethyl-1H-imidazo[4,5-c]pyridin-1-yl]ethoxy}ethyl)-N'-cyclohexylurea;

N-(2-{2-[4-amino-2-propyl-6,7-dimethyl-1H-imidazo[4,5-c]pyridin-1-yl]ethoxy}ethyl-N'-pyridin-3-ylurea;

N-(2-{2-[4-amino-2-propyl-6-methyl-1H-imidazo[4,5-c]pyridin-1-yl]ethoxy}ethyl)morpholine-4-carboxamide;

N-(2-{2-[4-amino-2-propyl-6-methyl-1H-imidazo[4,5-c]pyridin-1-yl]ethoxy}ethyl)-N'-cyclohexylurea;

N-(2-{2-[4-amino-2-propyl-6-methyl-1H-imidazo[4,5-c]pyridin-1-yl]ethoxy}ethyl)-N'-pyridin-3-ylurea;

N'-(2-{2-[4-amino-2-(cyclopropylmethyl)-6,7-dimethyl-1H-imidazo[4,5-c]pyridin-1-yl]ethoxy}ethyl)-N,N-diethylurea;

N-(2-{2-[4-amino-2-(cyclopropylmethyl)-6,7-dimethyl-1H-imidazo[4,5-c]pyridin-1-yl]ethoxy}ethyl)-N'-isopropylurea;

N'-(2-{2-[4-amino-2-(cyclopropylethyl)-6,7-dimethyl-1H-imidazo[4,5-c]pyridin-1-yl]ethoxy}ethyl)-N,N-diethylurea;

N-(2-{2-[4-amino-2-(cyclopropylethyl)-6,7-dimethyl-1H-imidazo[4,5-c]pyridin-1-yl]ethoxy}ethyl)-N'-isopropylurea;

N'-(2-{2-[4-amino-2-propyl-6,7-dimethyl-1H-imidazo[4,5-c]pyridin-1-yl]ethoxy}ethyl-N,N-diethylurea;

N-(2-{2-[4-amino-2-propyl-6,7-dimethyl-1H-imidazo[4,5-c]pyridin-1-yl]ethoxy}ethyl)-N'-isopropylurea;

N'-(2-{2-[4-amino-2-(methoxyethyl)-6,7-dimethyl-1H-imidazo[4,5-c]pyridin-1-yl]ethoxy}ethyl)-N,N-diethylurea;

N-(2-{2-[4-amino-2-(methoxyethyl)-6,7-dimethyl-1H-imidazo[4,5-c]pyridin-1-yl]ethoxy}ethyl)-N'-isopropylurea;

N'-(2-{2-[4-amino-2-(cyclopropylmethyl)-6-methyl-1H-imidazo[4,5-c]pyridin-1-yl]ethoxy}ethyl)-N,N-diethylurea;

N-(2-{2-[4-amino-2-(cyclopropylmethyl)-6-methyl-1H-imidazo[4,5-c]pyridin-1-yl]ethoxy}ethyl)-N'-isopropylurea;

N'-(2-{2-[4-amino-2-(cyclopropylethyl)-6-methyl-1H-imidazo[4,5-c]pyridin-1-yl]ethoxy}ethyl)-N,N-diethylurea;

N-(2-{2-[4-amino-2-(cyclopropylethyl)-6-methyl-1H-imidazo[4,5-c]pyridin-1-yl]ethoxy}ethyl)-N'-isopropylurea;

N'-(2-{2-[4-amino-2-propyl-6-methyl-1H-imidazo[4,5-c]pyridin-1-yl]ethoxy}ethyl)-N,N-diethylurea;

N-(2-{2-[4-amino-2-propyl-6-methyl-1H-imidazo[4,5-c]pyridin-1-yl]ethoxy}ethyl)-N'-isopropylurea;

N'-(2-{2-[4-amino-2-(methoxyethyl)-6-methyl-1H-imidazo[4,5-c]pyridin-1-yl]ethoxy}ethyl)-N,N-diethylurea;

N-(2-{2-[4-amino-2-(methoxyethyl)-6-methyl-1H-imidazo[4,5-c]pyridin-1-yl]ethoxy}ethyl)-N'-isopropylurea;

N-(2-{2-[4-amino-2-(cyclopropylmethyl)-6,7-dimethyl-1H-imidazo[4,5-c]pyridin-1-yl]ethoxy}ethyl)methanesulfonamide;

N-(2-{2-[4-amino-2-(cyclopropylmethyl)-6,7-dimethyl-1H-imidazo[4,5-c]pyridin-1-yl]ethoxy}ethyl)propane-2-sulfonamide;

N-(2-{2-[4-amino-2-(cyclopropylmethyl)-6,7-dimethyl-1H-imidazo[4,5-c]pyridin-1-yl]ethoxy}ethyl)quinoline-8-sulfonamide;

N-(2-{2-[4-amino-2-(cyclopropylmethyl)-6,7-dimethyl-1H-imidazo[4,5-c]pyridin-1-yl]ethoxy}ethyl)-N-methylmethanesulfonamide;

N-(2-{2-[4-amino-2-(cyclopropylmethyl)-6,7-dimethyl-1H-imidazo[4,5-c]pyridin-1-yl]ethoxy}ethyl)-N-methylpropane-2-sulfonamide;

N-(2-{2-[4-amino-2-(cyclopropylmethyl)-6,7-dimethyl-1H-imidazo[4,5-c]pyridin-1-yl]ethoxy}ethyl)-N-methylquinoline-8-sulfonamide;

N-(2-[2-[4-amino-2-(cyclopropylmethyl)-6-methyl-1H-imidazo[4,5-c]pyridin-1-yl]ethoxy}ethyl)methanesulfonamide;

N-(2-{2-[4-amino-2-(cyclopropylmethyl)-6-methyl-1H-imidazo[4,5-c]pyridin-1-yl]ethoxy}ethyl)propane-2-sulfonamide;

N-(2-{2-[4-amino-2-(cyclopropylmethyl)-6-methyl-1H-imidazo[4,5-c]pyridin-1-yl]ethoxy}ethyl)quinoline-8-sulfonamide;

N-(2-{2-[4-amino-2-(cyclopropylmethyl)-6-methyl-1H-imidazo[4,5-c]pyridin-1-yl]ethoxy}ethyl)-N-methylmethanesulfonamide;

N-(2-{2-[4-amino-2-(cyclopropylmethyl)-6-methyl-1H-imidazo[4,5-c]pyridin-1-yl]ethoxy}ethyl)-N-methylpropane-2-sulfonamide;

N-(2-{2-[4-amino-2-(cyclopropylmethyl)-6-methyl-1H-imidazo[4,5-c]pyridin-1-yl]ethoxy}ethyl)-N-methylquinoline-8-sulfonamide;

N-(2-{2-[4-amino-2-propyl-6,7-dimethyl-1H-imidazo[4,5-c]pyridin-1-yl]ethoxy}ethyl)methanesulfonamide;

N-(2-{2-[4-amino-2-propyl-6,7-dimethyl-1H-imidazo[4,5-c]pyridin-1-yl]ethoxy}ethyl)propane-2-sulfonamide;

N-(2-{2-[4-amino-2-propyl-6,7-dimethyl-1H-imidazo[4,5-c]pyridin-1-yl]ethoxy}ethyl)quinoline-8-sulfonamide;

N-(2-{2-[4-amino-2-propyl-6,7-dimethyl-1H-imidazo[4,5-c]pyridin-1-yl]ethoxy}ethyl)-N-methylmethanesulfonamide;

N-(2-{2-[4-amino-2-propyl-6,7-dimethyl-1H-imidazo[4,5-c]pyridin-1-yl]ethoxy}ethoxy)-N-methylpropane-2-sulfonamide;

N-(2-{2-[4-amino-2-propyl-6,7-dimethyl-1H-imidazo[4,5-c]pyridin-1-yl]ethoxy}ethoxy-N-methylquinoline-8-sulfonamide;

N-(2-{2-[4-amino-2-propyl-6-methyl-1H-imidazo[4,5-c]pyridin-1-yl]ethoxy}ethyl)methanesulfonamide;

N-(2-{2-[4-amino-2-propyl-6-methyl-1H-imidazo[4,5-c]pyridin-1-yl]ethoxy}ethyl)propane-2-sulfonamide;

N-(2-{2-[4-amino-2-propyl-6-methyl-1H-imidazo[4,5-c]pyridin-1-yl]ethoxy}ethyl)quinoline-8-sulfonamide;

N-(2-{2-[4-amino-2-propyl-6-methyl-1H-imidazo[4,5-c]pyridin-1-yl]ethoxy}ethyl)-N-methylmethanesulfonamide;

N-(2-{2-[4-amino-2-propyl-6-methyl-1H-imidazo[4,5-c]pyridin-1-yl]ethoxy}ethyl)-N-methylpropane-2-sulfonamide;

N-(2-{2-[4-amino-2-propyl-6-methyl-1H-imidazo[4,5-c]pyridin-1-yl]ethoxy}ethyl)-N-methylquinoline-8-sulfonamide;

N-(2-{2-[4-amino-2-methoxyethyl-6-methyl-1H-imidazo[4,5-c]pyridin-1-yl]ethoxy}ethyl)methanesulfonamide;

N-(2-{2-[4-amino-2-methoxyethyl-6-methyl-1H-imidazo[4,5-c]pyridin-1-yl]ethoxy}ethyl)propane-2-sulfonamide;

N-(2-{2-[4-amino-2-methoxyethyl-6-methyl-1H-imidazo[4,5-c]pyridin-1-yl]ethoxy}ethyl)quinoline-8-sulfonamide;

N-(2-{2-[4-amino-2-methoxyethyl-6-methyl-1H-imidazo[4,5-c]pyridin-1-yl]ethoxy}ethyl)-N-methylmethanesulfonamide;

N-(2-{2-[4-amino-2-methoxyethyl-6-methyl-1H-imidazo[4,5-c]pyridin-1-yl]ethoxy}ethyl)-N-methylpropane-2-sulfonamide;

N-(2-{2-[4-amino-2-methoxyethyl-6-methyl-1H-imidazo[4,5-c]pyridin-1-yl]ethoxy}ethyl)-N-methylquinoline-8-sulfonamide;

N-(2-{2-[4-amino-2-(cyclopropylethyl)-6-methyl-1H-imidazo[4,5-c]pyridin-1-yl]ethoxy}ethyl)methanesulfonamide;

N-(2-{2-[4-amino-2-(cyclopropylethyl)-6-methyl-1H-imidazo[4,5-c]pyridin-1-yl]ethoxy}ethyl)propane-2-sulfonamide;

N-(2-{2-[4-amino-2-(cyclopropylethyl)-6-methyl-1H-imidazo[4,5-c]pyridin-1-yl]ethoxy}ethyl)quinoline-8-sulfonamide;

N-(2-{2-[4-amino-2-(cyclopropylethyl)-6-methyl-1H-imidazo[4,5-c]pyridin-1-yl]ethoxy}ethyl)-N-methylmethanesulfonamide;

N-(2-{2-[4-amino-2-(cyclopropylethyl)-6-methyl-1H-imidazo[4,5-c]pyridin-1-yl]ethoxy}ethyl)-N-methylpropane-2-sulfonamide;

N-(2-{2-[4-amino-2-(cyclopropylethyl)-6-methyl-1H-imidazo[4,5-c]pyridin-1-yl]ethoxy}ethyl)-N-methylquinoline-8-sulfonamide;

2-butyl-1-{2-[3-(1,1-dioxidoisothiazolidin-2-yl)propoxy]ethyl}-6,7-dimethyl-1H-imidazo[4,5-c]pyridin-4-amine;

1-{2-[3-(1,1-dioxidoisothiazolidin-2-yl)propoxy]ethyl}-2-(ethoxymethyl)-6,7-dimethyl-1H-imidazo[4,5-c]pyridin-4-amine;

1-{2-[3-(1,1-dioxidoisothiazolidin-2-yl)propoxy]ethyl}-2-(methoxyethyl)-6,7-dimethyl-1H-imidazo[4,5-c]pyridin-4-amine;

2-(cyclopropylmethyl)-1-{2-[3-(1,1-dioxidoisothiazolidin-2-yl)propoxy]ethyl}-6,7-dimethyl-1H-imidazo[4,5-c]pyridin-4-amine;

2-(cyclopropylethyl)-1-{2-[3-(1,1-dioxidoisothiazolidin-2-yl)propoxy]ethyl}-6,7-dimethyl-1H-imidazo[4,5-c]pyridin-4-amine;

1-{2-[3-(1,1-dioxidoisothiazolidin-2-yl)propoxy]ethyl}-6,7-dimethyl-2-propyl-1H-imidazo[4,5-c]pyridin-4-amine;

1-{2-[3-(1,1-dioxidoisothiazolidin-2-yl)propoxy]ethyl}-6,7-dimethyl-2-ethyl-1H-imidazo[4,5-c]pyridin-4-amine;

1-{2-[3-(1,1-dioxidoisothiazolidin-2-yl)propoxy]ethyl}-2,6,7-trimethyl-1H-imidazo[4,5-c]pyridin-4-amine;

2-butyl-1-{2-[3-(1,1-dioxidoisothiazolidin-2-yl)propoxy]ethyl}-6-methyl-1H-imidazo[4,5-c]pyridin-4-amine;

1-{2-[3-(1,1-dioxidoisothiazolidin-2-yl)propoxy]ethyl}-2-(ethoxymethyl)-6-methyl-1H-imidazo[4,5-c]pyridin-4-amine;

1-{2-[3-(1,1-dioxidoisothiazolidin-2-yl)propoxy]ethyl}-2-(methoxyethyl)-6-methyl-1H-imidazo[4,5-c]pyridin-4-amine;

2-(cyclopropylmethyl)-1-{2-[3-(1,1-dioxidoisothiazolidin-2-yl)propoxy]ethyl}-6-methyl-1H-imidazo[4,5-c]pyridin-4-amine;

2-(cyclopropylethyl)-1-{2-[3-(1,1-dioxidoisothiazolidin-2-yl)propoxy]ethyl}-6-methyl-1H-imidazo[4,5-c]pyridin-4-amine;

1-{2-[3-(1,1-dioxidoisothiazolidin-2-yl)propoxy]ethyl}-6-methyl-2-propyl-1H-imidazo[4,5-c]pyridin-4-amine;

1-{2-[3-(1,1-dioxidoisothiazolidin-2-yl)propoxy]ethyl}-6-methyl-2-ethyl-1H-imidazo[4,5-c]pyridin-4-amine;

1-{2-[3-(1,1-dioxidoisothiazolidin-2-yl)propoxy]ethyl}-2,6-dimethyl-1H-imidazo[4,5-c]pyridin-4-amine;

1-[2-(benzyloxy)ethyl]-2-butyl-6,7-dimethyl-1H-imidazo[4,5-c]pyridin-4-amine;

1-[2-(benzyloxy)ethyl]-2-(cyclopropylmethyl)-6,7-dimethyl-1H-imidazo[4,5-c]pyridin-4-amine;

1-[2-(benzyloxy)ethyl]-2,6-dimethyl-1H-imidazo[4,5-c]pyridin-4-amine;

1-[2-(benzyloxy)ethyl]-6-methyl-2-propyl-1H-imidazo[4,5-c]pyridin-4-amine;
1-[2-(benzyloxy)ethyl]-2-(ethoxymethyl)-6-methyl-1H-imidazo[4,5-c]pyridin-4-amine;
1-[2-(benzyloxy)ethyl]-2-butyl-6-methyl-1H-imidazo[4,5-c]pyridin-4-amine;
1-[2-(benzyloxy)ethyl]-2-(cyclopropylmethyl)-6-methyl-1H-imidazo[4,5-c]pyridin-4-amine;
6,7-dimethyl-1-[2-(3-phenylpropoxy)ethyl]-2-propyl-1H-imidazo[4,5-c]pyridin-4-amine;
2-(cyclopropylmethyl)-6,7-dimethyl-1-[2-(3-phenylpropoxy)ethyl]-1H-imidazo[4,5-c]pyridin-4-amine;
2,6-dimethyl-1-[2-(3-phenylpropoxy)ethyl]-1H-imidazo[4,5-c]pyridin-4-amine;
2,6-dimethyl-1-(2-{[(2E)-3-phenylprop-2-enyl]oxy}ethyl)-1H-imidazo[4,5-c]pyridin-4-amine;
2,6-dimethyl-1-{2-[(3-phenylprop-2-ynyl)oxy]ethyl}-1H-imidazo[4,5-c]pyridin-4-amine;
6-methyl-1-[2-(3-phenylpropoxy)ethyl]-2-propyl-1H-imidazo[4,5-c]pyridin-4-amine;
2-(cyclopropylmethyl)-6-methyl-1-[2-(3-phenylpropoxy)ethyl]-1H-imidazo[4,5-c]pyridin-4-amine;
6,7-dimethyl-2-propyl-1-[2-(3-pyridin-3-ylpropoxy)ethyl]-1H-imidazo[4,5-c]pyridin-4-amine;
2-(cyclopropylmethyl)-6,7-dimethyl-1-[2-(3-pyridin-3-ylpropoxy)ethyl]-1H-imidazo[4,5-c]pyridin-4-amine;
2,6-dimethyl-1-[2-(3-pyridin-3-ylpropoxy)ethyl]-1H-imidazo[4,5-c]pyridin-4-amine;
2-(ethoxymethyl)-6-methyl-1-[2-(3-pyridin-3-ylpropoxy)ethyl]-1H-imidazo[4,5-c]pyridin-4-amine;
6-methyl-2-propyl-1-[2-(3-pyridin-3-ylpropoxy)ethyl]-1H-imidazo[4,5-c]pyridin-4-amine;
2-(cyclopropylmethyl)-6-methyl-1-[2-(3-pyridin-3-ylpropoxy)ethyl]-1H-imidazo[4,5-c]pyridin-4-amine;
6,7-dimethyl-2-propyl-1-{2-[3-(1,3-thiazol-2-yl)propoxy]ethyl}-1H-imidazo[4,5-c]pyridin-4-amine;
6,7-dimethyl-2-propyl-1-[2-(3-pyrimidin-5-ylpropoxy)ethyl]-1H-imidazo[4,5-c]pyridin-4-amine;
6-methyl-2-propyl-1-{2-[3-(1,3-thiazol-2-yl)propoxy]ethyl}-1H-imidazo[4,5-c]pyridin-4-amine;
6-methyl-2-propyl-1-[2-(3-pyrimidin-5-ylpropoxy)ethyl]-1H-imidazo[4,5-c]pyridin-4-amine;
6,7-dimethyl-2-propyl-1-[2-(3-pyrimidin-2-ylpropoxy)ethyl]-1H-imidazo[4,5-c]pyridin-4-amine;
6,7-dimethyl-1-[3-(methylthio)propyl]-1H-imidazo[4,5-c]pyridin-4-amine;
2,6,7-trimethyl-1-[3-(methylthio)propyl]-1H-imidazo[4,5-c]pyridin-4-amine;
2-ethyl-6,7-dimethyl-1-[3-(methylthio)propyl]-1H-imidazo[4,5-c]pyridin-4-amine;
6,7-dimethyl-1-[3-(methylthio)propyl]-2-propyl-1H-imidazo[4,5-c]pyridin-4-amine;
2-butyl-6,7-dimethyl-1-[3-(methylthio)propyl]-1H-imidazo[4,5-c]pyridin-4-amine;
2-ethoxymethyl-6,7-dimethyl-1-[3-(methylthio)propyl]-1H-imidazo[4,5-c]pyridin-4-amine;
2-methoxyethyl-6,7-dimethyl-1-[3-(methylthio)propyl]-1H-imidazo[4,5-c]pyridin-4-amine;
2-cyclopropylmethyl-6,7-dimethyl-1-[3-(methylthio)propyl]-1H-imidazo[4,5-c]pyridin-4-amine;
6,7-dimethyl-1-[3-(methylsulfonyl)propyl]-1H-imidazo[4,5-c]pyridin-4-amine;
2,6,7-trimethyl-1-[3-(methylsulfonyl)propyl]-1H-imidazo[4,5-c]pyridin-4-amine;
2-ethyl-6,7-dimethyl-1-[3-(methylsulfonyl)propyl]-1H-imidazo[4,5-c]pyridin-4-amine;
6,7-dimethyl-1-[3-(methylsulfonyl)propyl]-2-propyl-1H-imidazo[4,5-c]pyridin-4-amine;
2-butyl-6,7-dimethyl-1-[3-(methylsulfonyl)propyl]-1H-imidazo[4,5-c]pyridin-4-amine;
2-ethoxymethyl-6,7-dimethyl-1-[3-(methylsulfonyl)propyl]-1H-imidazo[4,5-c]pyridin-4-amine;
2-methoxyethyl-6,7-dimethyl-1-[3-(methylsulfonyl)propyl]-1H-imidazo[4,5-c]pyridin-4-amine;
2-cyclopropylmethyl-6,7-dimethyl-1-[3-(methylsulfonyl)propyl]-1H-imidazo[4,5-c]pyridin-4-amine;
6,7-dimethyl-1-[3-(methylsulfinyl)propyl]-1H-imidazo[4,5-c]pyridin-4-amine;
2,6,7-trimethyl-1-[3-(methylsulfinyl)propyl]-1H-imidazo[4,5-c]pyridin-4-amine;
2-ethyl-6,7-dimethyl-1-[3-(methylsulfinyl)propyl]-1H-imidazo[4,5-c]pyridin-4-amine;
6,7-dimethyl-1-[3-(methylsulfinyl)propyl]-2-propyl-1H-imidazo[4,5-c]pyridin-4-amine;
2-butyl-6,7-dimethyl-1-[3-(methylsulfinyl)propyl]-1H-imidazo[4,5-c]pyridin-4-amine;
2-ethoxymethyl-6,7-dimethyl-1-[3-(methylsulfinyl)propyl]-1H-imidazo[4,5-c]pyridin-4-amine;
2-methoxyethyl-6,7-dimethyl-1-[3-(methylsulfinyl)propyl]-1H-imidazo[4,5-c]pyridin-4-amine;
2-cyclopropylmethyl-6,7-dimethyl-1-[3-(methylsulfinyl)propyl]-1H-imidazo[4,5-c]pyridin-4-amine;
6,7-dimethyl-1-[3-(phenylthio)propyl]-1H-imidazo[4,5-c]pyridin-4-amine;
2,6,7-trimethyl-1-[3-(phenylthio)propyl]-1H-imidazo[4,5-c]pyridin-4-amine;
2-ethyl-6,7-dimethyl-1-[3-(phenylthio)propyl]-1H-imidazo[4,5-c]pyridin-4-amine;
6,7-dimethyl-1-[3-(phenylthio)propyl]-2-propyl-1H-imidazo[4,5-c]pyridin-4-amine;
2-butyl-6,7-dimethyl-1-[3-(phenylthio)propyl]-1H-imidazo[4,5-c]pyridin-4-amine;
2-ethoxymethyl-6,7-dimethyl-1-[3-(phenylthio)propyl]-1H-imidazo[4,5-c]pyridin-4-amine;
2-methoxyethyl-6,7-dimethyl-1-[3-(phenylthio)propyl]-1H-imidazo[4,5-c]pyridin-4-amine;
2-cyclopropylmethyl-6,7-dimethyl-1-[3-(phenylthio)propyl]-1H-imidazo[4,5-c]pyridin-4-amine;
6,7-dimethyl-1-[3-(phenylsulfonyl)propyl]-1H-imidazo[4,5-c]pyridin-4-amine;
2,6,7-trimethyl-1-[3-(phenylsulfonyl)propyl]-1H-imidazo[4,5-c]pyridin-4-amine;
2-ethyl-6,7-dimethyl-1-[3-(phenylsulfonyl)propyl]-1H-imidazo[4,5-c]pyridin-4-amine;
6,7-dimethyl-1-[3-(phenylsulfonyl)propyl]-2-propyl-1H-imidazo[4,5-c]pyridin-4-amine;
2-butyl-6,7-dimethyl-1-[3-(phenylsulfonyl)propyl]-1H-imidazo[4,5-c]pyridin-4-amine;
2-ethoxymethyl-6,7-dimethyl-1-[3-(phenylsulfonyl)propyl]-1H-imidazo[4,5-c]pyridin-4-amine;
2-methoxyethyl-6,7-dimethyl-1-[3-(phenylsulfonyl)propyl]-1H-imidazo[4,5-c]pyridin-4-amine;
2-cyclopropylmethyl-6,7-dimethyl-1-[3-(phenylsulfonyl)propyl]-1H-imidazo[4,5-c]pyridin-4-amine;
6,7-dimethyl-1-[3-(phenylsulfinyl)propyl]-1H-imidazo[4,5-c]pyridin-4-amine;
2,6,7-trimethyl-1-[3-(phenylsulfinyl)propyl]-1H-imidazo[4,5-c]pyridin-4-amine;
2-ethyl-6,7-dimethyl-1-[3-(phenylsulfinyl)propyl]-1H-imidazo[4,5-c]pyridin-4-amine;
6,7-dimethyl-1-[3-(phenylsulfinyl)propyl]-2-propyl-1H-imidazo[4,5-c]pyridin-4-amine;
2-butyl-6,7-dimethyl-1-[3-(phenylsulfinyl)propyl]-1H-imidazo[4,5-c]pyridin-4-amine;

2-ethoxymethyl-6,7-dimethyl-1-[3-(phenylsulfinyl)propyl]-1H-imidazo[4,5-c]pyridin-4-amine;
2-methoxyethyl-6,7-dimethyl-1-[3-(phenylsulfinyl)propyl]-1H-imidazo[4,5-c]pyridin-4-amine;
2-cyclopropylmethyl-6,7-dimethyl-1-[3-(phenylsulfinyl)propyl]-1H-imidazo[4,5-c]pyridin-4-amine;
6,7-dimethyl-1-[3-(pyrimidin-2-ylthio)propyl]-1H-imidazo[4,5-c]pyridin-4-amine;
2,6,7-trimethyl-1-[3-(pyrimidin-2-ylthio)propyl]-1H-imidazo[4,5-c]pyridin-4-amine;
2-ethyl-6,7-dimethyl-1-[3-(pyrimidin-2-ylthio)propyl]-1H-imidazo[4,5-c]pyridin-4-amine;
6,7-dimethyl-1-[3-(pyrimidin-2-ylthio)propyl]-2-propyl-1H-imidazo[4,5-c]pyridin-4-amine;
2-butyl-6,7-dimethyl-1-[3-(pyrimidin-2-yllthio)propyl]-1H-imidazo[4,5-c]pyridin-4-amine;
2-ethoxymethyl-6,7-dimethyl-1-[3-(pyrimidin-2-ylthio)propyl]-1H-imidazo[4,5-c]pyridin-4-amine;
2-methoxyethyl-6,7-dimethyl-1-[3-(pyrimidin-2-ylthio)propyl]-1H-imidazo[4,5-c]pyridin-4-amine;
2-cyclopropylmethyl-6,7-dimethyl-1-[3-(pyrimidin-2-ylthio)propyl]-1H-imidazo[4,5-c]pyridin-4-amine;
6,7-dimethyl-1-[3-(pyrimidin-2-ylsulfonyl)propyl]-1H-imidazo[4,5-c]pyridin-4-amine;
2,6,7-trimethyl-1-[3-(pyrimidin-2-ylsulfonyl)propyl]-1H-imidazo[4,5-c]pyridin-4-amine;
2-ethyl-6,7-dimethyl-1-[3-(pyrimidin-2-ylsulfonyl)propyl]-1H-imidazo[4,5-c]pyridin-4-amine;
6,7-dimethyl-1-[3-(pyrimidin-2-ylsulfonyl)propyl]-2-propyl-1H-imidazo[4,5-c]pyridin-4-amine;
2-butyl-6,7-dimethyl-1-[3-(pyrimidin-2-ylsulfonyl)propyl]-1H-imidazo[4,5-c]pyridin-4-amine;
2-ethoxymethyl-6,7-dimethyl-1-[3-(pyrimidin-2-ylsulfonyl)propyl]-1H-imidazo[4,5-c]pyridin-4-amine;
2-methoxyethyl-6,7-dimethyl-1-[3-(pyrimidin-2-ylsulfonyl)propyl]-1H-imidazo[4,5-c]pyridin-4-amine;
2-cyclopropylmethyl-6,7-dimethyl-1-[3-(pyrimidin-2-ylsulfonyl)propyl]-1H-imidazo[4,5-c]pyridin-4-amine;
6,7-dimethyl-1-[3-(pyrimidin-2-ylsulfinyl)propyl]-1H-imidazo[4,5-c]pyridin-4-amine;
2,6,7-trimethyl-1-[3-(pyrimidin-2-ylsulfinyl)propyl]-1H-imidazo[4,5-c]pyridin-4-amine;
2-ethyl-6,7-dimethyl-1-[3-(pyrimidin-2-ylsulfinyl)propyl]-1H-imidazo[4,5-c]pyridin-4-amine;
6,7-dimethyl-1-[3-(pyrimidin-2-ylsulfinyl)propyl]-2-propyl-1H-imidazo[4,5-c]pyridin-4-amine;
2-butyl-6,7-dimethyl-1-[3-(pyrimidin-2-ylsulfinyl)propyl]-1H-imidazo[4,5-c]pyridin-4-amine;
2-ethoxymethyl-6,7-dimethyl-1-[3-(pyrimidin-2-ylsulfinyl)propyl]-1H-imidazo[4,5-c]pyridin-4-amine;
2-methoxyethyl-6,7-dimethyl-1-[3-(pyrimidin-2-ylsulfinyl)propyl]-1H-imidazo[4,5-c]pyridin-4-amine;
2-cyclopropylmethyl-6,7-dimethyl-1-[3-(pyrimidin-2-ylsulfinyl)propyl]-1H-imidazo[4,5-c]pyridin-4-amine;
1-[3-(butylthio)propyl]-6,7-dimethyl-1H-imidazo[4,5-c]pyridin-4-amine;
1-[3-(butylthio)propyl]-2,6,7-trimethyl-1H-imidazo[4,5-c]pyridin-4-amine;
1-[3-(butylthio)propyl]-2-ethyl-6,7-dimethyl-1H-imidazo[4,5-c]pyridin-4-amine;
1-[3-(butylthio)propyl]-6,7-dimethyl-2-propyl-1H-imidazo[4,5-c]pyridin-4-amine;
2-butyl-1-[3-(butylthio)propyl]-6,7-dimethyl-1H-imidazo[4,5-c]pyridin-4-amine;
1-[3-(butylthio)propyl]-2-ethoxymethyl-6,7-dimethyl-1H-imidazo[4,5-c]pyridin-4-amine;
1-[3-(butylthio)propyl]-2-methoxyethyl-6,7-dimethyl-1H-imidazo[4,5-c]pyridin-4-amine;
1-[3-(butylthio)propyl]-2-cyclopropylmethyl-6,7-dimethyl-1H-imidazo[4,5-c]pyridin-4-amine;
1-[3-(butylsulfonyl)propyl]-6,7-dimethyl-1H-imidazo[4,5-c]pyridin-4-amine;
1-[3-(butylsulfonyl)propyl]-2,6,7-trimethyl-1H-imidazo[4,5-c]pyridin-4-amine;
1-[3-(butylsulfonyl)propyl]-2-ethyl-6,7-dimethyl-1H-imidazo[4,5-c]pyridin-4-amine;
1-[3-(butylsulfonyl)propyl]-6,7-dimethyl-2-propyl-1H-imidazo[4,5-c]pyridin-4-amine;
2-butyl-1-[3-(butylsulfonyl)propyl]-6,7-dimethyl-1H-imidazo[4,5-c]pyridin-4-amine;
1-[3-(butylsulfonyl)propyl]-2-ethoxymethyl-6,7-dimethyl-1H-imidazo[4,5-c]pyridin-4-amine;
1-[3-(butylsulfonyl)propyl]-2-methoxyethyl-6,7-dimethyl-1H-imidazo[4,5-c]pyridin-4-amine;
1-[3-(butylsulfonyl)propyl]-2-cyclopropylmethyl-6,7-dimethyl-1H-imidazo[4,5-c]pyridin-4-amine;
1-[3-(butylsulfinyl)propyl]-6,7-dimethyl-1H-imidazo[4,5-c]pyridin-4-amine;
1-[3-(butylsulfinyl)propyl]-2,6,7-trimethyl-1H-imidazo[4,5-c]pyridin-4-amine;
1-[3-(butylsulfinyl)propyl]-2-ethyl-6,7-dimethyl-1H-imidazo[4,5-c]pyridin-4-amine;
1-[3-(butylsulfinyl)propyl]-6,7-dimethyl-2-propyl-1H-imidazo[4,5-c]pyridin-4-amine;
2-butyl-1-[3-(butylsulfinyl)propyl]-6,7-dimethyl-1H-imidazo[4,5-c]pyridin-4-amine;
1-[3-(butylsulfinyl)propyl]-2-ethoxymethyl-6,7-dimethyl-1H-imidazo[4,5-c]pyridin-4-amine;
1-[3-(butylsulfinyl)propyl]-2-methoxyethyl-6,7-dimethyl-1H-imidazo[4,5-c]pyridin-4-amine;
1-[3-(butylsulfinyl)propyl]-2-cyclopropylmethyl-6,7-dimethyl-1H-imidazo[4,5-c]pyridin-4-amine;
1-{3-[(2,4-dichlorophenyl)thio]propyl}-6,7-dimethyl-1H-imidazo[4,5-c]pyridin-4-amine;
1-{3-[(2,4-dichlorophenyl)thio]propyl}-2,6,7-trimethyl-1H-imidazo[4,5-c]pyridin-4-amine;
1-{3-[(2,4-dichlorophenyl)thio]propyl}-2-ethyl-6,7-dimethyl-1H-imidazo[4,5-c]pyridin-4-amine;
1-{3-[(2,4-dichlorophenyl)thio]propyl}-6,7-dimethyl-2-propyl-1H-imidazo[4,5-c]pyridin-4-amine;
2-butyl-1-{3-[(2,4-dichlorophenyl)thio]propyl}-6,7-dimethyl-1H-imidazo[4,5-c]pyridin-4-amine;
1-{3-[(2,4-dichlorophenyl)thio]propyl}-2-ethoxymethyl-6,7-dimethyl-1H-imidazo[4,5-c]pyridin-4-amine;
1-{3-[(2,4-dichlorophenyl)thio]propyl}-2-methoxyethyl-6,7-dimethyl-1H-imidazo[4,5-c]pyridin-4-amine;
1-{3-[(2,4-dichlorophenyl)thio]propyl}-2-cyclopropylmethyl-6,7-dimethyl-1H-imidazo[4,5-c]pyridin-4-amine;
1-{3-[(2,4-dichlorophenyl)sulfonyl]propyl}-6,7-dimethyl-1H-imidazo[4,5-c]pyridin-4-amine;
1-{3-[(2,4-dichlorophenyl)sulfonyl]propyl}-2,6,7-trimethyl-1H-imidazo[4,5-c]pyridin-4-amine;
1-{3-[(2,4-dichlorophenyl)sulfonyl]propyl}-2-ethyl-6,7-dimethyl-1H-imidazo[4,5-c]pyridin-4-amine;
1-{3-[(2,4-dichlorophenyl)sulfonyl]propyl}-6,7-dimethyl-2-propyl-1H-imidazo[4,5-c]pyridin-4-amine;
2-butyl-1-{3-[(2,4-dichlorophenyl)sulfonyl]propyl}-6,7-dimethyl-1H-imidazo[4,5-c]pyridin-4-amine;
1-{3-[(2,4-dichlorophenyl)sulfonyl]propyl}-2-ethoxymethyl-6,7-dimethyl-1H-imidazo[4,5-c]pyridin-4-amine;
1-{3-[(2,4-dichlorophenyl)sulfonyl]propyl}-2-methoxyethyl-6,7-dimethyl-1H-imidazo[4,5-c]pyridin-4-amine;

1-{3-[(2,4-dichlorophenyl)sulfonyl]propyl}-2-cyclopropylmethyl-6,7-dimethyl-1H-imidazo[4,5-c]pyridin-4-amine;
1-{3-[(2,4-dichlorophenyl)sulfinyl]propyl}-6,7-dimethyl-1H-imidazo[4,5-c]pyridin-4-amine;
1-{3-[(2,4-dichlorophenyl)sulfinyl]propyl}-2,6,7-trimethyl-1H-imidazo[4,5-c]pyridin-4-amine;
1-{3-[(2,4-dichlorophenyl)sulfinyl]propyl}-2-ethyl-6,7-dimethyl-1H-imidazo[4,5-c]pyridin-4-amine;
1-{3-[(2,4-dichlorophenyl)sulfinyl]propyl}-6,7-dimethyl-2-propyl-1H-imidazo[4,5-c]pyridin-4-amine;
2-butyl-1-{3-[(2,4-dichlorophenyl)sulfinyl]propyl}-6,7-dimethyl-1H-imidazo[4,5-c]pyridin-4-amine;
1-{3-[(2,4-dichlorophenyl)sulfinyl]propyl}-2-ethoxymethyl-6,7-dimethyl-1H-imidazo[4,5-c]pyridin-4-amine;
1-{3-[(2,4-dichlorophenyl)sulfinyl]propyl}-2-methoxyethyl-6,7-dimethyl-1H-imidazo[4,5-c]pyridin-4-amine;
1-{3-[(2,4-dichlorophenyl)sulfinyl]propyl}-2-cyclopropylmethyl-6,7-dimethyl-1H-imidazo[4,5-c]pyridin-4-amine;
1-{3-[(2,4-difluorophenyl)thio]propyl}-6,7-dimethyl-1H-imidazo[4,5-c]pyridin-4-amine;
1-{3-[(2,4-difluorophenyl)thio]propyl}-2,6,7-trimethyl-1H-imidazo[4,5-c]pyridin-4-amine;
2-ethyl-1-{3-[(2,4-difluorophenyl)thio]propyl}-6,7-dimethyl-1H-imidazo[4,5-c]pyridin-4-amine;
1-{3-[(2,4-difluorophenyl)thio]propyl}-6,7-dimethyl-2-propyl-1H-imidazo[4,5-c]pyridin-4-amine;
2-butyl-1-{3-[(2,4-difluorophenyl)thio]propyl}-6,7-dimethyl-1H-imidazo[4,5-c]pyridin-4-amine;
2-ethoxymethyl-1-{3-[(2,4-difluorophenyl)thio]propyl}-6,7-dimethyl-1H-imidazo[4,5-c]pyridin-4-amine;
1-{3-[(2,4-difluorophenyl)thio]propyl}-2-methoxyethyl-6,7-dimethyl-1H-imidazo[4,5-c]pyridin-4-amine;
2-cyclopropylmethyl-1-{3-[(2,4-difluorophenyl)thio]propyl}-6,7-dimethyl-1H-imidazo[4,5-c]pyridin-4-amine;
1-{3-[(2,4-difluorophenyl)sulfonyl]propyl}-6,7-dimethyl-1H-imidazo[4,5-c]pyridin-4-amine;
1-{3-[(2,4-difluorophenyl)sulfonyl]propyl}-2,6,7-trimethyl-1H-imidazo[4,5-c]pyridin-4-amine;
2-ethyl-1-{3-[(2,4-difluorophenyl)sulfonyl]propyl}-6,7-dimethyl-1H-imidazo[4,5-c]pyridin-4-amine;
1-{3-[(2,4-difluorophenyl)sulfonyl]propyl}-6,7-dimethyl-2-propyl-1H-imidazo[4,5-c]pyridin-4-amine;
2-butyl-1-{3-[(2,4-difluorophenyl)sulfonyl]propyl}-6,7-dimethyl-1H-imidazo[4,5-c]pyridin-4-amine;
2-ethoxymethyl-1-{3-[(2,4-difluorophenyl)sulfonyl]propyl}-6,7-dimethyl-1H-imidazo[4,5-c]pyridin-4-amine;
1-{3-[(2,4-difluorophenyl)sulfonyl]propyl}-2-methoxyethyl-6,7-dimethyl-1H-imidazo[4,5-c]pyridin-4-amine;
2-cyclopropylmethyl-1-{3-[(2,4-difluorophenyl)sulfonyl]propyl}-6,7-dimethyl-1H-imidazo[4,5-c]pyridin-4-amine;
1-{3-[(2,4-difluorophenyl)sulfinyl]propyl}-6,7-dimethyl-1H-imidazo[4,5-c]pyridin-4-amine;
1-{3-[(2,4-difluorophenyl)sulfinyl]propyl}-2,6,7-trimethyl-1H-imidazo[4,5-c]pyridin-4-amine;
2-ethyl-1-{3-[(2,4-difluorophenyl)sulfinyl]propyl}-6,7-dimethyl-1H-imidazo[4,5-c]pyridin-4-amine;
1-{3-[(2,4-difluorophenyl)sulfinyl]propyl}-6,7-dimethyl-2-propyl-1H-imidazo[4,5-c]pyridin-4-amine;
2-butyl-1-{3-[(2,4-difluorophenyl)sulfinyl]propyl}-6,7-dimethyl-1H-imidazo[4,5-c]pyridin-4-amine;
2-ethoxymethyl-1-{3-[(2,4-difluorophenyl)sulfinyl]propyl}-6,7-dimethyl-1H-imidazo[4,5-c]pyridin-4-amine;
1-{3-[(2,4-difluorophenyl)sulfinyl]propyl}-2-methoxyethyl-6,7-dimethyl-1H-imidazo[4,5-c]pyridin-4-amine;
2-cyclopropylmethyl-1-{3-[(2,4-difluorophenyl)sulfinyl]propyl}-6,7-dimethyl-1H-imidazo[4,5-c]pyridin-4-amine;
7-methyl-1-[3-(methylthio)propyl]-1H-imidazo[4,5-c]pyridin-4-amine;
2,7-dimethyl-1-[3-(methylthio)propyl]-1H-imidazo[4,5-c]pyridin-4-amine;
2-ethyl-7-methyl-1-[3-(methylthio)propyl]-1H-imidazo[4,5-c]pyridin-4-amine;
6,7-dimethyl-1-[3-(methylthio)propyl]-2-propyl-1H-imidazo[4,5-c]pyridin-4-amine;
2-butyl-7-methyl-1-[3-(methylthio)propyl]-1H-imidazo[4,5-c]pyridin-4-amine;
2-ethoxymethyl-7-methyl-1-[3-(methylthio)propyl]-1H-imidazo[4,5-c]pyridin-4-amine;
2-methoxyethyl-7-methyl-1-[3-(methylthio)propyl]-1H-imidazo[4,5-c]pyridin-4-amine;
2-cyclopropylmethyl-7-methyl-1-[3-(methylthio)propyl]-1H-imidazo[4,5-c]pyridin-4-amine;
7-methyl-1-[3-(methylsulfonyl)propyl]-1H-imidazo[4,5-c]pyridin-4-amine;
2,7-dimethyl-1-[3-(methylsulfonyl)propyl]-1H-imidazo[4,5-c]pyridin-4-amine;
2-ethyl-7-methyl-1-[3-(methylsulfonyl)propyl]-1H-imidazo[4,5-c]pyridin-4-amine;
7-methyl-1-[3-(methylsulfonyl)propyl]-2-propyl-1H-imidazo[4,5-c]pyridin-4-amine;
2-butyl-7-methyl-1-[3-(methylsulfonyl)propyl]-1H-imidazo[4,5-c]pyridin-4-amine;
2-ethoxymethyl-7-methyl-1-[3-(methylsulfonyl)propyl]-1H-imidazo[4,5-c]pyridin-4-amine;
2-methoxyethyl-7-methyl-1-[3-(methylsulfonyl)propyl]-1H-imidazo[4,5-c]pyridin-4-amine;
2-cyclopropylmethyl-7-methyl-1-[3-(methylsulfonyl)propyl]-1H-imidazo[4,5-c]pyridin-4-amine;
7-methyl-1-[3-(methylsulfinyl)propyl]-1H-imidazo[4,5-c]pyridin-4-amine;
2,7-dimethyl-1-[3-(methylsulfinyl)propyl]-1H-imidazo[4,5-c]pyridin-4-amine;
2-ethyl-7-methyl-1-[3-(methylsulfinyl)propyl]-1H-imidazo[4,5-c]pyridin-4-amine;
7-methyl-1-[3-(methylsulfinyl)propyl]-2-propyl-1H-imidazo[4,5-c]pyridin-4-amine;
2-butyl-7-methyl-1-[3-(methylsulfinyl)propyl]-1H-imidazo[4,5-c]pyridin-4-amine;
2-ethoxymethyl-7-methyl-1-[3-(methylsulfinyl)propyl]-1H-imidazo[4,5-c]pyridin-4-amine;
2-methoxyethyl-7-methyl-1-[3-(methylsulfinyl)propyl]-1H-imidazo[4,5-c]pyridin-4-amine;
2-cyclopropylmethyl-7-methyl-1-[3-(methylsulfinyl)propyl]-1H-imidazo[4,5-c]pyridin-4-amine;
7-methyl-1-[3-(phenylthio)propyl]-1H-imidazo[4,5-c]pyridin-4-amine;
2,7-dimethyl-1-[3-(phenylthio)propyl]-1H-imidazo[4,5-c]pyridin-4-amine;
2-ethyl-7-methyl-1-[3-(phenylthio)propyl]-1H-imidazo[4,5-c]pyridin-4-amine;
7-methyl-1-[3-(phenylthio)propyl]-2-propyl-1H-imidazo[4,5-c]pyridin-4-amine;
2-butyl-7-methyl-1-[3-(phenylthio)propyl]-1H-imidazo[4,5-c]pyridin-4-amine;

2-ethoxymethyl-7-methyl-1-[3-(phenylthio)propyl]-1H-imidazo[4,5-c]pyridin-4-amine;
2-methoxyethyl-7-methyl-1-[3-(phenylthio)propyl]-1H-imidazo[4,5-c]pyridin-4-amine;
2-cyclopropylmethyl-7-methyl-1-[3-(phenylthio)propyl]-1H-imidazo[4,5-c]pyridin-4-amine;
7-methyl-1-[3-(phenylsulfonyl)propyl]-1H-imidazo[4,5-c]pyridin-4-amine;
2,7-dimethyl-1-[3-(phenylsulfonyl)propyl]-1H-imidazo[4,5-c]pyridin-4-amine;
2-ethyl-7-methyl-1-[3-(phenylsulfonyl)propyl]-1H-imidazo[4,5-c]pyridin-4-amine;
7-methyl-1-[3-(phenylsulfonyl)propyl]-2-propyl-1H-imidazo[4,5-c]pyridin-4-amine;
2-butyl-7-methyl-1-[3-(phenylsulfonyl)propyl]-1H-imidazo[4,5-c]pyridin-4-amine;
2-ethoxymethyl-7-methyl-1-[3-(phenylsulfonyl)propyl]-1H-imidazo[4,5-c]pyridin-4-amine;
2-methoxyethyl-7-methyl-1-[3-(phenylsulfonyl)propyl]-1H-imidazo[4,5-c]pyridin-4-amine;
2-cyclopropylmethyl-7-methyl-1-[3-(phenylsulfonyl)propyl]-1H-imidazo[4,5-c]pyridin-4-amine;
7-methyl-1-[3-(phenylsulfinyl)propyl]-1H-imidazo[4,5-c]pyridin-4-amine;
2,7-dimethyl-1-[3-(phenylsulfinyl)propyl]-1H-imidazo[4,5-c]pyridin-4-amine;
2-ethyl-7-methyl-1-[3-(phenylsulfinyl)propyl]-1H-imidazo[4,5-c]pyridin-4-amine;
7-methyl-1-[3-(phenylsulfinyl)propyl]-2-propyl-1H-imidazo[4,5-c]pyridin-4-amine;
2-butyl-7-methyl-1-[3-(phenylsulfinyl)propyl]-1H-imidazo[4,5-c]pyridin-4-amine;
2-ethoxymethyl-7-methyl-1-[3-(phenylsulfinyl)propyl]-1H-imidazo[4,5-c]pyridin-4-amine;
2-methoxyethyl-7-methyl-1-[3-(phenylsulfinyl)propyl]-1H-imidazo[4,5-c]pyridin-4-amine;
2-cyclopropylmethyl-7-methyl-1-[3-(phenylsulfinyl)propyl]-1H-imidazo[4,5-c]pyridin-4-amine;
7-methyl-1-[3-(pyrimidin-2-ylthio)propyl]-1H-imidazo[4,5-c]pyridin-4-amine;
2,7-dimethyl-1-[3-(pyrimidin-2-ylthio)propyl]-1H-imidazo[4,5-c]pyridin-4-amine;
2-ethyl-7-methyl-1-[3-(pyrimidin-2-ylthio)propyl]-1H-imidazo[4,5-c]pyridin-4-amine;
7-methyl-1-[3-(pyrimidin-2-ylthio)propyl]-2-propyl-1H-imidazo[4,5-c]pyridin-4-amine;
2-butyl-7-methyl-1-[3-(pyrimidin-2-yllthio)propyl]-1H-imidazo[4,5-c]pyridin-4-amine;
2-ethoxymethyl-7-methyl-1-[3-(pyrimidin-2-ylthio)propyl]-1H-imidazo[4,5-c]pyridin-4-amine;
2-methoxyethyl-7-methyl-1-[3-(pyrimidin-2-ylthio)propyl]-1H-imidazo[4,5-c]pyridin-4-amine;
2-cyclopropylmethyl-7-methyl-1-[3-(pyrimidin-2-ylthio)propyl]-1H-imidazo[4,5-c]pyridin-4-amine;
7-methyl-1-[3-(pyrimidin-2-ylsulfonyl)propyl]-1H-imidazo[4,5-c]pyridin-4-amine;
2,7-dimethyl-1-[3-(pyrimidin-2-ylsulfonyl)propyl]-1H-imidazo[4,5-c]pyridin-4-amine;
2-ethyl-7-methyl-1-[3-(pyrimidin-2-ylsulfonyl)propyl]-1H-imidazo[4,5-c]pyridin-4-amine;
7-methyl-1-[3-(pyrimidin-2-ylsulfonyl)propyl]-2-propyl-1H-imidazo[4,5-c]pyridin-4-amine;
2-butyl-7-methyl-1-[3-(pyrimidin-2-ylsulfonyl)propyl]-1H-imidazo[4,5-c]pyridin-4-amine;
2-ethoxymethyl-7-methyl-1-[3-(pyrimidin-2-ylsulfonyl)propyl]-1H-imidazo[4,5-c]pyridin-4-amine;
2-methoxyethyl-7-methyl-1-[3-(pyrimidin-2-ylsulfonyl)propyl]-1H-imidazo[4,5-c]pyridin-4-amine;
2-cyclopropylmethyl-7-methyl-1-[3-(pyrimidin-2-ylsulfonyl)propyl]-1H-imidazo[4,5-c]pyridin-4-amine;
7-methyl-1-[3-(pyrimidin-2-ylsulfinyl)propyl]-1H-imidazo[4,5-c]pyridin-4-amine;
2,7-dimethyl-1-[3-(pyrimidin-2-ylsulfinyl)propyl]-1H-imidazo[4,5-c]pyridin-4-amine;
2-ethyl-7-methyl-1-[3-(pyrimidin-2-ylsulfinyl)propyl]-1H-imidazo[4,5-c]pyridin-4-amine;
7-methyl-1-[3-(pyrimidin-2-ylsulfinyl)propyl]-2-propyl-1H-imidazo[4,5-c]pyridin-4-amine;
2-butyl-7-methyl-1-[3-(pyrimidin-2-ylsulfinyl)propyl]-1H-imidazo[4,5-c]pyridin-4-amine;
2-ethoxymethyl-7-methyl-1-[3-(pyrimidin-2-ylsulfinyl)propyl]-1H-imidazo[4,5-c]pyridin-4-amine;
2-methoxyethyl-7-methyl-1-[3-(pyrimidin-2-ylsulfinyl)propyl]-1H-imidazo[4,5-c]pyridin-4-amine;
2-cyclopropylmethyl-7-methyl-1-[3-(pyrimidin-2-ylsulfinyl)propyl]-1H-imidazo[4,5-c]pyridin-4-amine;
1-[3-(butylthio)propyl]-7-methyl-1H-imidazo[4,5-c]pyridin-4-amine;
1-[3-(butylthio)propyl]-2,7-dimethyl-1H-imidazo[4,5-c]pyridin-4-amine;
1-[3-(butylthio)propyl]-2-ethyl-7-methyl-1H-imidazo[4,5-c]pyridin-4-amine;
1-[3-(butylthio)propyl]-7-methyl-2-propyl-1H-imidazo[4,5-c]pyridin-4-amine;
2-butyl-1-[3-(butylthio)propyl]-7-methyl-1H-imidazo[4,5-c]pyridin-4-amine;
1-[3-(butylthio)propyl]-2-ethoxymethyl-7-methyl-1H-imidazo[4,5-c]pyridin-4-amine;
1-[3-(butylthio)propyl]-2-methoxyethyl-7-methyl-1H-imidazo[4,5-c]pyridin-4-amine;
1-[3-(butylthio)propyl]-2-cyclopropylmethyl-7-methyl-1H-imidazo[4,5-c]pyridin-4-amine;
1-[3-(butylsulfonyl)propyl]-7-methyl-1H-imidazo[4,5-c]pyridin-4-amine;
1-[3-(butylsulfonyl)propyl]-2,7-dimethyl-1H-imidazo[4,5-c]pyridin-4-amine;
1-[3-(butylsulfonyl)propyl]-2-ethyl-7-methyl-1H-imidazo[4,5-c]pyridin-4-amine;
1-[3-(butylsulfonyl)propyl]-7-methyl-2-propyl-1H-imidazo[4,5-c]pyridin-4-amine;
2-butyl-1-[3-(butylsulfonyl)propyl]-7-methyl-1H-imidazo[4,5-c]pyridin-4-amine;
1-[3-(butylsulfonyl)propyl]-2-ethoxymethyl-7-methyl-1H-imidazo[4,5-c]pyridin-4-amine;
1-[3-(butylsulfonyl)propyl]-2-methoxyethyl-7-methyl-1H-imidazo[4,5-c]pyridin-4-amine;
1-[3-(butylsulfonyl)propyl]-2-cyclopropylmethyl-7-methyl-1H-imidazo[4,5-c]pyridin-4-amine;
1-[3-(butylsulfinyl)propyl]-7-methyl-1H-imidazo[4,5-c]pyridin-4-amine;
1-[3-(butylsulfinyl)propyl]-2,7-dimethyl-1H-imidazo[4,5-c]pyridin-4-amine;
1-[3-(butylsulfinyl)propyl]-2-ethyl-7-methyl-1H-imidazo[4,5-c]pyridin-4-amine;
1-[3-(butylsulfinyl)propyl]-7-methyl-2-propyl-1H-imidazo[4,5-c]pyridin-4-amine;
2-butyl-1-[3-(butylsulfinyl)propyl]-7-methyl-1H-imidazo[4,5-c]pyridin-4-amine;
1-[3-(butylsulfinyl)propyl]-2-ethoxymethyl-7-methyl-1H-imidazo[4,5-c]pyridin-4-amine;
1-[3-(butylsulfinyl)propyl]-2-methoxyethyl-6,7-dimethyl-1H-imidazo[4,5-c]pyridin-4-amine;
1-[3-(butylsulfinyl)propyl]-2-cyclopropylmethyl-6,7-dimethyl-1H-imidazo[4,5-c]pyridin-4-amine;
1-{3-[(2,4-dichlorophenyl)thio]propyl}-7-methyl-1H-imidazo[4,5-c]pyridin-4-amine;

1-{3-[(2,4-dichlorophenyl)thio]propyl}-2,7-dimethyl-1H-imidazo[4,5-c]pyridin-4-amine;
1-{3-[(2,4-dichlorophenyl)thio]propyl}-2-ethyl-7-methyl-1H-imidazo[4,5-c]pyridin-4-amine;
1-{3-[(2,4-dichlorophenyl)thio]propyl}-7-methyl-2-propyl-1H-imidazo[4,5-c]pyridin-4-amine;
2-butyl-1-{3-[(2,4-dichlorophenyl)thio]propyl}-7-methyl-1H-imidazo[4,5-c]pyridin-4-amine;
1-{3-[(2,4-dichlorophenyl)thio]propyl}-2-ethoxymethyl-7-methyl-1H-imidazo[4,5-c]pyridin-4-amine;
1-{3-[(2,4-dichlorophenyl)thio]propyl}-2-methoxyethyl-7-methyl-1H-imidazo[4,5-c]pyridin-4-amine;
1-{3-[(2,4-dichlorophenyl)thio]propyl}-2-cyclopropylmethyl-7-methyl-1H-imidazo[4,5-c]pyridin-4-amine;
1-{3-[(2,4-dichlorophenyl)sulfonyl]propyl}-7-methyl-1H-imidazo[4,5-c]pyridin-4-amine;
1-{3-[(2,4-dichlorophenyl)sulfonyl]propyl}-2,7-dimethyl-1H-imidazo[4,5-c]pyridin-4-amine;
1-{3-[(2,4-dichlorophenyl)sulfonyl]propyl}-2-ethyl-7-methyl-1H-imidazo[4,5-c]pyridin-4-amine;
1-{3-[(2,4-dichlorophenyl)sulfonyl]propyl}-7-methyl-2-propyl-1H-imidazo[4,5-c]pyridin-4-amine;
2-butyl-1-{3-[(2,4-dichlorophenyl)sulfonyl]propyl}-7-methyl-1H-imidazo[4,5-c]pyridin-4-amine;
1-{3-[(2,4-dichlorophenyl)sulfonyl]propyl}-2-ethoxymethyl-7-methyl-1H-imidazo[4,5-c]pyridin-4-amine;
1-{3-[(2,4-dichlorophenyl)sulfonyl]propyl}-2-methoxyethyl-7-methyl-1H-imidazo[4,5c]pyridin-4-amine;
1-{3-[(2,4-dichlorophenyl)sulfonyl]propyl}-2-cyclopropylmethyl-7-methyl-1H-imidazo[4,5-c]pyridin-4-amine;
1-{3-[(2,4-dichlorophenyl)sulfinyl]propyl}-7-methyl-1H-imidazo[4,5-c]pyridin-4-amine;
1-{3-[(2,4-dichlorophenyl)sulfinyl]propyl}-2,7-dimethyl-1H-imidazo[4,5-c]pyridin-4-amine;
1-{3-[(2,4-dichlorophenyl)sulfinyl]propyl}-2-ethyl-7-methyl-1H-imidazo[4,5-c]pyridin-4-amine;
1-{3-[(2,4-dichlorophenyl)sulfinyl]propyl}-7-methyl-2-propy-1H-imidazo[4,5-c]pyridin-4-amine;
2-butyl-1-{3-[(2,4-dichlorophenyl)sulfinyl]propyl}-7-methyl-1H-imidazo[4,5-c]pyridin-4-amine;
1-{3-[(2,4-dichlorophenyl)sulfinyl]propyl}-2-ethoxymethyl-7-methyl-1H-imidazo[4,5-c]pyridin-4-amine;
1-{3-[(2,4-dichlorophenyl)sulfinyl]propyl}-2-methoxyethyl-7-methyl-1H-imidazo[4,5-c]pyridin-4-amine;
1-{3-[(2,4-dichlorophenyl)sulfinyl]propyl}-2-cyclopropylmethyl-7-methyl-1H-imidazo[4,5-c]pyridin-4-amine;
1-{3-[(2,4-difluorophenyl)thio]propyl}-6-methyl-1H-imidazo[4,5-c]pyridin-4-amine;
1-{3-[(2,4-difluorophenyl)thio]propyl}-2,7-dimethyl-1H-imidazo[4,5-c]pyridin-4-amine;
2-ethyl-1-{3-[(2,4-difluorophenyl)thio]propyl}-7-methyl-1H-imidazo[4,5-c]pyridin-4-amine;
1-{3-[(2,4-difluorophenyl)thio]propyl}-7-methyl-2-propyl-1H-imidazo[4,5-c]pyridin-4-amine;
2-butyl-1-{3-[(2,4-difluorophenyl)thio]propyl}-7-methyl-1H-imidazo[4,5-c]pyridin-4-amine;
2-ethoxymethyl-1-{3-[(2,4-difluorophenyl)thiolpropyl}-7-methyl-1H-imidazo[4,5-c]pyridin-4-amine;
1-{3-[(2,4-difluorophenyl)thio]propyl}-2-methoxyethyl-7-methyl-1H-imidazo[4,5-c]pyridin-4-amine;
2-cyclopropylmethyl-1-{3-[(2,4-difluorophenyl)thio]propyl}-7-methyl-1H-imidazo[4,5-c]pyridin-4-amine;
1-{3-[(2,4-difluorophenyl)sulfonyl]propyl}-7-methyl-1H-imidazo[4,5-c]pyridin-4-amine;
1-{3-[(2,4-difluorophenyl)sulfonyl]propyl}-2,7-dimethyl-1H-imidazo[4,5-c]pyridin-4-amine;
2-ethyl-1-{3-[(2,4-difluorophenyl)sulfonyl]propyl}-7-methyl-1H-imidazo[4,5-c]pyridin-4-amine;
1-{3-[(2,4-difluorophenyl)sulfonyl]propyl}-7-methyl-2-propyl-1H-imidazo[4,5-c]pyridin-4-amine;
2-butyl-1-{3-[(2,4-difluorophenyl)sulfonyl]propyl}-7-methyl-1H-imidazo[4,5-c]pyridin-4-amine;
2-ethoxymethyl-1-{3-[(2,4-difluorophenyl)sulfonyl]propyl}-7-methyl-1H-imidazo[4,5-c]pyridin-4-amine;
1-{3-[(2,4-difluorophenyl)sulfonyl]propyl}-2-methoxyethyl-7-methyl-1H-imidazo[4,5-c]pyridin-4-amine;
2-cyclopropylmethyl-1-{3-[(2,4-difluorophenyl)sulfonyl]propyl}-7-methyl-1H-imidazo[4,5-c]pyridin-4-amine;
1-{3-[(2,4-difluorophenyl)sulfinyl]propyl}-7-methyl-1H-imidazo[4,5-c]pyridin-4-amine;
1-{3-[(2,4-difluorophenyl)sulfinyl]propyl}-2,7-dimethyl-1H-imidazo[4,5-c]pyridin-4-amine;
2-ethyl-1-{3-[(2,4-difluorophenyl)sulfinyl]propyl}-7-methyl-1H-imidazo[4,5-c]pyridin-4-amine;
1-{3-[(2,4-difluorophenyl)sulfinyl]propyl}-7-methyl-2-propyl-1H-imidazo[4,5-c]pyridin-4-amine;
2-butyl-1-{3-[(2,4-difluorophenyl)sulfinyl]propyl}-7-methyl-1H-imidazo[4,5-c]pyridin-4-amine;
2-ethoxymethyl-1-{3-[(2,4-difluorophenyl)sulfinyl]propyl}-7-methyl-1H-imidazo[4,5-c]pyridin-4-amine;
1-{3-[(2,4-difluorophenyl)sulfinyl]propyl}-2-methoxyethyl-7-methyl-1H-imidazo[4,5-c]pyridin-4-amine;
2-cyclopropylmethyl-1-{3-[(2,4-difluorophenyl)sulfinyl]propyl}-7-methyl-1H-imidazo[4,5-c]pyridin-4-amine;
6,7-dimethyl-1-[4-(methylthio)butyl]-1H-imidazo[4,5-c]pyridin-4-amine;
2,6,7-trimethyl-1-[4-(methylthio)butyl]-1H-imidazo[4,5-c]pyridin-4-amine;
2-ethyl-6,7-dimethyl-1-[4-(methylthio)butyl]-1H-imidazo[4,5-c]pyridin-4-amine;
6,7-dimethyl-1-[4-(methylthio)butyl]-2-propyl-1H-imidazo[4,5-c]pyridin-4-amine;
2-butyl-6,7-dimethyl-1-[4-(methylthio)butyl]-1H-imidazo[4,5-c]pyridin-4-amine;
2-ethoxymethyl-6,7-dimethyl-1-[4-(methylthio)butyl]-1H-imidazo[4,5-c]pyridin-4-amine;
2-methoxyethyl-6,7-dimethyl-1-[4-(methylthio)butyl]-1H-imidazo[4,5-c]pyridin-4-amine;
2-cyclopropylmethyl-6,7-dimethyl-1-[4-(methylthio)butyl]-1H-imidazo[4,5-c]pyridin-4-amine;
6,7-dimethyl-1-[4-(methylsulfonyl)butyl]-1H-imidazo[4,5-c]pyridin-4-amine;
2,6,7-trimethyl-1-[4-(methylsulfonyl)butyl]-1H-imidazo[4,5-c]pyridin-4-amine;
2-ethyl-6,7-dimethyl-1-[4-(methylsulfonyl)butyl]-1H-imidazo[4,5-c]pyridin-4-amine;
6,7-dimethyl-1-[4-(methylsulfonyl)butyl]-2-propyl-1H-imidazo[4,5-c]pyridin-4-amine;
2-butyl-6,7-dimethyl-1-[4-(methylsulfonyl)butyl]-1H-imidazo[4,5-c]pyridin-4-amine;
2-ethoxymethyl-6,7-dimethyl-1-[4-(methylsulfonyl)butyl]-1H-imidazo[4,5-c]pyridin-4-amine;
2-methoxyethyl-6,7-dimethyl-1-[4-(methylsulfonyl)butyl]-1H-imidazo[4,5-c]pyridin-4-amine;
2-cyclopropylmethyl-6,7-dimethyl-1-[4-(methylsulfonyl)butyl]-1H-imidazo[4,5-c]pyridin-4-amine;

6,7-dimethyl-1-[4-(methylsulfinyl)butyl]-1H-imidazo[4,5-c]pyridin-4-amine;
2,6,7-trimethyl-1-[4-(methylsulfinyl)butyl]-1H-imidazo[4,5-c]pyridin-4-amine;
2-ethyl-6,7-dimethyl-1-[4-(methylsulfinyl)butyl]-1H-imidazo[4,5-c]pyridin-4-amine;
6,7-dimethyl-1-[4-(methylsulfinyl)butyl]-2-propyl-1H-imidazo[4,5-c]pyridin-4-amine;
2-butyl-6,7-dimethyl-1-[4-(methylsulfinyl)butyl]-1H-imidazo[4,5-c]pyridin-4-amine;
2-ethoxymethyl-6,7-dimethyl-1-[4-(methylsulfinyl)butyl]-1H-imidazo[4,5-c]pyridin-4-amine;
2-methoxyethyl-6,7-dimethyl-1-[4-(methylsulfinyl)butyl]-1H-imidazo[4,5-c]pyridin-4-amine;
2-cyclopropylmethyl-6,7-dimethyl-1-[4-(methylsulfinyl)butyl]-1H-imidazo[4,5-c]pyridin-4-amine;
6,7-dimethyl-1-[4-(phenylthio)butyl]-1H-imidazo[4,5-c]pyridin-4-amine;
2,6,7-trimethyl-1-[4-(phenylthio)butyl]-1H-imidazo[4,5-c]pyridin-4-amine;
2-ethyl-6,7-dimethyl-1-[4-(phenylthio)butyl]-1H-imidazo[4,5-c]pyridin-4-amine;
6,7-dimethyl-1-[4-(phenylthio)butyl]-2-propyl-1H-imidazo[4,5-c]pyridin-4-amine;
2-butyl-6,7-dimethyl-1-[4-(phenylthio)butyl]-1H-imidazo[4,5-c]pyridin-4-amine;
2-ethoxymethyl-6,7-dimethyl-1-[4-(phenylthio)butyl]-1H-imidazo[4,5-c]pyridin-4-amine;
2-methoxyethyl-6,7-dimethyl-1-[4-(phenylthio)butyl]-1H-imidazo[4,5-c]pyridin-4-amine;
2-cyclopropylmethyl-6,7-dimethyl-1-[4-(phenylthio)butyl]-1H-imidazo[4,5-c]pyridin-4-amine;
6,7-dimethyl-1-[4-(phenylsulfonyl)butyl]-1H-imidazo[4,5-c]pyridin-4-amine;
2,6,7-trimethyl-1-[4-(phenylsulfonyl)butyl]-1H-imidazo[4,5-c]pyridin-4-amine;
2-ethyl-6,7-dimethyl-1-[4-(phenylsulfonyl)butyl]-1H-imidazo[4,5-c]pyridin-4-amine;
6,7-dimethyl-1-[4-(phenylsulfonyl)butyl]-2-propyl-1H-imidazo[4,5-c]pyridin-4-amine;
2-butyl-6,7-dimethyl-1-[4-(phenylsulfonyl)butyl]-1H-imidazo[4,5-c]pyridin-4-amine;
2-ethoxymethyl-6,7-dimethyl-1-[4-(phenylsulfonyl)butyl]-1H-imidazo[4,5-c]pyridin-4-amine;
2-methoxyethyl-6,7-dimethyl-1-[4-(phenylsulfonyl)butyl]-1H-imidazo[4,5-c]pyridin-4-amine;
2-cyclopropylmethyl-6,7-dimethyl-1-[4-(phenylsulfonyl)butyl]-1H-imidazo[4,5-c]pyridin-4-amine;
6,7-dimethyl-1-[4-(phenylsulfinyl)butyl]-1H-imidazo[4,5-c]pyridin-4-amine;
2,6,7-trimethyl-1-[4-(phenylsulfinyl)butyl]-1H-imidazo[4,5-c]pyridin-4-amine;
2-ethyl-6,7-dimethyl-1-[4-(phenylsulfinyl)butyl]-1H-imidazo[4,5-c]pyridin-4-amine;
6,7-dimethyl-1-[4-(phenylsulfinyl)butyl]-2-propyl-1H-imidazo[4,5-c]pyridin-4-amine;
2-butyl-6,7-dimethyl-1-[4-(phenylsulfinyl)butyl]-1H-imidazo[4,5-c]pyridin-4-amine;
2-ethoxymethyl-6,7-dimethyl-1-[4-(phenylsulfinyl)butyl]-1H-imidazo[4,5-c]pyridin-4-amine;
2-methoxyethyl-6,7-dimethyl-1-[4-(phenylsulfinyl)butyl]-1H-imidazo[4,5-c]pyridin-4-amine;
2-cyclopropylmethyl-6,7-dimethyl-1-[4-(phenylsulfinyl)butyl]-1H-imidazo[4,5-c]pyridin-4-amine;
6,7-dimethyl-1-[4-(pyrimidin-2-ylthio)butyl]-1H-imidazo[4,5-c]pyridin-4-amine;
2,6,7-trimethyl-1-[4-(pyrimidin-2-ylthio)butyl]-1H-imidazo[4,5-c]pyridin-4-amine;
2-ethyl-6,7-dimethyl-1-[4-(pyrimidin-2-ylthio)butyl]-1H-imidazo[4,5-c]pyridin-4-amine;
6,7-dimethyl-1-[4-(pyrimidin-2-ylthio)butyl]-2-propyl-1H-imidazo[4,5-c]pyridin-4-amine;
2-butyl-6,7-dimethyl-1-[4-(pyrimidin-2-ylthio)butyl]-1H-imidazo[4,5-c]pyridin-4-amine;
2-ethoxymethyl-6,7-dimethyl-1-[4-(pyrimidin-2-ylthio)butyl]-1H-imidazo[4,5-c]pyridin-4-amine;
2-methoxyethyl-6,7-dimethyl-1-[4-(pyrimidin-2-ylthio)butyl]-1H-imidazo[4,5-c]pyridin-4-amine;
2-cyclopropylmethyl-6,7-dimethyl-1-[4-(pyrimidin-2-ylthio)butyl]-1H-imidazo[4,5-c]pyridin-4-amine;
6,7-dimethyl-1-[4-(pyrimidin-2-ylsulfonyl)butyl]-1H-imidazo[4,5-c]pyridin-4-amine;
2,6,7-trimethyl-1-[4-(pyrimidin-2-ylsulfonyl)butyl]-1H-imidazo[4,5-c]pyridin-4-amine;
2-ethyl-6,7-dimethyl-1-[4-(pyrimidin-2-ylsulfonyl)butyl]-1H-imidazo[4,5-c]pyridin-4-amine;
6,7-dimethyl-1-[4-(pyrimidin-2-ylsulfonyl)butyl]-2-propyl-1H-imidazo[4,5-c]pyridin-4-amine;
2-butyl-6,7-dimethyl-1-[4-(pyrimidin-2-ylsulfonyl)butyl]-1H-imidazo[4,5-c]pyridin-4-amine;
2-ethoxymethyl-6,7-dimethyl-1-[4-(pyrimidin-2-ylsulfonyl)butyl]-1H-imidazo[4,5-c]pyridin-4-amine;
2-methoxyethyl-6,7-dimethyl-1-[4-(pyrimidin-2-ylsulfonyl)butyl]-1H-imidazo[4,5-c]pyridin-4-amine;
2-cyclopropylmethyl-6,7-dimethyl-1-[4-(pyrimidin-2-ylsulfonyl)butyl]-1H-imidazo[4,5-c]pyridin-4-amine;
6,7-dimethyl-1-[4-(pyrimidin-2-ylsulfinyl)butyl]-1H-imidazo[4,5-c]pyridin-4-amine;
2,6,7-trimethyl-1-[4-(pyrimidin-2-ylsulfinyl)butyl]-1H-imidazo[4,5-c]pyridin-4-amine;
2-ethyl-6,7-dimethyl-1-[4-(pyrimidin-2-ylsulfinyl)butyl]-1H-imidazo[4,5-c]pyridin-4-amine;
6,7-dimethyl-1-[4-(pyrimidin-2-ylsulfinyl)butyl]-2-propyl-1H-imidazo[4,5-c]pyridin-4-amine;
2-butyl-6,7-dimethyl-1-[4-(pyrimidin-2-ylsulfinyl)butyl]-1H-imidazo[4,5-c]pyridin-4-amine;
2-ethoxymethyl-6,7-dimethyl-1-[4-(pyrimidin-2-ylsulfinyl)butyl]-1H-imidazo[4,5-c]pyridin-4-amine;
2-methoxyethyl-6,7-dimethyl-1-[4-(pyrimidin-2-ylsulfinyl)butyl]-1H-imidazo[4,5-c]pyridin-4-amine;
2-cyclopropylmethyl-6,7-dimethyl-1-[4-(pyrimidin-2-ylsulfinyl)butyl]-1H-imidazo[4,5-c]pyridin-4-amine;
1-[4-(butylthio)butyl]-6,7-dimethyl-1H-imidazo[4,5-c]pyridin-4-amine;
1-[4-(butylthio)butyl]-2,6,7-trimethyl-1H-imidazo[4,5-c]pyridin-4-amine;
1-[4-(butylthio)butyl]-2-ethyl-6,7-dimethyl-1H-imidazo[4,5-c]pyridin-4-amine;
1-[4-(butylthio)butyl]-6,7-dimethyl-2-propyl-1H-imidazo[4,5-c]pyridin-4-amine;
2-butyl-1-[4-(butylthio)butyl]-6,7-dimethyl-1H-imidazo[4,5-c]pyridin-4-amine;
1-[4-(butylthio)butyl]-2-ethoxymethyl-6,7-dimethyl-1H-imidazo[4,5-c]pyridin-4-amine;
1-[4-(butylthio)butyl]-2-methoxyethyl-6,7-dimethyl-1H-imidazo[4,5-c]pyridin-4-amine;
1-[4-(butylthio)butyl]-2-cyclopropylmethyl-6,7-dimethyl-1H-imidazo[4,5-c]pyridin-4-amine;
1-[4-(butylsulfonyl)butyl]-6,7-dimethyl-1H-imidazo[4,5-c]pyridin-4-amine;
1-[4-(butylsulfonyl)butyl]-2,6,7-trimethyl-1H-imidazo[4,5-c]pyridin-4-amine;
1-[4-(butylsulfonyl)butyl]-2-ethyl-6,7-dimethyl-1H-imidazo[4,5-c]pyridin-4-amine;
1-[4-(butylsulfonyl)butyl]-6,7-dimethyl-2-propyl-1H-imidazo[4,5-c]pyridin-4-amine;

2-butyl-1-[4-(butylsulfonyl)butyl]-6,7-dimethyl-1H-imidazo[4,5-c]pyridin-4-amine;
1-[4-(butylsulfonyl)butyl]-2-ethoxymethyl-6,7-dimethyl-1H-imidazo[4,5-c]pyridin-4-amine;
1-[4-(butylsulfonyl)butyl]-2-methoxyethyl-6,7-dimethyl-1H-imidazo[4,5-c]pyridin-4-amine;
1-[4-(butylsulfonyl)butyl]-2-cyclopropylmethyl-6,7-dimethyl-1H-imidazo[4,5-c]pyridin-4-amine;
1-[4-(butylsulfinyl)butyl]-6,7-dimethyl-1H-imidazo[4,5-c]pyridin-4-amine;
1-[4-(butylsulfinyl)butyl]-2,6,7-trimethyl-1H-imidazo[4,5-c]pyridin-4-amine;
1-[4-(butylsulfinyl)butyl]-2-ethyl-6,7-dimethyl-1H-imidazo[4,5-c]pyridin-4-amine;
1-[4-(butylsulfinyl)butyl]-6,7-dimethyl-2-propyl-1H-imidazo[4,5-c]pyridin-4-amine;
2-butyl-1-[4-(butylsulfinyl)butyl]-6,7-dimethyl-1H-imidazo[4,5-c]pyridin-4-amine;
1-[4-(butylsulfinyl)butyl]-2-ethoxymethyl-6,7-dimethyl-1H-imidazo[4,5-c]pyridin-4-amine;
1-[4-(butylsulfinyl)butyl]-2-methoxyethyl-6,7-dimethyl-1H-imidazo[4,5-c]pyridin-4-amine;
1-[4-(butylsulfinyl)butyl]-2-cyclopropylmethyl-6,7-dimethyl-1H-imidazo[4,5-c]pyridin-4-amine;
1-{4-[(2,4-dichlorophenyl)thio]butyl}-6,7-dimethyl-1H-imidazo[4,5-c]pyridin-4-amine;
1-{4-[(2,4-dichlorophenyl)thio]butyl}-2,6,7-trimethyl-1H-imidazo[4,5-c]pyridin-4-amine;
1-{4-[(2,4-dichlorophenyl)thio]butyl}-2-ethyl-6,7-dimethyl-1H-imidazo[4,5-c]pyridin-4-amine;
1-{4-[(2,4-dichlorophenyl)thio]butyl}-6,7-dimethyl-2-propyl-1H-imidazo[4,5-c]pyridin-4-amine;
2-butyl-1-{4-[(2,4-dichlorophenyl)thio]butyl}-6,7-dimethyl-1H-imidazo[4,5-c]pyridin-4-amine;
1-{4-[(2,4-dichlorophenyl)thio]butyl}-2-ethoxymethyl-6,7-dimethyl-1H-imidazo[4,5-c]pyridin-4-amine;
1-{4-[(2,4-dichlorophenyl)thio]butyl}-2-methoxyethyl-6,7-dimethyl-1H-imidazo[4,5-c]pyridin-4-amine;
1-{4-[(2,4-dichlorophenyl)thio]butyl}-2-cyclopropylmethyl-6,7-dimethyl-1H-imidazo[4,5-c]pyridin-4-amine;
1-{4-[(2,4-dichlorophenyl)sulfonyl]butyl}-6,7-dimethyl-1H-imidazo[4,5-c]pyridin-4-amine;
1-{4-[(2,4-dichlorophenyl)sulfonyl]butyl}-2,6,7-trimethyl-1H-imidazo[4,5-c]pyridin-4-amine;
1-{4-[(2,4-dichlorophenyl)sulfonyl]butyl}-2-ethyl-6,7-dimethyl-1H-imidazo[4,5-c]pyridin-4-amine;
1-{4-[(2,4-dichlorophenyl)sulfonyl]butyl}-6,7-dimethyl-2-propyl-1H-imidazo[4,5-c]pyridin-4-amine;
2-butyl-1-{4-[(2,4-dichlorophenyl)sulfonyl]butyl}-6,7-dimethyl-1H-imidazo[4,5-c]pyridin-4-amine;
1-{4-[(2,4-dichlorophenyl)sulfonyl]butyl}-2-ethoxymethyl-6,7-dimethyl-1H-imidazo[4,5-c]pyridin-4-amine;
1-{4-[(2,4-dichlorophenyl)sulfonyl]butyl}-2-methoxyethyl-6,7-dimethyl-1H-imidazo[4,5-c]pyridin-4-amine;
1-{4-[(2,4-dichlorophenyl)sulfonyl]butyl}-2-cyclopropylmethyl-6,7-dimethyl-1H-imidazo[4,5-c]pyridin-4-amine;
1-{4-[(2,4-dichlorophenyl)sulfinyl]butyl}-6,7-dimethyl-1H-imidazo[4,5-c]pyridin-4-amine;
1-{4-[(2,4-dichlorophenyl)sulfinyl]butyl}-2,6,7-trimethyl-1H-imidazo[4,5-c]pyridin-4-amine;
1-{4-[(2,4-dichlorophenyl)sulfinyl]butyl}-2-ethyl-6,7-dimethyl-1H-imidazo[4,5-c]pyridin-4-amine;
1-{4-[(2,4-dichlorophenyl)sulfinyl]butyl}-6,7-dimethyl-2-propyl-1H-imidazo[4,5-c]pyridin-4-amine;
2-butyl-1-{4-[(2,4-dichlorophenyl)sulfinyl]butyl}-6,7-dimethyl-1H-imidazo[4,5-c]pyridin-4-amine;
1-{4-[(2,4-dichlorophenyl)sulfinyl]butyl}-2-ethoxymethyl-6,7-dimethyl-1H-imidazo[4,5-c]pyridin-4-amine;
1-{4-[(2,4-dichlorophenyl)sulfinyl]butyl}-2-methoxyethyl-6,7-dimethyl-1H-imidazo[4,5-c]pyridin-4-amine;
1-{4-[(2,4-dichlorophenyl)sulfinyl]butyl}-2-cyclopropylmethyl-6,7-dimethyl-1H-imidazo[4,5-c]pyridin-4-amine;
1-{4-[(2,4-difluorophenyl)thio]butyl}-6,7-dimethyl-1H-imidazo[4,5-c]pyridin-4-amine;
1-{4-[(2,4-difluorophenyl)thio]butyl}-2,6,7-trimethyl-1H-imidazo[4,5-c]pyridin-4-amine;
2-ethyl-1-{4-[(2,4-difluorophenyl)thio]butyl}-6,7-dimethyl-1H-imidazo[4,5-c]pyridin-4-amine;
1-{4-[(2,4-difluorophenyl)thio]butyl}-6,7-dimethyl-2-propyl-1H-imidazo[4,5-c]pyridin-4-amine;
2-butyl-1-{4-[(2,4-difluorophenyl)thio]butyl}-6,7-dimethyl-1H-imidazo[4,5-c]pyridin-4-amine;
2-ethoxymethyl-1-{4-[(2,4-difluorophenyl)thio]butyl}-6,7-dimethyl-1H-imidazo[4,5-c]pyridin-4-amine;
1-{4-[(2,4-difluorophenyl)thio]butyl}-2-methoxyethyl-6,7-dimethyl-1H-imidazo[4,5-c]pyridin-4-amine;
2-cyclopropylmethyl-1-{4-[(2,4-difluorophenyl)thio]butyl}-6,7-dimethyl-1H-imidazo[4,5-c]pyridin-4-amine;
1-{4-[(2,4-difluorophenyl)sulfonyl]butyl}-6,7-dimethyl-1H-imidazo[4,5-c]pyridin-4-amine;
1-{4-[(2,4-difluorophenyl)sulfonyl]butyl}-2,6,7-trimethyl-1H-imidazo[4,5-c]pyridin-4-amine;
2-ethyl-1-{4-[(2,4-difluorophenyl)sulfonyl]butyl}-6,7-dimethyl-1H-imidazo[4,5-c]pyridin-4-amine;
1-{4-[(2,4-difluorophenyl)sulfonyl]butyl}-6,7-dimethyl-2-propyl-1H-imidazo[4,5-c]pyridin-4-amine;
2-butyl-1-{4-[(2,4-difluorophenyl)sulfonyl]butyl}-6,7-dimethyl-1H-imidazo[4,5-c]pyridin-4-amine;
2-ethoxymethyl-1-{4-[(2,4-difluorophenyl)sulfonyl]butyl}-6,7-dimethyl-1H-imidazo[4,5-c]pyridin-4-amine;
1-{4-[(2,4-difluorophenyl)sulfonyl]butyl}-2-methoxyethyl-6,7-dimethyl-1H-imidazo[4,5-c]pyridin-4-amine;
2-cyclopropylmethyl-1-{4-[(2,4-difluorophenyl)sulfonyl]butyl}-6,7-dimethyl-1H-imidazo[4,5-c]pyridin-4-amine;
1-{4-[(2,4-difluorophenyl)sulfinyl]butyl}-6,7-dimethyl-1H-imidazo[4,5-c]pyridin-4-amine;
1-{4-[(2,4-difluorophenyl)sulfinyl]butyl}-2,6,7-trimethyl-1H-imidazo[4,5-c]pyridin-4-amine;
2-ethyl-1-{4-[(2,4-difluorophenyl)sulfinyl]butyl}-6,7-dimethyl-1H-imidazo[4,5-c]pyridin-4-amine;
1-{4-[(2,4-difluorophenyl)sulfinyl]butyl}-6,7-dimethyl-2-propyl-1H-imidazo[4,5-c]pyridin-4-amine;
2-butyl-1-{4-[(2,4-difluorophenyl)sulfinyl]butyl}-6,7-dimethyl-1H-imidazo[4,5-c]pyridin-4-amine;
2-ethoxymethyl-1-{4-[(2,4-difluorophenyl)sulfinyl]butyl}-6,7-dimethyl-1H-imidazo[4,5-c]pyridin-4-amine;
1-{4-[(2,4-difluorophenyl)sulfinyl]butyl}-2-methoxyethyl-6,7-dimethyl-1H-imidazo[4,5-c]pyridin-4-amine;
2-cyclopropylmethyl-1-{4-[(2,4-difluorophenyl)sulfinyl]butyl}-6,7-dimethyl-1H-imidazo[4,5-c]pyridin-4-amine;
7-methyl-1-[4-(methylthio)butyl]-1H-imidazo[4,5-c]pyridin-4-amine;
2,7-dimethyl-1-[4-(methylthio)butyl]-1H-imidazo[4,5-c]pyridin-4-amine;
2-ethyl-7-methyl-1-[4-(methylthio)butyl]-1H-imidazo[4,5-c]pyridin-4-amine;
6,7-dimethyl-1-[4-(methylthio)butyl]-2-propyl-1H-imidazo[4,5-c]pyridin-4-amine;
2-butyl-7-methyl-1-[4-(methylthio)butyl]-1H-imidazo[4,5-c]pyridin-4-amine;
2-ethoxymethyl-7-methyl-1-[4-(methylthio)butyl]-1H-imidazo[4,5-c]pyridin-4-amine;

2-methoxyethyl-7-methyl-1-[4-(methylthio)butyl]-1H-imidazo[4,5-c]pyridin-4-amine;
2-cyclopropylmethyl-7-methyl-1-[4-(methylthio)butyl]-1H-imidazo[4,5-c]pyridin-4-amine;
7-methyl-1-[4-(methylsulfonyl)butyl]-1H-imidazo[4,5-c]pyridin-4-amine;
2,7-dimethyl-1-[4-(methylsulfonyl)butyl]-1H-imidazo[4,5-c]pyridin-4-amine;
2-ethyl-7-methyl-1-[4-(methylsulfonyl)butyl]-1H-imidazo[4,5-c]pyridin-4-amine;
7-methyl-1-[4-(methylsulfonyl)butyl]-2-propyl-1H-imidazo[4,5-c]pyridin-4-amine;
2-butyl-7-methyl-1-[4-(methylsulfonyl)butyl]-1H-imidazo[4,5-c]pyridin-4-amine;
2-ethoxymethyl-7-methyl-1-[4-(methylsulfonyl)butyl]-1H-imidazo[4,5-c]pyridin-4-amine;
2-methoxyethyl-7-methyl-1-[4-(methylsulfonyl)butyl]-1H-imidazo[4,5-c]pyridin-4-amine;
2-cyclopropylmethyl-7-methyl-1-[4-(methylsulfonyl)butyl]-1H-imidazo[4,5-c]pyridin-4-amine;
7-methyl-1-[4-(methylsulfinyl)butyl]-1H-imidazo[4,5-c]pyridin-4-amine;
2,7-dimethyl-1-[4-(methylsulfinyl)butyl]-1H-imidazo[4,5-c]pyridin-4-amine;
2-ethyl-7-methyl-1-[4-(methylsulfinyl)butyl]-1H-imidazo[4,5-c]pyridin-4-amine;
7-methyl-1-[4-(methylsulfinyl)butyl]-2-propyl-1H-imidazo[4,5-c]pyridin-4-amine;
2-butyl-7-methyl-1-[4-(methylsulfinyl)butyl]-1H-imidazo[4,5-c]pyridin-4-amine;
2-ethoxymethyl-7-methyl-1-[4-(methylsulfinyl)butyl]-1H-imidazo[4,5-c]pyridin-4-amine;
2-methoxyethyl-7-methyl-1-[4-(methylsulfinyl)butyl]-1H-imidazo[4,5-c]pyridin-4-amine;
2-cyclopropylmethyl-7-methyl-1-[4-(methylsulfinyl)butyl]-1H-imidazo[4,5-c]pyridin-4-amine;
7-methyl-1-[4-(phenylthio)butyl]-1H-imidazo[4,5-c]pyridin-4-amine;
2,7-dimethyl-1-[4-(phenylthio)butyl]-1H-imidazo[4,5-c]pyridin-4-amine;
2-ethyl-7-methyl-1-[4-(phenylthio)butyl]-1H-imidazo[4,5-c]pyridin-4-amine;
7-methyl-1-[4-(phenylthio)butyl]-2-propyl-1H-imidazo[4,5-c]pyridin-4-amine;
2-butyl-7-methyl-1-[4-(phenylthio)butyl]-1H-imidazo[4,5-c]pyridin-4-amine;
2-ethoxymethyl-7-methyl-1-[4-(phenylthio)butyl]-1H-imidazo[4,5-c]pyridin-4-amine;
2-methoxyethyl-7-methyl-1-[4-(phenylthio)butyl]-1H-imidazo[4,5-c]pyridin-4-amine;
2-cyclopropylmethyl-7-methyl-1-[4-(phenylthio)butyl]-1H-imidazo[4,5-c]pyridin-4-amine;
7-methyl-1-[4-(phenylsulfonyl)butyl]-1H-imidazo[4,5-c]pyridin-4-amine;
2,7-dimethyl-1-[4-(phenylsulfonyl)butyl]-1H-imidazo[4,5-c]pyridin-4-amine;
2-ethyl-7-methyl-1-[4-(phenylsulfonyl)butyl]-1H-imidazo[4,5-c]pyridin-4-amine;
7-methyl-1-[4-(phenylsulfonyl)butyl]-2-propyl-1H-imidazo[4,5-c]pyridin-4-amine;
2-butyl-7-methyl-1-[4-(phenylsulfonyl)butyl]-1H-imidazo[4,5-c]pyridin-4-amine;
2-ethoxymethyl-7-methyl-1-[4-(phenylsulfonyl)butyl]-1H-imidazo[4,5-c]pyridin-4-amine;
2-methoxyethyl-7-methyl-1-[4-(phenylsulfonyl)butyl]-1H-imidazo[4,5-c]pyridin-4-amine;
2-cyclopropylmethyl-7-methyl-1-[4-(phenylsulfonyl)butyl]-1H-imidazo[4,5-c]pyridin-4-amine;
7-methyl-1-[4-(phenylsulfinyl)butyl]-1H-imidazo[4,5-c]pyridin-4-amine;
2,7-dimethyl-1-[4-(phenylsulfinyl)butyl]-1H-imidazo[4,5-c]pyridin-4-amine;
2-ethyl-7-methyl-1-[4-(phenylsulfinyl)butyl]-1H-imidazo[4,5-c]pyridin-4-amine;
7-methyl-1-[4-(phenylsulfinyl)butyl]-2-propyl-1H-imidazo[4,5-c]pyridin-4-amine;
2-butyl-7-methyl-1-[4-(phenylsulfinyl)butyl]-1H-imidazo[4,5-c]pyridin-4-amine;
2-ethoxymethyl-7-methyl-1-[4-(phenylsulfinyl)butyl]-1H-imidazo[4,5-c]pyridin-4-amine;
2-methoxyethyl-7-methyl-1-[4-(phenylsulfinyl)butyl]-1H-imidazo[4,5-c]pyridin-4-amine;
2-cyclopropylmethyl-7-methyl-1-[4-(phenylsulfinyl)butyl]-1H-imidazo[4,5-c]pyridin-4-amine;
7-methyl-1-[4-(pyrimidin-2-ylthio)butyl]-1H-imidazo[4,5-c]pyridin-4-amine;
2,7-dimethyl-1-[4-(pyrimidin-2-ylthio)butyl]-1H-imidazo[4,5-c]pyridin-4-amine;
2-ethyl-7-methyl-1-[4-(pyrimidin-2-ylthio)butyl]-1H-imidazo[4,5-c]pyridin-4-amine;
7-methyl-1-[4-(pyrimidin-2-ylthio)butyl]-2-propyl-1H-imidazo[4,5-c]pyridin-4-amine;
2-butyl-7-methyl-1-[4-(pyrimidin-2-yllthio)butyl]-1H-imidazo[4,5-c]pyridin-4-amine;
2-ethoxymethyl-7-methyl-1-[4-(pyrimidin-2-ylthio)butyl]-1H-imidazo[4,5-c]pyridin-4-amine;
2-methoxyethyl-7-methyl-1-[4-(pyrimidin-2-ylthio)butyl]-1H-imidazo[4,5-c]pyridin-4-amine;
2-cyclopropylmethyl-7-methyl-1-[4-(pyrimidin-2-ylthio)butyl]-1H-imidazo[4,5-c]pyridin-4-amine;
7-methyl-1-[4-(pyrimidin-2-ylsulfonyl)butyl]-1H-imidazo[4,5-c]pyridin-4-amine;
2,7-dimethyl-1-[4-(pyrimidin-2-ylsulfonyl)butyl]-1H-imidazo[4,5-c]pyridin-4-amine;
2-ethyl-7-methyl-1-[4-(pyrimidin-2-ylsulfonyl)butyl]-1H-imidazo[4,5-c]pyridin-4-amine;
7-methyl-1-[4-(pyrimidin-2-ylsulfonyl)butyl]-2-propyl-1H-imidazo[4,5-c]pyridin-4-amine;
2-butyl-7-methyl-1-[4-(pyrimidin-2-ylsulfonyl)butyl]-1H-imidazo[4,5-c]pyridin-4-amine
2-ethoxymethyl-7-methyl-1-[4-(pyrimidin-2-ylsulfonyl)butyl]-1H-imidazo[4,5-c]pyridin-4-amine;
2-methoxyethyl-7-methyl-1-[4-(pyrimidin-2-ylsulfonyl)butyl]-1H-imidazo[4,5-c]pyridin-4-amine;
2-cyclopropylmethyl-7-methyl-1-[4-(pyrimidin-2-ylsulfonyl)butyl]-1H-imidazo[4,5-c]pyridin-4-amine;
7-methyl-1-[4-(pyrimidin-2-ylsulfinyl)butyl]-1H-imidazo[4,5-c]pyridin-4-amine;
2,7-dimethyl-1-[4-(pyrimidin-2-ylsulfinyl)butyl]-1H-imidazo[4,5-c]pyridin-4-amine;
2-ethyl-7-methyl-1-[4-(pyrimidin-2-ylsulfinyl)butyl]-1H-imidazo[4,5-c]pyridin-4-amine;
7-methyl-1-[4-(pyrimidin-2-ylsulfinyl)butyl]-2-propyl-1H-imidazo[4,5-c]pyridin-4-amine;
2-butyl-7-methyl-1-[4-(pyrimidin-2-ylsulfinyl)butyl]-1H-imidazo[4,5-c]pyridin-4-amine;
2-ethoxymethyl-7-methyl-1-[4-(pyrimidin-2-ylsulfinyl)butyl]-1H-imidazo[4,5-c]pyridin-4-amine;
2-methoxyethyl-7-methyl-1-[4-(pyrimidin-2-ylsulfinyl)butyl]-1H-imidazo[4,5-c]pyridin-4-amine;
2-cyclopropylmethyl-7-methyl-1-[4-(pyrimidin-2-ylsulfinyl)butyl]-1H-imidazo[4,5-c]pyridin-4-amine;
1-[4-(butylthio)butyl]-7-methyl-1H-imidazo[4,5-c]pyridin-4-amine;
1-[4-(butylthio)butyl]-2,7-dimethyl-1H-imidazo[4,5-c]pyridin-4-amine;

1-[4-(butylthio)butyl]-2-ethyl-7-methyl-1H-imidazo[4,5-c]pyridin-4-amine;

1-[4-(butylthio)butyl]-7-methyl-2-propyl-1H-imidazo[4,5-c]pyridin-4-amine;

2-butyl-1-[4-(butylthio)butyl]-7-methyl-1H-imidazo[4,5-c]pyridin-4-amine;

1-[4-(butylthio)butyl]-2-ethoxymethyl-7-methyl-1H-imidazo[4,5-c]pyridin-4-amine;

1-[4-(butylthio)butyl]-2-methoxyethyl-7-methyl-1H-imidazo[4,5-c]pyridin-4-amine;

1-[4-(butylthio)butyl]-2-cyclopropylmethyl-7-methyl-1H-imidazo[4,5-c]pyridin-4-amine;

1-[4-(butylsulfonyl)butyl]-7-methyl-1H-imidazo[4,5-c]pyridin-4-amine;

1-[4-(butylsulfonyl)butyl]-2,7-dimethyl-1H-imidazo[4,5-c]pyridin-4-amine;

1-[4-(butylsulfonyl)butyl]-2-ethyl-7-methyl-1H-imidazo[4,5-c]pyridin-4-amine;

1-[4-(butylsulfonyl)butyl]-7-methyl-2-propyl-1H-imidazo[4,5-c]pyridin-4-amine;

2-butyl-1-[4-(butylsulfonyl)butyl]-7-methyl-1H-imidazo[4,5-c]pyridin-4-amine;

1-[4-(butylsulfonyl)butyl]-2-ethoxymethyl-7-methyl-1H-imidazo[4,5-c]pyridin-4-amine;

1-[4-(butylsulfonyl)butyl]-2-methoxyethyl-7-methyl-1H-imidazo[4,5-c]pyridin-4-amine;

1-[4-(butylsulfonyl)butyl]-2-cyclopropylmethyl-7-methyl-1H-imidazo[4,5-c]pyridin-4-amine;

1-[4-(butylsulfinyl)butyl]-7-methyl-1H-imidazo[4,5-c]pyridin-4-amine;

1-[4-(butylsulfinyl)butyl]-2,7-dimethyl-1H-imidazo[4,5-c]pyridin-4-amine;

1-[4-(butylsulfinyl)butyl]-2-ethyl-7-methyl-1H-imidazo[4,5-c]pyridin-4-amine;

1-[4-(butylsulfinyl)butyl]-7-methyl-2-propyl-1H-imidazo[4,5-c]pyridin-4-amine;

2-butyl-1-[4-(butylsulfinyl)butyl]-7-methyl-1H-imidazo[4,5-c]pyridin-4-amine;

1-[4-(butylsulfinyl)butyl]-2-ethoxymethyl-7-methyl-1H-imidazo[4,5-c]pyridin-4-amine;

1-[4-(butylsulfinyl)butyl]-2-methoxyethyl-6,7-dimethyl-1H-imidazo[4,5-c]pyridin-4-amine;

1-[4-(butylsulfinyl)butyl]-2-cyclopropylmethyl-6,7-dimethyl-1H-imidazo[4,5-c]pyridin-4-amine;

1-{4-[(2,4-dichlorophenyl)thio]butyl}-7-methyl-1H-imidazo[4,5-c]pyridin-4-amine;

1-{4-[(2,4-dichlorophenyl)thio]butyl}-2,7-dimethyl-1H-imidazo[4,5-c]pyridin-4-amine;

1-{4-[(2,4-dichlorophenyl)thio]butyl}-2-ethyl-7-methyl-1H-imidazo[4,5-c]pyridin-4-amine;

1-{4-[(2,4-dichlorophenyl)thio]butyl}-7-methyl-2-propyl-1H-imidazo[4,5-c]pyridin-4-amine;

2-butyl-1-{4-[(2,4-dichlorophenyl)thio]butyl}-7-methyl-1H-imidazo[4,5-c]pyridin-4-amine;

1-{4-[(2,4-dichlorophenyl)thio]butyl}-2-ethoxymethyl-7-methyl-1H-imidazo[4,5-c]pyridin-4-amine;

1-{4-[(2,4-dichlorophenyl)thio]butyl}-2-methoxyethyl-7-methyl-1H-imidazo[4,5-c]pyridin-4-amine;

1-{4-[(2,4-dichlorophenyl)thio]butyl}-2-cyclopropylmethyl-7-methyl-1H-imidazo[4,5-c]pyridin-4-amine;

1-{4-[(2,4-dichlorophenyl)sulfonyl]butyl}-7-methyl-1H-imidazo[4,5-c]pyridin-4-amine;

1-{4-[(2,4-dichlorophenyl)sulfonyl]butyl}-2,7-dimethyl-1H-imidazo[4,5-c]pyridin-4-amine;

1-{4-[(2,4-dichlorophenyl)sulfonyl]butyl}-2-ethyl-7-methyl-1H-imidazo[4,5-c]pyridin-4-amine;

1-{4-[(2,4-dichlorophenyl)sulfonyl]butyl}-7-methyl-2-propyl-1H-imidazo[4,5-c]pyridin-4-amine;

2-butyl-1-{4-[(2,4-dichlorophenyl)sulfonyl]butyl}-7-methyl-1H-imidazo[4,5-c]pyridin-4-amine;

1-{4-[(2,4-dichlorophenyl)sulfonyl]butyl}-2-ethoxymethyl-7-methyl-1H-imidazo[4,5-c]pyridin-4-amine;

1-{4-[(2,4-dichlorophenyl)sulfonyl]butyl}-2-methoxyethyl-7-methyl-1H-imidazo[4,5-c]pyridin-4-amine;

1-{4-[(2,4-dichlorophenyl)sulfonyl]butyl}-2-cyclopropylmethyl-7-methyl-1H-imidazo[4,5-c]pyridin-4-amine;

1-{4-[(2,4-dichlorophenyl)sulfinyl]butyl}-7-methyl-1H-imidazo[4,5-c]pyridin-4-amine;

1-{4-[(2,4-dichlorophenyl)sulfinyl]butyl}-2,7-dimethyl-1H-imidazo[4,5-c]pyridin-4-amine;

1-{4-[(2,4-dichlorophenyl)sulfinyl]butyl}-2-ethyl-7-methyl-1H-imidazo[4,5-c]pyridin-4-amine;

1-{4-[(2,4-dichlorophenyl)sulfinyl]butyl}-7-methyl-2-propyl-1H-imidazo[4,5-c]pyridin-4-amine;

2-butyl-1-{4-[(2,4-dichlorophenyl)sulfinyl]butyl}-7-methyl-1H-imidazo[4,5-c]pyridin-4-amine;

1-{4-[(2,4-dichlorophenyl)sulfinyl]butyl}-2-ethoxymethyl-7-methyl-1H-imidazo[4,5-c]pyridin-4-amine;

1-{4-[(2,4-dichlorophenyl)sulfinyl]butyl}-2-methoxyethyl-7-methyl-1H-imidazo[4,5-c]pyridin-4-amine;

1-{4-[(2,4-dichlorophenyl)sulfinyl]butyl}-2-cyclopropylmethyl-7-methyl-1H-imidazo[4,5-c]pyridin-4-amine;

1-{4-[(2,4-difluorophenyl)thio]butyl}-6-methyl-1H-imidazo[4,5-c]pyridin-4-amine;

1-{4-[(2,4-difluorophenyl)thio]butyl}-2,7-dimethyl-1H-imidazo[4,5-c]pyridin-4-amine;

2-ethyl-1-{4-[(2,4-difluorophenyl)thio]butyl}-7-methyl-1H-imidazo[4,5-c]pyridin-4-amine;

1-{4-[(2,4-difluorophenyl)thio]butyl}-7-methyl-2-propyl-1H-imidazo[4,5-c]pyridin-4-amine;

2-butyl-1-{4-[(2,4-difluorophenyl)thio]butyl}-7-methyl-1H-imidazo[4,5-c]pyridin-4-amine;

2-ethoxymethyl-1-{4-[(2,4-difluorophenyl)thio]butyl}-7-methyl-1H-imidazo[4,5-c]pyridin-4-amine;

1-{4-[(2,4-difluorophenyl)thio]butyl}-2-methoxyethyl-7-methyl-1H-imidazo[4,5-c]pyridin-4-amine;

2-cyclopropylmethyl-1-{4-[(2,4-difluorophenyl)thio]butyl}-7-methyl-1H-imidazo[4,5-c]pyridin-4-amine;

1-{4-[(2,4-difluorophenyl)sulfonyl]butyl}-7-methyl-1H-imidazo[4,5-c]pyridin-4-amine;

1-{4-[(2,4-difluorophenyl)sulfonyl]butyl}-2,7-dimethyl-1H-imidazo[4,5-c]pyridin-4-amine;

2-ethyl-1-{4-[(2,4-difluorophenyl)sulfonyl]butyl}-7-methyl-1H-imidazo[4,5-c]pyridin-4-amine;

1-{4-[(2,4-difluorophenyl)sulfonyl]butyl}-7-methyl-2-propyl-1H-imidazo[4,5-c]pyridin-4-amine;

2-butyl-1-{4-[(2,4-difluorophenyl)sulfonyl]butyl}-7-methyl-1H-imidazo[4,5-c]pyridin-4-amine;

2-ethoxymethyl-1-{4-[(2,4-difluorophenyl)sulfonyl]butyl}-7-methyl-1H-imidazo[4,5-c]pyridin-4-amine;

1-{4-[(2,4-difluorophenyl)sulfonyl]butyl}-2-methoxyethyl-7-methyl-1H-imidazo[4,5-c]pyridin-4-amine;

2-cyclopropylmethyl-1-{4-[(2,4-difluorophenyl)sulfonyl]butyl}-7-methyl-1H-imidazo[4,5-c]pyridin-4-amine;

1-{4-[(2,4-difluorophenyl)sulfinyl]butyl}-7-methyl-1H-imidazo[4,5-c]pyridin-4-amine;

1-{4-[(2,4-difluorophenyl)sulfinyl]buyl}-2,7-dimethyl-1H-imidazo[4,5-c]pyridin-4-amine;

2-ethyl-1-{4-[(2,4-difluorophenyl)sulfinyl]butyl}-7-methyl-1H-imidazo[4,5-c]pyridin-4-amine;

1-{4-[(2,4-difluorophenyl)sulfinyl]butyl}-7-methyl-2-propyl-1H-imidazo[4,5-c]pyridin-4-amine;

2-butyl-1-{4-[(2,4-difluorophenyl)sulfinyl]butyl}-7-methyl-1H-imidazo[4,5-c]pyridin-4-amine;
2-ethoxymethyl-1-{4-[(2,4-difluorophenyl)sulfinyl]butyl}-7-methyl-1H-imidazo[4,5-c]pyridin-4-amine;
1-{4-[(2,4-difluorophenyl)sulfinyl]butyl}-2-methoxyethyl-7-methyl-1H-imidazo[4,5-c]pyridin-4-amine;
2-cyclopropylmethyl-1-{4-[(2,4-difluorophenyl)sulfinyl]butyl}-7-methyl-1H-imidazo[4,5-c]pyridin-4-amine;
6,7-dimethyl-1-[5-(methylthio)pentyl]-1H-imidazo[4,5-c]pyridin-4-amine;
2,6,7-trimethyl-1-[5-(methylthio)pentyl]-1H-imidazo[4,5-c]pyridin-4-amine;
2-ethyl-6,7-dimethyl-1-[5-(methylthio)pentyl]-1H-imidazo[4,5-c]pyridin-4-amine;
6,7-dimethyl-1-[5-(methylthio)pentyl]-2-propyl-1H-imidazo[4,5-c]pyridin-4-amine;
2-butyl-6,7-dimethyl-1-[5-(methylthio)pentyl]-1H-imidazo[4,5-c]pyridin-4-amine;
2-ethoxymethyl-6,7-dimethyl-1-[5-(methylthio)pentyl]-1H-imidazo[4,5-c]pyridin-4-amine;
2-methoxyethyl-6,7-dimethyl-1-[5-(methylthio)pentyl]-1H-imidazo[4,5-c]pyridin-4-amine;
2-cyclopropylmethyl-6,7-dimethyl-1-[5-(methylthio)pentyl]-1H-imidazo[4,5-c]pyridin-4-amine;
6,7-dimethyl-1-[5-(methylsulfonyl)pentyl]-1H-imidazo[4,5-c]pyridin-4-amine;
2,6,7-trimethyl-1-[5-(methylsulfonyl)pentyl]-1H-imidazo[4,5-c]pyridin-4-amine;
2-ethyl-6,7-dimethyl-1-[5-(methylsulfonyl)pentyl]-1H-imidazo[4,5-c]pyridin-4-amine;
6,7-dimethyl-1-[5-(methylsulfonyl)pentyl]-2-propyl-1H-imidazo[4,5-c]pyridin-4-amine;
2-butyl-6,7-dimethyl-1-[5-(methylsulfonyl)pentyl]-1H-imidazo[4,5-c]pyridin-4-amine;
2-ethoxymethyl-6,7-dimethyl-1-[5-(methylsulfonyl)pentyl]-1H-imidazo[4,5-c]pyridin-4-amine;
2-methoxyethyl-6,7-dimethyl-1-[5-(methylsulfonyl)pentyl]-1H-imidazo[4,5-c]pyridin-4-amine;
2-cyclopropylmethyl-6,7-dimethyl-1-[5-(methylsulfonyl)pentyl]-1H-imidazo[4,5-c]pyridin-4-amine;
6,7-dimethyl-1-[5-(methylsulfinyl)pentyl]-1H-imidazo[4,5-c]pyridin-4-amine;
2,6,7-trimethyl-1-[5-(methylsulfinyl)pentyl]-1H-imidazo[4,5-c]pyridin-4-amine;
2-ethyl-6,7-dimethyl-1-[5-(methylsulfinyl)pentyl]-1H-imidazo[4,5-c]pyridin-4-amine;
6,7-dimethyl-1-[5-(methylsulfinyl)pentyl]-2-propyl-1H-imidazo[4,5-c]pyridin-4-amine;
2-butyl-6,7-dimethyl-1-[5-(methylsulfinyl)pentyl]-1H-imidazo[4,5-c]pyridin-4-amine;
2-ethoxymethyl-6,7-dimethyl-1-[5-(methylsulfinyl)pentyl]-1H-imidazo[4,5-c]pyridin-4-amine;
2-methoxyethyl-6,7-dimethyl-1-[5-(methylsulfinyl)pentyl]-1H-imidazo[4,5-c]pyridin-4-amine;
2-cyclopropylmethyl-6,7-dimethyl-1-[5-(methylsulfinyl)pentyl]-1H-imidazo[4,5-c]pyridin-4-amine;
6,7-dimethyl-1-[5-(phenylthio)pentyl]-1H-imidazo[4,5-c]pyridin-4-amine;
2,6,7-trimethyl-1-[5-(phenylthio)pentyl]-1H-imidazo[4,5-c]pyridin-4-amine;
2-ethyl-6,7-dimethyl-1-[5-(phenylthio)pentyl]-1H-imidazo[4,5-c]pyridin-4-amine;
6,7-dimethyl-1-[5-(phenylthio)pentyl]-2-propyl-1H-imidazo[4,5-c]pyridin-4-amine;
2-butyl-6,7-dimethyl-1-[5-(phenylthio)pentyl]-1H-imidazo[4,5-c]pyridin-4-amine;
2-ethoxymethyl-6,7-dimethyl-1-[5-(phenylthio)pentyl]-1H-imidazo[4,5-c]pyridin-4-amine;
2-methoxyethyl-6,7-dimethyl-1-[5-(phenylthio)pentyl]-1H-imidazo[4,5-c]pyridin-4-amine;
2-cyclopropylmethyl-6,7-dimethyl-1-[5-(phenylthio)pentyl]-1H-imidazo[4,5-c]pyridin-4-amine;
6,7-dimethyl-1-[5-(phenylsulfonyl)pentyl]-1H-imidazo[4,5-c]pyridin-4-amine;
2,6,7-trimethyl-1-[5-(phenylsulfonyl)pentyl]-1H-imidazo[4,5-c]pyridin-4-amine;
2-ethyl-6,7-dimethyl-1-[5-(phenylsulfonyl)pentyl]-1H-imidazo[4,5-c]pyridin-4-amine;
6,7-dimethyl-1-[5-(phenylsulfonyl)pentyl]-2-propyl-1H-imidazo[4,5-c]pyridin-4-amine;
2-butyl-6,7-dimethyl-1-[5-(phenylsulfonyl)pentyl]-1H-imidazo[4,5-c]pyridin-4-amine;
2-ethoxymethyl-6,7-dimethyl-1-[5-(phenylsulfonyl)pentyl]-1H-imidazo[4,5-c]pyridin-4-amine;
2-methoxyethyl-6,7-dimethyl-1-[5-(phenylsulfonyl)pentyl]-1H-imidazo[4,5-c]pyridin-4-amine;
2-cyclopropylmethyl-6,7-dimethyl-1-[5-(phenylsulfonyl)pentyl]-1H-imidazo[4,5-c]pyridin-4-amine;
6,7-dimethyl-1-[5-(phenylsulfinyl)pentyl]-1H-imidazo[4,5-c]pyridin-4-amine;
2,6,7-trimethyl-1-[5-(phenylsulfinyl)pentyl]-1H-imidazo[4,5-c]pyridin-4-amine;
2-ethyl-6,7-dimethyl-1-[5-(phenylsulfinyl)pentyl]-1H-imidazo[4,5-c]pyridin-4-amine;
6,7-dimethyl-1-[5-(phenylsulfinyl)pentyl]-2-propyl-1H-imidazo[4,5-c]pyridin-4-amine;
2-butyl-6,7-dimethyl-1-[5-(phenylsulfinyl)pentyl]-1H-imidazo[4,5-c]pyridin-4-amine;
2-ethoxymethyl-6,7-dimethyl-1-[5-(phenylsulfinyl)pentyl]-1H-imidazo[4,5-c]pyridin-4-amine;
2-methoxyethyl-6,7-dimethyl-1-[5-(phenylsulfinyl)pentyl]-1H-imidazo[4,5-c]pyridin-4-amine;
2-cyclopropylmethyl-6,7-dimethyl-1-[5-(phenylsulfinyl)pentyl]-1H-imidazo[4,5-c]pyridin-4-amine;
6,7-dimethyl-1-[5-(pyrimidin-2-ylthio)pentyl]-1H-imidazo[4,5-c]pyridin-4-amine;
2,6,7-trimethyl-1-[5-(pyrimidin-2-ylthio)pentyl]-1H-imidazo[4,5-c]pyridin-4-amine;
2-ethyl-6,7-dimethyl-1-[5-(pyrimidin-2-ylthio)pentyl]-1H-imidazo[4,5-c]pyridin-4-amine;
6,7-dimethyl-1-[5-(pyrimidin-2-ylthio)pentyl]-2-propyl-1H-imidazo[4,5-c]pyridin-4-amine;
2-butyl-6,7-dimethyl-1-[5-(pyrimidin-2-ylthio)pentyl]-1H-imidazo[4,5-c]pyridin-4-amine;
2-ethoxymethyl-6,7-dimethyl-1-[5-(pyrimidin-2-ylthio)pentyl]-1H-imidazo[4,5-c]pyridin-4-amine;
2-methoxyethyl-6,7-dimethyl-1-[5-(pyrimidin-2-ylthio)pentyl]-1H-imidazo[4,5-c]pyridin-4-amine;
2-cyclopropylmethyl-6,7-dimethyl-1-[5-(pyrimidin-2-ylthio)pentyl]-1H-imidazo[4,5-c]pyridin-4-amine;
6,7-dimethyl-1-[5-(pyrimidin-2-ylsulfonyl)pentyl]-1H-imidazo[4,5-c]pyridin-4-amine;
2,6,7-trimethyl-1-[5-(pyrimidin-2-ylsulfonyl)pentyl]-1H-imidazo[4,5-c]pyridin-4-amine;
2-ethyl-6,7-dimethyl-1-[5-(pyrimidin-2-ylsulfonyl)pentyl]-1H-imidazo[4,5-c]pyridin-4-amine;
6,7-dimethyl-1-[5-(pyrimidin-2-ylsulfonyl)pentyl]-2-propyl-1H-imidazo[4,5-c]pyridin-4-amine;
2-butyl-6,7-dimethyl-1-[5-(pyrimidin-2-ylsulfonyl)pentyl]-1H-imidazo[4,5-c]pyridin-4-amine;
2-ethoxymethyl-6,7-dimethyl-1-[5-(pyrimidin-2-ylsulfonyl)pentyl]-1H-imidazo[4,5-c]pyridin-4-amine;
2-methoxyethyl-6,7-dimethyl-1-[5-(pyrimidin-2-ylsulfonyl)pentyl]-1H-imidazo[4,5-c]pyridin-4-amine;
2-cyclopropylmethyl-6,7-dimethyl-1-[5-(pyrimidin-2-ylsulfonyl)pentyl]-1H-imidazo[4,5-c]pyridin-4-amine;

6,7-dimethyl-1-[5-(pyrimidin-2-ylsulfinyl)pentyl]-1H-imidazo[4,5-c]pyridin-4-amine;
2,6,7-trimethyl-1-[5-(pyrimidin-2-ylsulfinyl)pentyl]-1H-imidazo[4,5-c]pyridin-4-amine;
2-ethyl-6,7-dimethyl-1-[5-(pyrimidin-2-ylsulfinyl)pentyl]-1H-imidazo[4,5-c]pyridin-4-amine;
6,7-dimethyl-1-[5-(pyrimidin-2-ylsulfinyl)pentyl]-2-propyl-1H-imidazo[4,5-c]pyridin-4-amine;
2-butyl-6,7-dimethyl-1-[5-(pyrimidin-2-ylsulfinyl)pentyl]-1H-imidazo[4,5-c]pyridin-4-amine;
2-ethoxymethyl-6,7-dimethyl-1-[5-(pyrimidin-2-ylsulfinyl)pentyl]-1H-imidazo[4,5-c]pyridin-4-amine;
2-methoxyethyl-6,7-dimethyl-1-[5-(pyrimidin-2-ylsulfinyl)pentyl]-1H-imidazo[4,5-c]pyridin-4-amine;
2-cyclopropylmethyl-6,7-dimethyl-1-[5-(pyrimidin-2-ylsulfinyl)pentyl]-1H-imidazo[4,5-c]pyridin-4-amine;
1-[5-(butylthio)pentyl]-6,7-dimethyl-1H-imidazo[4,5-c]pyridin-4-amine;
1-[5-(butylthio)pentyl]-2,6,7-trimethyl-1H-imidazo[4,5-c]pyridin-4-amine;
1-[5-(butylthio)pentyl]-2-ethyl-6,7-dimethyl-1H-imidazo[4,5-c]pyridin-4-amine;
1-[5-(butylthio)pentyl]-6,7-dimethyl-2-propyl-1H-imidazo[4,5-c]pyridin-4-amine;
2-butyl-1-[5-(butylthio)pentyl]-6,7-dimethyl-1H-imidazo[4,5-c]pyridin-4-amine;
1-[5-(butylthio)pentyl]-2-ethoxymethyl-6,7-dimethyl-1H-imidazo[4,5-c]pyridin-4-amine;
1-[5-(butylthio)pentyl]-2-methoxyethyl-6,7-dimethyl-1H-imidazo[4,5-c]pyridin-4-amine;
1-[5-(butylthio)pentyl]-2-cyclopropylmethyl-6,7-dimethyl-1H-imidazo[4,5-c]pyridin-4-amine;
1-[5-(butylsulfonyl)pentyl]-6,7-dimethyl-1H-imidazo[4,5-c]pyridin-4-amine;
1-[5-(butylsulfonyl)pentyl]-2,6,7-trimethyl-1H-imidazo[4,5-c]pyridin-4-amine;
1-[5-(butylsulfonyl)pentyl]-2-ethyl-6,7-dimethyl-1H-imidazo[4,5-c]pyridin-4-amine;
1-[5-(butylsulfonyl)pentyl]-6,7-dimethyl-2-propyl-1H-imidazo[4,5-c]pyridin-4-amine;
2-butyl-1-[5-(butylsulfonyl)pentyl]-6,7-dimethyl-1H-imidazo[4,5-c]pyridin-4-amine;
1-[5-(butylsulfonyl)pentyl]-2-ethoxymethyl-6,7-dimethyl-1H-imidazo[4,5-c]pyridin-4-amine;
1-[5-(butylsulfonyl)pentyl]-2-methoxyethyl-6,7-dimethyl-1H-imidazo[4,5-c]pyridin-4-amine;
1-[5-(butylsulfonyl)pentyl]-2-cyclopropylmethyl-6,7-dimethyl-1H-imidazo[4,5-c]pyridin-4-amine;
1-[5-(butylsulfinyl)pentyl]-6,7-dimethyl-1H-imidazo[4,5-c]pyridin-4-amine;
1-[5-(butylsulfinyl)pentyl]-2,6,7-trimethyl-1H-imidazo[4,5-c]pyridin-4-amine;
1-[5-(butylsulfinyl)pentyl]-2-ethyl-6,7-dimethyl-1H-imidazo[4,5-c]pyridin-4-amine;
1-[5-(butylsulfinyl)pentyl]-6,7-dimethyl-2-propyl-1H-imidazo[4,5-c]pyridin-4-amine;
2-butyl-1-[5-(butylsulfinyl)pentyl]-6,7-dimethyl-1H-imidazo[4,5-c]pyridin-4-amine;
1-[5-(butylsulfinyl)pentyl]-2-ethoxymethyl-6,7-dimethyl-1H-imidazo[4,5-c]pyridin-4-amine;
1-[5-(butylsulfinyl)pentyl]-2-methoxyethyl-6,7-dimethyl-1H-imidazo[4,5-c]pyridin-4-amine;
1-[5-(butylsulfinyl)pentyl]-2-cyclopropylmethyl-6,7-dimethyl-1H-imidazo[4,5-c]pyridin-4-amine;
1-{5-[(2,4-dichlorophenyl)thio]pentyl}-6,7-dimethyl-1H-imidazo[4,5-c]pyridin-4-amine;
1-{5-[(2,4-dichlorophenyl)thio]pentyl}-2,6,7-trimethyl-1H-imidazo[4,5-c]pyridin-4-amine;
1-{5-[(2,4-dichlorophenyl)thio]pentyl}-2-ethyl-6,7-dimethyl-1H-imidazo[4,5-c]pyridin-4-amine;
1-{5-[(2,4-dichlorophenyl)thio]pentyl}-6,7-dimethyl-2-propyl-1H-imidazo[4,5-c]pyridin-4-amine;
2-butyl-1-{5-[(2,4-dichlorophenyl)thio]pentyl}-6,7-dimethyl-1H-imidazo[4,5-c]pyridin-4-amine;
1-{5-[(2,4-dichlorophenyl)thio]pentyl}-2-ethoxymethyl-6,7-dimethyl-1H-imidazo[4,5-c]pyridin-4-amine;
1-{5-[(2,4-dichlorophenyl)thio]pentyl}-2-methoxyethyl-6,7-dimethyl-1H-imidazo[4,5-c]pyridin-4-amine;
1-{5-[(2,4-dichlorophenyl)thio]pentyl}-2-cyclopropylmethyl-6,7-dimethyl-1H-imidazo[4,5-c]pyridin-4-amine;
1-{5-[(2,4-dichlorophenyl)sulfonyl]pentyl}-6,7-dimethyl-1H-imidazo[4,5-c]pyridin-4-amine;
1-{5-[(2,4-dichlorophenyl)sulfonyl]pentyl}-2,6,7-trimethyl-1H-imidazo[4,5-c]pyridin-4-amine;
1-{5-[(2,4-dichlorophenyl)sulfonyl]pentyl}-2-ethyl-6,7-dimethyl-1H-imidazo[4,5-c]pyridin-4-amine;
1-{5-[(2,4-dichlorophenyl)sulfonyl]pentyl}-6,7-dimethyl-2-propyl-1H-imidazo[4,5-c]pyridin-4-amine;
2-butyl-1-{5-[(2,4-dichlorophenyl)sulfonyl]pentyl}-6,7-dimethyl-1H-imidazo[4,5-c]pyridin-4-amine;
1-{5-[(2,4-dichlorophenyl)sulfonyl]pentyl}-2-ethoxymethyl-6,7-dimethyl-1H-imidazo[4,5-c]pyridin-4-amine;
1-{5-[(2,4-dichlorophenyl)sulfonyl]pentyl}-2-methoxyethyl-6,7-dimethyl-1H-imidazo[4,5-c]pyridin-4-amine;
1-{5-[(2,4-dichlorophenyl)sulfonyl]pentyl}-2-cyclopropylmethyl-6,7-dimethyl-1H-imidazo[4,5-c]pyridin-4-amine;
1-{5-[(2,4-dichlorophenyl)sulfinyl]pentyl}-6,7-dimethyl-1H-imidazo[4,5-c]pyridin-4-amine;
1-{5-[(2,4-dichlorophenyl)sulfinyl]pentyl}-2,6,7-trimethyl-1H-imidazo[4,5-c]pyridin-4-amine;
1-{5-[(2,4-dichlorophenyl)sulfinyl]pentyl}-2-ethyl-6,7-dimethyl-1H-imidazo[4,5-c]pyridin-4-amine;
1-{5-[(2,4-dichlorophenyl)sulfinyl]pentyl}-6,7-dimethyl-2-propyl-1H-imidazo[4,5-c]pyridin-4-amine;
2-butyl-1-{5-[(2,4-dichlorophenyl)sulfinyl]pentyl}-6,7-dimethyl-1H-imidazo[4,5-c]pyridin-4-amine;
1-{5-[(2,4-dichlorophenyl)sulfinyl]pentyl}-2-ethoxymethyl-6,7-dimethyl-1H-imidazo[c]pyridin-4-amine;
1-{5-[(2,4-dichlorophenyl)sulfinyl]pentyl}-2-methoxyethyl-6,7-dimethyl-1H-imidazo[c]pyridin-4-amine;
1-{5-[(2,4-dichlorophenyl)sulfinyl]pentyl}-2-cyclopropylmethyl-6,7-dimethyl-1H-imidazo[4,5-c]pyridin-4-amine;
1-{5-[(2,4-difluorophenyl)thio]pentyl}-6,7-dimethyl-1H-imidazo[4,5-c]pyridin-4-amine;
1-{5-[(2,4-difluorophenyl)thio]pentyl}-2,6,7-trimethyl-1H-imidazo[4,5-c]pyridin-4-amine;
2-ethyl-1-{5-[(2,4-difluorophenyl)thio]pentyl}-6,7-dimethyl-1H-imidazo[4,5-c]pyridin-4-amine;
1-{5-[(2,4-difluorophenyl)thio]pentyl}-6,7-dimethyl-2-propyl-1H-imidazo[4,5-c]pyridin-4-amine;
2-butyl-1-{5-[(2,4-difluorophenyl)thio]pentyl}-6,7-dimethyl-1H-imidazo[4,5-c]pyridin-4-amine;
2-ethoxymethyl-1-{5-[(2,4-difluorophenyl)thio]pentyl}-6,7-dimethyl-1H-imidazo[4,5-c]pyridin-4-amine;
1-{5-[(2,4-difluorophenyl)thio]pentyl}-2-methoxyethyl-6,7-dimethyl-1H-imidazo[4,5-c]pyridin-4-amine;
2-cyclopropylmethyl-1-{5-[(2,4-difluorophenyl)thio]pentyl}-6,7-dimethyl-1H-imidazo[4,5-c]pyridin-4-amine;

1-{5-[(2,4-difluorophenyl)sulfonyl]pentyl}-6,7-dimethyl-1H-imidazo[4,5-c]pyridin-4-amine;
1-{5-[(2,4-difluorophenyl)sulfonyl]pentyl}-2,6,7-trimethyl-1H-imidazo[4,5-c]pyridin-4-amine;
2-ethyl-1-{5-[(2,4-difluorophenyl)sulfonyl]pentyl}-6,7-dimethyl-1H-imidazo[4,5-c]pyridin-4-amine;
1-{5-[(2,4-difluorophenyl)sulfonyl]pentyl}-6,7-dimethyl-2-propyl-1H-imidazo[4,5-c]pyridin-4-amine;
2-butyl-1-{5-[(2,4-difluorophenyl)sulfonyl]pentyl}-6,7-dimethyl-1H-imidazo[4,5-c]pyridin-4-amine;
2-ethoxymethyl-1-{5-[(2,4-difluorophenyl)sulfonyl]pentyl}-6,7-dimethyl-1H-imidazo[4,5-c]pyridin-4-amine;
1-{5-[(2,4-difluorophenyl)sulfonyl]pentyl}-2-methoxyethyl-6,7-dimethyl-1H-imidazo[4,5-c]pyridin-4-amine;
2-cyclopropylmethyl-1-{5-[(2,4-difluorophenyl)sulfonyl]pentyl}-6,7-dimethyl-1H-imidazo[4,5-c]pyridin-4-amine;
1-{5-[(2,4-difluorophenyl)sulfinyl]pentyl}-6,7-dimethyl-1H-imidazo[4,5-c]pyridin-4-amine;
1-{5-[(2,4-difluorophenyl)sulfinyl]pentyl}-2,6,7-trimethyl-1H-imidazo[4,5-c]pyridin-4-amine;
2-ethyl-1-{5-[(2,4-difluorophenyl)sulfinyl]pentyl}-6,7-dimethyl-1H-imidazo[4,5-c]pyridin-4-amine;
1-{5-[(2,4-difluorophenyl)sulfinyl]pentyl}-6,7-dimethyl-2-propyl-1H-imidazo[4,5-c]pyridin-4-amine;
2-butyl-1-{5-[(2,4-difluorophenyl)sulfinyl]pentyl}-6,7-dimethyl-1H-imidazo[4,5-c]pyridin-4-amine;
2-ethoxymethyl-1-{5-[(2,4-difluorophenyl)sulfinyl]pentyl}-6,7-dimethyl-1H-imidazo[4,5-c]pyridin-4-amine;
1-{4-[(2,4-difluorophenyl)sulfinyl]pentyl}-2-methoxyethyl-6,7-dimethyl-1H-imidazo[4,5-c]pyridin-4-amine;
2-cyclopropylmethyl-1-{5-[(2,4-difluorophenyl)sulfinyl]pentyl}-6,7-dimethyl-1H-imidazo[4,5-c]pyridin-4-amine;
7-methyl-1-[4-(methylthio)pentyl]-1H-imidazo[4,5-c]pyridin-4-amine;
2,7-dimethyl-1-[5-(methylthio)pentyl]-1H-imidazo[4,5-c]pyridin-4-amine;
2-ethyl-7-methyl-1-[5-(methylthio)pentyl]-1H-imidazo[4,5-c]pyridin-4-amine;
6,7-dimethyl-1-[5-(methylthio)pentyl]-2-propyl-1H-imidazo[4,5-c]pyridin-4-amine;
2-butyl-7-methyl-1-[5-(methylthio)pentyl]-1H-imidazo[4,5-c]pyridin-4-amine;
2-ethoxymethyl-7-methyl-1-[5-(methylthio)pentyl]-1H-imidazo[4,5-c]pyridin-4-amine;
2-methoxyethyl-7-methyl-1-[5-(methylthio)pentyl]-1H-imidazo[4,5-c]pyridin-4-amine;
2-cyclopropylmethyl-7-methyl-1-[5-(methylthio)pentyl]-1H-imidazo[4,5-c]pyridin-4-amine;
7-methyl-1-[5-(methylsulfonyl)pentyl]-1H-imidazo[4,5-c]pyridin-4-amine;
2,7-dimethyl-1-[5-(methylsulfonyl)pentyl]-1H-imidazo[4,5-c]pyridin-4-amine;
2-ethyl-7-methyl-1-[5-(methylsulfonyl)pentyl]-1H-imidazo[4,5-c]pyridin-4-amine;
7-methyl-1-[5-(methylsulfonyl)pentyl]-2-propyl-1H-imidazo[4,5-c]pyridin-4-amine;
2-butyl-7-methyl-1-[5-(methylsulfonyl)pentyl]-1H-imidazo[4,5-c]pyridin-4-amine;
2-ethoxymethyl-7-methyl-1-[5-(methylsulfonyl)pentyl]-1H-imidazo[4,5-c]pyridin-4-amine;
2-methoxyethyl-7-methyl-1-[5-(methylsulfonyl)pentyl]-1H-imidazo[4,5-c]pyridin-4-amine;
2-cyclopropylmethyl-7-methyl-1-[5-(methylsulfonyl)pentyl]-1H-imidazo[4,5-c]pyridin-4-amine;
7-methyl-1-[5-(methylsulfinyl)pentyl]-1H-imidazo[4,5-c]pyridin-4-amine;
2,7-dimethyl-1-[5-(methylsulfinyl)pentyl]-1H-imidazo[4,5-c]pyridin-4-amine;
2-ethyl-7-methyl-1-[5-(methylsulfinyl)pentyl]-1H-imidazo[4,5-c]pyridin-4-amine;
7-methyl-1-[5-(methylsulfinyl)pentyl]-2-propyl-1H-imidazo[4,5-c]pyridin-4-amine;
2-butyl-7-methyl-1-[5-(methylsulfinyl)pentyl]-1H-imidazo[4,5-c]pyridin-4-amine;
2-ethoxymethyl-7-methyl-1-[5-(methylsulfinyl)pentyl]-1H-imidazo[4,5-c]pyridin-4-amine;
2-methoxyethyl-7-methyl-1-[5-(methylsulfinyl)pentyl]-1H-imidazo[4,5-c]pyridin-4-amine;
2-cyclopropylmethyl-7-methyl-1-[5-(methylsulfinyl)pentyl]-1H-imidazo[4,5-c]pyridin-4-amine;
7-methyl-1-[5-(phenylthio)pentyl]-1H-imidazo[4,5-c]pyridin-4-amine;
2,7-dimethyl-1-[4-(phenylthio)pentyl]-1H-imidazo[4,5-c]pyridin-4-amine;
2-ethyl-7-methyl-1-[5-(phenylthio)pentyl]-1H-imidazo[4,5-c]pyridin-4-amine;
7-methyl-1-[5-(phenylthio)pentyl]-2-propyl-1H-imidazo[4,5-c]pyridin-4-amine;
2-butyl-7-methyl-1-[5-(phenylthio)pentyl]-1H-imidazo[4,5-c]pyridin-4-amine;
2-ethoxymethyl-7-methyl-1-[5-(phenylthio)pentyl]-1H-imidazo[4,5-c]pyridin-4-amine;
2-methoxyethyl-7-methyl-1-[5-(phenylthio)pentyl]-1H-imidazo[4,5-c]pyridin-4-amine;
2-cyclopropylmethyl-7-methyl-1-[5-(phenylthio)pentyl]-1H-imidazo[4,5-c]pyridin-4-amine;
7-methyl-1-[5-(phenylsulfonyl)pentyl]-1H-imidazo[4,5-c]pyridin-4-amine;
2,7-dimethyl-1-[5-(phenylsulfonyl)pentyl]-1H-imidazo[4,5-c]pyridin-4-amine;
2-ethyl-7-methyl-1-[5-(phenylsulfonyl)pentyl]-1H-imidazo[4,5-c]pyridin-4-amine;
7-methyl-1-[5-(phenylsulfonyl)pentyl]-2-propyl-1H-imidazo[4,5-c]pyridin-4-amine;
2-butyl-7-methyl-1-[5-(phenylsulfonyl)pentyl]-1H-imidazo[4,5-c]pyridin-4-amine;
2-ethoxymethyl-7-methyl-1-[5-(phenylsulfonyl)pentyl]-1H-imidazo[4,5-c]pyridin-4-amine;
2-methoxyethyl-7-methyl-1-[5-(phenylsulfonyl)pentyl]-1H-imidazo[4,5-c]pyridin-4-amine;
2-cyclopropylmethyl-7-methyl-1-[5-(phenylsulfonyl)pentyl]-1H-imidazo[4,5-c]pyridin-4-amine;
7-methyl-1-[5-(phenylsulfinyl)pentyl]-1H-imidazo[4,5-c]pyridin-4-amine;
2,7-dimethyl-1-[5-(phenylsulfinyl)pentyl]-1H-imidazo[4,5-c]pyridin-4-amine;
2-ethyl-7-methyl-1-[5-(phenylsulfinyl)pentyl]-1H-imidazo[4,5-c]pyridin-4-amine;
7-methyl-1-[5-(phenylsulfinyl)pentyl]-2-propyl-1H-imidazo[4,5-c]pyridin-4-amine;
2-butyl-7-methyl-1-[5-(phenylsulfinyl)pentyl]-1H-imidazo[4,5-c]pyridin-4-amine;
2-ethoxymethyl-7-methyl-1-[5-(phenylsulfinyl)pentyl]-1H-imidazo[4,5-c]pyridin-4-amine;
2-methoxyethyl-7-methyl-1-[5-(phenylsulfinyl)pentyl]-1H-imidazo[4,5-c]pyridin-4-amine;
2-cyclopropylmethyl-7-methyl-1-[5-(phenylsulfinyl)pentyl]-1H-imidazo[4,5-c]pyridin-4-amine;
7-methyl-1-[5-(pyrimidin-2-ylthio)pentyl]-1H-imidazo[4,5-c]pyridin-4-amine;

2,7-dimethyl-1-[5-(pyrimidin-2-ylthio)pentyl]-1H-imidazo[4,5-c]pyridin-4-amine;
2-ethyl-7-methyl-1-[5-(pyrimidin-2-ylthio)pentyl]-1H-imidazo[4,5-c]pyridin-4-amine;
7-methyl-1-[5-(pyrimidin-2-ylthio)pentyl]-2-propyl-1H-imidazo[4,5-c]pyridin-4-amine;
2-butyl-7-methyl-1-[5-(pyrimidin-2-yllthio)pentyl]-1H-imidazo[4,5-c]pyridin-4-amine;
2-ethoxymethyl-7-methyl-1-[5-(pyrimidin-2-ylthio)pentyl]-1H-imidazo[4,5-c]pyridin-4-amine;
2-methoxyethyl-7-methyl-1-[5-(pyrimidin-2-ylthio)pentyl]-1H-imidazo[4,5-c]pyridin-4-amine;
2-cyclopropylmethyl-7-methyl-1-[5-(pyrimidin-2-ylthio)pentyl]-1H-imidazo[4,5-c]pyridin-4-amine;
7-methyl-1-[5-(pyrimidin-2-ylsulfonyl)pentyl]-1H-imidazo[4,5-c]pyridin-4-amine;
2,7-dimethyl-1-[5-(pyrimidin-2-ylsulfonyl)pentyl]-1H-imidazo[4,5-c]pyridin-4-amine;
2-ethyl-7-methyl-1-[5-(pyrimidin-2-ylsulfonyl)pentyl]-1H-imidazo[4,5-c]pyridin-4-amine;
7-methyl-1-[5-(pyrimidin-2-ylsulfonyl)pentyl]-2-propyl-1H-imidazo[4,5-c]pyridin-4-amine;
2-butyl-7-methyl-1-[5-(pyrimidin-2-ylsulfonyl)pentyl]-1H-imidazo[4,5-c]pyridin-4-amine;
2-ethoxymethyl-7-methyl-1-[5-(pyrimidin-2-ylsulfonyl)pentyl]-1H-imidazo[4,5-c]pyridin-4-amine;
2-methoxyethyl-7-methyl-1-[5-(pyrimidin-2-ylsulfonyl)pentyl]-1H-imidazo[4,5-c]pyridin-4-amine;
2-cyclopropylmethyl-7-methyl-1-[5-(pyrimidin-2-ylsulfonyl)pentyl]-1H-imidazo[4,5-c]pyridin-4-amine;
7-methyl-1-[5-(pyrimidin-2-ylsulfinyl)pentyl]-1H-imidazo[4,5-c]pyridin-4-amine;
2,7-dimethyl-1-[5-(pyrimidin-2-ylsulfinyl)pentyl]-1H-imidazo[4,5-c]pyridin-4-amine;
2-ethyl-7-methyl-1-[5-(pyrimidin-2-ylsulfinyl)pentyl]-1H-imidazo[4,5-c]pyridin-4-amine;
7-methyl-1-[5-(pyrimidin-2-ylsulfinyl)pentyl]-2-propyl-1H-imidazo[4,5-c]pyridin-4-amine;
2-butyl-7-methyl-1-[5-(pyrimidin-2-ylsulfinyl)pentyl]-1H-imidazo[4,5-c]pyridin-4-amine;
2-ethoxymethyl-7-methyl-1-[5-(pyrimidin-2-ylsulfinyl)pentyl]-1H-imidazo[4,5-c]pyridin-4-amine;
2-methoxyethyl-7-methyl-1-[5-(pyrimidin-2-ylsulfinyl)pentyl]-1H-imidazo[4,5-c]pyridin4-amine;
2-cyclopropylmethyl-7-methyl-1-[5-(pyrimidin-2-ylsulfinyl)pentyl]-1H-imidazo[4,5-c]pyridin-4-amine;
1-[5-(butylthio)pentyl]-7-methyl-1H-imidazo[4,5-c]pyridin-4-amine;
1-[5-(butylthio)pentyl]-2,7-dimethyl-1H-imidazo[4,5-c]pyridin-4-amine;
1-[5-(butylthio)pentyl]-2-ethyl-7-methyl-1H-imidazo[4,5-c]pyridin-4-amine;
1-[5-(butylthio)pentyl]-7-methyl-2-propyl-1H-imidazo[4,5-c]pyridin-4-amine;
2-butyl-1-[5-(butylthio)pentyl]-7-methyl-1H-imidazo[4,5-c]pyridin-4-amine;
1-[5-(butylthio)pentyl]-2-ethoxymethyl-7-methyl-1H-imidazo[4,5-c]pyridin-4-amine;
1-[5-(butylthio)pentyl]-2-methoxyethyl-7-methyl-1H-imidazo[4,5-c]pyridin-4-amine;
1-[5-(butylthio)pentyl]-2-cyclopropylmethyl-7-methyl-1H-imidazo[4,5-c]pyridin-4-amine;
1-[5-(butylsulfonyl)pentyl]-7-methyl-1H-imidazo[4,5-c]pyridin-4-amine;
1-[5-(butylsulfonyl)pentyl]-2,7-dimethyl-1H-imidazo[4,5-c]pyridin-4-amine;
1-[5-(butylsulfonyl)pentyl]-2-ethyl-7-methyl-1H-imidazo[4,5-c]pyridin-4-amine;
1-[5-(butylsulfonyl)pentyl]-7-methyl-2-propyl-1H-imidazo[4,5-c]pyridin-4-amine;
2-butyl-1-[5-(butylsulfonyl)pentyl]-7-methyl-1H-imidazo[4,5-c]pyridin-4-amine;
1-[5-(butylsulfonyl)pentyl]-2-ethoxymethyl-7-methyl-1H-imidazo[4,5-c]pyridin-4-amine;
1-[5-(butylsulfonyl)pentyl]-2-methoxyethyl-7-methyl-1H-imidazo[4,5-c]pyridin-4-amine;
1-[5-(butylsulfonyl)pentyl]-2-cyclopropylmethyl-7-methyl-1H-imidazo[4,5-c]pyridin-4-amine;
1-[5-(butylsulfinyl)bpenyl]-7-methyl-1H-imidazo[4,5-c]pyridin-4-amine;
1-[5-(butylsulfinyl)pentyl]-2,7-dimethyl-1H-imidazo[4,5-c]pyridin-4-amine;
1-[5-(butylsulfinyl)pentyl]-2-ethyl-7-methyl-1H-imidazo[4,5-c]pyridin-4-amine;
1-[5-(butylsulfinyl)pentyl]-7-methyl-2-propyl-1H-imidazo[4,5-c]pyridin-4-amine;
2-butyl-1-[5-(butylsulfinyl)pentyl]-7-methyl-1H-imidazo[4,5-c]pyridin-4-amine;
1-[5-(butylsulfinyl)pentyl]-2-ethoxymethyl-7-methyl-1H-imidazo[4,5-c]pyridin-4-amine;
1-[5-(butylsulfinyl)pentyl]-2-methoxyethyl-6,7-dimethyl-1H-imidazo[4,5-c]pyridin-4-amine;
1-[5-(butylsulfinyl)pentyl]-2-cyclopropylmethyl-6,7-dimethyl-1H-imidazo[4,5-c]pyridin-4-amine;
1-{5-[(2,4-dichlorophenyl)thio]pentyl}-7-methyl-1H-imidazo[4,5-c]pyridin-4-amine;
1-{5-[(2,4-dichlorophenyl)thio]pentyl}-2,7-dimethyl-1H-imidazo[4,5-c]pyridin-4-amine;
1-{5-[(2,4-dichlorophenyl)thio]pentyl}-2-ethyl-7-methyl-1H-imidazo[4,5-c]pyridin-4-amine;
1-{5-[(2,4-dichlorophenyl)thio]pentyl}-7-methyl-2-propyl-1H-imidazo[4,5-c]pyridin-4-amine;
2-butyl-1-{5-[(2,4-dichlorophenyl)thio]pentyl}-7-methyl-1H-imidazo[4,5-c]pyridin-4-amine;
1-{5-[(2,4-dichlorophenyl)thio]pentyl}-2-ethoxymethyl-7-methyl-1H-imidazo[4,5-c]pyridin-4-amine;
1-{5-[(2,4-dichlorophenyl)thio]pentyl}-2-methoxyethyl-7-methyl-1H-imidazo[4,5-c]pyridin-4-amine;
1-{5-[(2,4-dichlorophenyl)thio]pentyl}-2-cyclopropylmethyl-7-methyl-1H-imidazo[4,5-c]pyridin-4-amine;
1-{5-[(2,4-dichlorophenyl)sulfonyl]pentyl}-7-methyl-1H-imidazo[4,5-c]pyridin-4-amine;
1-{5-[(2,4-dichlorophenyl)sulfonyl]pentyl}-2,7-dimethyl-1H-imidazo[4,5-c]pyridin-4-amine;
1-{5-[(2,4-dichlorophenyl)sulfonyl]pentyl}-2-ethyl-7-methyl-1H-imidazo[4,5-c]pyridin-4-amine;
1-{5-[(2,4-dichlorophenyl)sulfonyl]pentyl}-7-methyl-2-propyl-1H-imidazo[4,5-c]pyridin-4-amine;
2-butyl-1-{5-[(2,4-dichlorophenyl)sulfonyl]pentyl}-7-methyl-1H-imidazo[4,5-c]pyridin-4-amine;
1-{5-[(2,4-dichlorophenyl)sulfonyl]pentyl}-2-ethoxymethyl-7-methyl-1H-imidazo[4,5-c]pyridin-4-amine;
1-{5-[(2,4-dichlorophenyl)sulfonyl]pentyl}-2-methoxyethyl-7-methyl-1H-imidazo[4,5-c]pyridin-4-amine;
1-{5-[(2,4-dichlorophenyl)sulfonyl]pentyl}-2-cyclopropylmethyl-7-methyl-1H-imidazo[4,5-c]pyridin-4-amine;
1-{5-[(2,4-dichlorophenyl)sulfinyl]pentyl}-7-methyl-1H-imidazo[4,5-c]pyridin-4-amine;
1-{5-[(2,4-dichlorophenyl)sulfinyl]pentyl}-2,7-dimethyl-1H-imidazo[4,5-c]pyridin-4-amine;
1-{5-[(2,4-dichlorophenyl)sulfinyl]pentyl}-2-ethyl-7-methyl-1H-imidazo[4,5-c]pyridin-4-amine;

1-{5-[(2,4-dichlorophenyl)sulfinyl]pentyl}-7-methyl-2-propyl-1H-imidazo[4,5-c]pyridin-4-amine;
2-butyl-1-{5-[(2,4-dichlorophenyl)sulfinyl]pentyl}-7-methyl-1H-imidazo[4,5-c]pyridin-4-amine;
1-{5-[(2,4-dichlorophenyl)sulfinyl]pentyl}-2-ethoxymethyl-7-methyl-1H-imidazo[4,5-c]pyridin-4-amine;
1-{5-[(2,4-dichlorophenyl)sulfinyl]pentyl}-2-methoxyethyl-7-methyl-1H-imidazo[4,5-c]pyridin-4-amine;
1-{5-[(2,4-dichlorophenyl)sulfinyl]pentyl}-2-cyclopropylmethyl-7-methyl-1H-imidazo[4,5-c]pyridin-4-amine;
1-{5-[(2,4-difluorophenyl)thio]pentyl}-6-methyl-1H-imidazo[4,5-c]pyridin-4-amine;
1-{5-[(2,4-difluorophenyl)thio]pentyl}-2,7-dimethyl-1H-imidazo[4,5-c]pyridin-4-amine;
2-ethyl-1-{5-[(2,4-difluorophenyl)thio]pentyl}-7-methyl-1H-imidazo[4,5-c]pyridin-4-amine;
1-{5-[(2,4-difluorophenyl)thio]pentyl}-7-methyl-2-propyl-1H-imidazo[4,5-c]pyridin-4-amine;
2-butyl-1-{5-[(2,4-difluorophenyl)thio]pentyl}-7-methyl-1H-imidazo[4,5-c]pyridin-4-amine;
2-ethoxymethyl-1-{5-[(2,4-difluorophenyl)thio]pentyl}-7-methyl-1H-imidazo[4,5-c]pyridin-4-amine;
1-{5-[(2,4-difluorophenyl)thio]pentyl}-2-methoxyethyl-7-methyl-1H-imidazo [4,5-c]pyridin-4-amine;
2-cyclopropylmethyl-1-{5-[(2,4-difluorophenyl)thio]pentyl}-7-methyl-1H-imidazo[4,5-c]pyridin-4-amine;
1-{5-[(2,4-difluorophenyl)sulfonyl]pentyl}-7-methyl-1H-imidazo[4,5-c]pyridin-4-amine;
1-{5-[(2,4-difluorophenyl)sulfonyl]pentyl}-2,7-dimethyl-1H-imidazo[4,5-c]pyridin-4-amine;
2-ethyl-1-{5-[(2,4-difluorophenyl)sulfonyl]pentyl}-7-methyl-1H-imidazo[4,5-c]pyridin-4-amine;
1-{5-[(2,4-difluorophenyl)sulfonyl]pentyl}-7-methyl-2-propyl-1H-imidazo[4,5-c]pyridin-4-amine;
2-butyl-1-{5-[(2,4-difluorophenyl)sulfonyl]pentyl}-7-methyl-1H-imidazo[4,5-c]pyridin-4-amine;
2-ethoxymethyl-1-{5-[(2,4-difluorophenyl)sulfonyl]pentyl}-7-methyl-1H-imidazo[4,5-c]pyridin-4-amine;
1-{5-[(2,4-difluorophenyl)sulfonyl]pentyl}-2-methoxyethyl-7-methyl-1H-imidazo[4,5-c]pyridin-4-amine;
2-cyclopropylmethyl-1-{5-[(2,4-difluorophenyl)sulfonyl]pentyl}-7-methyl-1H-imidazo[4,5-c]pyridin-4-amine;
1-{5-[(2,4-difluorophenyl)sulfinyl]pentyl}-7-methyl-1H-imidazo[4,5-c]pyridin-4-amine;
1-{5-[(2,4-difluorophenyl)sulfinyl]pentyl}-2,7-dimethyl-1H-imidazo[4,5-c]pyridin-4-amine;
2-ethyl-1-{5-[(2,4-difluorophenyl)sulfinyl]pentyl}-7-methyl-1H-imidazo[4,5-c]pyridin-4-amine;
1-{5-[(2,4-difluorophenyl)sulfinyl]pentyl}-7-methyl-2-propyl-1H-imidazo[4,5-c]pyridin-4-amine;
2-butyl-1-{5-[(2,4-difluorophenyl)sulfinyl]pentyl}-7-methyl-1H-imidazo[4,5-c]pyridin-4-amine;
2-ethoxymethyl-1-{5-[(2,4-difluorophenyl)sulfinyl]pentyl}-7-methyl-1H-imidazo[4,5-c]pyridin-4-amine;
1-{5-[(2,4-difluorophenyl)sulfinyl]pentyl}-2-methoxyethyl-7-methyl-1H-imidazo[4,5-c]pyridin-4-amine;
2-cyclopropylmethyl-1-{5-[(2,4-difluorophenyl)sulfinyl]pentyl}-7-methyl-1H-imidazo[4,5-c]pyridin-4-amine;
6-methyl-2-propyl-1-[2-(3-pyrimidin-2-ylpropoxy)ethyl]-1H-imidazo[4,5-c]pyridin-4-amine;
N-{2-[2-(4-amino-7-nitro-2-propyl-1H-imidazo[4,5-c]pyridin-1-yl)ethoxy]ethyl}methanesulfonamide;
N-{2-[2-(4-amino-7-nitro-2-propyl-1H-imidazo[4,5-c]pyridin-1-yl)ethoxy]ethyl}-4-chlorobenzamide;
N-{2-[2-(4-amino-7-nitro-2-propyl-1H-imidazo[4,5-c]pyridin-1-yl)ethoxy]ethyl}-N'-cyclohexylurea;
N-{2-[2-(4-amino-7-hex-1-ynyl-2-propyl-1H-imidazo[4,5-c]pyridin-1-yl)ethoxy]ethyl}-4-chlorobenzamide;
N-{2-[2-(4-amino-7-hex-1-ynyl-2-propyl-1H-imidazo[4,5-c]pyridin-1-yl)ethoxy]ethyl}-N'-cyclohexylurea;
N-{2-[2-(4-amino-7-hexyl-2-propyl-1H-imidazo[4,5-c]pyridin-1-yl)ethoxy]ethyl}-4-chlorobenzamide;
N-{2-[2-(4-amino-7-hexyl-2-propyl-1H-imidazo[4,5-c]pyridin-1-yl)ethoxy]ethyl}-N'-cyclohexylurea;
N-{2-[2-(4,7-diamino-2-propyl-1H-imidazo[4,5-c]pyridin-1-yl)ethoxy]ethyl}methanesulfonamide;
N-{2-[2-(4,7-diamino-2-propyl-1H-imidazo[4,5-c]pyridin-1-yl)ethoxy]ethyl}-4-chlorobenzamide;
N-{2-[2-(4,7-diamino-2-propyl-1H-imidazo[4,5-c]pyridin-1-yl)ethoxy]ethyl}-N'-cyclohexylurea;
N-{2-[2-(4-amino-7-methylamino-2-propyl-1H-imidazo[4,5-c]pyridin-1-yl)ethoxy]ethyl}methanesulfonamide;
N-{2-[2-(4-amino-7-methylamino-2-propyl-1H-imidazo[4,5-c]pyridin-1-yl)ethoxy]ethyl}-4-chlorobenzamide;
N-{2-[2-(4-amino-7-methylamino-2-propyl-1H-imidazo[4,5-c]pyridin-1-yl)ethoxy]ethyl}-N'-cyclohexylurea;
N-{2-[2-(4-amino-7-ethylamino-2-propyl-1H-imidazo[4,5-c]pyridin-1-yl)ethoxy]ethyl}methanesulfonamide;
N-{2-[2-(4-amino-7-ethylamino-2-propyl-1H-imidazo[4,5-c]pyridin-1-yl)ethoxy]ethyl}-chlorobenzamide;
N-{2-[2-(4-amino-7-ethylamino-2-propyl-1H-imidazo[4,5-c]pyridin-1-yl)ethoxy]ethyl}-N'-cyclohexylurea;
N-{2-[2-(4-amino-7-dimethylamino-2-propyl-1H-imidazo[4,5-c]pyridin-1-yl)ethoxy]ethyl}methanesulfonamide;
N-{2-[2-(4-amino-7-dimethylamino-2-propyl-1H-imidazo[4,5-c]pyridin-1-yl)ethoxy]ethyl}-4-chlorobenzamide;
N-{2-[2-(4-amino-7-dimethylamino-2-propyl-1H-imidazo[4,5-c]pyridin-1-yl)ethoxy]ethyl}-N'-cyclohexylurea;
5N-{2-[2-(4-amino-7-diethylamino-2-propyl-1H-imidazo[4,5-c]pyridin-1-yl)ethoxy]ethyl}methanesulfonamide;
N-{2-[2-(4-amino-7-diethylamino-2-propyl-1H-imidazo[4,5-c]pyridin-1-yl)ethoxy]ethyl}-4-chlorobenzamide;
N-{2-[2-(4-amino-7-diethylamino-2-propyl-1H-imidazo[4,5-c]pyridin-1-yl)ethoxy]ethyl}-N'-cyclohexylurea;
6,7-dimethyl-2-ethoxymethyl-1-(2-{2-[(pyridin-2-yl)sulfonyl]ethoxy}ethyl)-1H-imidazo[4,5-c]pyridin-4-amine;
4-{[3-(4-amino-6,7-dimethyl-2-propyl-1H-imidazo[4,5-c]pyridin-1-yl)propyl]sulfonyl}-N-butylbenzamide;
4-{[3-(4-amino-6,7-dimethyl-2-propyl-1H-imidazo[4,5-c]pyridin-1-yl)propyl]sulfonyl}-butyl-N-methylbenzamide;
N-{2-[2-(4-amino-2-ethyl-6,7-dimethyl-1H-imidazo[4,5-c]pyridin-1-yl)ethoxy]ethyl}-N'-benzoylurea;
1-[2-(2-aminoethoxy)ethyl]-6-chloro-7-methyl-2-propyl-1H-imidazo[4,5-c]pyridin-4-amine;
N-{2-[2-(4-amino-6-chloro-7-methyl-2-propyl-1H-imidazo[4,5-c]pyridin-1-yl)ethoxy]ethyl}benzamide;
N-{2-[2-(4-amino-2-ethyl-6,7-dimethyl-1H-imidazo[4,5-c]pyridin-1-yl)ethoxy]ethyl}-N'-benzenesulfonylurea;
1-{2-[2-(4-amino-2-ethyl-6,7-dimethyl-1H-imidazo[4,5-c]pyridin-1-yl)ethoxy]ethyl}pyrrolidin-2-one;
2-ethoxymethyl-6,7-dimethyl-1-[2-(3-phenylprop-2-ynyloxy)ethyl]-1H-imidazo[4,5-c]pyridin-4-amine;
2-ethoxymethyl-6,7-dimethyl-1-[2-(3-phenylpropoxy)ethyl]-1H-imidazo[4,5-c]pyridin-4-amine;
2-ethoxymethyl-6,7-dimethyl-1-{2-[(4-phenylbut-3-ynyl)sulfonyl]ethyl}-1H-imidazo[4,5-c]pyridin-4-amine;
2-ethoxymethyl-6,7-dimethyl-1-{2-[(4-phenylbutyl)sulfonyl]ethyl}-1H-imidazo[4,5-c]pyridin-4-amine;

2-ethoxymethyl-6,7-dimethyl-1-[2-(4-phenylbut-3-ynyloxy)ethyl]-1H-imidazo[4,5-c]pyridin-4-amine; and
2-ethoxymethyl-6,7-dimethyl-1-[2-(4-phenylbutoxy)ethyl]-1H-imidazo[4,5-c]pyridin-4-amine;

or pharmaceutically acceptable salts thereof.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" means an amount of the compound sufficient to induce a therapeutic effect, such as cytokine induction, antitumor activity, and/or antiviral activity. Although the exact amount of active compound used in a pharmaceutical composition of the invention will vary according to factors known to those of skill in the art, such as the physical and chemical nature of the compound, the nature of the carrier, and the intended dosing regimen, it is anticipated that the compositions of the invention will contain sufficient active ingredient to provide a dose of about 100 ng/kg to about 50 mg/kg, preferably about 10 μg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL), including IL-1, IL-6, IL-10 and IL-12, and a variety of other cytokines. Among other effects, these and other cytokines can inhibit virus production and tumor cell growth, making the compounds useful in the treatment of viral diseases and tumors. Accordingly, the invention provides a method of inducing cytokine biosynthesis in an animal comprising administering an effective amount of a compound or composition of the invention to the animal.

Certain compounds of the invention have been found to preferentially induce the expression of IFN-α in a population of hematopoietic cells such as PBMCs (peripheral blood mononuclear cells) containing pDC2cells (precursor dendritic cell-type 2) without concomitant production of significant levels of inflammatory cytokines.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines.

Compounds of the invention also have an effect on the acquired immune response. For example, the compounds may cause proliferation and differentiation of B lymphocytes. In addition, the compounds induce responses from T lymphocytes, as discussed below.

Although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; varriola major; HIV; CMV; VZV; rhinovirus; adenovirus; influenza; and para-influenza; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia areata; the inhibition of Keloid formation after surgery and other types of post-surgical scars. In addition, these compounds could enhance or stimulate the healing of wounds, including chronic wounds. The compounds may be useful for treating the opportunistic infections and tumors that occur after suppression of cell mediated immunity in, for example, transplant patients, cancer patients and HIV patients.

An amount of a compound effective to induce cytokine biosynthesis is an amount sufficient to cause one or more cell types, such as monocytes, macrophages, dendritic cells and B cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

The invention is further described by the following examples, which are provided for illustration only and are not intended to be limiting in any way.

EXAMPLE 1

6,7-Dimethyl-1-(2-phenoxyethyl)-1H-imidazo[4,5-c]pyridin-4-amine

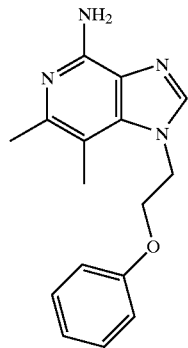

Part A
2,4-dichloro-5,6-dimethyl-3-nitropyridine

Phosphorous oxychloride (105 ml) and 2,4-dihydroxy-5,6-dimethyl-3-nitropyridine (10.53 g) were combined and heated to reflux for 2 hours. The reaction mixture was cooled and the phosphorous oxychloride was removed under reduced pressure. The resulting black solid was dissolved in ethyl acetate (300 ml) and washed with a saturated aqueous solution of sodium bicarbonate. The basic aqueous layer was washed 2 times with ethyl acetate. The combined organic layers were dried with magnesium sulfate and concentrated under reduced pressure. The resulting brown solid was run through a column using 60/40 ethyl acetate/hexane as the eluant. The product was found to be pure by NMR analysis.

Part B
2-chloro-5,6-dimethyl-3-nitro-N-(2-phenoxyethyl)pyridin-4-amine 2,4-Dichloro-5,6-dimethyl-3-nitropyridine (1.00 g), anhydrous N,N-dimethylformamide (5 ml), triethylamine (0.63 ml), and 2-phenoxyethylamine (0.59 ml) were combined and the resulting mixture was heated to 55° C. for 24 hours. Thin layer chromatography (TLC) monitoring of the reaction indicated that it was complete. The solvent was removed under reduced pressure and the remaining oil was dissolved in dichloromethane (DCM) and washed once with water. Following 2 additional extractions with DCM, the organic layers were combined, dried with magnesium sulfate, and the solvent was removed under reduced pressure. The product was passed through a column using 20/80 ethyl acetate/hexane as the eluant. NMR analysis of the resulting yellow solid indicated sufficient purity for use in the next step.

Part C
2,3-dimethyl-5-nitro-6-phenoxy-N-(2-phenoxyethyl)pyridin-4-amine

2-Methoxyethyl ether (diglyme) (3 ml) and sodium hydride (60% in oil) (0.56 g) were combined and cooled to 0° C. Phenol (1.24 g) was added slowly in portions to allow for controlled release of hydrogen gas. A solution of 2-chloro-5,6-dimethyl-3-nitro-N-(2-phenoxyethyl)pyridin-4-amine (4.00 g) and diglyme (37 ml) was then added and the reaction mixture was heated to 150° C. for 16 hours. At this time, the reaction stalled at 85% completion. The reaction mixture was allowed to cool and the solvent was removed under reduced pressure. The oil was dissolved in ethyl acetate, washed with water, dried with magnesium sulfate, and concentrated under reduced pressure. The product was run through a column using 20/80 ethyl acetate/hexane as the eluant. HPLC analysis of the resulting orange solid indicated sufficient purity for use in the next step.

Part D
5,6-dimethyl-2-phenoxy-$N^4$-(2-phenoxyethyl)pyridine-3,4-diamine

Anhydrous toluene (100 ml), 5% platinum on carbon (Pt/C) (1.5 g), and 2,3-dimethyl-5-nitro-6-phenoxy-N-(2-phenoxyethyl)pyridin-4-amine (2.97 g) from Part C were placed in a Parr hydrogenation flask at a hydrogen pressure of 345 kPa for 4 hours with shaking. Additional 5% Pt/C (1.5 g) was added and the reaction was allowed to continue for 3 hours. The reaction mixture was filtered through a fluted filter paper and then through a folded No. 2 Whatman filter. The solvent was removed from the filtrate under reduced pressure and the resulting oil was used in the next step.

Part E
6,7-dimethyl-4-phenoxy-1-(2-phenoxyethyl)-1H-imidazo[4,5-c]pyridine 5,6-Dimethyl-2-phenoxy-$N^4$-(2-phenoxyethyl)pyridine-3,4-diamine (2.41 g), triethyl orthoacetate (1.60 ml), toluene (20 ml), and a catalytic amount of pyridine HCl were combined and heated to reflux for 2 hours. HPLC and MS analysis indicated that the reaction was complete. The reaction mixture was allowed to cool and the resulting solid was filtered and dried. NMR analysis of the dried solid indicated a pure product.

Part F
6,7-dimethyl-1-(2-phenoxyethyl)-1H-imidazo[4,5-c]pyridin-4-amine

A sealed tube containing ammonium acetate (12.7 g) and 6,7-dimethyl-4-phenoxy-1-(2-phenoxyethyl)-1H-imidazo[4,5-c]pyridine (1.27 g) from Part E was heated to 150° C. for 36 hours. HPLC and TLC analysis indicated that the reaction was complete. The reaction was allowed to cool to room temperature. The resulting reaction mixture was then dissolved in dichloromethane (DCM) and washed with 20% aqueous sodium hydroxide. The basic layer was washed with DCM and the combined organic layers were dried with magnesium sulfate and concentrated under reduced pressure. The resulting oil was passed through a silica gel column using 95/5 dichloromethane/methanol as the eluant. The product was recrystallized from isopropyl alcohol, and the resulting white solid was dried under vacuum to provide 6,7-dimethyl-1-(2-phenoxyethyl)-1H-imidazo[4,5-c]pyridin-4-amine, m.p. 197.0–199.0° C.

Analysis: Calculated for $C_{16}H_{18}N_4O$: % C, 68.06; % H, 6.43; % N, 19.84 Found: % C, 67.85; % H, 6.33; % N, 19.74.

EXAMPLE 2

2,6,7-Trimethyl-1-(2-phenoxyethyl)-1H-imidazo[4,5-c]pyridin-4-amine

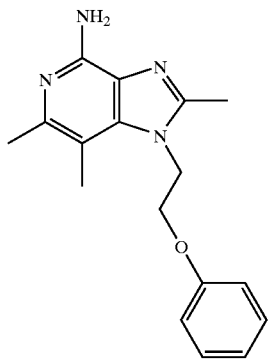

Part A 2-chloro-5,6-dimethyl-$N^4$-(2-phenoxyethyl)pyridine-3,4-diamine

Toluene (150 ml), 5% platinum on carbon (5.0 g), and 2-chloro-5,6-dimethyl-3-nitro-N-(2-phenoxyethyl)pyridin-4-amine (3.32 g) from Part B of Example 1 were placed in a Parr hydrogenation flask at a hydrogen pressure of 345 kPa for 4 hours with shaking. HPLC analysis indicated that the reaction was complete. The reaction mixture was filtered through a fluted filter paper and then through a folded No. 2 Whatman filter. The solvent was removed from the filtrate under reduced pressure and the resulting brown oil was used in the next step.

Part B 4-chloro-2,6,7-trimethyl-1-(2-phenoxyethyl)-1H-imidazo[4,5-c]pyridine

2-Chloro-5,6-dimethyl-$N^4$-(2-phenoxyethyl)pyridine-3,4-diamine (2.41 g), triethyl orthoacetate (1.60 ml), toluene (20 ml), and a catalytic amount of pyridine HCl were combined and heated to reflux for 2 hours. Methanol (15 ml) was then added and the reaction mixture was allowed to cool. The resulting white needles were filtered and dried. NMR analysis of the dried solid indicated a pure product.

Part C 2,6,7-trimethyl-4-phenoxy-1-(2-phenoxyethyl)-1H-imidazo[4,5-c]pyridine

A solution of sodium phenoxide was prepared by adding phenol (0.60 g) in portions over a period of 1 hour to a chilled solution of 2-methoxyethyl ether (diglyme) (40 ml) and sodium hydride (60% in oil) (0.27 g). After 1 hour, 4-chloro-2,6,7-trimethyl-1-(2-phenoxyethyl)-1H-imidazo[4,5-c]pyridine (1.91 g) from Part B was added to the sodium phenoxide solution and the resulting dark brown mixture was heated to reflux for 7 days. At this time, the reaction was 80% complete. Remaining sodium hydride was quenched by the addition of methanol (5 ml), and the solvents were then removed under reduced pressure. The oil was dissolved in ethyl acetate, washed with water and brine, dried with magnesium sulfate, and concentrated under reduced pressure. The resulting brown solid was run through a silica gel column using 80/20ethyl acetate/hexane as the eluant. NMR analysis of the dried solid indicated sufficient purity for carrying the product on to the next step.

Part D 2,6,7-trimethyl-1-(2-phenoxyethyl)-1H-imidazo[4,5-c]pyridin-4-amine

A sealed tube containing anhydrous ammonium acetate (11.4 g) and 2,6,7-trimethyl-4-phenoxy-1-(2-phenoxyethyl)-1H-imidazo[4,5-c]pyridine (1.14 g) from Part C was heated to 150° C. for 40 hours. The reaction was allowed to cool to room temperature. The resulting reaction mixture was then dissolved in ethyl acetate and washed with a saturated aqueous solution of sodium bicarbonate. The basic layer was washed twice with ethyl acetate. The organic layers were combined, dried with magnesium sulfate, and the solvents were removed under reduced pressure. The resulting orange solid was passed through a silica gel column using 94/6dichloromethane/methanol as the eluant. Because NMR analysis indicated that the white solid contained ammonium acetate, the product was dissolved in chloroform and washed with 25% aqueous sodium hydroxide. The resulting basic aqueous layer was extracted twice with chloroform. The organic layers were combined, washed with water, dried with magnesium sulfate, and concentrated under reduced pressure. The resulting white solid was dried under vacuum at 60° C. for 24hours to provide 2,6,7-trimethyl-1-(2-phenoxyethyl)-1H-imidazo[4,5-c]pyridin-4-amine, m.p. 176.0–177.0° C.

Analysis: Calculated for $C_{17}H_{20}N_4O$: % C, 68.90; % H, 6.80; % N, 18.90 Found: % C, 68.71; % H, 6.95; % N, 18.89.

EXAMPLE 3

2-Butyl-6,7-dimethyl-1-(2-phenoxyethyl)-1H-imidazo[4,5-c]pyridin-4-amine

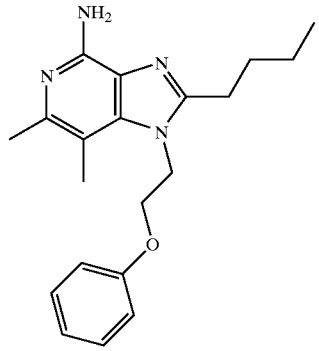

Part A

N-{2-chloro-5,6-dimethyl-4-[(2-phenoxyethyl)amino]pyridin-3-yl}pentanamide

Triethylamine (1.39 ml), anhydrous acetonitrile (100 ml), and 2-chloro-5,6-dimethyl-$N^4$-(2-phenoxyethyl)pyridine-3,4-diamine (2.92 g) from Part A of Example 2 were combined and cooled to 0° C. in an ice bath. Valeryl chloride (0.59 ml) was slowly added to the reaction mixture. After 2hours, the reaction mixture was heated to 55° C. for 24 hours, at which point HPLC analysis indicated the reaction was complete. The reaction mixture was cooled and the solvent was removed under reduced pressure. The resulting oil was dissolved in dichloromethane and washed with water. The organic layer was dried with magnesium sulfate and the solvent was removed under reduced pressure. The product was then passed through a silica gel column using 50/50 ethyl acetate/hexane as the eluant. The resulting light brown solid was used in the next step.

Part B 2-butyl-4-chloro-6,7-dimethyl-1-(2-phenoxyethyl)-1H-imidazo[4,5-c]pyridine Triethylamine (1.93 ml), anhydrous ethanol (35 ml), and N-{2-chloro-5,6-dimethyl-4-[(2-phenoxyethyl)amino]pyridin-3-yl}pentanamide (1.32 g) from Part A were combined and heated to reflux for 24 hours. The reaction stalled, so the mixture was cooled and the solvent was removed under reduced pressure. Pyridine (75 ml) and an equivalent of pyridine HCl was added and the reaction mixture was heated to reflux for 16 hours. TLC analysis indicated that the reaction was complete. The reaction was allowed to cool and the solvent was removed under reduced pressure. The resulting product was dissolved in ethyl acetate and washed 4 times with water (150 ml each) to remove the pyridine HCl. The organic layer was dried with magnesium sulfate and the solvent was removed under reduced pressure. NMR analysis of the dried brown solid indicated sufficient purity for use of the product in the next step.

Part C 2-butyl-6,7-dimethyl-4-phenoxy-1-(2-phenoxyethyl)-1H-imidazo[4,5-c]pyridine 2-Methoxyethyl ether (diglyme) (1.50 ml) and sodium hydride (60% in oil) (0.12 g) were combined and cooled to 0° C. Phenol (0.27 g) was added slowly in portions over 1 hour to allow for controlled release of hydrogen gas. 2-Butyl-4-chloro-6,7-dimethyl-1-(2-phenoxyethyl)-1H-imidazo[4,5-c]pyridine (0.96 g) from Part B was then added and the reaction mixture became dark brown. The reaction mixture was heated to reflux for 5 days, at which time HPLC analysis indicated the reaction was complete. The reaction mixture was cooled and washed with water. The mixture was filtered and the resulting solid was dried under vacuum at 60° C. overnight. NMR analysis of the product indicated sufficient purity for use of the product in the next step.

Part D 2-butyl-6,7-dimethyl-1-(2-phenoxyethyl)-1H-imidazo[4,5-c]pyridin-4-amine

A sealed tube containing ammonium acetate (7.5 g) and 2-butyl-6,7-dimethyl-4-phenoxy-1-(2-phenoxyethyl)-1H-imidazo[4,5-c]pyridine (0.75 g) from Part C was heated in an oil bath to 150° C. for 48hours. The reaction reached 70% completion and was allowed to cool to room temperature. The reaction mixture was then dissolved in ethyl acetate and washed with a saturated aqueous solution of sodium bicarbonate. The organic layer was dried with magnesium sulfate and concentrated under reduced pressure. The product was passed through a silica gel column using 10/90 methanol/ethyl acetate as the eluant. To remove impurities, the product was recrystallized twice from acetonitrile with charcoal. The resulting white crystals were crushed and dried to yield 2-butyl-6,7-dimethyl-1-(2-phenoxyethyl)-1H-imidazo[4,5-c]pyridin-4-amine, m.p. 130.0–132.0° C.

Analysis: Calculated for $C_{20}H_{26}N_4O$: % C, 70.98; % H, 7.74; % N, 16.55 Found: % C, 70.80; % H, 7.43; % N, 16.56.

EXAMPLES 4

1-[2-(Benzyloxy)ethyl]-2-(ethoxymethyl)-6,7-dimethyl-1H-imidazo[4,5-c]pyridin-4-amine

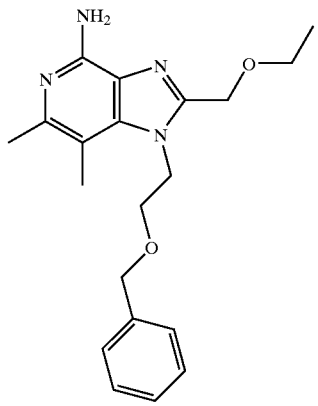

Part A tert-butyl 2-(benzyloxy)ethylcarbamate

To a mechanically stirred mixture of tert-butyl 2-(hydroxy)ethylcarbamate (32.2 g, 200.4 mmol) and sodium hydroxide (300 mL of 50%) was added benzyltrimethylammonium chloride (3.79 g, 20.4 mmol) and benzyl bromide (23.8 mL, 200.4 mmol). After stirring at room temperature for 12 hours TLC monitoring, using 1/1 hexane/ethyl acetate and ninhydrin stain, indicated complete reaction. The resulting clear solution was diluted with ice water (1 L), and the organic layer was separated. The aqueous layer was washed with chloroform (4x). The organic layers were combined and washed with water (2x) and brine (2x), dried with sodium sulfate, and concentrated under reduced pressure to provide 45.4 g of clear liquid. NMR analysis confirmed the product, which was used in the next step.

Part B 2-(benzyloxy)ethylamine HCl

The product from Part A (45.4 g, 180.6 mmol), 2.2 M hydrochloric acid in ethanol (200 mL), and 10% aqueous hydrochloric acid (20 mL) were combined and stirred for 62 hours. The reaction was determined to be complete by TLC and HPLC analysis. The volatiles were removed under reduced pressure, and the resulting solids were recrytallized from ethyl acetate. The resulting white fluffy crystals were filtered off, rinsed with diethyl ether, and dried for 1 hour to provide 27.4 g of white solids. NMR analysis confirmed the hydrochloride salt of 2-(benzyloxy)ethylamine, which was used in the next step.

Part C

N-[2-(Benzyloxy)ethyl]-2-chloro-5,6-dimethyl-3-nitropyridin-4-amine 2,4-Dichloro-6,7-dimethyl-3-nitropyridine (26.89 g, 121.7 mmol), anhydrous N,N-dimethylformamide (400 mL), anhydrous triethylamine (48.84 mL), and the benzyloxyethylamine hydrochloride salt (27.4 g, 146.0 mmol) from Part B were combined under nitrogen and heated to 90° C. for 20 minutes, 60 ° C. for 1 hour, and then 90° C. for 1 hour. The reaction was complete as determined by TLC analysis using 8/2 hexane/ethyl acetate. The reaction mixture was concentrated under reduced pressure, and the resulting orange solids were triturated with water. The resulting solids were filtered off and recrystalized from ethyl acetate. Recrystallized solids were rinsed with hexane and dried under vacuum at 50° C. for 30 minutes to provide 21.8 g of yellow fluffy solid for use in the next step. NMR analysis confirmed the N-[2-(benzyloxy)ethyl]-2-chloro-5,6-dimethyl-3-nitropyridin-4-amine and a minor amount of residual salts.

Part D

N-[2-(Benzyloxy)ethyl]-5,6-dimethyl-3-nitro-2-phenoxypyridin-4-amine

To a stirred solution of sodium hydride (4.75 g, 118.8 mmol, 60% in mineral oil) in diglyme (50 mL) under a nitrogen purge was added phenol (11.56 g, 122.8 mmol) dissolved in diglyme (50 mL) by cannula over a 10 minute period. The flask from which the phenol solution was transferred was washed with diglyme (2×20 mL), and the washings were added to the reaction mixture. Because the reaction was exothermic, an ice bath was used to cool the reaction mixture. After 15 minutes, addition of a solution of N-[2-(benzyloxy)ethyl]-2-chloro-5,6-dimethyl-3-nitropyridin-4-amine (26.6 g, 79.2 mmol) in diglyme (100 mL) to the clear solution of sodium phenoxide was begun. The flask from which the pyridine-4-amine starting material was transferred was rinsed with diglyme (3×20 mL), and the rinsings were transferred to the sodium phenoxide solution as well. The transfer was complete after 15 minutes, and the resulting orange solution was heated to about 150° C. for 4.5 hours when the reaction was determined to be essentially complete by HPLC. The resulting reaction solution was concentrated under reduced pressure, and the resulting dark oil was dissolved in ethyl acetate. The ethyl acetate solution was wased with ammonium chloride (1×), 1 N potassium hydroxide (3×), and brine (2×). The potassium hydroxide fractions were combined and extracted with dichloromethane (4×). The organic fractions were combined, dried with magnesium sulfate, and concentrated under reduced pressure. The resulting dark oil was passed through a column containing 400 g silica using 8/2 hexane/ethyl acetate. The resulting isolated product was an orange oil, which was triturated with hexane/diethyl ether. The resulting yellow solids were dried in a vacuum oven at 60° C. to provide 21 g of product. NMR and LC/MS analyses confirmed the N-[2-(benzyloxy)ethyl]-2,3-dimethyl-5-nitro-6-phenoxypyridin-4-amine with good purity.

Part E $N^4$-[2-(Benzyloxy)ethyl]-5,6-dimethyl-2-phenoxypyridine-3,4-diamine

N-[2-(Benzyloxy)ethyl]-5,6-dimethyl-3-nitro-2-phenoxypyridin-4-amine (12 g, 30.499 mmol) from Part D was combined with 5% platinum on carbon (2.2 g) in a Parr flask under a nitrogen purge. Toluene was slowly added to the resulting reaction mixture, which was then pressurized with hydrogen at 310 kPa. After 2 hours the reaction was complete. The resulting reaction mixture was filtered through Celite™ filter agent, and the filtrate was concentrated under reduced pressure to provide 10.6 g of brown oil. NMR analysis confirmed the $N^4$-[2-(benzyloxy)ethyl]-5,6-dimethyl-2-phenoxypyridine-3,4-diamine at a purity of 99+%.

Part F 2-(Ethoxymethyl)-1-[2-(benzyloxy)ethyl]-6,7-dimethyl-4-phenoxy-1H-imidazo[4,5-c]pyridine $N^4$-[2-(Benzyloxy)ethyl]-5,6-dimethyl-2-phenoxypyridin-3,4-amine (5.3 g, 14.582 mmol) from Part E, pyridine (50 mL), and pyridine hydrochloride (0.034 g, 0.2916 mmol) were combined with stirring under nitrogen and cooled with an ice bath to about 7° C. Ethoxyacetyl chloride (1.876 g, 15.311 mmol) was added dropwise over 1 minute, and the resulting reaction mixture was stirred for 30 minutes. The ice bath was removed. LC/MS analysis of the resulting reaction solution confirmed the molecular weight of the expected amide, and TLC (with 1/1 hexane/ethyl acetate) and HPLC analysis indicated no starting material or other by-products present.

The resulting reaction solution was heated to reflux (~90° C.) for about 10 hours. HPLC analysis of the resulting reaction solution indicated about 4% of the amide remaining along with the desired product. The reaction solution was cooled to room temperature and concentrated under reduced pressure. The resulting oil was triturated with hexane/diethyl ether, and the resulting solid was filtered off and dried to provide 4.33 g of pure product. A second crop from the hexane/diethyl ether was recovered to provide an additional 0.3157 g of desired product.

Part G

1-[2-(Benzyloxy)ethyl]-2-(ethoxymethyl)-6,7-dimethyl-1H-imidazo[4,5-c]pyridin-4-amine 2-(Ethoxymethyl)-1-[2-(benzyloxy)ethyl]-6,7-dimethyl-4-phenoxy-1H-imidazo[4,5-c]pyridine (4.33 g, 10.03 mm01) was placed in a glass reaction flask, and then ammonium acetate (45 g) was added. The flask was sealed with a teflon screw cap and heated to 156° C. for 44 hours. The reaction was determined to be complete by HPLC analysis, and the desired product's molecular weight was confirmed by LC/MS. The resulting solution was basified with 1 N potassium hydroxide to a pH of about 14. The basic solution was extracted with dichloromethane (5×), and the organic layers were combined, washed with water (3×) and brine (3×), dried with magnesium sulfate, filtered, and concentrated under reduced pressure. The resulting oil was triturated with diethyl ether. After the resulting solids were filtered off and dried, they were recrystallized from ethyl acetate/diethyl ether and again dried. NMR analysis or the recrystallized solids indicated impurities. The recrystallized solids were dissolved in ethanol. Hydrochloric acid (10 mL, 1 N) was added to the ethanol solution, and the resulting salt was filtered off and dissolved in water. The resulting aqueous solution was basified with 1 N potassium hydroxide to a pH of about 14 and extracted with dichloromethane (4×). The organic layers were combined, washed with water (2×) and brine (3×), dried with magnesium sulfate, filtered, and concentrated under reduced pressure to a white solid. The white solid was dried to provide 1.4285 g of 1-[2-(benzyloxy)ethyl]-2-(ethoxymethyl)-6,7-dimethyl-1H-imidazo[4,5-c]pyridin-4-amine, m.p. 107.3–108.2° C.

Analysis: Calculated for $C_{20}H_{26}N_4O_2$: % C, 67.77; % H, 7.39; % N, 15.81; Found: % C, 67.88; % H, 7.44; % N, 15.79. $^1$H NMR (300 MHz, DMSO-$d_6$) δ 7.22–7.31 (m, 3H), 7.14 (dd, J=9.4, 1.9 Hz, 2H), 5.81 (s, 2H), 4.67 (s, 2H), 4.57 (t, J=5.6 Hz, 2H), 4.42 (s, 2H), 3.76 (t, J=5.6 Hz, 2H), 3.47 (q, J=7.2 Hz, 2H), 2.34 (s, 3H), 2.30 (s, 3H), 1.12 (t, J=7.2 Hz, 3H)

EXAMPLE 5

1-[2-(Benzyloxy)ethyl]-2,6,7-trimethyl-1H-imidazo[4,5-c]pyridin-4-amine

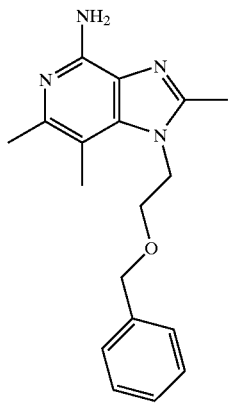

Part A

1-[2-(benzyloxy)ethyl]-2,6,7-trimethyl-4-phenoxy-1H-imidazo[4,5-c]pyridine $N^4$-[2-(Benzyloxy)ethyl]-5,6-dimethyl-2-phenoxypyridin-3,4-amine (5.3 g, 14.582 mmol) from Part E of Example 4, anhydrous toluene (50 mL), pyridine hydrochloride (0.034 g, 0.2916 mmol), and triethyl orthoacetate (4.00 mL, 21.873 mmol) were combined with stirring under nitrogen. After the resulting solution was heated to 90° C. (gentle reflux) for 1 hour, the reaction was complete. The reaction solution was concentrated under reduced pressure, and the resulting oil was dissolved in ethyl acetate. The ethyl acetate solution was washed with water (3x) and brine (2x), dried with magnesium sulfate, filtered, and concentrated under reduced pressure. The resulting solid was triturated with diethyl ether, filtered off, and dried to provide 5.113 g of pure white product, which was used in the next step.

Part B

1-[2-(benzyloxy)ethyl]-2,6,7-trimethyl-1H-imidazo[4,5-c]pyridin-4-amine

1-[2-(Benzyloxy)ethyl]-2,6,7-trimethyl-4-phenoxy-1H-imidazo[4,5-c]pyridine (5.113 g, 13.195 mmol) from Part A and ammonium acetate (51 g) were combined in a dried glass pressure flask under nitrogen. The flask was sealed and heated to 150° C. for 46 hours. The reaction was complete, and the resulting solution was cooled and basified to a pH of about 12 with 1 N potassium hydroxide. The basic solution was extracted with dichloromethane (3x), and the organic layers were combined, washed with water (3x) and brine (3x), dried with magnesium sulfate, filtered, and concentrated under reduced pressure. The resulting oil was triturated with diethyl ether, and the resulting solids were filtered off. NMR analysis of the solids indicated residual phenol. The solids were dissolved in ethyl acetate. The ethyl acetate solution was washed with 1 N potassium hydroxide (4x), water (3x) and brine (3x), dried with magnesium sulfate, filtered, and concentrated under reduced pressure. The resulting oil was diluted with diethyl ether, and after several hours the resulting crystals were filtered off and rinsed with diethyl ether. The resulting solids, which by NMR analysis were free of the phenol, were dried at 60° C. for 17 hours under high vacuum to provide 2.2515 g of 1-[2-(benzyloxy)ethyl]-2,6,7-trimethyl-1H-imidazo[4,5-c]pyridin-4-amine, m.p. 136.8–137.5° C.

Analysis: Calculated for $C_{18}H_{22}N_4O$: % C, 69.65; % H, 7.14; % N, 18.05; Found: % C, 69.71; % H, 7.06; % N, 18.03. $^1$H NMR (300 MHz, DMSO-$d_6$) δ 7.24–7.31 (m, 3H), 7.15 (dd, J=9.4, 1.9 Hz, 2H), 5.61 (s, 2H), 4.45 (t, J=5.3 Hz, 2H), 4.42 (s, 2H), 3.73 (t, J=5.3 Hz, 2H), 2.47 (s, 3H), 2.32 (s, 3H), 2.29 (s, 3H)

EXAMPLE 6

1-[2-(Benzyloxy)ethyl]-6,7-dimethyl-2-propyl-1H-imidazo[4,5-c]pyridin-4-amine

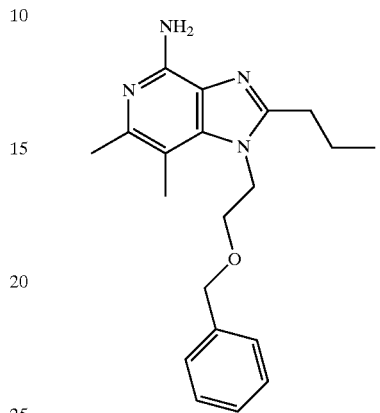

Part A

1-[2-(benzyloxy)ethyl]-6,7-dimethyl-4-phenoxy-2-propyl-1H-imidazo[4,5-c]pyridine Pyridine hydrochloride (0.04 g, 0.380 mmol), and trimethyl orthobutyrate (4.6 mL, 28.48 mmol) were added to a stirred solution of $N^4$-[2-(benzyloxy)ethyl]-5,6-dimethyl-2-phenoxypryridine-3,4-diamine (6.9 g, 18.984 mmol) prepared as in Part E of Example 4 in toluene (65 mL). After the resulting solution was heated to reflux for 2 hours, the reaction was complete as determined by TLC (using 1/1 hexane/ethyl acetate), HPLC, and LC/MS. The reaction solution was then concentrated under reduced pressure, and the resulting oil was dissolved in ethyl acetate. The ethyl acetate solution was washed with brine (3x), dried with magnesium sulfate, filtered, and concentrated under reduced pressure. The resulting tan solids were triturated with diethyl ether, filtered off, and dried to provide 6.5862 g of pure product (by NMR and LC/MS), which was used in the next step.

Part B

1-[2-(benzyloxy)ethyl]-6,7-dimethyl-2-propyl-1H-imidazo[4,5-c]pyridin-4-amine

1-[2-(Benzyloxy)ethyl]-6,7-dimethyl-4-phenoxy-2-propyl-1H-imidazo[4,5-c]pyridine (6.6 g, 15.8 mmol) and ammonium acetate (66 g) were combined in a dried glass pressure flask under nitrogen with stirring. The flask was sealed with a teflon screw cap and heated to 156° C. for 44 hours. The reaction was complete as determined by HPLC and LC/MS, and the resulting solution was cooled and basified to a pH of about 14 with 1 N potassium hydroxide. The basic solution was extracted with dichloromethane (5x), and the organic layers were combined, washed with 1 N potassium hydroxide (3x), water (1x) and brine (3x), dried with magnesium sulfate, filtered, and concentrated under reduced pressure. The resulting residue was triturated with ethyl acetate/diethyl ether, and the resulting solids were filtered off and dried. NMR analysis of the solids indicated impurities. The solids were recrystallized from isopropyl alcohol and dried. Impurities were found in the resulting solids (3.2982 g), which were then recrystallized from ethyl acetate/hexane and again dried. The resulting solids (2.4076 g), still with impurities, were dissolved in ethanol, and the resulting solution was treated with 1 M hydrochloric acid in diethyl ether (10 mL). The resulting hydrochloride salt was filtered off, dissolved in water, and the aqueous solution was basified with 1N potassium hydroxide to a pH of about 14. The resulting aqueous mixture was extracted with dichloromethane (5×), and the combined organic layers were washed with water (3×) and brine (3×), dried with magnesium sulfate, filtered, and concentrated under reduced pressure. The resulting white solid was dried to provide 1.5999 g of 1-[2-(benzyloxy)ethyl]-6,7-dimethyl-2-propyl-1H-imidazo[4,5-c]pyridin-4-amine, m.p. 99.5–100.0° C.

Analysis: Calculated for $C_{20}H_{26}N_4O$: % C, 70.98; % H, 7.74; % N, 16.55; Found: % C, 70.79; % H, 7.71; % N, 16.80. $^1$H NMR (300 MHz, DMSO-$d_6$) δ 7.24–7.31 (m, 3H), 7.14 (dd, J=9.4, 2.3 Hz, 2H), 5.60 (s, 2H), 4.46 (t, J=5.6 Hz, 2H), 4.41 (s, 2H), 3.71 (t, J=5.3 Hz, 2H), 2.78 (t, J=7.5 Hz, 2H), 2.32 (s, 3H), 2.29 (s, 3H), 1.76 (sextet, J=7.5 Hz, 2H), 0.95 (t, J=7.2 Hz, 3H)

EXAMPLE 7

2,6,7-Trimethyl-1-{2-[(3-phenylprop-2-ynyl)oxy]ethyl}-1H-imidazo[4,5-c]pyridin-4-amine

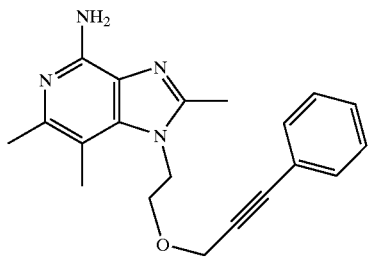

Part A
3-Bromo-1-phenylpropyne

3-Phenyl-2-propyn-1-ol (5 g, 37.83 mmol), anyhdrous diethyl ether (10 mL), and anhydrous pyridine (0.76 mL) were combined with stirring under nitrogen. To the resulting reaction mixture cooled to about 7° C. with an ice bath was added dropwise over 20 minutes a solution of phosphorous tribromide (1.8 mL (18.92 mmol) in anhydrous diethyl ether (20 mL). The ice bath was then removed, and the solution was stirred at room temperature for 2 hours. The reaction was complete, and the resulting reaction mixture was diluted with ice water. The organic layer was separated, and the aqueous layer was washed with diethyl ether (3×). The combined organic layers were washed with water (2×), saturated aqueous sodium bicarbonate (2×), and brine (2×), dried with magnesium sulfate, diluted with 8/2 hexane/ethyl acetate (100 mL), filtered through silica, and concentrated under reduced pressure. The resulting oil was filtered through silica with a dichloromethane rinse. The filtrate was concentrated under reduced pressure to provide a slightly cloudy oil (7.22 g). 3-Bromo-1-phenylpropyne was confirmed by NMR analysis.

Part B
1-[(2-Chloro-5,6-dimethyl-3-nitropyridin-4-yl)amino]ethan-2-ol 2,4-Dichloro-5,6-dimethyl-3-nitropyridine (60 g, 271.4 mmol), anhydrous N,N-dimethylformamide (900 mL), ethanolamine (19.6 mL, 325.8 mmol), and anhydrous triethylamine (45.4 mL, 325.8 mmol) were combined with stirring under nitrogen. The reaction mixture was held at 40° C. for 17 hours when TLC and HPLC monitoring indicated complete reaction with no starting material present. The resulting reaction mixture was concentrated under reduced pressure, the resulting yellowish orange solids were triturated with water (3×1 L), filtered off, and dried by dissolving the solids in methanol/diethyl ether, followed by removal of the solvents under reduced pressure. The resulting solids were slurried in diethyl ether, followed by removal of the diethyl ether under reduced pressure. After repeating the slurrying and solvent removal several times, the resulting solid was dried at 85° C. for 16 hours under high vacuum to provide 55.2 g of yellow solid, which was carried on to the next step. NMR analysis confirmed 1-[(2-chloro-5,6-dimethyl-3-nitropyridin-4-yl)amino]ethan-2-ol.

Part C
1-[(2,3-Dimethyl-5-nitro-6-phenoxypyridin-4-yl)amino]ethan-2-ol

A solution of phenol (94 g, 998.9 mmol) in diglyme (200 mL) was added slowly over 45 minutes to a solution of sodium hydride (38.06 g, 951.5 mmol, 60% in mineral oil) in diglyme (100 mL) cooled to 4° C. with an ice bath. Hydrogen gas evolved, and the temperature increased to a maximum of 34° C., but was immediately reduced by slowing the rate of phenol addition. After addition was complete, the reaction mixture was stirred for 1 hour. About 200 mL of the resulting clear solution was removed and set aside. The ice bath was removed, and 1-[(2-chloro-5,6-dimethyl-3-nitropyridin-4-yl)amino]ethan-2-ol (55.2 g, 224.69 mmol) dissolved in diglyme (400 mL) was added to the clear reaction solution under nitrogen. The flask from which the starting material was transferred was rinsed with diglyme (2×100 mL), and the rinsings were added to the resulting reaction mixture. This reaction mixture was heated to 110° C. for 4 hours under a flow of nitrogen, and then the resulting reaction mixture was concentrated under reduced pressure. The resulting oil was cooled to about 5° C. for 2 days, triturated with hexane, and passed through a silica gel column using 8/2 hexane/ethyl acetate, then 7/3 hexane/ethyl acetate, and ending with 6/4 hexane ethyl acetate over 3 days. A first 10.5 g fraction of impure product and a second 3.9 g fraction of pure product were isolated. The first fraction (9.6510 g) was dissolved in ethyl acetate/hexane and the product allowed to crystallize. The crystals were filtered off and dried to provide 9.6510 g of product, which was combined with the previous 3.9 g of pure product and carried on to the next step.

Part D
1-[(2,3-Dimethyl-5-nitro-6-phenoxypyridin-4-yl)amino]eth-2-yl Acetate

1-[(2,3-Dimethyl-5-nitro-6-phenoxypyridin-4-yl)amino]ethan-2-ol (13.55 g, 44.67 mmol), anhydrous dichloromethane (150 mL), pyridine (21.7 mL), and dimethylaminopyridine (0.11 g) were combined, and then acetic anhydried was added under nitrogen. The resulting solution was stirred at room temperature for 30 minutes. The reaction was complete, and the reaction solution was concentrated under reduced pressure. The resulting oil was dissolved in dichloromethane, and the dichloromethane solution was washed with 4% sodium bicarbonate (3×), water (3×), and brine (3×), dried with magnesium sulfate, filtered, and concentrated under reduced pressure. The resulting yellow solid was triturated with diethyl ether, and the solids were filtered off and dried to provide 11.5 g of product. The 1-[(2,3-Dimethyl-5-nitro-6-phenoxypyridin-4-yl)amino]eth-2-yl acetate structure was confirmed by NMR and its molecular weight was confirmed by LC/MS.

Part E

1-[(3-Amino-5,6-dimethyl-2-phenoxypyridin-4-yl)amino]eth-2-yl Acetate

1-[(2,3-Dimethyl-5-nitro-6-phenoxypyridin-4-yl)amino]eth-2-yl acetate (11.5 g, 33.30 mmol) was combined with 5% platinum on carbon (5.0 g) in a Parr flask. Toluene was added to the flask (120 mL) and the resulting mixture was pressurized with hydrogen at 310 kPa at room temperature for 1.6 hours. The reaction was complete as determined by LC/MS and HPLC. The resulting reaction mixture was filtered through Celite™ filter agent, and the filter cake was rinsed with more toluene. The volatiles were removed under reduced pressure, and the resulting oil was carried on to the next step.

Part F

1-[2,6,7-Trimethyl-4-phenoxy-1H-imidazo[4,5-c]pyridin-1-yl]eth-2-yl Acetate

1-[(3-Amino-5,6-dimethyl-2-phenoxypyridin-4-yl)amino]eth-2-yl acetate (10.5 g, 33.29 mmol), toluene (100 mL), pyridine hydrochloride (0.077 g, 0.6659 mmol), and triethyl orthoacetate (9.1 mL, 49.94 mmol) were combined with stirring and the resulting mixture was heated to a gentle reflux (about 95° C.) for 1.5 hours. The reaction was complete. The resulting reaction mixture was concentrated under reduced pressure to white solids, which were dissolved in ethyl acetate. The ethyl acetate solution was washed with water (3×) and brine (2×), dried with magnesium sulfate, filtered, and concentrated under reduced pressure. The resulting solid was triturated with diethyl ether, filtered off, and dried at 60° C. overnight to provide 11 g of pure product, which was carried on to the next step.

Part G

1-[2,6,7-Trimethyl-4-phenoxy-1H-imidazo[4,5-c]pyridin-1-yl]ethan-2-ol

1-[2,6,7-Trimethyl-4-phenoxy-1H-imidazo[4,5-c]pyridin-1-yl]eth-2-yl acetate (11.1 g, 33.0 mmol), methanol (250 mL), and potassium carbonate (1.14 g, 8.25 mmol) were combined with stirring and heated to 45° C. under nitrogen. The reaction was complete after 30 minutes, and the reaction mixture was concentrated under reduced pressure to a solid, which was dissolved in dichloromethane. The resulting solution was subjected to flash chromatography using 9/1 dichloromethane/methanol. A white solid was isolated and dried to provide 9.1 g of product.

Part H

1-[2,6,7-Trimethyl-4-phenoxy-1H-imidazo[4,5-c]pyridin-1-yl]eth-2-yl (3-Phenylprop-2-ynyl) Ether Sodium hydride (0.82 g, 20.48 mmol, 60% in mineral oil) and anhydrous N,N-dimethylformamide (20 mL) were combined and stirred for 5 minutes under nitrogen. A solution of 1-[2,6,7-trimethyl-4-phenoxy-1H-imidazo[4,5-c]pyridin-1-yl]ethan-2-ol (5.8 g, 19.50 mmol) from Part G in N,N-dimethylformamide (30 mL) was then added to the sodium hydride over 5 minutes. After stirring the resulting reaction solution for 10 minutes at room temperature, a solution of 3-bromo-1-phenylpropyne (4.18 g, 21.45 mmol) from Part A in N,N-dimethylformamide (15 mL) was added to the reaction solution, and the resulting reaction mixture was stirred for 4 hours and 10 minutes. Sodium hydride (0.10 g, 60% in mineral oil) and then 3-bromo-1-phenylpropyne (1 g) were added to the reaction mixture, and after stirring for 30 minutes, HPLC monitoring of the reaction mixture indicated about 7% starting material remaining. The reaction mixture was concentrated under reduced pressure, and the resulting oil was dissolved in dichloromethane. The dichloromethane solution was washed with saturated ammonium chloride (3×), water (3×), and brine (3×), dried with magnesium sulfate, filtered, and concentrated under reduced pressure to a brown solid, which was triturated with diethyl ether. The resulting solid was filtered off, and a second crop was collected from the mother liquor. The combined solids were passed through a column of silica (120 g, 40×200 mm) using 95/5 ethyl acetate/dichloromethane. A white solid (5.4 g) was isolated and carried on to the next step. HPLC analysis indicated the presence of about 9% starting material in the white solid.

Part I 2,6,7-Trimethyl-1-{2-[(3-phenylprop-2-ynyl)oxy]ethyl}-1H-imidazo[4,5-c]pyridin-4-amine 1-[2,6,7-Trimethyl-4-phenoxy-1H-imidazo[4,5-c]pyridin-1-yl]eth-2-yl (3-phenylprop-2-ynyl) ether (5.4 g, 13.122 mmol) from Part H and ammonium acetate (54 g) were combined in a glass pressure vessel. The vessel was sealed with a teflon screw cap, and the reaction mixture was heated to 150° C. for 45 hours. The reaction was essentially complete, and the resulting reaction solution was cooled with an ice bath, acidified to a pH of 1 with 10% hydrochloric acid, and washed with dichloromethane (3×500 mL). The combined organic portions were washed with 10% hydrochloric acid (4×). The acidic aqueous portions were combined, basified with potassium hydroxide pellets to a pH of 14. The resulting brown solids were filtered off and recrystallized from methanol. A first crop of 0.6 g was collected for use in Example 5, and a second crop was collected and found to contain about 2% of the 4-hydroxy compound by NMR analysis. The second crop was returned to the mother liquor, and dichloromethane was added until all solids were dissolved. 1M Hydrochloric acid in diethyl ether (20 mL) was added to the resulting solution, and the solids that formed were filtered off, and dissolved in water, which was basified to a pH of 14 with potassium hydroxide pellets. The resulting solution was washed with dichloromethane (3×). The organic portions were combined, washed with water (2×) and brine (2×), dried with magnesium sulfate, filtered, and concentrated under reduced pressure. The resulting white solid (1.8 g) was dissolved in dichloromethane (150 mL), and 1M hydrochloric acid in diethyl ether (5.3 mL) was added to the resulting solution. The acidified solution was concentrated under reduced pressure. The resulting solids were dissolved in water, and this aqueous solution was filtered to remove an oily sludge. The filtrate was basified with a few drops of 20% potassium hydroxide and then 1N potassium hydroxide to a pH of 13. The fine white precipitate that formed was filtered off, rinsed with diethyl ether, and dried under vacuum for 18 hours to provide 1.8064 g of 2,6,7-trimethyl-1-{2-[(3-phenylprop-2-ynyl)oxy]ethyl}-1H-imidazo[4,5-c]pyridin-4-amine, m.p. 186.8–187.5° C.

Analysis: Calculated for $C_{20}H_{22}N_4O$: % C, 71.83; % H, 6.63; % N, 16.75; Found: % C, 71.51; % H, 6.50; % N, 16.71. $^1$H NMR (300 MHz, DMSO-$d_6$) 67 7.32–7.40 (m, 5H), 5.61 (s, 2H), 4.47 (t, J=5.3 Hz, 2H), 4.36 (s, 2H), 3.83 (t, J=5.6 Hz, 2H), 2.50 (s, 3H), 2.36 (s, 3H), 2.28 (s, 3H)

EXAMPLE 8

2,6,7-Trimethyl-1-[2-(3-phenylpropoxy)ethyl]-1H-imidazo[4,5-c]pyridin-4-amine

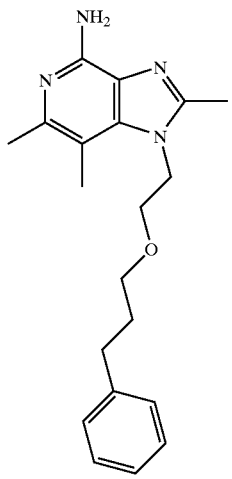

2,6,7-Trimethyl-1-{2-[(3-phenylprop-2-ynyl)oxy]ethyl}-1H-imidazo[4,5-c]pyridin-4-amine (0.55 g, 1.645 mmol) from Part I of Example 7 was combined with 10% palladium on carbon (0.10 g) in a Parr reactor. Methanol (30 mL) was added to the resulting mixture under a nitrogen purge, and then the mixture was placed under hydrogen at a pressure of 310 kPa for 4 hours. The resulting reaction mixture was filtered through a layer of Celite™ filter agent, and the filtrate was concentrated under reduced pressure to a clear oil. The oil was dissolved in 5% methanol in diethyl ether (~50 mL), and 1M hydrochloric acid in diethyl ether (1.7 mL) was added to the resulting solution. Volatiles were removed under reduced pressure, and the resulting solids were dissolved in water. The aqueous solution was stirred for 10 minutes when the product oiled out of solution. The aqueous portion was washed with dichloromethane (3×). The combined organic portions were washed with water (2×) and brine (3×), dried with magnesium sulfate, filtered, and concentrated to a glassy oil under reduced pressure. The oil was triturated with diethyl ether. The solids that formed after 10 minutes of stirring were filtered off and dried for 18 hours to provide 0.3185 g of 2,6,7-trimethyl-1-[2-(3-phenylpropoxy)ethyl]-1H-imidazo[4,5-c]pyridin-4-amine, m.p. 118.1–119.0° C.

Analysis: Calculated for $C_{20}H_{26}N_4O$: % C, 70.98; % H, 7.74; % N, 16.55; Found: % C, 70.72; % H, 7.77; % N, 16.65. $^1$H NMR (300 MHz, DMSO-$d_6$) δ 7.09–7.22 (m, 3H), 6.99 (d, J=8.1 Hz, 2H), 5.66 (s, 2H), 4.43 (t, J=5.3 Hz, 2H), 3.64 (t, J=5.3 Hz, 2H), 3.27 (t, J=6.2 Hz, 2H), 2.51 (s, 3H), 2.45 (t, J=7.8 Hz, 2H), 2.36 (s, 3H), 2.31 (s, 3H), 1.68 (p, J=7.0 Hz, 2H)

EXAMPLE 9

2,6,7-Trimethyl-1-(2-{[(2E)-3-phenylprop-2-enyl]oxy}ethyl)-1H-imidazo[4,5-c]pyridin-4-amine

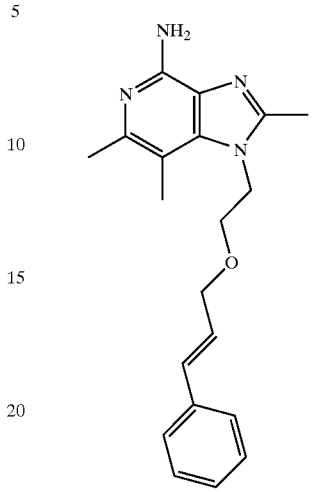

Part A
1-[2,6,7-Trimethyl-4-phenoxy-1H-imidazo[4,5-c]pyridin-1-yl]eth-2-yl [(2E)-3-Phenylprop-2-enyl]Ether Sodium hydride (0.41 g, 10.24 mmol, 60% in mineral oil) and anhydrous N,N-dimethylformamide (10 mL) were combined and stirred for 5 minutes under nitrogen. A solution of 1-[2,6,7-trimethyl-4-phenoxy-1H-imidazo[4,5-c]pyridin-1-yl]ethan-2-ol (2.9 g, 9.752 mmol) from Part G of Example 7 in N,N-dimethylformamide (15 mL) was then added to the sodium hydride over 5 minutes. After stirring the resulting reaction solution for 10 minutes at room temperature, a solution of cinnamyl bromide (2.11 g, 10.73 mmol) in N,N-dimethylformamide (15 mL) was added to the reaction solution, and the resulting reaction mixture was stirred for 4 hours and 10 minutes. Sodium hydride (0.10 g, 60% in mineral oil) and then cinnamyl bromide (0.1 g) were added to the reaction mixture, and after stirring for 30 minutes, HPLC monitoring of the reaction mixture indicated about 9% starting material remaining. The reaction mixture was concentrated under reduced pressure, and the resulting oil was dissolved in dichloromethane. The dichloromethane solution was washed with saturated ammonium chloride (3×), water (3×), and brine (3×), dried with magnesium sulfate, filtered, and concentrated under reduced pressure to a white solid, which contained about 6% starting material by HPLC analysis. The white solid was passed through a column of silica (120 g, 40×200 mm) using 95/5 ethyl acetate/dichloromethane. The isolated product was triturated with diethyl ether, filtered off, and dried to provide 2.9 g of product with no starting material. This was carried on to the next step.

Part B
2,6,7-Trimethyl-1-(2-{[(2E)-3-phenylprop-2-enyl]oxy}ethyl)-1H-imidazo[4,5-c]pyridin-4-amine 1-[2,6,7-Trimethyl-4-phenoxy-1H-imidazo[4,5-c]pyridin-1-yl]eth-2-yl [(2E)-3-phenylprop-2-enyl]ether (2.9 g, 7.013 mmol) from Part A and ammonium acetate (54 g) were combined in a glass pressure vessel. The vessel was sealed with a teflon screw cap, and the reaction mixture was heated to 150° C. for 45 hours. The reaction was complete, and the resulting reaction solution was cooled with an ice bath, basified to a pH of about 13 with 1N potassium hydroxide, and washed with dichloromethane (4×500 mL).

The combined organic portions were washed with water (3x) and brine (3x), dried with magnesium sulfate, filtered, and concentrated under reduced pressure to a white solid. The resulting white solid was slowly passed through a column containing 200 g silica that had been heated with 1% diethyl ether in dichloromethane using 98/2 dichloromethane/methanol. Two crops of product were isolated from the eluted solution, and both were recrystallized from isopropyl alcohol. The resulting white powder was dried under vacuum for 18 hours to provide 0.7479 g of 2,6,7-trimethyl-1-(2-{[(2E)-3-phenylprop-2-enyl]oxy}ethyl)-1H-imidazo[4,5-c]pyridin-4-amine, m.p. 143.7–144.8° C.

Analysis: Calculated for $C_{20}H_{24}N_4O$: % C, 71.40; % H, 7.19; % N, 16.65; Found: % C, 71.36; % H, 7.10; % N, 16.74. $^1$H NMR (300 MHz, DMSO-$d_6$) δ 7.30–7.33 (m, 4H), 7.20–7.25 (m, 1H), 6.37 (d, J=16.2 Hz, 1H), 6.20 (dt, J=16.2, 5.3 Hz, 1H), 5.62 (s, 2H), 4.46 (t, J=5.3 Hz, 2H), 4.05 (dd, J=6.2, 1.2 Hz, 2H), 3.74 (t, J=5.3 Hz, 2H), 2.51 (s, 3H), 2.36 (s, 3H), 2.28 (s, 3H)

EXAMPLE 10

2,6,7-Trimethyl-1-[2-(3-pyridin-3-ylpropoxy)ethyl]-1H-imidazo[4,5-c]pyridin-4-amine

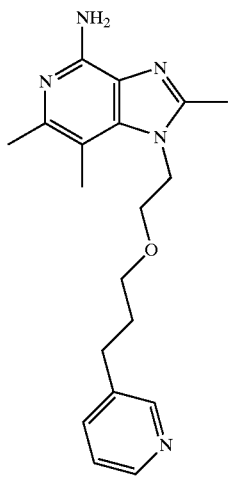

Part A
2-chloro-5,6-dimethyl-3-nitro-N-[2-(3-pyridin-3-ylpropoxy)ethyl]pyridin-4-amine Anhydrous N,N-dimethylformamide (200 ml), anhydrous triethylamine (12.1 ml), and 2,4-dichloro-5,6-dimethyl-3-nitropyridine (16.05 g) were combined and 2-(3-pyridin-3-ylpropoxy)ethylamine (14.4 g) was then added with stirring. The pale yellow reaction mixture was heated to 45° C. under a nitrogen atmosphere for 1 hour. HPLC analysis indicated that the reaction was sufficiently complete to proceed. The reaction mixture was allowed to cool and the solvent was removed under reduced pressure. The resulting oil was dissolved in ethyl acetate and washed twice: once with a saturated aqueous solution of ammonium chloride and once with water. The organic layer was then extracted 3 times with brine, dried with magnesium sulfate, and concentrated under reduced pressure. The product was passed through a silica gel column using 90/10 ethyl acetate/hexane as the eluant. The resulting oil was dried under vacuum at 60° C. for 2 hours. NMR analysis indicated sufficient purity for use of the product in the next step.

Part B
2,3-dimethyl-5-nitro-6-phenoxy-N-[2-(3-pyridin-3-ylpropoxy)ethyl]pyridin-4-amine 2-Methoxyethyl ether (diglyme) (50 ml) and sodium hydride (60% in oil) (5.77 g) were combined. Under a nitrogen atmosphere, a solution of phenol (13.58 g) and diglyme (250 ml) was added slowly over 10 minutes to allow for controlled gas evolution. 2-chloro-5,6-dimethyl-3-nitro-N-[2-(3-pyridin-3-ylpropoxy)ethyl]pyridin-4-amine (35.1 g) from Part A was then added and the reaction mixture was heated to 90° C. After 1.25 hours, the reaction mixture clouded and the temperature was increased to 110° C. After an additional 3.75 hours, HPLC and TLC analysis indicated the reaction was complete. The reaction mixture was cooled and the solvent was removed under reduced pressure. The resulting oil was dissolved in ethyl acetate and washed once with 20% potassium hydroxide, once with 1N potassium hydroxide, 3 times with water, and 3 times with brine. The combined organic layers were dried with magnesium sulfate and concentrated under reduced pressure. The residue was purified by flash chromatography over silica, eluting with 90/10 ethyl acetate/hexane. The fractions containing purified product were concentrated under reduced pressure and dried under vacuum at 70° C. overnight. NMR analysis of the resulting yellow oil indicated sufficient purity for use of the product in the next step.

Part C
5,6-dimethyl-2-phenoxy-$N^4$-[2-(3-pyridin-3-ylpropoxy)ethyl]pyridine-3,4-diamine Under a nitrogen atmosphere, a solution of 2,3-dimethyl-5-nitro-6-phenoxy-N-[2-(3-pyridin-3-ylpropoxy)ethyl]pyridin-4-amine (27.1 g) in toluene (300 ml) was added to a Parr hydrogenation flask containing 5% platinum on carbon (10 g). After 4 hours at a hydrogen pressure of 207 kPa, the reaction was judged complete by HPLC and TLC analysis. The molecular weight and structure of the product were confirmed by LC/MS and NMR analysis, respectively. The reaction mixture was filtered through filter paper, Celite™, and magnesium sulfate. The filtrate was used in the next step.

Part D
2,6,7-trimethyl-4-phenoxy-1-[2-(3-pyridin-3-ylpropoxy)ethyl]-1H-imidazo[4,5-c]pyridine A solution of 5,6-dimethyl-2-phenoxy-$N^4$-[2-(3-pyridin-3-ylpropoxy)ethyl]pyridine-3,4-diamine (12 g) in toluene (300 ml) from Part C was combined with pyridine HCl (0.08 g) and triethyl orthoacetate (8.4 ml). Under a nitrogen atmosphere, the reaction mixture was heated to reflux (99° C.) for 1.5 hours. TLC and HPLC analysis indicated that the reaction was complete. The solvent was removed under reduced pressure. The resulting yellow oil was dissolved in dichloromethane and washed once with saturated potassium carbonate, 3 times with water, and 3 times with brine. The combined organic layers were dried with magnesium sulfate and concentrated under reduced pressure. The resulting yellow oil darkened slightly after being dried under vacuum at 70° C. overnight. The product was purified by column chromatography over silica using 95/5 ethyl acetate/methanol as the eluant. The product was dried and then triturated with diethyl ether to yield a white solid that was dried under vacuum at 80° C. overnight. NMR analysis of the dried solid indicated a pure product.

Part E 2,6,7-trimethyl-1-[2-(3-pyridin-3-ylpropoxy)ethyl]-1H-imidazo[4,5-c]pyridin-4-amine Under a nitrogen atmosphere, 2,6,7-trimethyl-4-phenoxy-1-[2-(3-pyridin-3-ylpropoxy)ethyl]-1H-imidazo[4,5-c]pyridine (4 g) from Part D and ammonium acetate (40 g) were heated in a sealed tube to 150° C. After 46.5 hours, NMR analysis indicated that only 7% of the starting material remained. The reaction mixture was cooled to ambient temperature, diluted with ethyl acetate, and washed 3 times with 1N potassium hydroxide and once with water. The organic layers were dried with magnesium sulfate and concentrated under reduced pressure. The resulting oil was triturated with 90/10 diethyl ether/toluene and the filtered solids were dried under vacuum at 45° C. The pale yellow solid was dissolved in 10% hydrochloric acid and extracted 3 times with dichloromethane (DCM). Potassium hydroxide was added to the aqueous layer to bring the pH to 14, and this was subsequently washed 3 times with DCM. The combined organic layers were washed once with water, 3 times with brine, dried with magnesium sulfate, and concentrated under reduced pressure. The oil was purified by column chromatography over silica using 97/3 DCM/methanol as the eluant. The oil was then triturated with diethyl ether/toluene and the resulting solid was recrystallized from ethyl acetate/hexane to yield 2,6,7-trimethyl-1-[2-(3-pyridin-3-ylpropoxy)ethyl]-1H-imidazo[4,5-c]pyridin-4-amine, m.p. 108.6–109.5° C.

Analysis: Calculated for $C_{19}H_{25}N_5O$: % C, 65.49; % H, 7.52; % N, 20.10 Found: % C, 65.69; % H, 7.58; % N, 20.36. $^1$H NMR (300 MHz, DMSO-$d_6$) δ 8.36 (dd, J=6.2 , 4.7 Hz, 1H), 8.30 (d, J=1.9, 1H), 7.38 (dt, J=8.1, 1.9 Hz, 1H), 7.21 (dd, J=7.8, 4.7 Hz, 1H), 5.78 (s, 2H), 4.44 (t, J=5.3 Hz, 2H), 3.66 (t, J=5.3 Hz, 2H), 3.29 (t, J=6.2 Hz, 2H), 2.51 (s, 3H), 2.46 (t, J=8.1 Hz, 2H), 2.36 (s, 3H), 2.31 (s, 3H), 1.70 (p, J=7.0 Hz, 2H)

EXAMPLE 11

2-(Ethoxymethyl)-6,7-dimethyl-1-[2-(3-pyridin-3-ylpropoxy)ethyl]-1H-imidazo[4,5-c]pyridin-4-amine

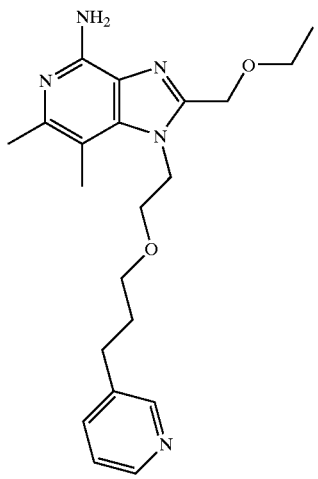

Part A 2-(ethoxymethyl)-6,7-dimethyl-4-phenoxy-1-[2-(3-pyridin-3-ylpropoxy)ethyl]-1H-imidazo[4,5-c]pyridine A solution of 5,6-dimethyl-2-phenoxy-$N^4$-[2-(3-pyridin-3-ylpropoxy)ethyl]pyridine-3,4-diamine (12 g) in toluene (300 ml) from Part C of Example 10 was concentrated under pressure to yield a pale yellow liquid. Under a nitrogen atmosphere, this product was combined with anhydrous pyridine (100 ml) and pyridine HCl (0.08 g) and the reaction mixture was cooled to 0° C. in an ice bath. Ethoxyacetyl chloride was added dropwise to the reaction mixture over 5 minutes, which induced the formation of a precipitate and changed the color of the solution from clear to pale yellow. After 30 minutes, TLC and HPLC analysis indicated the reaction was complete. The reaction mixture was gently heated to reflux (100° C.) for 17.5 hours under a nitrogen atmosphere. The mixture was allowed to cool and was then concentrated under reduced pressure. The oil was dissolved in ethyl acetate and washed once with saturated potassium carbonate, 3 times with water, and 3 times with brine. The brownish red organic layer was purified by column chromatography over silica using ethyl acetate as the eluant. The resulting oil was triturated with diethyl ether and dried to yield a white solid. NMR and LC/MS analysis indicated sufficient purity for use of the product in the next step.

Part B 2-(ethoxymethyl)-6,7-dimethyl-1-[2-(3-pyridin-3-ylpropoxy)ethyl]-1H-imidazo[4,5-c]pyridin-4-amine Under a nitrogen atmosphere, 2-(ethoxymethyl)-6,7-dimethyl-4-phenoxy-1-[2-(3-pyridin-3-ylpropoxy)ethyl]-1H-imidazo[4,5-c]pyridine (4.6 g) from Part A and ammonium acetate (46 g) were heated in a sealed tube to 150° C. After 65 hours, NMR analysis indicated that the reaction was complete. The reaction mixture was cooled to ambient temperature, dissolved in ethyl acetate, and washed 3 times with 1N potassium hydroxide and once with water. The organic layers were dried with magnesium sulfate and concentrated under reduced pressure. The resulting residue was dissolved in 10% hydrochloric acid and washed 3 times with dichloromethane (DCM). Potassium hydroxide was added to the aqueous layer to bring the pH to 14, and this was subsequently washed 4 times with DCM. The combined organic layers were washed twice with water, twice with brine, dried with magnesium sulfate, and concentrated under reduced pressure. The oil was purified by column chromatography over silica using 98/2 DCM/methanol as the eluant. The oil was then triturated with ethyl acetate/hexane and the resulting solid was recrystallized from ethyl acetate/hexane to yield 2-(ethoxymethyl)-6,7-dimethyl-1-[2-(3-pyridin-3-ylpropoxy)ethyl]-1H-imidazo[4,5-c]pyridin-4-amine as a white solid, m.p. 78.0 78.5° C.

Analysis: Calculated for $C_{21}H_{29}N_5O_2$: % C, 65.77; % H, 7.62; % N, 18.26 Found: % C, 65.74; % H, 7.83; % N, 18.31. $^1$H NMR (300 MHz, DMSO-$d_6$) δ 8.36 (dd, J=3.1, 1.9 Hz, 1H), 8.30 (d, J=1.9, 1H), 7.39 (dt, J=8.1, 1.9 Hz, 1H), 7.22 (dd, J=7.5, 5.0 Hz, 1H), 5.81 (s, 2H), 4.70 (s, 2H), 4.55 (t, J=5.3 Hz, 2H), 3.69 (t, J=5.6 Hz, 2H), 3.50 (q, J=6.8 Hz, 2H), 3.30 (t, J=5.9 Hz, 2H), 2.46 (t, J=7.8 Hz, 2H), 2.39 (s, 3H), 2.31 (s, 3H), 1.70 (q, J=6.9 Hz, 2H), 1.13 (t, J=6.9 Hz, 3H)

EXAMPLE 12

2,6,7-Trimethyl-1-[5-(methylthio)pentyl]-1H-imidazo[4,5-c]pyridin-4-amine

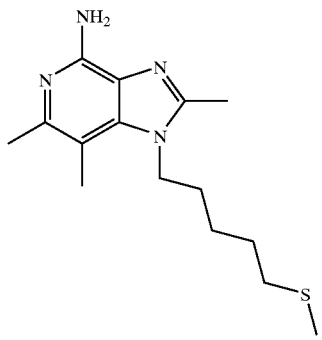

Part A

A mixture of 2,4-dihydroxy-5,6-dimethyl-3-nitropyridine (245 g, 1.33 mol) and phosphorous oxychloride (2.2 L) was heated at 85° C. overnight. The bulk of the phosphorous oxychloride (1.75 L) was removed under reduced pressure to provide a black oil. The oil was poured into water (2.5 L) and the mixture was cooled in an ice bath to 5° C. The resulting tan precipitate was isolated by filtration, dissolved in dichloromethane (~3 L) and filtered to remove some black solids. The filtrate was washed with 10% sodium carbonate and brine, dried over magnesium sulfate and then concentrated under reduced pressure to provide 272 g of a light tan solid. This solid was recrystallized from heptane (2.5 mL/g) to provide 248 g of 2,4-dichloro-5,6-dimethyl-3-nitropyridine as large amber rods.

Part B

A solution of 5-amino-1-pentanol (28.03 g, 271.4 mmol) in N,N-dimethylformamide (200 mL) was added over a period of 45 minutes to a solution of 2,4-dichloro-5,6-dimethyl-3-nitropyridine (60.01 g, 271.4 mmol) in N,N-dimethylformamide. The reaction was stirred overnight and then the N,N-dimethylformamide was removed by vacuum distillation. The residue was dissolved in ethyl acetate (500 mL), washed with water (4×75 mL), dried over magnesium sulfate and then concentrated under reduced pressure. The crude product was dissolved in hot ethyl acetate (400 mL). Hexane was added until a clear solution was obtained then the mixture was allowed to cool to ambient temperature. The resulting precipitate was isolated by filtration and washed with cold hexane to provide 26. 87 g of 5-[(2-chloro-5,6-dimethyl-3-nitropyridin-4-yl)amino]pentan-1-ol as a solid. An additional 4.41 g was isolated from the filtrate.

Part C

Sodium hydride (6.63 g of 60%, 166 mmol) was added to chilled (0° C.) anhydrous tetrahydrofuran (200 mL) and the mixture was allowed to stir for 15 minutes. A solution of phenol (15.07 g, 160 mmol) in tetrahydrofuran (150 mL) was added dropwise over a period of 1 hour. A solution of 5-[(2-chloro-5,6-dimethyl-3-nitropyridin-4-yl)amino]pentan-1-ol (31.723 g, 110 mmol) in tetrahydrofuran (150 mL) was added dropwise over a period of 30 minutes while maintaining the reaction temperature at 0° C. The reaction mixture was allowed to warm to ambient temperature and then it was heated at reflux overnight. Analysis by thin layer chromatography indicated that the reaction was 50–60% complete. An additional equivalent of phenoxide was prepared and added to the reaction mixture at ambient temperature; then the reaction mixture was heated at reflux overnight. The reaction mixture was concentrated under reduced pressure. The residue was dissolved in ethyl acetate (300 mL); washed sequentially with water (2×50 mL), 5% sodium hydroxide (2×50 mL)) and 1N sodium hydroxide (2×50 mL); dried over magnesium sulfate and then concentrated under reduced pressure. The residue was divided into two portions and purified by column chromatography (450 g of silica gel eluting with 1:1 hexanes:ethyl acetate to 1:3 hexanes:ethyl acetate) to provide 38.13 g of 5-[(2,3-dimethyl-5-nitro-6-phenoxypyridin-4-yl)amino]pentan-1-ol.

Part D

Thionyl chloride (10.72 mL, 147 mmol) was added dropwise to a mixture of 5-[(2,3-dimethyl-5-nitro-6-phenoxypyridin-4-yl)amino]pentan-1-ol (34.0 g, 98 mmol) and dichloromethane (250 mL). The reaction mixture was heated at reflux for 2 hours and then it was placed in an ice bath and quenched with water. The reaction mixture was concentrated under reduced pressure. The residue was combined with water (300 mL). Solid sodium bicarbonate was slowly added to pH 10; then the mixture was extracted with ethyl acetate (250 mL). The extract was washed sequentially with saturated sodium bicarbonate (2×100 mL) and brine (1×100 mL), dried over magnesium sulfate and then concentrated under reduced pressure to provide 30.96 g of N-(5-chloropentyl)-2,3-dimethyl-5-nitro-6-phenoxypyridin-4-amine.

Part E

A solution of N-(5-chloropentyl)-2,3-dimethyl-5-nitro-6-phenoxypyridin-4-amine (30.86 g, 85 mmol) in toluene (200 mL) was added to a Parr vessel containing a mixture of 5% platinum on carbon (25.24 g) and toluene (100 mL). The vessel was placed under hydrogen pressure (30 psi, $2.0 \times 10^5$ Pa) and allowed to shake overnight. The reaction mixture was filtered through a layer of Celite® filter aid. The filtrate was concentrated under reduced pressure to provide 24.97 g of $N^4$-(5-chloropentyl)-5,6-dimethyl-2-phenoxypyridine-3,4-diamine as a thick off white oil.

Part F

Pyridine hydrochloride (2 g) and trimethyl orthoacetate (10.5 mL, 82 mmol) were added to a solution of $N^4$-(5-chloropentyl)-5,6-dimethyl-2-phenoxypyridine-3,4-diamine (24.97 g, 75 mmol) in anhydrous tetrahydrofuran (200 mL). The reaction mixture was heated at reflux for 25 hours, cooled to ambient temperature and then concentrated under reduced pressure. The residue was dissolved in hot ethyl acetate, titrated with hexanes and then cooled. The resulting precipitate was isolated by filtration and then it was dissolved in ethyl acetate (300 mL), washed with water (2×100 mL) and with brine (1×100 mL), dried over magnesium sulfate and then concentrated under reduced pressure to provide 21.09 g of 1-(5-chloropentyl)-2,6,7-trimethyl-4-phenoxy-1H-imidazo[4,5-c]pyridine.

Part G

Sodium thiomethoxide (1.5 g, 21 mmol) was added to a solution of 1-(5-chloropentyl)-2,6,7-trimethyl-4-phenoxy-1H-imidazo[4,5-c]pyridine (7.00 g, 19 mmol) in anhydrous N,N-dimethylformamide (80 mL). The reaction mixture was stirred at ambient temperature for 1.5 hours, then it as quenched with water and extracted with ethyl acetate (250 mL). The extract was washed with water (5×50 mL), dried over magnesium sulfate and then concentrated under reduced pressure to provide 6.73 g of 2,6,7-trimethyl-1-[5-(methylthio)pentyl]-4-phenoxy-1H-imidazo[4,5-c]pyridine.

Part H

Ammonium acetate (25 g) and 2,6,7-trimethyl-1-[5-(methylthio)pentyl]-4-phenoxy-1H-imidazo[4,5-c]pyridine (2.75 g, 7.45 mmol) were combined and heated at 160° C. overnight. The reaction mixture was cooled to 0° C. and then diluted with water (50 mL). The pH was adjusted to >13 with 15% sodium hydroxide and then the mixture was extracted with chloroform (2×100 mL). The combined extracts were dried over magnesium sulfate and then concentrated under reduced pressure. The residue was purified on deactivated silica gel (triethylamine) eluting with 2% methanol in chloroform and then recrystallized from ethyl acetate/hexanes to provide 1.089 g of 2,6,7-trimethyl-1-[5-(methylthio)pentyl]-1H-imidazo[4,5-c]pyridin-4-amine as an off white solid, m.p. 121–122° C.

Analysis: Calculated for $C_{15}H_{24}N_4S$: % C, 61.61; % H, 8.27; % N, 19.16; Found: % C, 61.40; % H, 8.43; % N, 18.92.

EXAMPLE 13

2,6,7-Trimethyl-1-[5-(phenylthio)pentyl]-1H-imidazo[4,5-c]pyridin-4-amine

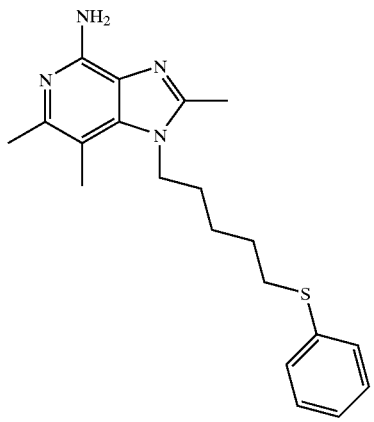

Part A

Benzenethiol (2.42 mL, 23.6 mmol) was added dropwise to a suspension of sodium hydride (0.944 g of 60%, 23.6 mmol) in anhydrous N,N-dimethylformamide (50 mL) and stirred until a clear solution was obtained. A solution of 1-(5-chloropentyl)-2,6,7-trimethyl-4-phenoxy-1H-imidazo[4,5-c]pyridine (6.5 g, 18.2 mmol) in anhydrous N,N-dimethylformamide (50 mL) was added dropwise. The reaction mixture was stirred at ambient temperature for 2 hours, then it was quenched with water and extracted with ethyl acetate (300 mL). The extract was washed with water (5×75 mL), dried over magnesium sulfate and then concentrated under reduced pressure to provide 7.20 g of 2,6,7-trimethyl-4-phenoxy-1-[5-(phenylthio)pentyl]-1H-imidazo[4,5-c]pyridine.

Part B

Ammonium acetate (25 g) and 2,6,7-trimethyl-4-phenoxy-1-[5-(phenylthio)pentyl]-1H-imidazo[4,5-c]pyridine (2.50 g, 5.80 mmol) were combined and heated at 160° C. in a sealed tube for 2 days. The reaction mixture was cooled to ambient temperature and diluted with water (100 mL). Sodium hydroxide (15%) was added and the mixture was extracted with chloroform (2×150 mL). The combined extracts were dried over magnesium sulfate and then concentrated under reduced pressure. The residue was purified by column chromatography (silica gel eluting with 2% methanol in dichloromethane) followed by recrystallization from methanol/dichloromethane/hexanes to provide 2,6,7-trimethyl-1-[5-(phenylthio)pentyl]-1H-imidazo[4,5-c]pyridin-4-amine as an off white powder, m.p. 181–183° C.

Analysis: Calculated for $C_{20}H_{26}N_4S$: % C, 67.76; % H, 7.39; % N, 15.8; Found: % C, 67.41; % H, 7.53; % N, 15.54.

EXAMPLE 14

1-[2-(2-Aminoethoxy)ethyl]-2,6,7-trimethyl-1H-imidazo[4,5-c]pyridin-4-amine

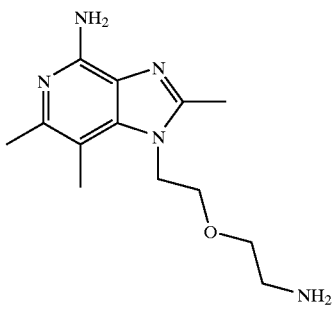

Part A

Under a nitrogen atmosphere, a solution of 2-(2-aminoethoxy)ethanol (27.8 mL, 277 mmol) in tetrahydrofuran (180 mL) was cooled to 0° C. Sodium hydroxide (140 mL of 2N) was added. A solution of di-tert-butyl dicarbonate (60.27 g, 277 mmol) in tetrahydrofuran (180 mL) was added dropwise over a period of 1 hour with rapid stirring. The reaction was allowed to warm to ambient temperature and stir overnight. The tetrahydrofuran was removed under reduced pressure. The pH of the resulting slurry was adjusted to ~3 by adding sulfuric acid (150 mL of 1M). The mixture was extracted with ethyl acetate (6×100 mL). The combined extracts were washed with water (2×100 mL) and brine (1×100 mL), dried over magnesium sulfate and then concentrated under reduced pressure to provide 48.53 g of tert-butyl 2-(2-hydroxyethoxy)ethylcarbamate as a colorless oil.

Part B

Under a nitrogen atmosphere, a solution of tert-butyl 2-(2-hydroxyethoxy)ethylcarbamate (48.53 g, 236 mmol) in anhydrous dichloromethane (1 L) was cooled to 0° C. Triethylamine (49.4 mL, 354 mmol)) was added. Methanesulfonyl chloride (20.10 mL, 260 mmol) was added dropwise over a period of 10 minutes. The reaction was allowed to warm to ambient temperature and stir overnight. The reaction was quenched with saturated sodium bicarbonate solution (500 mL). The organic layer was washed with water (3×500 mL) and brine (1×500 mL), dried over sodium sulfate and then concentrated under reduced pressure to provide 66.9 g of 2-{2-[(tert-butoxycarbonyl)amino]ethoxy}ethyl methanesulfonate as a brown oil.

Part C

Sodium azide (16.8 g, 259 mmol) was added to a solution of 2-t2-[(tert-butoxycarbonyl)amino]ethoxy}ethyl methanesulfonate (66.9 g, 236 mmol) in N,N-dimethylformamide (400 mL). The reaction was heated at 90° C. for 1.5 hours. The reaction mixture was allowed to cool to ambient temperature, diluted with cold water (500 mL) and then extracted with diethyl ether (4×300 mL). The combined extracts were washed with water (4×100 mL) and brine (1×200 mL), dried over magnesium sulfate and then concentrated under reduced pressure to provide 52 g of tert-butyl 2-(2-azidoethoxy)ethylcarbamate.

Part D

A solution of tert-butyl 2-(2-azidoethoxy)ethylcarbamate (52 g, 226 mmol) in methanol (500 mL) was added to a Parr vessel containing 10% palladium on carbon (4 g) which had been wetted with toluene (30 mL). The mixture was placed under hydrogen pressure (30 psi; $2.0 \times 10^5$ Pa). After 18.5 hours analysis by thin layer chromatography indicated that the reaction was not complete. Catalyst (0.5 g) was added and the hydrogenation was continued for an additional 4 hours. The reaction mixture was filtered through a layer of Celite® filter aid and a glass wool filter pad. The filter cake was rinsed with a mixture of isopropanol and methanol. The filtrate was concentrated under reduced pressure to provide tert-butyl 2-(2-aminoethoxy)ethylcarbamate.

Part E

A mixture of 2,4-dihydroxy-5,6-dimethyl-3-nitropyridine (245 g, 1.33 mol) and phosphorous oxychloride (2.2 L) was heated at 85° C. overnight. The bulk of the phosphorous oxychloride (1.75 L) was removed under reduced pressure to provide a black oil. The oil was poured into water (2.5 L) and the mixture was cooled in an ice bath to 5° C. The resulting tan precipitate was isolated by filtration, dissolved in dichloromethane (~3 L) and filtered to remove some black solids. The filtrate was washed with 10% sodium carbonate and brine, dried over magnesium sulfate and then concentrated under reduced pressure to provide 272 g of a light tan solid. This solid was recrystallized from heptane (2.5 mL/g) to provide 248 g of 2,4-dichloro-5,6-dimethyl-3-nitropyridine as large amber rods.

Part F

Under a nitrogen atmosphere, a solution of tert-butyl 2-(2-aminoethoxy)ethylcarbamate (23.1 g, 113 mmol) in N,N-dimethylformamide (100 mL) was added over a 1 hour period to a solution of 2,4-dichloro-5,6-dimethyl-3-nitropyridine (25.02 g, 113 mmol) in N,N-dimethylformamide (400 mL) containing triethylamine (24 mL, 175 mmol). The reaction mixture was allowed to stir at ambient temperature overnight. The N,N-dimethylformamide was removed under reduced pressure. The residue was dissolved in ethyl acetate (500 mL), washed with water (3×100 ml), dried over magnesium sulfate, and then concentrated under reduced pressure. The residue was purified by column chromatography (450 g of silica gel eluting sequentially with 3/1 hexanes/ethyl acetate (1.2 L), 2/1 hexanes/ethyl acetate (1.2 L), and 1/1 hexanes/ethyl acetate (1 L)) to provide 20.67 g of tert-butyl 2-{2-[(2-chloro-5,6-dimethyl-3-nitropyridin-4-yl)amino]ethoxy}ethylcarbamate.

Part G

Phenol (5.33 g, 56.63 mmol) was added in small portions over a period of 10 minutes to a chilled (0°) suspension of sodium hydride (2.39 g of 60%, 59.75 mmol) in anhydrous tetrahydrofuran (100 mL). After the addition was complete, the reaction was allowed to stir at 0° for 30 minutes. A solution tert-butyl 2-{2-[(2-chloro-5,6-dimethyl-3-nitropyridin-4-yl)amino]ethoxy}ethylcarbamate (20.67 g, 53.16 mmol) in tetrahydrofuran (100 mL) was added over a period of 1 hour while maintaining the temperature at 0° C. The ice bath was removed and the reaction mixture was heated to reflux. At 46 and 52 hours additional fresh sodium phenoxide (11.3 mmol) was added. Refluxing was continued for 2 hours after the second addition. The reaction mixture was diluted with ethyl acetate (500 mL); washed sequentially with water (3×100 mL), 1N sodium hydroxide (2×100 mL), and brine; dried over magnesium sulfate and then concentrated under reduced pressure. The residue was purified by column chromatography (450 g of silica gel eluting with 1/1 hexanes/ethyl acetate) to provide 19.85 g of tert-butyl 2-{2-[(2,3-dimethyl-5-nitro-6-phenoxypyridin-4-yl)amino]ethoxy}ethylcarbamate.

Part H

A solution of of tert-butyl 2-{2-[(2,3-dimethyl-5-nitro-6-phenoxypyridin-4-yl)amino]ethoxy}ethylcarbamate (15.34 g, 34.35 mmol) in absolute ethanol (500 mL) was combined with 5% platinum on carbon (12.02 g) in a Parr vessel and placed under hydrogen pressure overnight. The reaction mixture was filtered through a layer of Celite® filter aid. The filtrate was concentrated under reduced pressure. The resulting residue was purified by column chromatography (250 g of silica gel eluting with 1/1 ethyl acetate/hexanes) to provide 11.21 g of tert-butyl 2-{2-[(3-amino-5,6-dimethyl-2-phenoxypyridin-4-yl)amino]ethoxy}ethylcarbamate.

Part I

Trimethyl orthoacetate (3.55 mL, 28.27 mmol), tert-butyl 2-{2-[(3-amino-5,6-dimethyl-2-phenoxypyridin-4-yl)amino]ethoxy}ethylcarbamate (11.21 g, 26.92 mmol), pyridine hydrochloride (1.12 g) and toluene (120 mL) were combined and heated at reflux for 2.5 hours. The reaction mixture was concentrated under reduced pressure. The residue was dissolved in ethyl acetate (300 mL), washed with water (3×100 mL) and brine (1×100 mL), dried over magnesium sulfate and then concentrated under reduced pressure to provide 9.85 g of tert-butyl 2-[2-(2,6,7-trimethyl-4-phenoxy-1H-imidazo[4,5-c]pyridin-1-yl)ethoxy]ethylcarbamate.

Part J

A mixture of ammonium acetate (100 g) and tert-butyl 2-[2-(2,6,7-trimethyl-4-phenoxy-1H-imidazo[4,5-c]pyridin-1-yl)ethoxy]ethylcarbamate (9.85 g) was heated at 160° C. for 18.5 hours. The reaction mixture was diluted with water (100 mL), made basic (pH 13) with 15% sodium hydroxide (160 mL), saturated with sodium chloride and then extracted with chloroform (9×100 mL). The combined extracts were dried over magnesium sulfate and then concentrated under reduced pressure. Analysis by high performance liquid chromatography and NMR showed that the residue contained about 13% of N-{2-[2,6,7-trimethyl-4-phenxoy-1H-imidazo[4,5-c]pyridin-1-yl)ethoxy]ethyl}acetamide. The residue was combined with ammonium acetate (71 g) in a pressure vessel and heated at 160° C. for 20 hours. The reaction was worked up as before. Residual ammonium acetate was removed by sublimation (high vacuum at 35° C.) to provide 7.36 g of N-{2-[4-amino-2,6,7-trimethyl-1H-imidazo[4,5-c]pyridin-1-yl)ethoxy]ethyl}acetamide.

Part K

N-{2-[4-amino-2,6,7-trimethyl-1H-imidazo[4,5-c]pyridin-1-yl)ethoxy]ethyl}acetamide (7.36 g), concentrated hydrochloric acid (45 mL) and absolute ethanol (100 mL) were combined and heated at 90° C. After 26.5 hours additional concentrated hydrochloric acid (2 mL) was added. The reaction was stopped after 29 hours and concentrated under reduced pressure. In order to remove excess hydrochloric acid, the residue was twice diluted with ethanol (100 mL) and concentrated under reduced pressure. The residue was dissolved in water (100 mL) and washed with chloroform (3×50 mL). The aqueous layer was adjusted to pH≧12 with 15% sodium hydroxide, saturated with solid sodium chloride and then extracted with chloroform (9×100 mL). The combined extracts were dried over magnesium sulfate and then concentrated under reduced pressure. The residue was purified by column chromatography (100 g of silica gel eluting with 4% methanol in chloroform containing 1% triethylamine) to provide 4.18 g of 1-[2-(2-aminoethoxy)ethyl]-2,6,7-trimethyl-1H-imidazo[4,5-c]pyridin-4-amine as a white powder, m.p. 130–133° C.

Analysis: Calculated for C₁₃H₂₁N₅O.0.03 HCl: % C, 59.05; % H, 8.01; % N, 26.48; Found: % C, 58.70; % H, 7.99; % N, 26.37. ¹H NMR (300 MHz, CDCl₃) δ 4.79 (s, 2 H), 4.43 (t, J=5.6 Hz, 2 H), 3.75 (t, J=5.3 Hz, 2 H), 3.38 (t, J=5.3 Hz, 2 H), 2.78 (t, J 5.3 Hz, 2 H), 2.59 (s, 3 H), 2.43 (d, J=6.9 Hz, 6 H), 1.07 (bs, 2 H);

MS(CI) m/e 264 (M+H)

EXAMPLE 15

N-{2-[2-(4-Amino-2,6,7-trimethyl-1H-imidazo[4,5-c]pyridin-1-yl)ethoxy]ethyl}morpholine-4-carboxamide

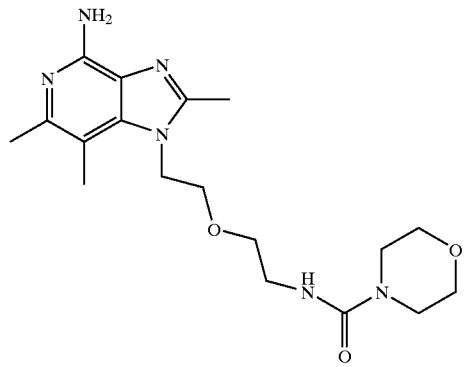

Under a nitrogen atmosphere, 4-morpholinecarbonyl chloride (370 μL) was added to a solution of 1-[2-(2-aminoethoxy)ethyl]-2,6,7-trimethyl-1H-imidazo[4,5-c]pyridin-4-amine (0.757 g) in chloroform (11 mL) and triethylamine (520 μL). The reaction mixture was stirred at ambient temperature for about 3 hours; then it was diluted with chloroform (20 mL) and washed with saturated sodium bicarbonate solution. The organic layer was dried over magnesium sulfate and concentrated under reduced pressure. The crude product was recrystallized from acetonitrile and dried in a vacuum oven at 60° C. for 24 hours to provide 0.7014 g of N-{2-[2-(4-amino-2,6,7-trimethyl-1H-imidazo[4,5-c]pyridin-1-yl)ethoxy]ethyl}morpholine-4-carboxamide as a white powder, m.p. 205–207° C.

Analysis: Calculated for C₁₈H₂₈N₆O₃.0.05 HCl: % C, 57.15; % H, 7.47; % N, 22.22; Found: % C, 56.75; % H, 7.47; % N, 21.98. ¹H NMR (300 MHz, CDCl₃) δ 4.80 (s, 2 H), 4.45 (t, J=5.3 Hz, 2 H), 4.30 (s, 1 H), 3.75 (t, J=4.9Hz, 2 H), 3.62 (t, J=4.9 Hz, 4 H), 3.44 (t, J=4.7 Hz, 2 H), 3.34 (m, 2 H), 3.09 (t, J=4.7 Hz, 4 H), 2.57 (s, 3 H), 2.43 (d, J=3.1 Hz, 6 H); MS(CI) m/e 377 (M+H)

EXAMPLE 16

N-{2-[2-(4-Amino-2,6,7-trimethyl-1H-imidazo[4,5-c]pyridin-1-yl)ethoxy]ethyl}-2-methylpropanamide

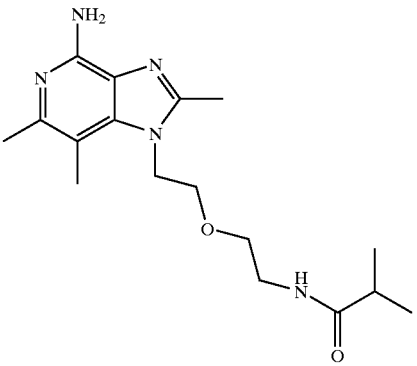

Under a nitrogen atmosphere, isobutyryl chloride (330 μL, 3.15 mmol) was added to a solution of 1-[2-(2-aminoethoxy)ethyl]-2,6,7-trimethyl-1H-imidazo[4,5-c]pyridin-4-amine (0.757 g, 2.875 mmol) in chloroform (11 mL) and triethylamine (520 μL, 3.78 mmol). The reaction mixture was stirred at ambient temperature for about 3 hours; then it was diluted with chloroform (20 mL) and washed with saturated sodium bicarbonate solution. The organic layer was dried over magnesium sulfate and concentrated under reduced pressure. The residue was purified by column chromatography (10 g of silica gel eluting with 2% methanol in chloroform containing 0.5% triethylamine) to provide 0.3486 g of N-{2-[2-(4-amino-2,6,7-trimethyl-1H-imidazo[4,5-c]pyridin-1-yl)ethoxy]ethyl}-2-methylpropanamide as a solid, m.p. 179.5–182° C.

Analysis: Calculated for C₁₇H₂₇N₅O₂.0.06 HCl: % C, 60.84; % H, 8.13; % N, 20.87; Found: % C, 60.67; % H, 7.89; % N, 20.57. ¹H NMR (300 MHz, CDCl₃) δ 5.23 (bs, 1 H), 4.93 (bs, 2 H), 4.44 (t, J=5.3 Hz, 2 H), 3.74 (t, J=5.6 Hz, 2 H), 3.42 (t, J=5.3 Hz, 2 H), 3.32 (m, 2 H), 2.58 (s, 3 H), 2.44 (d, J=8.1 Hz, 6 H), 2.15 (quintet, J=6.7 Hz, 1 H), 1.04 (d, J=6.8 Hz, 6 H); MS(CI) m/e 334 (M+H).

In the examples below the compounds were purified either by preparative high performance liquid chromatography (Method A) or by flash chromatography (Method B).

In Method A the compounds were purified by preparative high performance liquid chromatography using a Waters Fraction Lynx automated purification system. The prep HPLC fractions were analyzed using a Micromass LC-TOFMS and the appropriate fractions were combined and centrifuge evaporated to provide the trifluoroacetate salt of the desired compound. Column: Phenomenex Luna C18 (2), 21.2×50 mm, 10 micron particle size, 100 Å pore; flow rate: 25 mL/min.; non-linear gradient elution from 5–95% B in 12 min, then hold at 95% B for 2 min., where A is 0.05% trifluoroacetic acid/water and B is 0.05% trifluoroactic acid/acetonitrile; fraction collection by mass-selective triggering.

In Method B the compounds were purified by flash chromatography using a 4 g silica gel cartridge (RediSep, ISCO, 230–400 mesh, 6.25 cm×1.27 cm diameter) attached to a gradient pump system, 254 nm UV detector and fraction collector (ISCO CombiFlash Sg100c system). The column was equilibrated with dichloromethane and the reaction mixture was injected onto the column. The mixture was eluted at 30 mL/minute, with a gradient program consisting of 100% dichloromethane for 12 seconds, a linear gradient to 10% methanol/dichloromethane over 1 minute and holding at 10% methanol/dichloromethane to elute the desired compound. Fractions were examined by thin layer chromatography and those containing the desired compound were pooled and evaporated. In cases where the reaction mixture was a suspension, the mixture was treated with ~125 mg of tris-(aminoethyl)amine polystyrene (Argonaut PS-Trisamine, 3.85 meq/g), shaken for several minutes and then filtered prior to injection into the column.

EXAMPLES 17–32

The compounds in the table below were prepared using the following method. The appropriate acid chloride (1.1 eq.) was added to a test tube containing a solution of 1-[2-(2-aminoethoxy)ethyl]-2,6,7-trimethyl-1H-imidazo[4,5-c]pyridin-4-amine (25 mg) in chloroform (5 mL). The test tube was capped, vortexed and then placed on a shaker at ambient temperature overnight (~18 hours). The solvent was removed by vacuum centrifugation. The table below shows the structure of the free base (compounds purified by Method A were isolated as trifluoroacetate salts), the observed accurate mass and the purification method that was used for that particular compound.

| Example Number | $R_a$ | Accurate Mass (observed) | Purification Method |
|---|---|---|---|
| 17 | butyl | 348.2391 | B |
| 18 | phenyl | 368.2095 | B |
| 19 | cyclohexyl | 374.2520 | B |
| 20 | benzyl | 382.2239 | B |
| 21 | 4-fluorophenyl | 386.1984 | B |
| 22 | 2-thienylmethyl | 388.1808 | B |
| 23 | 4-cyanophenyl | 393.2031 | B |
| 24 | 3-cyanophenyl | 393.2025 | B |
| 25 | 2-phenylethyl | 396.2413 | B |
| 26 | 3-methoxyphenyl | 398.2194 | B |
| 27 | 4-methoxyphenyl | 398.2173 | B |
| 28 | 2-chloro-5-pyridyl | 403.1654 | B |
| 29 | benzyloxymethyl | 412.2364 | B |
| 30 | 2-naphthyl | 418.2225 | B |
| 31 | 3-trifluoromethylphenyl | 436.1938 | B |
| 32 | 4-trifluoromethoxyphenyl | 452.1924 | B |

EXAMPLE 33

(1R*,2R*)-N-{2-[2-(4-Amino-2,6,7-trimethyl-1H-imidazo[4,5-c]pyridin-1-yl)ethoxy]ethyl}-2-phenylcyclopropanecarboxamide

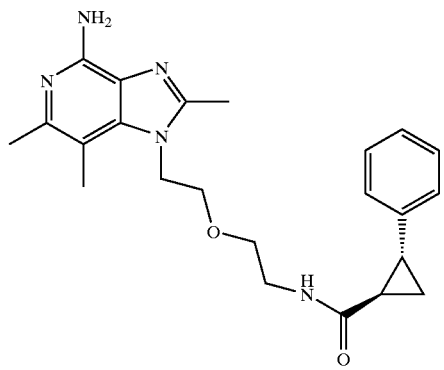

Using the method of Examples 17–32, trans-2-phenylcyclopropylcarbonyl chloride was reacted with 1-[2-(2-aminoethoxy)ethyl]-2,6,7trimethyl1H-imidazo[4,5-c]pyridin-4-amine to provide the desired compound. The product was purified using Method B. The observed accurate mass was 408.2392.

EXAMPLES 34–50

The compounds in the table below were prepared using the following method. The appropriate sulfonyl chloride (1.1eq.) was added to a test tube containing a solution of 1-[2-(2-aminoethoxy)ethyl]-2,6,7-trimethyl-1H-imidazo[4,5-c]pyridin-4-amine (25 mg) in chloroform (5 mL). The test tube was capped, vortexed and then placed on a shaker at ambient temperature overnight (18 hours). The solvent was removed by vacuum centrifugation. The table below shows the structure of the free base (compounds purified by Method A were isolated as trifluoroacetate salts), the observed accurate mass and the purification method that was used for that particular compound.

| Example Number | $R_a$ | Accurate Mass (observed) | Purification Method |
|---|---|---|---|
| 34 | ethyl | 356.1729 | A |
| 35 | 1-methylethyl | 370.1901 | A |
| 36 | butyl | 384.2092 | A |

-continued

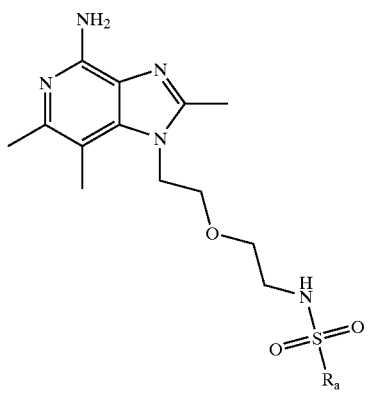

| Example Number | $R_a$ | Accurate Mass (observed) | Purification Method |
|---|---|---|---|
| 37 | phenyl | 404.1767 | B |
| 38 | 2-thienyl | 410.1327 | B |
| 39 | benzyl | 418.1900 | A |
| 40 | 3-fluorophenyl | 422.1646 | B |
| 41 | 4-cyanophenyl | 429.1709 | B |
| 42 | 3-cyanophenyl | 429.1704 | B |
| 43 | 4-methoxyphenyl | 434.1857 | B |
| 44 | 2,4-difluorophenyl | 440.1559 | B |
| 45 | 1-naphthyl | 454.1910 | B |
| 46 | 2-naphthyl | 454.1916 | B |
| 47 | 4-trifluoromethylphenyl | 472.1639 | A |
| 48 | 4-biphenyl | 480.2050 | A |
| 49 | 4-methylsulfonylphenyl | 482.1506 | A |
| 50 | 4-trifluoromethoxyphenyl | 488.1624 | A |

EXAMPLE 51

N'-{2-[2-(4-Amino-2,6,7-trimethyl-1H-imidazo[4,5-c]pyridin-1-yl)ethoxy)ethyl}-N,N-dimethylsulfamide

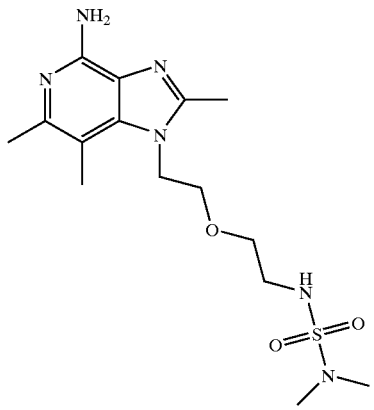

Using the method of Examples 34–50, dimethylsulfamoyl chloride was reacted with 1-[2-(2-aminoethoxy)ethyl]-2,6,7-trimethyl-1H-imidazo[4,5-c]pyridin-4-amine to provide the desired compound. The product was purified using Method A. The observed accurate mass was 371.1861.

EXAMPLE 52

N-{2-[2-(4-Amino-2,6,7-trimethyl-imidazo[4,5-c]pyridin-1-yl)-ethoxy]-ethyl}-C-(7,7-dimethyl-2-oxo-bicyclo[2.2.1]hept-1-yl)methanesulfonamide

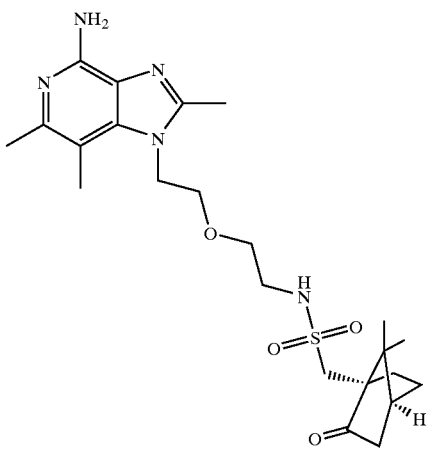

Using the method of Examples 34–50, D-(+)-10-camphorsulfonyl chloride was reacted with 1-[2-(2-aminoethoxy)ethyl]-2,6,7-trimethyl-1H-imidazo[4,5-c]pyridin-4-amine to provide the desired compound. The product was purified using Method A. The observed accurate mass was 478.2455.

EXAMPLE 53

N-{2-[2-(4-Amino-2,6,7-trimethyl-1H-imidazo[4,5-c]pyridin-1-yl)ethoxy]ethyl}-4-{[4-(dimethylamino)phenyl]diazenyl}benzenesulfonamide

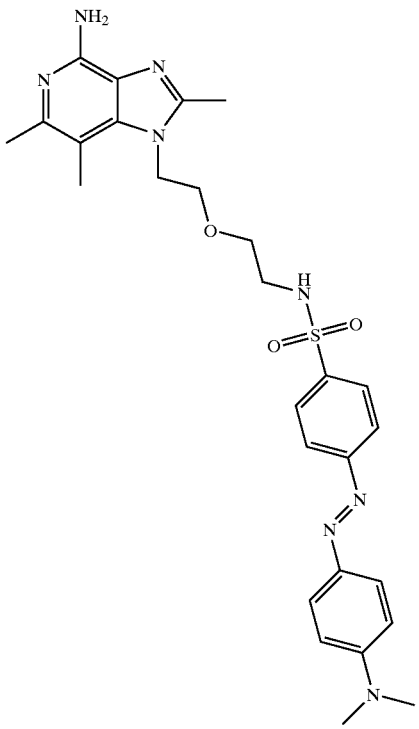

Using the method of Examples 34–50, 4-dimethylaminoazobenzene-4'-sulfonyl chloride was reacted with 1-[2-(2-aminoethoxy)ethyl]-2,6,7-trimethyl-1H-imidazo[4,5-c]pyridin-4-amine to provide the desired compound. The product was purified using Method A. The observed accurate mass was 551.2551.

EXAMPLES 54–68

The compounds in the table below were prepared using the following method. The appropriate isocyanate (1.1 eq.) was added to a test tube containing a solution of 1-[2-(2-aminoethoxy)ethyl]-2,6,7-trimethyl-1H-imidazo[4,5-c]pyridin-4-amine (25 mg) in chloroform (5 mL). The test tube was capped, vortexed and then placed on a shaker at ambient temperature overnight (~18 hours). The solvent was removed by vacuum centrifugation. The table below shows the structure of the free base (compounds purified by Method A were isolated as trifluoroacetate salts), the observed accurate mass and the purification method that was used for that particular compound.

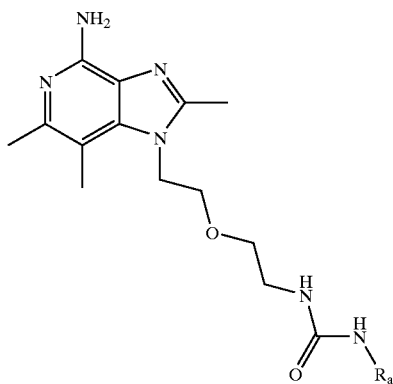

| Example Number | $R_a$ | Accurate Mass (observed) | Purification Method |
|---|---|---|---|
| 54 | 1-methylethyl | 349.2360 | B |
| 55 | 1,1-dimethylethyl | 363.2506 | B |
| 56 | butyl | 363.2511 | B |
| 57 | phenyl | 383.2200 | B |
| 58 | cyclohexyl | 389.2638 | A |
| 59 | ethoxycarbonylmethyl | 393.2236 | A |
| 60 | 3-cyanophenyl | 408.2141 | A |
| 61 | 3-methoxyphenyl | 413.2319 | A |
| 62 | 3-acetylphenyl | 425.2293 | A |
| 63 | 4-(dimethylamino)phenyl | 426.2644 | A |
| 64 | 3-(methylthio)phenyl | 429.2057 | A |
| 65 | 2,4-dimethoxyphenyl | 443.2390 | A |
| 66 | phenylsulfonyl | 447.1819 | A |
| 67 | 4-methylphenylsulfonyl | 461.1969 | A |
| 68 | 2-chlorophenylsulfonyl | 481.1418 | A |

EXAMPLE 69

N-{2-[2-(4-Amino-2,6,7-trimethyl-1H-imidazo[4,5-c]pyridin-1-yl)ethoxy]ethyl}morpholine-4-carboxamide

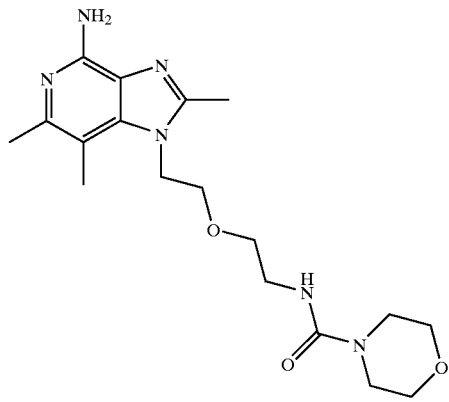

Using the method of Examples 54–68, 4-morpholinecarbonyl chloride was reacted with 1-[2-(2-aminoethoxy)ethyl]-2,6,7-trimethyl-1H-imidazo[4,5-c]pyridin-4-amine to provide the desired compound. The product was purified using Method A. The observed accurate mass was 377.2295.

EXAMPLE 70

N-{2-[2-(4-Amino-2,6,7-trimethyl-1H-imidazo[4,5-c]pyridin-1-yl)ethoxy]ethyl}-N'-[(1R*,2S*)-2-phenylcyclopropyl]urea

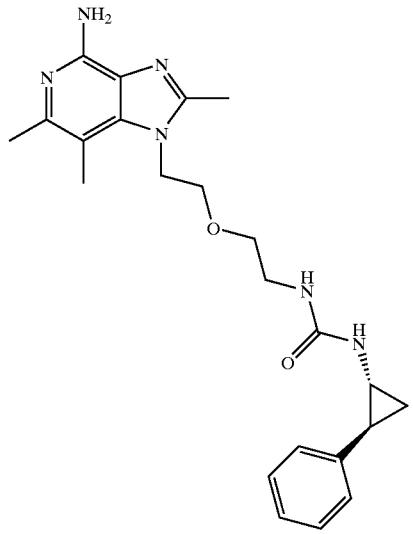

Using the method of Examples 54–68, trans-2-phenylcyclopropyl isocyanate was reacted with 1-[2-(2-aminoethoxy)ethyl]-2,6,7-trimethyl-1H-imidazo[4,5-c]pyridin-4-amine to provide the desired compound. The product was purified using Method A. The observed accurate mass was 423.2508.

EXAMPLE 71

N'-{2-[2-(4-Amino-2,6,7-trimethyl-1H-imidazo[4,5-c]pyridin-1-yl)ethoxy]ethyl}-N-methyl-N-phenylurea

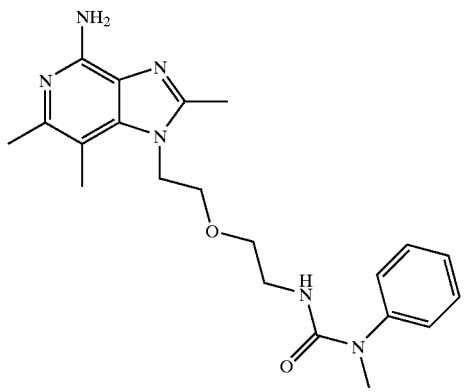

Using the method of Examples 54–68, N-methyl-N-phenylcarbamoyl chloride was reacted with 1-[2-(2-aminoethoxy)ethyl]-2,6,7-trimethyl-1H-imidazo[4,5-c]pyridin-4-amine to provide the desired compound. The product was purified using Method A. The observed accurate mass was 397.2343.

EXAMPLES 72–76

The compounds in the table below were prepared using the following method. The appropriate isothiocyanate (1.1 eq.) was added to a test tube containing a solution of 1-[2-(2-aminoethoxy)ethyl]-2,6,7-trimethyl-1H-imidazo[4,5-c]pyridin-4-amine (25 mg) in chloroform (5 mL). The test tube was capped, vortexed and then placed on a shaker at ambient temperature overnight (~18 hours). The solvent was removed by vacuum centrifugation. The table below shows the structure of the free base (compounds purified by Method A were isolated as trifluoroacetate salts), the observed accurate mass and the purification method that was used for that particular compound.

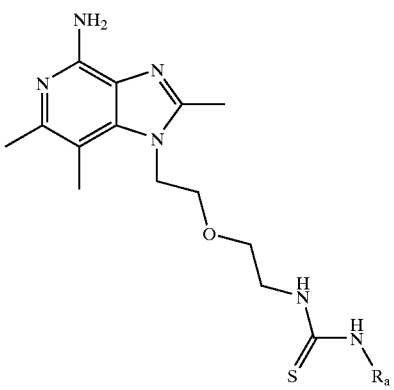

| Example Number | $R_a$ | Accurate Mass (observed) | Purification Method |
|---|---|---|---|
| 72 | 3-(dimethylamino)propyl | 436.2851 | A |
| 73 | phenyl | 399.1946 | A |
| 74 | 2-furoyl | 417.1715 | A |
| 75 | 2-phenylethyl | 427.2289 | A |
| 76 | 4-methoxyphenyl | 429.2057 | A |

EXAMPLE 77

N-{2-[2-(4-Amino-2,6,7-trimethyl-1H-imidazo[4,5-c]pyridin-1-yl)ethoxy]ethyl}methanesulfonamide

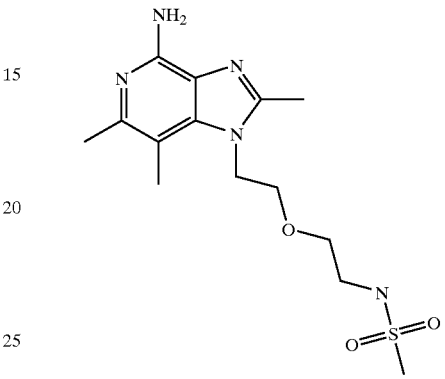

Under a nitrogen atmosphere, methane sulfonic anhydride (550 mg) was added to a solution of 1-[2-(2-aminoethoxy)ethyl]-2,6,7-trimethyl-1H-imidazo[4,5-c]pyridin-4-amine (757 mg, 2.875 mmol), triethylamine (520 μL) and chloroform (11 mL). The reaction mixture was allowed to stir at ambient temperature for about 3 hours. The reaction mixture was diluted with chloroform (20 mL) and washed with saturated sodium bicarbonate solution (10 mL). The organic layer was dried over magnesium sulfate and then concentrated under reduced pressure to provide crude product as a light yellow oil. The oil was purified by column chromatography (10 g of silica gel eluting with 2% methanol in chloroform containing 0.5 % triethylamine). The fractions containing product were combined and concentrated under reduced pressure. The residue was purified using Method A described above to provide 0.2753 g of N-{2-[2-(4-amino-2,6,7-trimethyl-1H-imidazo[4,5-c]pyridin-1-yl)ethoxy]ethyl}methanesulfonamide.

EXAMPLE 78

1-[5-(Methanesulfonyl)pentyl]-2,6,7-trimethyl-1H-imidazo[4,5-c]pyridin-4-amine

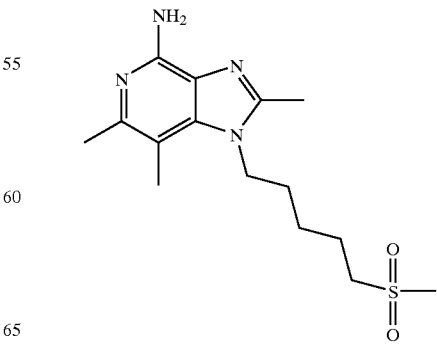

3-Chloroperoxybenzoic acid, available as an approximately 75% pure mixture (mCPBA), (2.727 g, 15.80 mmol) was slowly added to a solution of 2,6,7-trimethyl-1-[5-(methylthio)pentyl]-1H-imidazo[4,5-c]pyridin-4-amine (1.442 g, 4.938 mmol), described in Example 12, in dichloromethane (60 mL), and the reaction was stirred for three hours. The volatiles were removed under reduced pressure, and the residue was dissolved in dichloromethane (100 mL). The solution was washed with 10% aqueous sodium hydroxide (2×100 mL), dried over magnesium sulfate, filtered, and concentrated under reduced pressure. The product was recrystallized first from a mixture of dichloromethane, hexanes, and ethanol and secondly from a mixture of methanol, ethyl acetate, and hexanes to provide 0.738 g of 1-[5-(methanesulfonyl)pentyl]-2,6,7-trimethyl-1H-imidazo[4,5-c]pyridin-4-amine as a solid, m.p. 199–200° C. Analysis: Calculated for $C_{15}H_{24}N_4O_2S$: % C, 55.53; % H, 7.45; % N, 17.27; % S 9.88. Found: % C, 55.17; % H, 7.67; % N, 16.99; % S 9.75.

EXAMPLE 79

1-[5-(Benzenesulfonyl)pentyl]-2,6,7-trimethyl-1H-imidazo[4,5-c]pyridin-4-amine

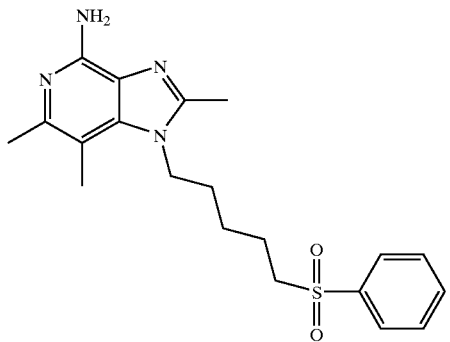

The reaction was carried out as described in Example 78 with the following exceptions. mCPBA (2.01 g, 11.65 mmol) was added to a solution of 2,6,7-trimethyl-1-[5-(phenylthio)pentyl]-1H-imidazo[4,5-c]pyridin-4-amine (1.32 g, 3.72 mmol), described in Example 13, in dichloromethane (100 mL). The crude product (1.45 g) was purified by column chromatography on silica gel (eluting sequentially with 99:1 dichloromethane:methanol and 95:5 dichloromethane:methanol) to provide 0.245 g of 1-[5-(benzenesulfonyl)pentyl]-2,6,7-trimethyl-1H-imidazo[4,5-c]pyridin-4-amine as a solid, m.p. 166–167° C. Analysis: Calculated for $C_{20}H_{26}N_4O_2S$: % C, 62.15; % H, 6.78; % N, 14.05; %S 8.30. Found: % C, 61.83; % H, 6.69; % N, 14.39; % S, 7.98.

EXAMPLE 80

1-[2-(Benzyloxy)ethyl]-2-(ethoxymethyl)-6-methyl-1H-imidazo[4,5-c]pyridin-4-amine

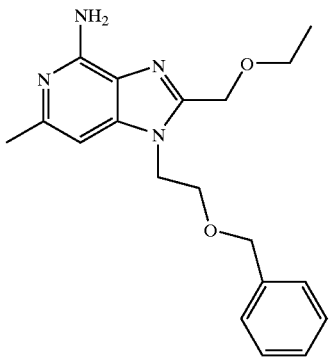

Part A

Aqueous sodium hydroxide (510 mL of 2 M) was added to a solution of ethanol amine (61.0 g, 1.00 mol) in tetrahydrofuran (500 mL). The temperature of the reaction was maintained at 25° C. using a water bath. A solution of di-tert-butyl dicarbonate (218 g, 1.00 mol) in tetrahydrofuran (500 mL) was added dropwise over a period of one hour with rapid stirring, and a white precipitate formed. The reaction was stirred for 17 hours, and the tetrahydrofuran was removed under reduced pressure. The pH of the resulting slurry was adjusted to ~2 by adding sulfuric acid (550 mL of 1M), and the resulting clear solution was extracted with ethyl acetate (3×500 mL). The combined extracts were washed thrice with water and twice with brine, dried over sodium sulfate, filtered, and concentrated under reduced pressure to provide 142.2 g of tert-butyl 2-hydroxyethylcarbamate as a colorless oil.

Part B

Benzyltrimethylammonium chloride (4.61 g, 24.8 mmol) was added to a mixture of tert-butyl 2-hydroxyethylcarbamate (40.0 g, 248 mmol), dichloromethane (600 mL), and 50% aqueous sodium hydroxide (400 mL). Benzyl bromide (29.5 mL, 248 mmol) was then added, and the reaction was stirred for three hours. Ice water was added (1 L), and the aqueous solution was extracted with chloroform (5×). The combined organic solutions were washed with water (2×) and brine (3×), dried over magnesium sulfate, filtered, and concentrated under reduced pressure. Upon concentration, a white precipitate formed, and the organic solution was washed again with water (3×100 mL). The combined washings were extracted with chloroform (3×50 mL). The combined organic solutions were washed with brine (3×50 mL), dried over magnesium sulfate, filtered, and concentrated under reduced pressure to provide 59.1 g of tert-butyl 2-(benzyloxy)ethylcarbamate as a colorless oil.

Part C

A solution of 7% hydrochloric acid in ethanol (245 g of ~1.6 M) was added to tert-butyl 2-(benzyloxy) ethylcarbamate (59.1 g, 235 mmol), and the solution was stirred at room temperature for 17 hours. The volatiles were removed under reduced pressure to provide 52.1 g of a white solid, which was recrystallized from ethyl acetate (650 mL)

and a small amount of methanol. The crystals were isolated by filtration and dried for three days at 78° C. and 39.9 Pa to provide 32.2 g of 2-(benzyloxy)ethylamine hydrochloride as a white solid.

Part D

Under a nitrogen atmosphere, triethylamine (40.4 mL, 290 mmol) was added to a solution of 2,4-dichloro-6-methyl-3-nitropyridine (12.0 g, 58.0 mmol), prepared according to the general method of Part A of Example 1 using 2,4-dihydroxy-6-methyl-3-nitropyridine in lieu of 2,4-dihydroxy-5,6-dimethyl-3-nitropyridine, in anhydrous N,N-dimethylformamide (DMF) (200 mL). To the resulting dark brown solution was added 2-(benzyloxy)ethylamine hydrochloride (11.97 g, 63.76 mmol), and the mixture was stirred at room temperature for 23 hours. The volatiles were then removed under reduced pressure, and the residue was mixed with water and ethyl acetate. The organic layer was washed with water (3×200 mL), aqueous sodium bicarbonate (2×200 mL), and brine (3×250 mL), dried over magnesium sulfate, filtered, and concentrated under reduced pressure to provide a brown oil. The crude product (18.1 g) was purified by column chromatography on silica gel (700 g, eluting with 80:20 hexane:ethyl acetate) to provide an oil which was triturated with 80:20 hexane:ethyl acetate. The resulting crystals were isolated by filtration and dried to provide 4.7 g of [2-(benzyloxy)ethyl]-(2-chloro-6-methyl-3-nitropyridin-4-yl)amine as a yellow solid.

Part E

Under a nitrogen atmosphere, diglyme (20 mL) was added to sodium hydride (0.548 g, 13.7 mmol), which is available as a 60% dispersion in mineral oil, and the mixture was cooled to 0° C. A solution of phenol (1.35 g, 14.4 mmol) in diglyme (20 mL) was added, and the addition flask was rinsed with additional diglyme (2×5 mL), which was added to the reaction flask. The reaction became homogeneous and was stirred for 30 minutes. Solid [2-(benzyloxy)ethyl]-(2-chloro-6-methyl-3-nitropyridin-4-yl)amine (4.2 g, 13 mmol) was added, and the resulting dark solution was heated at 60° C. for 90 minutes. The reaction was allowed to cool and then slowly poured into water (500 mL) and stirred rapidly for 90 minutes. A yellow solid formed, which was isolated by filtration and dissolved in ethyl acetate. The solution was then dried over magnesium sulfate, filtered, and concentrated under reduced pressure to provide a yellow oil, which began to crystallize over three days. The product was triturated with hexane, and the resulting solid was isolated by filtration and dried for two hours under high vacuum at 55° C. to provide 4.44 g of [2-(benzyloxy)ethyl]-(6-methyl-3-nitro-2-phenoxy-pyridin-4-yl)amine as a yellow solid.

Part F

Under a nitrogen purge, 5% platinum on carbon (1.0 g) and toluene (20 mL) were added to a Parr vessel. [2-(Benzyloxy)ethyl](6-methyl-3-nitro-2-phenoxy-pyridin-4-yl)amine (4.91 g, 12.9 mmol) and additional toluene (40 mL) were then added. The vessel was placed under hydrogen pressure (49 psi, 3.3×10$^5$ Pa) for three hours. The reaction mixture was filtered through a layer of CELITE filter aid, and the filtrate was concentrated under reduced pressure to yield 4.9 g of $N^4$-[2-(benzyloxy)ethyl]-6-methyl-2-phenoxypyridine-3,4-diamine as a milky oil, contaminated with a small amount of toluene.

Part G

Under a nitrogen atmosphere, a solution of $N^4$-[2-(benzyloxy)ethyl]-6-methyl-2-phenoxypyridine-3,4-diamine (3.80 g, 10.9 mmol), anhydrous dichloromethane (75 mL), and anhydrous triethylamine (1.8 mL, 13 mmol) was cooled to 5° C. Ethoxyacetyl chloride (1.40 g, 11.4 mmol) was then added over a period of 30 seconds, and the reaction was stirred for 20 minutes. The reaction mixture was washed with aqueous sodium bicarbonate (3×), and the combined aqueous washings were extracted with chloroform (3×). The combined organic solutions were dried over sodium sulfate, filtered, and concentrated under reduced pressure to provide a white powder. The powder was dried for three days under vacuum at room temperature to provide 4.01 g of N-{4-[2-(benzyloxy)ethylamino]-6-methyl-2-phenoxypyridin-3-yl}-2-ethoxyacetamide as a white solid.

Part H

Under a nitrogen atmosphere, a solution of N-{4-[2-(benzyloxy)ethylamino]-6-methyl-2-phenoxypyridin-3-yl}-2-ethoxyacetamide (3.98 g, 9.13 mmol) and pyridine hydrochloride (4.0 g, 35 mmol) in anhydrous pyridine (30 mL) was heated at reflux. After 22 hours, an analysis by high-performance liquid chromatography (HPLC) indicated the presence of starting material, and additional pyridine hydrochloride (0.05 g, 0.4 mmol) was added. After an additional hour, an HPLC analysis again indicated the presence of starting material, and additional pyridine hydrochloride (0.05 g, 0.4 mmol) was added. The reaction was heated at reflux for an additional four days and then was allowed to cool to room temperature. The volatiles were removed under reduced pressure, and the residue was dissolved in dichloromethane. The resulting solution was washed with water (3×) and brine (3×), dried over sodium sulfate, filtered, and concentrated under reduced pressure to provide 3.7 g of a brown oil. The oil was purified by column chromatography on silica gel (eluting with 95:5 dichloromethane:ethyl acetate) to provide 2.5 g of 1-[2-(benzyloxy)ethyl]-2-(ethoxymethyl)-6-methyl-4-phenoxy-1H-imidazo[4,5-c]pyridine as a yellow oil.

Part I

Ammonium acetate (25 g, 0.32 mol) and 1-[2-(benzyloxy)ethyl]-2-(ethoxymethyl)-6-methyl-4-phenoxy-1H-imidazo[4,5-c]pyridine (2.5 g, 6.0 mmol) were heated at 150° C. in a sealed tube for 22 hours. The resulting solution was adjusted to pH 14 with the addition of 20% sodium hydroxide, and water (50 mL) was added. The mixture was stirred for several hours to provide a yellow precipitate, which was isolated by filtration. The precipitate (1.75 g) was recrystallized from a 50:50 mixture of hexane:ethyl acetate (29 mL/g), and the crystals were isolated by filtration and dried under vacuum for 23 hours at 60° C. to provide 1.05 g of 1-[2-(benzyloxy)ethyl]-2-(ethoxymethyl)-6-methyl-1H-imidazo[4,5-c]pyridin-4-amine as small white crystals, mp. 127–128° C.

$^1$H NMR (300 MHz, DMSO) δ 7.24–7.31 (m, 3H), 7.15–7.19 (m, 2H), 6.61 (s, 1H), 6.05 (s, 2H), 4.67 (s, 2H), 4.44 (s, 2H), 4.35 (t, J=5.6 Hz, 2H), 3.73 (t, J=5.3 Hz, 2H), 3.46 (q, J=6.9 Hz, 2H), 2.29 (s, 3H), 1.09 (t, J=7.2 Hz, 3H); MS (APCI) m/z 341 (M+H)$^+$; Anal. Calcd for $C_{19}H_{24}N_4O_2$: C, 67.04; H, 7.11; N, 16.46; Found: C, 67.17; H, 7.13; N, 16.49.

EXAMPLE 81

2-(Ethoxymethyl)-6-methyl-1-{2-[3-(pyridin-3-yl)propoxy]ethyl}-1H-imidazo[4,5-c]pyridin-4-amine

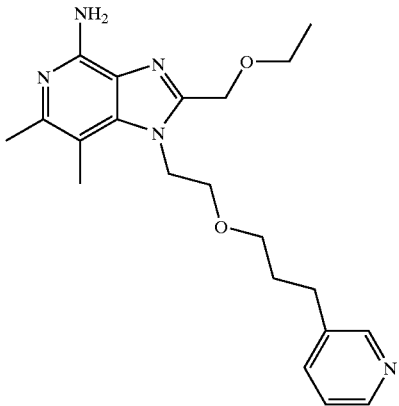

Part A

The preparation of tert-butyl 2-hydroxyethylcarbamate is described in Example 80, Part A. Benzyltrimethylammonium chloride (18 g, 97 mmol) and 50% aqueous sodium hydroxide (1.5 L) were added to a solution of tert-butyl 2-hydroxyethylcarbamate (156.4 g, 970.0 mmol) in dichloromethane (2.4 L), and the mixture was stirred rapidly. Propargyl bromide (109 mL, 979 mmol), available as an 80% solution in toluene, was then added, and the reaction was stirred for three hours. The layers were separated, and the aqueous layer was cooled to ~0° C. in an ice bath. Water was slowly added (1.2 L), and the aqueous solution was extracted with chloroform (2×300 mL). The combined organic solutions were washed with water (3×500 mL) and brine (2×500 mL), dried over sodium sulfate, filtered, and concentrated under reduced pressure to provide 173 g of tert-butyl 2-(prop-2-ynyloxy)ethylcarbamate as an orange oil, which was used without purification.

Part B

Under a nitrogen atmosphere, anhydrous triethylamine (45.5 mL, 326 mmol) and 3-bromopyridine (12.9 mL, 138 mmol) were added to a solution of tert-butyl 2-(prop-2-ynyloxy)ethylcarbamate (26.0 g, 125 mmol) in anhydrous DMF (400 mL), and the reaction was heated at 80° C. Dichlorobis(triphenylphosphine)palladium (II) (1.76 g, 2.51 mmol) and copper (I) iodide (0.96 g, 5.02 mmol) were then added, and the reaction was heated at 80° C. for one hour. The volatiles were removed under reduced pressure, and the residual black oil was dissolved in ethyl acetate (500 mL). The solution was washed with dilute aqueous sodium bicarbonate (1×200 mL) and brine (2×100 mL), dried over sodium sulfate, filtered, and concentrated under reduced pressure to provide a dark brown oil. The oil was purified by column chromatography on silica gel (350 g, eluting with 50:50 ethyl acetate:hexane), and the resulting dark oil was dissolved in hot methanol (200 mL) and treated with 10 g of activated charcoal. The mixture was filtered through a layer of CELITE filter aid, and the filtrate was treated with additional activated charcoal (10 g) and filtered in the same way to provide 25.4 g of tert-butyl {2-[3-(pyridin-3-yl)prop-2-ynyloxy]ethyl}carbamate as a light amber-colored oil.

Part C

Under a nitrogen purge, 10% palladium on carbon (5.0 g) and 2-propanol (20 mL) were added to a pressure vessel. A solution of tert-butyl {2-[3-(pyridin-3-yl)prop-2-ynyloxy]ethyl}carbamate (22.7 g, 82.1 mmol) in methanol (200 mL) were then added. The vessel was purged three times with nitrogen and then placed under hydrogen pressure (50 psi, $3.4 \times 10^5$ Pa) for five hours. The reaction mixture was filtered through a layer of CELITE filter aid, and the filtrate was concentrated under reduced pressure to yield 21.3 g of tert-butyl {2-[3-(pyridin-3-yl)propoxy]ethyl}carbamate as a brown oil.

Part D

A solution of tert-butyl {2-[3-(pyridin-3-yl)prop-2-ynyloxy]ethyl}carbamate (21.3 g, 76.0 mmol) in methanol (50 mL) was cooled to 6° C. A solution of 4 M hydrochloric acid in dioxane (114 mL, 456 mmol) was added over a period of ten minutes, and the reaction was stirred for six hours. The volatiles were removed under reduced pressure, and the residue was dissolved in water (200 mL). The solution was washed with dichloromethane (2×100 mL), and then adjusted to pH 14 with the addition of 20% aqueous sodium hydroxide (100 mL). The basic solution was then extracted with chloroform (5×100 mL). The combined extracts were washed with brine (2×100 mL), dried over magnesium sulfate, filtered, and concentrated under reduced pressure to provide a dark oil (8.5 g). The basic solution was then extracted with chloroform for six hours using a continuous extractor. The extracts were concentrated under reduced pressure to provide a yellow oil (1 g). The oils were combined and purified by distillation (108–110° C. at $2.1 \times 10^2$ Pa) to yield 7.74 g of 2-[3-(pyridin-3-yl)propoxy]ethylamine as a pale yellow oil.

Part E

Under a nitrogen atmosphere, triethylamine (6.1 mL, 44 mmol) was added to a solution of 2,4-dichloro-6-methyl-3-nitropyridine (7.50 g, 36.2 mmol), prepared as described in Part A of Example 1, in anhydrous DMF (160 mL). Neat 2-[3-(pyridin-3-yl)propoxy]ethylamine (6.60 g, 36.6 mmol) was then added, and the mixture was stirred at room temperature for 1.5 hours. The volatiles were then removed under reduced pressure, and the residue was dissolved in chloroform. The solution was washed with 2% aqueous potassium bicarbonate (1×), water (1×), and brine (1×), dried over sodium sulfate, filtered, and concentrated under reduced pressure to provide an oil. The crude product was purified by column chromatography on silica gel (600 g, eluting with methanol:ethyl acetate in various ratios) to afford an oil which was dried under reduced pressure to yield 4.9 g of (2-chloro-6-methyl-3-nitropyridin-4-yl)-{2-[3-(pyridin-3-yl)propoxy]ethyl}amine.

Part F

The general method described in Part E of Example 80 was used with the following modifications. A solution of phenol (1.45 g, 15.4 mmol) in diglyme (10 mL) was added to a cooled mixture of the sodium hydride dispersion (0.59 g, 14.7 mmol) in diglyme (15 mL), and the addition flask was rinsed twice with diglyme (5 mL), which was added to the reaction. A solution of (2-chloro-6-methyl-3-nitropyridin-4-yl)-{2-[3-(pyridin-3-yl)propoxy]ethyl}amine (4.9 g, 14 mmol) was added, and the reaction was heated at 60° C. for 20 hours. Additional reagent prepared from phenol (0.50 g, 5.3 mmol) and 60% sodium hydride (0.21 g, 5.3 mmol) in diglyme was added, and the reaction was heated at 60° C. for 2.5 hours. The reaction was allowed to cool to room temperature and slowly added to 800 mL of water and stirred for one hour to form a bright yellow solid. The solid was isolated by filtration and washed with hexane (50 mL) to provide 7.4 g of (6-methyl-3-nitro-2-phenoxypyridin-4-yl)-{2-[3-(pyridin-3-yl)propoxy]ethyl}amine as a yellow solid contaminated with water.

Part G

Under a nitrogen purge, 5% platinum on carbon (2.0 g), toluene (5 mL), and 2-propanol (5 mL) were added to a Parr vessel. A solution of (6-methyl-3-nitro-2-phenoxypyridin-4-yl)-{2-[3-(pyridin-3-yl)propoxy]ethyl}amine (5.71 g, 14.0 mmol) in toluene (45 mL) was then added. The vessel was placed under hydrogen pressure (49 psi, 3.4×10$^5$ Pa) for three hours. An analysis by liquid chromatography/mass spectrometry indicated the presence of starting material, and additional 5% platinum on carbon (0.1 g) was added. The reaction was continued for an additional 6 hours. The reaction mixture was filtered through a layer of CELITE filter aid, and the filtrate was concentrated under reduced pressure to yield 5.2 g of 6-methyl-2-phenoxy-N$^4$-{2-[3-(pyridin-3-yl)propoxy]ethyl}pyridine-3,4-diamine as a dark oil.

Part H

Under a nitrogen atmosphere, a solution of 6-methyl-2-phenoxy-N$^4$-{2-[3-(pyridin-3-yl)propoxy]ethyl}pyridine-3,4-diamine (5.2 g, 14 mmol), anhydrous dichloromethane (40 mL), and anhydrous triethylamine (2.3 mL, 16.5 mmol) was cooled to 5° C. A solution of ethoxyacetyl chloride (1.77 g, 14.4 mmol) in dichloromethane (10 mL) was then added over a period of ten minutes, and the reaction was stirred for 30 minutes. The reaction mixture was diluted with dichloromethane (25 mL), washed with aqueous saturated sodium bicarbonate (3×) and brine (3×), dried over sodium sulfate, filtered, and concentrated under reduced pressure to provide 5.8 g of 2-ethoxy-N-(6-methyl-2-phenoxy-4-{2-[3-(pyridin-3-yl)propoxy]ethylamino}pyridin-3-yl)acetamide as an oil.

Part I

Under a nitrogen atmosphere, a solution of 2-ethoxy-N-(6-methyl-2-phenoxy-4-{2-[3-(pyridin-3-yl)propoxy]ethylamino}pyridin-3-yl)acetamide (3.70 g, 7.96 mmol) and pyridine hydrochloride (3.70 g, 32.0 mmol) in anhydrous pyridine (25 mL) was heated at 140° C. for 38.5 hours and then was allowed to cool to room temperature. The volatiles were removed under reduced pressure, and the residue was dissolved in dichloromethane. The resulting solution was washed with saturated aqueous sodium bicarbonate (1×), water (1×) and brine (1×), dried over sodium sulfate, filtered, and concentrated under reduced pressure to provide 4.13 g of a brown oil. The crude product was purified by column chromatography on silica gel (220 g, eluting with ethyl acetate) to provide 2.72 g of 2-(ethoxymethyl)-6-methyl-4-phenoxy-1-{2-[3-(pyridin-3-yl)propoxy]ethyl}-1H-imidazo[4,5-c]pyridine as an oil.

Part J

Ammonium acetate (27.0 g, 0.350 mol) and 2-(ethoxymethyl)-6-methyl-4-phenoxy-1-{2-[3-(pyridin-3-yl)propoxy]ethyl}-1H-imidazo[4,5-c]pyridine (2.72 g, 6.09 mmol) were heated at 155° C. in a sealed tube for 21.5 hours. The solution was allowed to cool to room temperature and adjusted to pH 14 with the addition of 1 N sodium hydroxide. The solution was extracted with dichloromethane (3×). The combined extracts were washed with water (3×) and brine (3×), dried over sodium sulfate, filtered, and concentrated under reduced pressure to provide 2.19 g an amber-colored oil. The crude oil was purified by column chromatography on silica gel (200 g, eluting with 89:11 ethyl acetate:methanol) to provide 0.858 g of an oil. The oil was dissolved in 2-propanol treated with a 1.0 M solution of hydrochloric acid in diethyl ether (4.64 mL), and the resulting salt was recrystallized from 2-propanol. The salt was treated with aqueous sodium hydroxide to make the free base, which was isolated by filtration and dried for 48 hours at 80° C. to yield 0.348 g of 2-(ethoxymethyl)-6-methyl-1-{2-[3-(pyridin-3-yl)propoxy]ethyl}-1H-imidazo[4,5-c]pyridin-4-amine as a colorless oil.

$^1$H NMR (300 MHz, DMSO) δ 8.36 (d, J=4.4 Hz, 1H), 8.309 (s, 1H), 7.39 (d, J=7.5 Hz, 1H), 7.20–7.24 (m, 1H), 6.64 (s, 1H), 6.10 (s, 2H), 4.69 (s, 2H), 4.32 (t, J=5.3 Hz, 2H), 3.65 (t, J=5.3 Hz, 2H), 3.50 (q, J=7.1 Hz, 2H), 3.30 (t, J=6.24 Hz, 2H), 2.47 (t, J=8.1 Hz, 2H) 2.31 (s, 3H), 1.70 (p, J=7.5, 6.2 Hz, 2H), 1.12 (t, J=639 Hz, 3H); MS (APCI) m/z 341 (M +H)$^+$; Anal. Calcd for C$_{20}$H$_{27}$N$_5$O$_2$.0.8 H$_2$O: C, 62.58; H, 7.51; N, 18.24; Found: C, 62.85; H, 7.6; N, 18.12.

EXAMPLE 82

2-(Ethoxymethyl)-6,7-dimethyl-1-{2-[3-(1,3-thiazol-2-yl)propoxy]ethyl}-1H-imidazo[4,5-c]pyridin-4-amine

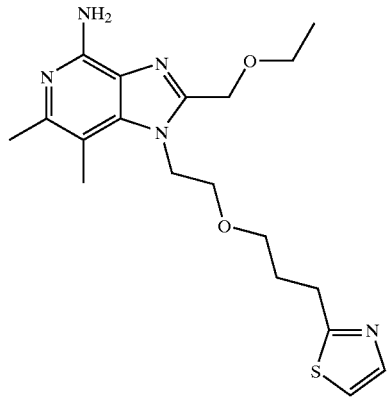

Part A

2-[3-(1,3-Thiazol-2-yl)propoxy]ethylamine was prepared using the general methods of Parts A through D of Example 81. In Part B tert-butyl 2-(prop-2-ynyloxy)ethylcarbamate (151.2 g, 0.759 mol) was coupled with 2-bromothiazole (124 g, 0.759 mmol) in lieu of 3-bromopyridine. After Part D, the product was purified by distillation (113–115° C. at 1.7×10$^2$ Pa) to yield 43 g of the desired product as an oil.

Part B

Under a nitrogen atmosphere, triethylamine (3.4 mL, 24 mmol) was added dropwise to a solution of 2,4-dichloro-5,6-dimethyl-3-nitropyridine (4.50 g, 20.4 mmol) in anhydrous DMF (45 mL). 2-[3-(1,3-Thiazol-2-yl)propoxy]ethylamine (4.55 g, 24.4 mmol) was then added, and the addition funnel was rinsed with additional DMF (15 mL). The reaction was heated at 60° C. for 3.5 hours. The volatiles were then removed under reduced pressure, and the residue was partitioned between water (100 mL) and diethyl ether (250 mL). The organic layer was washed with water (2×50 mL) and brine (3×50 mL), dried over magnesium sulfate, filtered, and concentrated under reduced pressure to provide an orange oil. The crude product (7.41 g) was purified by column chromatography on silica gel (375 g, eluting with 50:50 hexane:ethyl acetate) to provide a solid, which was dried overnight under high vacuum at room temperature to provide 4.6 g of (2-chloro-5,6-dimethyl-3-nitropyridin-4-yl)-{2-[3-(1,3-thiazol-2-yl)propoxy]ethyl}amine as a yellow solid.

Part C

The method described in Example 80, Part E was used with the following exceptions. A solution of phenol (2.11 g, 22.4 mmol) in diglyme (5 mL) was added to the sodium hydride dispersion (0.87 g, 22 mmol) in diglyme (10 mL). A solution of (2-chloro-5,6-dimethyl-3-nitropyridin-4-yl)-

{2-[3-(1,3-thiazol-2-yl)propoxy]ethyl}amine (4.6 g, 15 mmol) in diglyme (25 mL) was added, and the addition flask was rinsed with additional diglyme (2×5 mL), which was added to the reaction flask. The resulting amber solution was heated at 110° C. for 3.25 hours and then allowed to cool to room temperature. The volatiles were removed under reduced pressure, and the residue was dissolved in ethyl acetate (100 mL). The solution was washed with saturated aqueous ammonium chloride (1×50 mL), 1 N potassium hydroxide (2×50 mL), and brine (2×50 mL), and then dried over magnesium sulfate, filtered, and concentrated under reduced pressure to provide an oil. The oil was dried for three days under high vacuum at room temperature to provide 4.7 g of (2,3-dimethyl-5-nitro-6-phenoxypyridin-4-yl)-{2-[3-(1,3-thiazol-2-yl)propoxy]ethyl}amine as an oil.

Part D

Under a nitrogen purge, 5% platinum on carbon (0.5 g) and toluene (5 mL) were added to a pressure vessel. A solution of (2,3-dimethyl-5-nitro-6-phenoxypyridin-4-yl)-{2-[3-(1,3-thiazol-2-yl)propoxy]ethyl} amine (4.7 g, 11 mmol) in toluene (35 mL) was then added. The vessel was placed under hydrogen pressure (50 psi, 3.4×10$^5$ Pa) for 24 hours. The reaction mixture was filtered through a layer of CELITE filter aid, and the filtrate was concentrated under reduced pressure to yield 4.12 g of 5,6-dimethyl-2-phenoxy-N$^4$-{2-[3-(1,3-thiazol-2-yl)propoxy]ethyl}pyridine-3,4-diamine as a pale yellow oil.

Part E

Under a nitrogen atmosphere, a solution of 5,6-dimethyl-2-phenoxy-N$^4$-{2-[3-(1,3-thiazol-2-yl)propoxy]ethyl}pyridine-3,4-diamine (4.12 g, 10.3 mmol) and pyridine hydrochloride (0.024 g, 0.21 mmol) in pyridine (30 mL) was cooled to 7° C. Ethoxyacetyl chloride (1.33 g, 10.9 mmol) was added, and the reaction was stirred for 30 minutes. The cloudy solution was then heated at 100° C. for 20 hours and then allowed to cool to room temperature. The volatiles were removed under reduced pressure, and the residue was partitioned between water and dichloromethane. The organic layer was washed with potassium carbonate (2×50 mL) and brine (2×50 mL), dried over magnesium sulfate, filtered, and concentrated under reduced pressure. The resulting oil was triturated with heptane to provide a solid that was isolated by filtration. 2-(Ethoxymethyl)-6,7-dimethyl-4-phenoxy-1-{2-[3-(1,3-thiazol-2-yl)propoxy]ethyl)}-1H-imidazo[4,5-c]pyridine (3.68 g) was obtained as a tan solid.

Part F

Ammonium acetate (37 g, 0.48 mol) and 2-(ethoxymethyl)-6,7-dimethyl-4-phenoxy-1-{2-[3-(1,3-thiazol-2-yl)propoxy]ethyl}-1H-imidazo[4,5-c]pyridine (3.68 g, 7.89 mmol) were heated at 150° C. in a sealed tube for 29.5 hours. The resulting solution was allowed to cool, and the pH was adjusted to 14 with the addition of 1 N potassium hydroxide. The solution was stirred for one hour and was then extracted with ethyl acetate (1×200 mL). The extract was washed with 1 N potassium hydroxide (3×50 mL) and brine (3×50 mL), dried over magnesium sulfate, filtered, and concentrated under reduced pressure to provide a brown solid. The solid was triturated with diethyl ether, isolated by filtration, and purified by column chromatography on silica gel (100 g, eluting with 96:4 dichloromethane:methanol) to provide an oil, which was triturated with hexane to form a solid (0.60 g). The solid was dissolved in ethyl acetate, filtered through a 4 μm syringe filter, and concentrated under reduced pressure to provide a solid. The solid was triturated with hexane, isolated by filtration, and dried to provide 0.446 g of 2-(ethoxymethyl)-6,7-dimethyl-1-{2-[3-(1,3-thiazol-2-yl)propoxy]ethyl}-1H-imidazo[4,5-c]pyridin-4-amine as a white powder, mp. 91–92° C.

$^1$H NMR (300 MHz, DMSO) δ 7.66 (d, J=3.7 Hz, 1H), 7.53 (d, J=3.1 Hz, 1H), 5.77 (s, 2H), 4.69 (s, 2H), 4.53 (t, J=5.a6 Hz, 2H), 3.70 (t, J=5.6 Hz, 2H), 3.50 (q, J=7.0 Hz, 2H), 3.38 (t, J=5.9 Hz, 2H), 2.89 (t, J=7.5 Hz, 2H), 2.38 (s, 3H), 2.31 (s, 3H), 1.86 (p, J=7.5, 6.2 Hz, 2H) 1.13 (t, J=6.9 Hz, 3H); MS (APCI) m/z 390 (M+H)$^+$; Anal. Calcd for C$_{19}$H$_{27}$N$_5$O$_2$S: C, 58.59; H, 6.99; N, 17.98; Found: C, 58.53; H, 7.01; N, 17.88.

EXAMPLE 83

6,7-Dimethyl-1-{2-[3-(1,3-thiazol-2-yl)propoxy]ethyl}-1H-imidazo[4,5-c]pyridin--4-amine hydrochloride

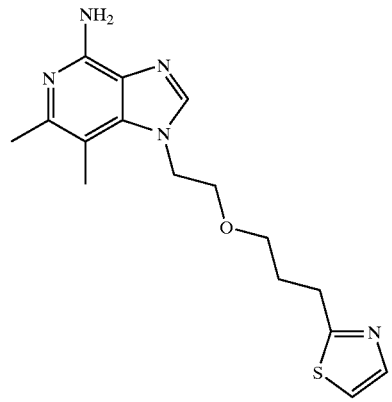

Part A

The preparation of 5,6-dimethyl-2-phenoxy-N$^4$-{2-[3-(1,3-thiazol-2-yl)propoxy]ethyl}pyridine-3,4-diamine is described in Example 82, parts A through D. Under a nitrogen atmosphere, a solution of 5,6-dimethyl-2-phenoxy-N$^4$-{2-[3-(1,3-thiazol-2-yl)propoxy]ethyl}pyridine-3,4-diamine (2.9 g, 7.3 mmol), pyridine hydrochloride (0.017 g, 0.145 mmol), and triethylorthoformate (1.8 mL, 11 mmol) in toluene (75 mL) was heated at reflux for 30 minutes. The volatiles were removed under reduced pressure, and the residue was dissolved in dichloromethane. The resulting solution was washed with saturated aqueous sodium bicarbonate (2×20 mL) and brine (2×50 mL), dried over sodium sulfate, filtered, and concentrated under reduced pressure to provide an oil. The oil was triturated with diethyl ether to form a solid that was isolated by filtration to provide 2.15 g of 6,7-dimethyl-4-phenoxy-1-{2-[3-(1,3-thiazol-2-yl)propoxy]ethyl}-1H-imidazo[4,5-c]pryridine as an off-white powder.

Part B

Ammonium acetate (15.9 g, 0.206 mol) and 6,7-dimethyl-4-phenoxy-1-{2-[3-(1,3-thiazol-2-yl)propoxy]ethyl}-1H-imidazo[4,5-c]pryridine (1.59 g, 3.89 mmol) were heated at 150° C. in a sealed tube for 20 hours. The amber-colored solution was allowed to cool to room temperature and diluted with water (10 mL). The resulting solution was adjusted to pH 14 with the addition of 20% sodium hydroxide and stirred for 30 minutes. The solution was extracted with dichloromethane (3×30 mL). The combined extracts were washed with brine (3×25 mL), dried over sodium sulfate, filtered, and concentrated under reduced pressure to provide an oil. Diethyl ether was added to the oil and subsequently removed under reduced pressure to provide a solid, which was purified by column chromatography on silica gel (eluting with 95:5 dichloromethane:methanol) to provide two portions of slightly impure product. One portion (0.13 g) was treated with a 1.0 M solution of hydrochloric acid in diethyl ether (1 equivalent), and the resulting salt was recrystallized from 2-propanol to provide 0.056 g of 6,7-dimethyl-1-{2-[3-(1,3-thiazol-2-yl)propoxy]ethyl}-1H-imidazo[4,5-c]pyridin-4-amine hydrochloride as a white powder, decomp. ~180° C.

$^1$H NMR (300 MHz, DMSO) δ 13.52 (m, 1H), 8.32 (s, 1H), 8.03 (s, 1H), 7.65 (d, J=3.1 Hz, 1H), 7.54 (d, J=3.7 Hz, 1H), 4.61 (t, J=5.0 Hz, 2H), 3.73 (t, J=5.0 Hz, 2H), 3.40 (t, J=5.9 Hz, 2H), 2.84 (t, J=7.5 Hz, 2H), 2.44 (s, 3H), 2.42 (s, 3H), 1.84 (p, J=7.5, 6.2 Hz,2H); MS (APCI) m/z 332 (M+H)$^+$; Anal. Calcd for $C_{16}H_{21}N_5OS \cdot HCl \cdot 0.5\ H_2O$: C, 50.99; H, 6.15; N, 18.58; Found: c, 50.93; H, 6.00; N, 18.55.

EXAMPLE 84

6,7-Dimethyl-1-[2-(pyridin-4-ylmethoxy)ethyl]-1H-imidazo[4,5-c]pyridin-4-amine

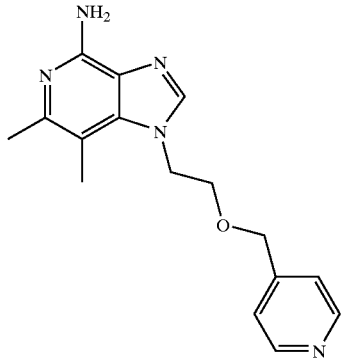

Part A

The general methods described in Parts A and B in Example 80 were employed to convert ethanol amine (40.00 g, 655 mmol) to tert-butyl (2-pyridin-4-ylmethoxy) ethylcarbamate. In Part B, 4-(chloromethyl)pyridine hydrochloride (102 g, 633 mmol) was used in lieu of benzyl bromide.

Part B

To a solution of tert-butyl (2-pyridin-4-ylmethoxy) ethylcarbamate (157 g, 622 mmol) was added a solution of 25% by volume hydrochloric acid in anhydrous ethanol (1600 mL) at 0° C., and the reaction was allowed to warm to room temperature and stirred overnight. The volatiles were removed under reduced pressure, and the residue was dissolved in water (1 L). The solution was washed with dichloromethane (2×500 mL), and then adjusted to pH 13 with the addition of solid potassium carbonate and 50% aqueous sodium hydroxide. The basic solution was then extracted with chloroform (2×2000 mL) and overnight using a continuous extractor. The combined extracts were concentrated under reduced pressure to a volume of 2 L, washed with brine (2×1000 mL), dried over sodium sulfate, filtered, and concentrated under reduced pressure to provide a yellow oil (83.2 g). The oil was purified by distillation (103–105° C. at 63 Pa) to yield 47.5 g of 2-(pyridin-4-ylmethoxy) ethylamine as a colorless oil.

Part C

Under a nitrogen atmosphere, triethylamine (7.4 mL, 53 mmol) was added to a solution of 2,4-dichloro-5,6-dimethyl-3-nitropyridine (9.78 g, 44.2 mmol) in anhydrous DMF (200 mL). 2-(Pyridin-4-ylmethoxy)ethylamine (6.8 g, 45 mmol) was added, and the reaction was stirred at room temperature for 17.5 hours. The reaction solution was slowly added to water (1.8 L) and stirred for two hours to form a precipitate, which was isolated by filtration and washed with cold hexane (200 mL). The solid was dried under reduced pressure for one hour to provide 10.15 g of (2-chloro-5,6-dimethyl-3-nitropyridin-4-yl)-[2-(pyridin-4-ylmethoxy) ethyl]amine as a yellow solid. An analysis by HPLC indicated that starting material and an isomer were present as impurities.

Part D

Under a nitrogen atmosphere, diglyme (25 mL) was added to sodium hydride (1.81 g, 45.2 mmol), which is available as a 60% dispersion in mineral oil, and the mixture was cooled to 5° C. A solution of phenol (4.54 g, 48.2 mmol) in diglyme (50 mL) was added dropwise over a period of 15 minutes. The reaction became homogeneous after 15 minutes. A solution of (2-chloro-5,6-dimethyl-3-nitropyridin-4-yl)-[2-(pyridin-4-ylmethoxy)ethyl]amine (10.15 g, 30.14 mmol) was added, and the reaction was heated at 160° C. for 13 hours. An analysis by HPLC indicated the presence of starting material. Additional phenol (3.12 g, 33.2 mmol) was added to 60% sodium hydride (1.24 g, 31.1 mmol) in diglyme, and the mixture was stirred until it became homogeneous. This solution was added to the cooled reaction flask, and the reaction was heated at 160° C. for 9.5 hours. The reaction was allowed to cool to room temperature, and the volatiles were removed under reduced pressure to provide a black oil. The oil was dissolved in ethyl acetate, and the solution was washed with 1 N potassium hydroxide (3×) and brine (3×), dried over magnesium sulfate, filtered, and concentrated under reduced pressure. The crude product was purified by column chromatography on silica gel (eluting with 80:20 ethyl acetate:hexane) to provide 2.47 g of (2,3-dimethyl-5-nitro-6-phenoxypyridin-4-yl)-[2-(pyridin-4-ylmethoxy)ethyl]amine.

Part E

The procedure described in Part F of Example 80 was followed using (2,3-dimethyl-5-nitro-6-phenoxypyridin-4-yl)-[2-(pyridin-4-ylmethoxy)ethyl]amine (2.47 g, 6.26 mmol) as the starting material. The reaction product, 5,6-dimethyl-2-phenoxy-$N^4$-[2-(pyridin-4-ylmethoxy)ethyl]pyridine-3,4-diamine (1.99 g), was obtained as an amber-colored oil.

Part F

Under a nitrogen atmosphere, pyridine hydrochloride (0.013 g, 0.11 mmol) and triethylorthoformate (1.4 mL, 8.2 mmol) were added to a solution of 5,6-dimethyl-2-phenoxy-$N^4$-[2-(pyridin-4-ylmethoxy)ethyl]pyridine-3,4-diamine (1.99 g, 5.46 mmol) in toluene, and the reaction was heated at 84° C. for one hour. The volatiles were removed under reduced pressure to provide a solid (2.0 g), which was purified by column chromatography on silica gel (70 g, eluting with ethyl acetate). The resulting solid was dried to yield 1.52 g of 6,7-dimethyl-4-phenoxy-1-[2-(pyridin-4-ylmethoxy)ethyl]-1H-imidazo[4,5-c]pyridine as a white solid.

Part G

Ammonium acetate (15 g, 0.19 mol) and 6,7-dimethyl-4-phenoxy-1-[2-(pyridin-4-ylmethoxy)ethyl]-1H-imidazo[4,5-c]pyridine (1.52 g, 4.06 mmol) were heated at 155° C. in a sealed tube for 23.5 hours. The solution was allowed to cool to room temperature and adjusted to pH 14 with the addition of 1 N sodium hydroxide. The solution was extracted with dichloromethane, and the combined extracts were washed with aqueous sodium bicarbonate (1×), water (1×), and brine (2×), dried over sodium sulfate, filtered, and concentrated under reduced pressure to provide an orange solid. The solid was recrystallized from acetonitrile and then from 2-propanol to yield 0.407 g of a white solid, which was further purified by column chromatography on silica gel (treated with diethylamine, eluting with 95:5 dichloromethane:methanol). The product was washed with water, isolated by filtration, and dried to provide 0.247 g of 6,7-dimethyl-1-[2-(pyridin-4-ylmethoxy)ethyl]1H-imidazo[4,5-c]pyridin-4-amine as a white powder, mp 195–196° C.

$^1$H NMR (300 MHz, DMSO) δ 8.45 (d, J=5.6 Hz, 2H), 7.93 (s, 1H), 7.14 (d, J=6.2 Hz, 2H), 5.75 (s, 2H), 4.56 (t, J=5.3 Hz, 2H), 4.51 (s, 2H), 3.79 (t, J=5.3 Hz, 2H), 2.35 (s, 3H), 2.30 (s, 3H); MS (APCI) m/z 298 (M+H)$^+$; Anal. Calcd for $C_{16}H_{19}N_5O$: C, 64.63; H, 6.44; N, 23.55; Found: C, 64.42; H, 6.64; N, 23.31.

EXAMPLE 85

1-[5-(4-Chlorobenzenesulfonyl)pentyl]-6,7-dimethyl-2-propyl-1H-imidazo[4,5-c]pyridin-4-amine

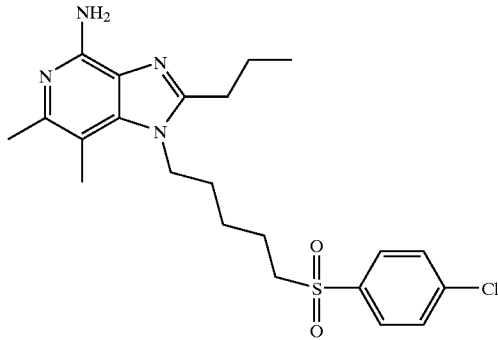

Part A

Under a nitrogen atmosphere, triethylamine (65.0 mL, 475 mmol) was added to a solution of 2,4-dichloro-5,6-dimethyl-3-nitropyridine (70.0 g, 317 mmol) in anhydrous DMF (760 mL), and the reaction was stirred for 15 minutes. A solution of 5-amino-1-pentanol (35.9 g, 348 mmol) in anhydrous DMF (200 mL) was slowly added over a period of 2 hours, and the reaction was stirred overnight at room temperature. A white precipitate had formed and was removed by filtration. The filtrate was concentrated under reduced pressure to provide an orange-red oil, which was dissolved in ethyl acetate (600 mL). The solution was washed with water (3×60 mL), dried over magnesium sulfate, filtered, and concentrated under reduced pressure to provide 96.7 g of an orange solid. The solid was recrystallized twice from a mixture of ethyl acetate and hexanes to afford a yellow solid, which was isolated by filtration and washed with cold hexanes to provide 44.6 g of 5-(2-chloro-5,6-dimethyl-3-nitropyridin-4-ylamino)pentan-1-ol as a yellow solid.

Part B

Under a nitrogen atmosphere, tetrahydrofuran (THF) (150 mL) was cooled to 0° C. Sodium hydride (9.30 g, 233 mmol), available as a 60% dispersion in mineral oil, was added with stirring. A solution of phenol (21.1 g, 225 mmol) in THF (80 mL) was added dropwise over a period of one hour. A solution of 5-(2-chloro-5,6-dimethyl-3-nitropyridin-4-ylamino)pentan-1-ol (44.5 g, 155 mmol) in THF (80 mL) was then added dropwise over a period of 40 minutes. The reaction was allowed to warm to room temperature and heated at reflux overnight. An analysis by thin layer chromatography (TLC) indicated that the reaction was incomplete. Additional reagent was prepared as described above by adding phenol (7.1 g, 75 mmol) to sodium hydride (3.2 g, 80 mmol) in THF (50 mL), and the reagent was added to the reaction solution at room temperature. The reaction was heated at reflux overnight and then allowed to cool to room temperature. Water (50 mL) was added, and the solvent was removed under reduced pressure. The aqueous solution was extracted with ethyl acetate. The organic solution was washed with water (3×) and brine (1×), dried over magnesium sulfate, filtered, and concentrated under reduced pressure to provide the crude product. The crude product was purified twice by column chromatography on silica gel (eluting sequentially with 50:50 hexane:ethyl acetate and 25:75 hexane:ethyl acetate) to provide 40.24 g of 5-(2,3-dimethyl-5-nitro-6-phenoxy-pyridin-4-ylamino)pentan-1-ol as a yellow oil.

Part C

Under a nitrogen atmosphere, a solution of 5-(2,3-dimethyl-5-nitro-6-phenoxy-pyridin-4-ylamino)pentan-1-ol (40.24 g, 114.6 mmol) in dichloromethane (350 mL) was cooled to 0° C. Thionyl chloride (12.5 mL, 172 mmol) was added dropwise, and the reaction was heated at reflux for one hour. The reaction was cooled to 0° C., and water (200 mL) was slowly added followed by solid sodium bicarbonate until the pH of the solution was basic. The solvent was partially removed under reduced pressure, and the aqueous solution was extracted with ethyl acetate (500 mL). The combined organic solutions washed with saturated aqueous sodium bicarbonate (3×50 mL), water (1×50 mL), and brine (2×20 mL), and then dried over magnesium sulfate, filtered, and concentrated under reduced pressure to afford a yellow oil, which crystallized overnight. The solid was dried for one hour in a vacuum oven at 70° C. to provide 40.1 g of (5-chloropentyl)-(2,3-dimethyl-5-nitro-6-phenoxy-pyridin-4-yl)amine as a yellow solid.

Part D

A solution of sodium dithionite (90.5 g, 520 mmol), available as approximately 85% pure sodium hydrosulfite, in water (200 mL) was added to a solution of (5-chloropentyl)-(2,3-dimethyl-5-nitro-6-phenoxy-pyridin-4-yl)amine (37.8 g, 104 mmol) in ethanol (575 mL), and the mixture was stirred rapidly for five hours. The mixture did not become homogeneous, and additional ethanol (200 mL) was added. The mixture remained heterogeneous and was separated into two batches. A solution of sodium dithionite (40 g, 230 mmol) in water (150 mL) was partitioned evenly between the two batches, and the reactions were stirred for an additional hour. An analysis by TLC indicated that the reactions were complete. A white solid was removed from the reaction mixtures by filtration and was washed with methanol. The solvents were removed under reduced pressure, and the residue was partitioned between dichloromethane (400 mL) and water (100 mL). Saturated aqueous sodium bicarbonate was added to the aqueous layer until it was basic, and the resulting solution was extracted with dichloromethane (2×100 mL). The combined organic extracts were washed with brine, dried over magnesium sulfate, filtered, and concentrated under reduced pressure to provide 34.7 g of $N^4$-(5-chloropentyl)-5,6-dimethyl-2-phenoxypyridine-3,4-diamine as an orange-red liquid.

Part E

Under a nitrogen atmosphere, pyridine hydrochloride (4.2 g, 36.4 mmol) was added in small amounts to a solution of $N^4$-(5-chloropentyl)-5,6-dimethyl-2-phenoxypyridine-3,4-diamine (32.4 g, 97.0 mmol) in toluene (500 mL). Trimethylorthobutyrate (17 mL, 107 mmol) was then added, and the reaction was heated at reflux for two hours. The solvent was removed under reduced pressure, and the residue was dissolved in ethyl acetate (500 mL). The solution was washed with water (3×80 mL) and brine (1×40 mL), dried over magnesium sulfate, filtered, and concentrated under reduced pressure to afford an oil, which was dissolved in hexanes (20 mL) and concentrated under reduced pressure to provide an off-white solid. The crude solid was purified by column chromatography on silica gel (eluting with 2:1 hexane:ethyl acetate) to provide 30.8 g of 1-(5-chloropentyl)-6,7-dimethyl-4-phenoxy-2-propyl-1H-imidazo[4,5-c]pyridine as white crystals.

Part F

Under a nitrogen atmosphere, a solution of 4-chlorobenzenethiol (868 mg, 6.00 mmol) in DMF (5 mL) was added to a mixture of sodium hydride (60% dispersion, 240 mg, 6.00 mmol) in DMF (15 mL); the reaction became homogeneous and was stirred for 15 minutes. Solid 1-(5-chloropentyl)-6,7-dimethyl-4-phenoxy-2-propyl-1H-imidazo[4,5-c]pyridine (1.93 g, 5.00 mmol) was added in small amounts, and the reaction was stirred for 1.5 hours. Water (25 mL) was added, and the resulting solution was extracted with ethyl acetate (3×50 mL). The combined extracts were washed with water (5×30 mL) and brine (2×10 mL), dried over magnesium sulfate, filtered, and concentrated under reduced pressure to provide a colorless oil, which crystallized overnight. The solid was dried for three hours under high vacuum to provide 2.58 g of 1-[5-(4-chlorophenylsulfanyl)pentyl]-6,7-dimethyl-4-phenoxy-2-propyl-1H-imidazo[4,5-c]pyridine as a white solid.

Part G

Under a nitrogen atmosphere, a solution of 1-[5-(4-chlorophenylsulfanyl)pentyl]-6,7-dimethyl-4-phenoxy-2-propyl-1H-imidazo[4,5-c]pyridine (2.47 g, 5.00 mmol) in chloroform (25 mL) was cooled to 0° C. mCPBA (2.47 g, 11 mmol) was added in one portion, and the cloudy reaction was stirred for 30 minutes at room temperature. The volatiles were removed under reduced pressure, and the residue was partitioned between ethyl acetate (300 mL) and saturated aqueous sodium bicarbonate (75 mL). The organic layer was washed with saturated aqueous sodium bicarbonate (5×30 mL), water (2×30 mL), and brine (2×10 mL), and then dried over magnesium sulfate, filtered, and concentrated under reduced pressure to provide a solid. The product was triturated with ethyl acetate, isolated by filtration, and dried under high vacuum to provide 2.31 g of 1-[5-(4-chlorobenzenesulfonyl)pentyl]-6,7-dimethyl-4-phenoxy-2-propyl-1H-imidazo[4,5-c]pyridine as a white powder.

Part H

Ammonium acetate (20.2 g, 0.262 mol) and 1-[5-(4-chlorobenzenesulfonyl)pentyl]-6,7-dimethyl-4-phenoxy-2-propyl-1H-imidazo[4,5-c]pyridine (2.20 g, 4.18 mmol) were stirred at 160° C. in a sealed tube for 18 hours. The solution was allowed to cool to room temperature and partitioned between chloroform (50 mL) and water (25 mL). The aqueous solution was adjusted to pH 11 with the addition of 1 M sodium hydroxide and two solid sodium hydroxide pellets. The aqueous solution was then extracted with chloroform (4×50 mL). The combined organic solutions were washed with 1 M sodium hydroxide (2×25 mL), dried over sodium sulfate, filtered, and concentrated under reduced pressure to provide the crude product as a tan foam. The crude product was purified by column chromatography on silica gel (eluting with 94:5:1 dichloromethane:methanol:triethylamine) to provide a product that was impure as determined by HPLC analysis. A second purification by column chromatography on silica gel (eluting with 96:3:1 dichloromethane:methanol:triethylamine) also resulted in impure material. The solid was recrystallized from acetonitrile, and the crystals were isolated by filtration, washed with cold acetonitrile and ethyl acetate, dried under high vacuum to provide 0.53 g of 1-[5-(4-chlorobenzenesulfonyl)pentyl]-6,7-dimethyl-2-propyl-1H-imidazo[4,5-c]pyridin-4-amine as white needles, mp 147.0–149.0° C.

$^1$H NMR (300 MHz, CDCl$_3$) δ 7.83 (d, J=8.6, 2H), 7.55 (d, J=8.6, 2H), 4.82 (br s, 2H), 4.17 (dd, J=7.7, 7.7, 2H), 3.07 (dd, J=7.8, 7.8, 2H), 2.72 (dd, J=7.7, 7.7, 2H), 2.43 (s, 3H), 2.39 (s, 3H), 1.95–1.65 (m, 6H), 1.55–1.42 (m, 2H), 1.05 (t, J=7.4, 3H); MS (APCI) m/z 449 (M)$^+$; Anal. Calcd for C$_{22}$H$_{29}$ClN$_4$ O$_2$S: C, 58.85; H, 6.51; N, 12.48; Found: C, 58.79; H, 6.50; N, 12.29.

EXAMPLES 86–88

The general methods described in Example 85 were used for Examples 86–88. The thiol selected in lieu of 4-chlorobenzenethiol in Part F of Example 85 is shown in the table below for Examples 86–88. The isolation of the final products is described below.

| Example Number | Thiol | R |
|---|---|---|
| 86 | 4-trifluoromethylthiophenol | 4-CF$_3$-phenyl |
| 87 | 2-mercaptopyridine | 2-pyridyl |
| 88 | thiophenol | phenyl |

EXAMPLE 86

6,7-Dimethyl-2-propyl-1-{5-[4-(trifluoromethyl)benzenesulfonyl]pentyl}-1H-imidazo[4,5-c]pyridin-4-amine Ammonium acetate (6.25 g, 81.1 mmol) and 6,7-dimethyl-4-phenoxy-2-propyl-1-{5-[4-(trifluoromethyl)benzenesulfonyl]pentyl}-1H-imidazo[4,5-c]pyridine (0.70 g, 1.25 mmol) were used as described in Part H of Example 85. The reaction solution was partitioned between chloroform (75 mL) and 1 M sodium hydroxide (75 mL). The aqueous solution was extracted with chloroform (2×75 mL).

The combined organic solutions were washed with 1 M sodium hydroxide (4×30 mL) and brine, dried, filtered, and concentrated as described in Example 85. The crude product was purified by column chromatography on silica gel (eluting sequentially with 99:1:0.1 dichloromethane:methanol:ammonium hydroxide and 94:6:0.1 dichloromethane:methanol:ammonium hydroxide) to provide a product that was impure as determined by nuclear magnetic resonance (NMR) spectroscopy analysis. The solid was dissolved in hot 2-propanol and treated with one equivalent of a 1 M solution of hydrochloric acid in diethyl ether. Chloroform and water were added, and the aqueous layer was extracted with chloroform (3×). The combined organic solutions were dried over sodium sulfate, filtered, and concentrated under reduced pressure to provide a solid. The solid was stirred with 2-propanol, isolated by filtration, washed with cold 2-propanol, and dried under high vacuum. The solid was then dissolved in dichloromethane (100 mL), and the resulting solution was washed with 1 M sodium hydroxide (2×40 mL). The basic solution was extracted with dichloromethane (2×30 mL), and the combined extracts were dried over sodium sulfate, filtered, and concentrated under reduced pressure to provide 198 mg of 6,7-dimethyl-2-propyl-1-{5-[4-(trifluoromethyl)benzenesulfonyl]pentyl}-1H-imidazo[4,5-c]pyridin-4-amine as a white powder, mp 172.0–173.5° C.

$^1$H NMR (300 MHz, CDCl$_3$) δ 8.04 (d, J=8.6, 2H), 7.85 (d, J=8.6, 2H), 4.82 (br s, 2H) 4.18 (dd, J=7.7, 7.7, 2H), 3.10 (dd, J=7.8, 7.8, 2H), 2.73 (dd J=7.7, 7.7, 2H), 2.43 (s, 3H), 2.39 (s, 3H), 1.96–1.65 (m, 6H), 1.58–1.43 (m, 2H), 1.05 (t, J=7.4, 3H); MS (APCI) m/z 483 (M+H)$^+$; Anal. Calcd for C$_{23}$H$_{29}$F$_3$N$_4$O$_2$S: C, 57.25; H, 6.06; N, 11.61; Found: C, 56.75; H, 6.20; N, 11.25.

EXAMPLE 87

6,7-Dimethyl-2-propyl-1-[5-(pyridine-2-sulfonyl)pentyl]-1H-imidazo[4,5-c]pyridin-4-amine The crude product (2.47 g), obtained after the oxidation procedure as described in Part G of Example 85, was purified by column chromatography on silica gel (eluting sequentially with 2:1 ethyl acetate:hexane and 4:1 ethyl acetate:hexane to provide 1.86 g of 6,7-dimethyl-4-phenoxy-2-propyl-1-[5-(pyridine-2-sulfonyl)pentyl]-1H-imidazo[4,5-c]pyridine as a white solid.

Ammonium acetate (15 g, 0.20 mol) and 6,7-dimethyl-4-phenoxy-2-propyl-1-[5-(pyridine-2-sulfonyl)pentyl]-1H-imidazo[4,5-c]pyridine (1.54 g, 3.13 mmol) were heated at 160° C. in a sealed tube for 16 hours. The solution was allowed to cool to room temperature and partitioned between chloroform (30 mL) and 1 M sodium hydroxide (30 mL). The aqueous solution was then extracted with chloroform (3×30 mL). The combined organic solutions were washed, dried, filtered, and concentrated as described in Example 85 to provide 1.47 g of an off-white foam. The crude product was recrystallized from acetonitrile to provide 672 mg of 6,7-dimethyl-2-propyl-1-[5-(pyridine-2-sulfonyl)pentyl]-1H-imidazo[4,5-c]pyridin-4-amine as a white powder, mp 143.0–144.5° C.

$^1$H NMR (300 MHz, CDCl$_3$) δ 8.74 (ddd, J=4.6, 1.7, 1.1, 1H), 8.08 (ddd, J=7.8, 1.1, 1.1, 1H), 7.98 (ddd, J=7.8, 7.5, 1.7, 1H), 7.55 (ddd, J=7.5, 4.6, 1.1, 1H), 4.80 (br s, 2H), 4.18 (dd, J=7.7, 7.7, 2H), 3.40 (dd, J=7.7, 7.7, 2H), 2.73 (dd, J=7.7, 7.7, 2H), 2.43 (s, 3H), 1.95–1.68 (m, 6H), 1.60–1.48 (m, 2H), 1.05 (t, J=7.4, 3H); MS (APCI) m/z 416 (M+H)$^+$; Anal. Calcd for C$_{21}$H$_{29}$N$_5$O$_2$S: C, 60.70; H, 7.03; N, 16.85; Found: C, 60.54; H, 6.97; N 16.76.

EXAMPLE 88

1-[5-(Benzenesulfonyl)pentyl]-6,7-dimethyl-2-propyl-1H-imidazo[4,5-c]pyridin-4-amine Ammonium acetate (18 g, 0.23 mol) and 1-[5-(benzenesulfonyl)pentyl]-6,7-dimethyl-4-phenoxy-2-propyl-1H-imidazo[4,5-c]pyridine (1.74 g, 3.54 mmol) were heated at 165° C. in a sealed tube for 8 hours with stirring. Following the work-up, an analysis by NMR indicated that starting material was present; additional ammonium acetate was added (18 g, 0.23 mol), and the reaction was continued overnight at 160° C. The solution was allowed to cool to room temperature and partitioned between chloroform (100 mL) and 1 M sodium hydroxide (75 mL). Following the work-up, the crude product (1.37 g) was purified by column chromatography on silica gel (eluting with 97:3:0.1 dichloromethane:methanol:ammonium hydroxide) and then recrystallized from acetonitrile to provide 0.715 g of 1-[5-(benzenesulfonyl)pentyl]-6,7-dimethyl-2-propyl-1H-imidazo[4,5-c]pyridin-4-amine as a white powder, mp 134.0–136.0° C. with a phase change at 122–125° C.

$^1$H NMR (300 MHz, CDCl$_3$) δ 7.89 (d, J=7.7, 2H), 7.67 (t, J=7.7, 1H), 7.57 (t, J=7.7, 2H), 4.80 (br s, 2H), 4.16 (dd, J=7.8, 7.8, 2H), 3.08 (dd, J=7.7, 7.7, 2H), 2.72 (dd, J=7.7, 7.7, 2H), 2.43 (s, 3H), 2.39 (s, 3H), 1.91–1.65 (m, 6H), 1.53–1.41 (m, 2H), 1.05 (t, J=7.3, 3H); MS (APCI) m/z 415 (M+H)$^+$; Anal. Calcd for C$_{22}$H$_{30}$N$_4$O$_2$S: C, 63.74; H, 7.29; N, 13.51; Found: C, 63.77; H, 7.57; N 13.55.

EXAMPLE 89

1-[4-(Methanesulfonyl)butyl]-6,7-dimethyl-2-propyl-1H-imidazo[4,5-c]pyridin-4-amine

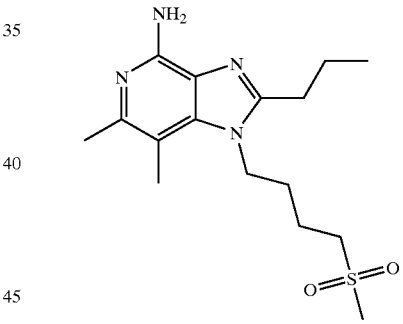

Part A

Triethylamine (18.9 g, 136 mmol) was added to a solution of 2,4-dichloro-5,6-dimethyl-3-nitropyridine (25 g, 113 mmol) in N,N-dimethylformamide (100 mL). 4-Aminobutan-1-ol (11.1 g, 124. mmol) was added with a syringe and the reaction mixture was allowed to stir under a nitrogen atmosphere at ambient temperature for 17 hours. A portion (85 mL) of the solvent was removed under reduced pressure. The residue was diluted with ethyl acetate (200 mL), washed with water (2×50 mL) then with brine (75 mL), dried over magnesium sulfate, filtered and then concentrated under reduced pressure to provide a solid. This material was recrystallized from ethyl acetate/hexanes to provide 15.07 g of 4-[(2-chloro-5,6-dimethyl-3-nitropyridin-4-yl)amino]butan-1-ol as yellow powder. An additional 5.70 g was isolated from the mother liquor.

Part B

Sodium hydride (4.38 g of 60% dispersion in mineral oil, 109.6 mmol) was added to chilled dioxane (73 mL). Phenol (10.31 g, 109.6 mmol) was added in portions with cooling.

4-[(2-Chloro-5,6-dimethyl-3-nitropyridin-4-yl)amino] butan-1-ol (20.00 g, 93.07 mmol) and additional dioxane (~30 mL) were added. The reaction mixture was heated at reflux for 3 hours and then allowed to stand at ambient temperature overnight. The reaction mixture was concentrated under reduced pressure. The residue was diluted with water (200 mL) and then extracted with ethyl acetate (300 mL). The extract was washed with water (2×100 mL) then with brine, dried over magnesium sulfate, filtered and then concentrated under reduced pressure to provide an oil. The oil was purified by flash chromatography (600 mL of silica gel, eluting initially with 2000 mL 1:3 ethyl acetate:hexanes, then with 2000 mL 1:1 ethyl acetate:hexanes and finally with 1000 mL 3:1 ethyl acetate: hexanes) to provide 13.46 g of 4-[(2,3-dimethyl-5-nitro-6-phenoxypyridin-4-yl)amino] butan-1-ol as a yellow solid.

Part C

Thionyl chloride (3.14 mL, 43 mmol) was added over a period of 5 minutes to a chilled (0° C.) solution of 4-[(2,3-dimethyl-5-nitro-6-phenoxypyridin-4-yl)amino]butan-1-ol (12.95 g, 39.08 mmol) in dichloromethane (130 mL). The reaction was allowed to warm to ambient temperature and was stirred overnight under a nitrogen atmosphere. The reaction mixture was diluted with dichloromethane (130 mL), washed sequentially with saturated aqueous sodium bicarbonate (2×65 mL), water (80 mL) and brine (100 mL), dried over magnesium sulfate, filtered and then concentrated under reduced pressure to provide 12.57 g of N-(4-chlorobutyl)-2,3-dimethyl-5-nitro-6-phenoxypyridin-4-amine as a yellow solid.

Part D

A solution of sodium dithionite (35.13 g, 171.5 mmol), available as approximately 85% pure sodium hydrosulfite, in water (130 mL) was added to a mixture of N-(4-chlorobutyl)-2,3-dimethyl-5-nitro-6-phenoxypyridin-4-amine (12 g, 34 mmol) and ethanol (340 mL). The mixture was stirred for 1.5 hours. Analysis by thin layer chromatography indicated that the reaction was not complete. Solid sodium dithionite (5 g) was added and the reaction was allowed to stir for an additional 3 hours. The reaction mixture was filtered to remove solids. The filtrate was concentrated under reduced pressure until ~50 mL of solvent remained. The residue was diluted with dichloromethane (300 mL), washed sequentially with aqueous sodium bicarbonate, water and brine, dried over magnesium sulfate, filtered and then concentrated under reduced pressure to provide 9.5 g of $N^4$-(4-chlorobutyl)-5,6-dimethyl-2-phenoxypyridine-3,4-diamine as a brown oil.

Part E

The oil from Part D was combined with toluene (90 mL), trimethyl orthobutyrate (6.04 mL, 148 mmol), and pyridine hydrochloride (0.9 g). The reaction mixture was heated at reflux for 30 minutes; trimethyl orthobutyrate (1 mL) was added and the reaction mixture was heated at reflux for 1.5 hr and then allowed to cool to ambient temperature. The reaction mixture was diluted with ethyl acetate, washed sequentially with water and brine, dried over magnesium sulfate, filtered and then concentrated under reduced pressure. The residue was purified by flash chromatography (silica gel eluting with 1:4 to 1:1 ethyl acetate:hexanes) to provide 5.44 g of 1-(4-chlorobutyl)-6,7-dimethyl-4-phenoxy-2-propyl-1H-imidazo[4,5-c]pyridine.

Part F

Sodium thiomethoxide (0.927 g, 13.2 mmol) was added to a solution of 1-(4-chlorobutyl)-6,7-dimethyl-4-phenoxy-2-propyl-1H-imidazo[4,5-c]pyridine (4.1 g, 11.0 mmol) in N,N-dimethylformamide (30 mL). The reaction mixture was stirred under a nitrogen atmosphere at ambient temperature for 75 minutes. Sodium thiomethoxide (0.08 g) was added and the reaction was stirred for an additional 105 minutes. The reaction mixture was diluted with ethyl acetate (300 mL), washed sequentially with water (3×50 mL) and brine (50 mL), dried over magnesium sulfate, filtered and then concentrated under reduced pressure to provide 4.53 g of 6,7-dimethyl-1-[4-(methanethio)butyl]-4-phenoxy-2-propyl-1H-imidazo[4,5-c]pyridine as a brown oil that solidified after a few hours.

Part G

3-Chloroperoxybenzoic acid (2.72 g of 77%) was added to a chilled (0° C.) solution of the material from Part F in dichloromethane (55 mL). A short time later more 3-chloroperoxybenzoic acid (2.72 g of 77%) was added and the reaction mixture was stirred at 0° C. for 30 minutes. The reaction mixture was diluted with dichloromethane (250 mL), washed sequentially with aqueous sodium bicarbonate (2×100 mL), water (100 mL) and brine (100 mL), dried over magnesium sulfate, filtered and then concentrated under reduced pressure to provide a pink oil. The oil was dissolved in dichloromethane, diluted with ethyl acetate and hexanes, and then concentrated under reduced pressure until a precipitate formed. The precipitate was isolated by filtration, washed with 1:1 ethyl acetate: hexanes (40 mL), and dried under high vacuum to provide 3.84 g of 1-[4-(methanesulfonyl)butyl]-6,7-dimethyl-4-phenoxy-2-propyl-1H-imidazo[4,5-c]pyridine as a white solid.

Part H

Ammonium acetate (45.24 g) and 1-[4-(methanesulfonyl) butyl]-6,7-dimethyl-4-phenoxy-2-propyl-1H-imidazo[4,5-c]pyridine (3.77 g, 9.07 mmol) were combined and heated at 160° C. for about 19 hours. The reaction mixture was allowed to stand at ambient temperature for 2 days. The reaction mixture was partitioned between dichloromethane (300 mL) and water. The layers were separated. The aqueous layer was made basic with 5% sodium hydroxide and then extracted with dichloromethane (2×100 mL). The combined organics were washed with aqueous 5% sodium hydroxide, dried over sodium sulfate, filtered and then concentrated under reduced pressure to provide a white solid. This material was recrystallized from acetonitrile to provide ~2 g of a white solid. This material was further purified by flash chromatography (silica gel, eluting sequentially with 1% methanol in dichloromethane containing 0.1% ammonium hydroxide, 2% methanol in dichloromethane containing 0.1% ammonium hydroxide, 4% methanol in dichloromethane containing 0.1% ammonium hydroxide and 10% methanol in dichloromethane containing 0.1% ammonium hydroxide) to provide a white solid. This material was recrystallized from acetonitrile and dried under high vacuum at 60° C. to provide 1.3 g of 1-[4-(methanesulfonyl)butyl]-6,7-dimethyl-2-propyl-1H-imidazo[4,5-c]pyridin-4-amine as white needles, mp 152.0–153.0° C.

$^1$H NMR (300 MHz, CDCl$_3$) δ 4.82 (br s, 2H), 4.25 (m, 2H), 3.03 (t, J=6.9 Hz, 2H), 2.92 (s, 3H), 2.76 (m, 2H), 2.44 (s, 3H), 2.43 (s, 3H), 2.00–1.81 (m, 6H), 1.07 (t, J=7.5 Hz, 3H); $^{13}$C NMR (75 MHz, CDCl$_3$) δ 153.0, 148.2, 146.5, 138.8, 125.2, 103.9, 53.7, 43.8, 40.8, 30.4, 29.3, 21.9, 21.2, 19.1, 13.9, 12.9; MS (APCI) m/z 339 (M+H)$^+$; Anal. Calcd for $C_{16}H_{26}O_2N_4S$: C, 56.77; H, 7.74; N, 16.56; S, 9.47. Found: C, 56.46; H, 7.67; N, 16.36; S, 9.29.

EXAMPLE 90

1-[3-(Methanesulfonyl)propyl]-6,7-dimethyl-2-propyl-1H-imidazo[4,5-c]pyridin-4-amine

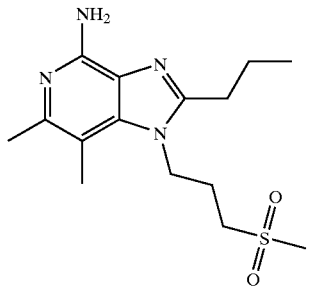

Part A

Using the general method of Example 89 Part A, 3-aminopropan-1-ol (9.52 mL, 124 mmol) was reacted with 2,4-dichloro-5,6-dimethyl-3-nitropyridine (25 g, 113 mmol) to provide 17.35 g of 3-[(2-chloro-5,6-dimethyl-3-nitropyridin-4-yl)amino]propan-1-ol as a yellow solid.

Part B

Sodium hydride (7.80 g of a 60% dispersion in mineral oil, 195 mmol) was added in portions to a chilled (0° C.) solution of phenol (18.36 g, 195 mmol) in tetrahydrofuran (200 mL). After the addition was completed the reaction mixture was allowed to stir at ambient temperature for 30 minutes. Solid 3-[(2-chloro-5,6-dimethyl-3-nitropyridin-4-yl)amino]propan-1-ol (16.89 g, 65.0 mmol) was added and the reaction mixture was heated at reflux for 5 days. The reaction mixture was concentrated under reduced pressure. The residue was partitioned between ethyl acetate (400 mL) and water (100 mL). The organic layer was separated, washed with brine, dried over sodium sulfate, filtered and then concentrated under reduced pressure. The residue was purified by flash chromatography (500 mL silica gel eluting with a gradient of 30–75% ethyl acetate in hexanes) and then heated under high vacuum until it melted. The melt solidified to provide 11.54 g of 3-[(2,3-dimethyl-5-nitro-6-phenoxypyridin-4-yl)amino]propan-1-ol.

Part C

Thionyl chloride (2.86 mL, 39.2 mmol) was added to a chilled (0° C.) solution of 3-[(2,3-dimethyl-5-nitro-6-phenoxypyridin-4-yl)amino]propan-1-ol (11.3 g, 35.6 mmol) in dichloromethane (170 mL). The reaction mixture was stirred at ambient temperature for 0.5 hr and then heated at reflux for 0.5 hr. The reaction mixture was allowed to cool to ambient temperature. A precipitate was isolated by filtration and then dried under vacuum to provide 13.64 g of N-(3-chloropropyl)-2,3-dimethyl-5-nitro-6-phenoxypyridin-4-amine hydrochloride.

Part D

N-(3-chloropropyl)-2,3-dimethyl-5-nitro-6-phenoxypyridin-4-amine hydrochloride (12.62 g, 33.72 mmol), 1,1'-di-n-octyl-4,4'-bipyridinium dibromide (dioctyl viologen) (910 mg, 1.69 mmol), dichloromethane (227 mL), water (28 mL) and potassium carbonate (2.33 g, 16.9 mmol) were added sequentially to a 1 L round bottom flask. The reaction mixture was allowed to stir under nitrogen. A solution of of potassium carbonate (23.30 g, 168.6 mmol) and sodium dithionite (26.42 g, 174.1 mmol) in water (114 mL) was added to the reaction mixture. The reaction mixture was heated at reflux for about 2.5 hr and then allowed to cool to ambient temperature. The layers were separated. The aqueous layer was extracted with dichloromethane (100 mL). The combined organics were dried over sodium sulfate, filtered and then concentrated under reduced pressure to provide $N^4$-(3-chloropropyl)-5,6-dimethyl-2-phenoxypyridine-3,4-diamine as a brown sludge. This material was used directly in the next step.

Part E

Using the general method of Example 89 Part E, the material from Part D was reacted with trimethyl orthobutyrate (6.48 mL, 40.5 mmol) and purified to provide 9.10 g of 1-(3-chloropropyl)-6,7-dimethyl-4-phenoxy-2-propyl-1H-imidazo[4,5-c]pyridine as a white solid.

Part F

Using the general method of Example 89 Part F, 1-(3-chloropropyl)-6,7-dimethyl-4-phenoxy-2-propyl-1H-imidazo[4,5-c]pyridine (4 g, 11.2 mmol)) was reacted with sodium thiomethoxide (0.940 g, 13.4 mmol) to provide 3.54 g of 6,7-dimethyl-1-[3-(methanethio)propyl]-4-phenoxy-2-propyl-1H-imidazo[4,5-c]pyridine as a white solid.

Part G

Using the general method of Example 89 Part G, 6,7-dimethyl-1-[3-(methylthio)propyl]-4-phenoxy-2-propyl-1H-imidazo[4,5-c]pyridine (3.41 g, 9.23 mmol) was oxidized to provide 2.39 g of 1-[3-(methanesulfonyl)propyl]-6,7-dimethyl-4-phenoxy-2-propyl-1H-imidazo[4,5-c]pyridine as a white solid.

Part H

Using the general method of Example 89 Part H, 1-[3-(methanesulfonyl)propyl]-6,7-dimethyl-4-phenoxy-2-propyl-1H-imidazo[4,5-c]pyridine (2.1 g, 5.23 mmol) was reacted with ammonium acetate (25 g) and purified to provide 1.14 g of 1-[3-(methanesulfonyl)propyl]-6,7-dimethyl-2-propyl-1H-imidazo[4,5-c]pyridin-4-amine as white needles, mp 153.5–155.0 C. $^1$H NMR (300 MHz, CDCl$_3$) 67 4.83 (br s, 2H), 4.48–4.42 (m, 2H), 3.07 (t, J=7.1 Hz, 2H), 2.95 (s, 3H), 2.82–2.77 (m, 2H), 2.45–2.25 (m, 2H), 1.94–1.81 (m, 2H), 1.07 (t, J=7.3 Hz, 3H); $^{13}$C NMR (75 MHz, CDCl$_3$) δ 153.2, 148.3, 147.1, 138.9, 125.4, 104.0, 51.2, 42.9, 41.3, 29.5, 24.3, 22.1, 21.5, 14.0, 13.1; MS (APCI) m/z 325 (M+H)$^+$; Anal. Calcd for $C_{15}H_{24}O_2N_4S$: C, 55.53; H, 7.46; N, 17.27; S, 9.87. Found: C, 55.53; H 7.44; N, 17.27; S, 9.90.

EXAMPLE 91

1-[6-(Methanesulfonyl)hexyl]-6,7-dimethyl-2-propyl-1H-imidazo[4,5-c]pyridin-4-amine

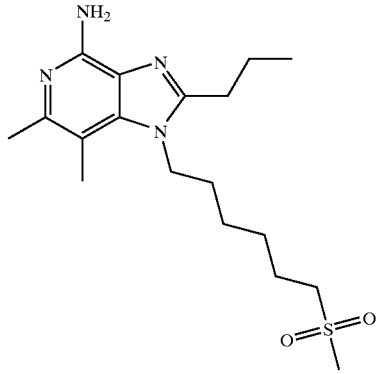

Part A

Using the general method of Example 89 Part A, 6-aminohexan-1-ol (15.91 g, 135.7 mmol) was reacted with 2,4-dichloro-5,6-dimethyl-3-nitropyridine (30 g, 136 mmol) to provide 14.79 g of 6-[(2-chloro-5,6-dimethyl-3-nitropyridin-4-yl)amino]hexan-1-ol as a yellow solid.

155

Part B

Using the general method of Example 90 Part B, 6-[(2-chloro-5,6-dimethyl-3-nitropyridin-4-yl)amino]hexan-1-ol (14.00 g, 46.39 mmol) was reacted with sodium phenoxide to provide 12.40 g of 6-[(2,3-dimethyl-5-nitro-6-phenoxypyridin-4-yl)amino]hexan-1-ol as a yellow powder.

Part C

Using the general method of Example 89 Part C, 6-[(2,3-dimethyl-5-nitro-6-phenoxypyridin-4-yl)amino]hexan-1-ol (11.97 g, 33.30 mmol) was chlorinated to provide 12.24 g of N-(6-chlorohexyl)-2,3-dimethyl-5-nitro-6-phenoxypyridin-4-amine as a yellow solid.

Part D

A solution of sodium dithionite (24.01 g, 137.9 mmol) in water (90 mL) was added to a mixture of N-(6-chlorohexyl)-2,3-dimethyl-5-nitro-6-phenoxypyridin-4-amine (10.42 g, 27.58 mmol) and ethanol (276 mL). After about 4 hours sodium dithionite (6.71 g) in water (20 mL) was added to the reaction mixture. About 1 hour later tetrahydrofuran (100 mL) was added. When analysis by thin layer chromatography indicated that the reaction was complete, the reaction mixture was filtered to remove solids. The solids were rinsed with ethanol. The rinses and the filtrate were concentrated under reduced pressure. The residue was diluted with toluene (200 mL) and then concentrated under reduced pressure to remove the bulk of the solvent. The residue was partitioned between ethyl acetate (200 mL) and water (50 mL). The aqueous layer was separated, combined with saturated aqueous sodium bicarbonate to adjust to pH 8 and then extracted with ethyl acetate. The combined organics were washed with brine (100 mL), dried over sodium sulfate, filtered and then concentrated under reduced pressure. The residue was combined with toluene and then concentrated under reduced pressure to provide 12.12 g of $N^4$-(6-chlorohexyl)-5,6-dimethyl-2-phenoxypyridine-3,4-diamine.

Part E

Using the general method of Example 89 Part E, the material from Part D was reacted with trimethyl orthobutyrate (4.86 mL, 30.3 mmol) and purified to provide 2.4 g of 1-(6-chlorohexyl)-6,7-dimethyl-4-phenoxy-2-propyl-1H-imidazo[4,5-c]pyridine as an off-white solid.

Part F

Using the general method of Example 89 Part F, 1-(6-chlorohexyl)-6,7-dimethyl-4-phenoxy-2-propyl-1H-imidazo[4,5-c]pyridine (2.0 g, 5.0 mmol) was reacted with sodium thiomethoxide (0.421 g, 6.00 mmol) to provide 2.17 g of 6,7-dimethyl-1-[6-(methanethio)hexyl]-4-phenoxy-2-propyl-1H-imidazo[4,5-c]pyridine as a yellow oil.

Part G

Using the general method of Example 89 Part G, the material form Part F was oxidized to provide ~1 g of 1-[6-(methanesulfonyl)hexyl]-6,7-dimethyl-4-phenoxy-2-propyl-1H-imidazo[4,5-c]pyridine as a colorless oil.

Part H

Using the general method of Example 89 Part H, the material form Part H was reacted with ammonium acetate (12.36 g) and purified to provide 0.37 g of 1-[6-(methanesulfonyl)hexyl]-6,7-dimethyl-2-propyl-1H-imidazo[4,5-c]pyridin-4-amine as off white crystals, mp 157.0–158.0° C.

$^1$H NMR (300 MHz, CDCl$_3$) δ 4.81 (br s, 2H), 4.18 (m, 2H), 2.99 (m, 2H), 2.89 (s, 3H), 2.76 (m, 2H), 2.44 (s, 3H), 2.42 (s, 3H), 1.93–1.71 (m, 6H), 1.57–1.40 (m, 4H), 1.07 (t, J=7.5 Hz, 3H); $^{13}$C NMR (75 MHz, CDCl$_3$) δ 153.3, 148.1, 146.6, 139.1, 125.4, 104.2, 54.4, 44.5, 40.6, 31.6, 29.5, 28.1, 26.1, 22.1, 21.4, 14.0, 13.0; MS (APCI) m/z 367 (M+H)$^+$; Anal. Calcd for C$_{18}$H$_{30}$O$_2$N$_4$S: C, 58.98; H, 8.25; N, 15.29; S, 8.75. Found: C, 58.85; H, 8.55; N, 15.34; S, 8.75.

156

EXAMPLE 92

1-[5-(4-Fluorobenzenesulfonyl)pentyl]-6,7-dimethyl-2-propyl-1H-imidazo[4,5-c]pyridin-4-amine

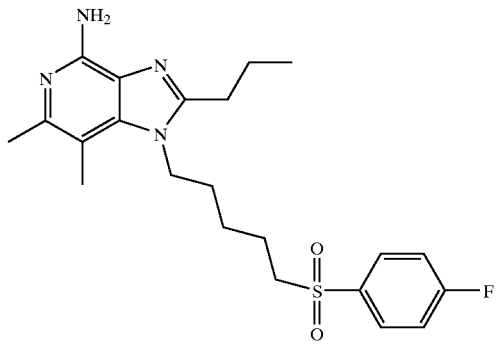

Part A

The preparation of 5-(2-chloro-5,6-dimethyl-3-nitropyridin-4-ylamino)pentan-1-ol was described in Part A of Example 85. Under a nitrogen atmosphere, cerium (III) chloride heptahydrate (8.08 g, 21.7 mmol) and sodium azide (5.64 g, 86.8 mmol) were added to a solution of 5-(2-chloro-5,6-dimethyl-3-nitropyridin-4-ylamino)pentan-1-ol (12.48 g, 43.38 mmol) in a 9:1 mixture of acetonitrile and water (145 mL). The reaction was stirred and heated at reflux for two days then allowed to cool to room temperature. A precipitate was removed by filtration and washed with acetonitrile. The filtrate was concentrated under reduced pressure to provide 12.13 g of 5-[(5,6-dimethyl-8-nitrotetrazolo[1,5-a]pyridin-7-yl)amino]pentan-1-ol as a yellow solid.

Part B

Using the general method described in Part C of Example 85, 5-[(5,6-dimethyl-8-nitrotetrazolo[1,5-a]pyridin-7-yl)amino]pentan-1-ol (12.1 g, 41.2 mmol) was converted to 13.3 g of (5-chloropentyl)-5,6-dimethyl-8-nitrotetrazolo[1,5-a]pyridin-7-yl)amine, which was isolated as a dark brown semi-solid.

Part C

Under a nitrogen atmosphere, a solution of potassium carbonate (28.46 g, 205.9 mmol) and sodium dithionite (32.26 g, 185.3 mmol) in water (100 mL) was added dropwise to a solution of the material from Part B (13.8 g, 42 mmol) and dioctyl viologen (1.17 g, 2.06 mmol) in dichloromethane (275 mL) and water (35 mL). The addition funnel was rinsed with additional water (37 mL), which was added to the reaction. The reaction was heated at reflux for three hours. The aqueous layer was extracted with dichloromethane (3×50 mL), and the combined organic solutions were dried over sodium sulfate, filtered, and concentrated under reduced pressure to provide 11.5 g of $N^7$-(5-chloropentyl)-5,6-dimethyl-tetrazolo[1,5-a]pyridine-7,8-diamine as a brown solid.

Part D

The general method described in Part E of Example 85 was used to convert $N^7$-(5-chloropentyl)-5,6-dimethyl-tetrazolo[1,5-a]pyridine-7,8-diamine (11.5 g, 40.7 mmol) to 7-(5-chloropentyl)-5,6-dimethyl-8-propyl-7H-imidazo[4,5-c]tetrazolo[1,5-a]pyridine. The crude product was purified by column chromatography on silica gel (eluting sequentially with 3:1 ethyl acetate:hexane and ethyl acetate) to yield a yellow solid, which was recrystallized from ethyl acetate:hexane to provide 9.2 g of the product as a white solid.

Part E

The general method described in Parts F and G of Example 85 was used to convert 7-(5-chloropentyl)-5,6-dimethyl-8-propyl-7H-imidazo[4,5-c]tetrazolo[1,5-a]pyridine (1.68 g, 5.0 mmol) to 7-[5-(4-fluorobenzenesulfonyl)pentyl]-5,6-dimethyl-8-propyl-7H-imidazo[4,5-c]tetrazolo[1,5-a]pyridine. 4-Fluorobenzenethiol was used in lieu of 4-chlorobenzenethiol. Following the oxidation with mCPBA, the crude product was purified by column chromatography on silica gel (eluting with ethyl acetate) to yield 1.71 g of the pure product as a white solid.

Part F

A mixture of 7-[5-(4-fluorobenzenesulfonyl)pentyl]-5,6-dimethyl-8-propyl-7H-imidazo[4,5-c]tetrazolo[1,5-a]pyridine (1.61 g, 3.51 mmol), trifluoroacetic acid (15 mL) and platinum (IV) oxide were added to a Parr vessel and agitated under hydrogen pressure (50 psi, $3.4 \times 10^5$ Pa) for two days. The reaction mixture was filtered through a layer of CELITE filter aid, and the filter cake was washed with methanol. The filtrate was concentrated under reduced pressure, and the black residue was stirred in concentrated hydrochloric acid (10 mL) for 1.5 hours. The solution was treated with 1 N aqueous sodium hydroxide (100 mL) and solid sodium hydroxide until the solution exhibited a pH of 14. The solution was extracted with chloroform (3×80 mL), and the combined extracts were dried over sodium sulfate, filtered, and concentrated under reduced pressure to provide 1.8 g of the crude product as a white foam. The crude product was purified by column chromatography on silica gel (eluting with 98:2 chloroform:methanol) and recrystallized from ethyl acetate:hexane. The solid was triturated with ethyl acetate and dried at 70° C. in a vacuum oven overnight to provide 0.57 g of 1-[5-(4-fluorobenzenesulfonyl)pentyl]-6,7-dimethyl-2-propyl-1H-imidazo[4,5-c]pyridin-4-amine as a white powder, mp 130.0–132.0° C.

$^1$H NMR (300 MHz, CDCl$_3$) δ 7.94–7.88 (m, 2H), 7.29–7.20 (m, 2H), 4.81 (br s, 2H), 4.17 (dd, J=7.7, 7.7, 2H), 3.07 (dd, J=7.7, 7.7, 2H), 2.73 (dd, J=7.7, 7.7, 2H), 2.43 (s, 3H), 2.40 (s, 3H), 1.91–1.69 (m, 6H), 1.54–1.43 (m, 2H), 1.05 (t, J=7.4, 3H); MS (APCI) m/z 433 (M+H)$^+$; Anal. Calcd for C$_{22}$H$_{29}$FN$_4$O$_2$S: C, 61.09; H, 6.76; N, 12.95; Found: C, 61.05; H, 7.04; N, 13.00.

EXAMPLE 93–96

The general methods described in Example 92 were used for Examples 93–96. The reagent selected in lieu of 4-chlorobenzenethiol in Part E of Example 92 is shown in the table below for Examples 93–96. The oxidation products from Part E were purified by trituration with ethyl acetate. A description of the isolation of the final compounds, obtained after Part F, follows.

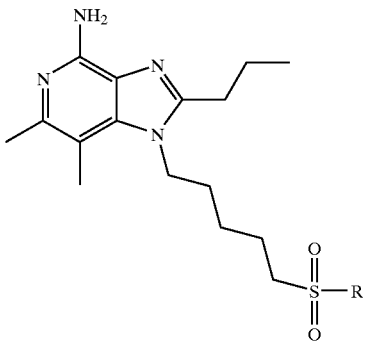

| Example Number | Reagent for Part E | R |
|---|---|---|
| 93 | 2,4-difluorobenzenethiol | ![F, F phenyl] |
| 94 | 4-methoxythiophenol | ![4-methoxyphenyl] |
| 95 | 2,4-dichlorobenzenethiol | ![Cl, Cl phenyl] |
| 96 | Sodium thiomethoxide | —CH$_3$ |

EXAMPLE 93

1-[5-(2,4-Difluorobenzenesulfonyl)pentyl]-6,7-dimethyl-2-propyl-1H-imidazo[4,5-c]pyridin-4-amine The crude product was purified by flash chromatography on silica gel (eluting with 98:2 chloroform:methanol) to yield a white foam that was recrystallized from 2-propanol. After the product was dried under reduced pressure, 1.27 g of the product was obtained as a white powder, mp 130.0–132.0° C.

$^1$H NMR (300 MHz, CDCl$_3$) 8.01–7.89 (m, 1H), 7.12–6.94 (m, 2H), 4.82 (br s, 2H), 4.18 (dd, J=7.7, 7.7, 2H), 3.26 (dd, J=7.7, 7.7, 2H), 2.73 (dd, J=7.7, 7.7, 2H), 2.43 (s, 3H), 2.39 (s, 3H), 1.91–1.64 (m, 6H), 1.54–1.41 (m, 2H), 1.06 (t, J=7.4, 3H); MS (APCI) m/z 451 (M+H)$^+$; Anal. Calcd for C$_{22}$H$_{28}$F$_2$N$_4$O$_2$S: C, 58.65; H, 6.26; N, 12.44; Found: C, 58.75; H, 6.42; N, 12.32.

EXAMPLE 94

1-[5-(4-Methoxybenzenesulfonyl)pentyl]-6,7-dimethyl-2-propyl-1H-imidazo[4,5-c]pyridin-4-amine The crude product was purified by flash chromatography on silica gel (eluting with 98:2 chloroform:methanol) to yield a colorless oil that was recrystallized from acetonitrile. After the product was dried under reduced pressure, 0.725 g of the product was obtained as a white powder, mp 130.5–132.0° C.

¹H NMR (300 MHz, CDCl₃) δ 7.81 (d, J=8.9, 2H), 7.02 (d, J=8.9, 2H), 4.82 (br s, 2H), 4.16 (dd, J=7.7, 7.7, 2H), 3.05 (dd, J=7.7, 7.7, 2H), 2.73 (dd, J=7.7, 7.7, 2H), 2.43 (s, 3H), 2.39 (s, 3H), 1.91–1.64 (m, 6H), 1.55–1.41 (m, 2H), 1.05 (t, J=7.4, 3H); MS (APCI) m/z 445 (M+H)⁺; Anal. Calcd for C₂₃H₃₂N₄O₃S: C, 62.14; H, 7.26; N, 12.60; Found: C, 62.14; H, 7.43; N, 12.60.

EXAMPLE 95

1-[5-(2,4-Dichlorobenzenesulfonyl)pentyl]-6,7-dimethyl-2-propyl-1H-imidazo[4,5-c]pyridin-4-amine After the crude product was recrystallized from acetonitrile, 0.614 g of the product was obtained as a white powder, mp 130.0–131.5° C.

¹H NMR (300 MHz, CDCl₃) δ 8.04 (d, J=8.6, 1H), 7.57 (d, J=2.0, 1H), 7.46 (dd, J=8.6, 2.0, 1H), 4.83 (br s, 2H), 4.18 (dd, J=7.7, 7.7, 2H), 3.37 (dd, J=7.6, 7.6, 2H), 2.73 (dd, J=7.7, 7.7, 2H), 2.44 (s, 3H), 2.40 (s, 3H), 1.92–1.66 (m, 6H), 1.59–1.46 (m, 2H), 1.06 (t, J=7.4, 3H); MS (APCI) m/z 483 (M)⁺; Anal. Calcd for C₂₂H₂₈Cl₂N₄O₂S: C, 54.66; H, 5.84; N, 11.59; Found: C, 54.58; H, 5.65; N, 11.58.

EXAMPLE 96

1-[5-(Methanesulfonyl)pentyl]-6,7-dimethyl-2-propyl-1H-imidazo[4,5-c]pyridin-4-amine A modification of Part E of Example 92 was used; a slurry of sodium methoxide (0.64 g, 9.1 mmol) in DMF (10 mL) was added to a solution of 7-(5-chloropentyl)-5,6-dimethyl-8-propyl-7H-imidazo[4,5-c]tetrazolo[1,5-a]pyridine (2.35 g, 7.02 mmol) at 0° C. The synthesis was completed as described in Parts E and F or Example 92. The crude product was recrystallized from acetonitrile and dried under reduced pressure to yield 1.73 g of the desired product as a white powder, mp 145.0–146.0° C.

¹H NMR (300 MHz, CDCl₃) δ 4.82 (br s, 2H), 4.18 (dd, J=7.7, 7.7, 2H), 3.01 (dd, J=7.7, 7.7, 2H), 2.90 (s, 3H), 2.75 (dd, J=7.7, 7.7, 2H), 2.44 (s, 3H), 2.42 (s, 3H), 1.96–1.74 (m, 6H), 1.61–1.51 (m, 2H), 1.07 (t, J=7.4, 3H); MS (APCI) m/z 353 (M+H)⁺; Anal. Calcd for C₁₇H₂₈N₄O₂S: C, 57.93; H, 8.01; N, 15.89; Found: C, 57.82; H, 8.26; N, 15.76.

EXAMPLES 97–99

The general methods described in Example 92 were used for Examples 97–99. In Part A, 3-amino-1-propanol was used in lieu of 5-amino-1-pentanol. The purification in Part D was carried out by column chromatography on silica gel (eluting with 95:5 chloroform:methanol) followed by trituration with ethyl acetate:hexane. The thiol selected in Part E of Example 92 is shown in the table below for Examples 97–99. The oxidation products from Part E were purified by trituration with ethyl acetate.

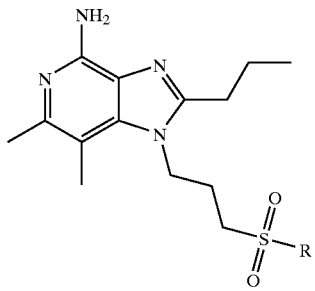

| Example Number | Thiol | R |
|---|---|---|
| 97 | 4-chlorobenzenethiol | 4-chlorophenyl |
| 98 | 2-mercaptopyridine | pyridin-2-yl |
| 99 | 4-mercaptoethylbenzoate[a] | 4-(ethoxycarbonyl)phenyl |

[a]preparation described below

EXAMPLE 97

1-[3-(4-Chlorobenzenesulfonyl)propyl]-6,7-dimethyl-2-propyl-1H-imidazo[4,5-c]pyridin-4-amine The crude product was triturated with ethyl acetate and dried at 60° C. under high vacuum for three days to provide 1.037 g of the desired product as a white powder, mp 186.5–188.0° C.

¹H NMR (300 MHz, CDCl₃) δ 7.81 (d, J=8.8, 2H), 7.55 (d, J=8.7, 2H), 4.83 (br s, 2H), 4.39 (dd, J=7.8, 7.8, 2H), 3.10 (dd, J=7.3, 7.3, 2H), 2.75 (dd, J=7.7, 7.7, 2H), 2.42 (s, 3H), 2.35 (s, 3H), 2.24–2.14 (m, 2H), 1.91–1.78 (m, 2H), 1.05 (t, J=7.3, 3H); MS (APCI) m/z 421 (M)⁺; Anal. Calcd for C₂₀H₂₅ClN₄O₂S: C, 57.06; H, 5.99; N, 13.31; Found: C, 57.04; H, 6.14; N, 13.23.

EXAMPLE 98

6,7-Dimethyl-2-propyl-1-[3-(pyridine-2-sulfonyl)propyl]-1H-imidazo[4,5-c]pyridin-4-amine The crude product was recrystallized from acetonitrile and then purified by column chromatography on a Biotage Horizon™ High-Performance Flash Chromatography instrument. A second recrystallization from acetonitrile provided 0.180 g of the desired product as a off-white powder, mp 172.0–173.5° C.

¹H NMR (300 MHz, CDCl₃) δ 8.69 (ddd, J=4.7, 1.7, 1.0, 1H), 8.09 (ddd, J=7.8, 1.2, 1.0, 1H), 7.98 (ddd, J=7.8, 7.8, 1.7, 1H), 7.57 (ddd, J=7.8, 4.7, 1.2, 1H), 4.83 (br s, 2H), 4.42 (dd, J=7.9, 7.9, 2H), 3.49 (dd, J=7.3, 7.3, 2H), 2.77 (dd, J=7.7, 7.7, 2H), 2.42 (s, 3H), 2.38 (s, 3H), 2.29–2.17 (m, 2H), 1.92–1.78 (m, 2H), 1.06 (t, J=7.4, 3H); MS (APCI) m/z 388 (M+H)⁺; Anal. Calcd for C₁₉H₂₅N₅O₂S: C, 58.89; H, 6.503; N, 18.07; Found: C, 58.51; H, 6.37; N, 17.80.

EXAMPLE 99

4-[3-(4-Amino-6,7-dimethyl-2-propyl-1H-imidazo[4,5-c]pyridin-1-yl)propane-1-sulfonyl]benzoic acid ethyl ester Ethyl-4-mercaptobenzoate was prepared by treating 4-mercaptobenzoic acid (1.50 g, 9.73 mmol) with ethanol (97 mL) in the presence of catalytic concentrated sulfuric acid under a nitrogen atmosphere. The reaction was heated at reflux for three hours. The volume of the reaction was reduced to 10 mL under reduced pressure and then partitioned between water (100 mL) and ethyl acetate (100 mL). The aqueous layer was extracted with ethyl acetate (3×100 mL), and the combined organic solutions were washed with water (75 mL) and saturated aqueous sodium bicarbonate (2×75 mL), dried over magnesium sulfate, filtered, and concentrated under reduced pressure to provide an oil. The oil was dissolved in dichloromethane (100 mL), and the resulting solution was extracted with saturated aqueous sodium carbonate (3×100 mL). The combined extracts were washed with dichloromethane (3×50 mL) and then treated with concentrated hydrochloric acid to adjust to pH 7. The solution was then extracted with dichloromethane (3×100 mL), and the combined extracts were washed with water (50 mL), dried over magnesium sulfate, filtered, and concentrated under reduced pressure to provide 1.23 g of ethyl-4-mercaptobenzoate as a colorless oil.

The ethyl-4-mercaptobenzoate was used as described in Part E of Example 92 in lieu of 4-fluorobenzenethiol, and the synthesis was completed using the methods described in Parts E and F of Example 92. The crude product was purified by column chromatography on silica gel (eluting sequentially with 98:2 dichloromethane:methanol and 95:5 dichloromethane:methanol, and the resulting yellow solid was triturated with acetonitrile. The solid was isolated and recrystallized from 2-propanol to provide 1.4 g of 4-[3-(4-amino-6,7-dimethyl-2-propyl-1H-imidazo[4,5-c]pyridin-1-yl)propane-1-sulfonyl]benzoic acid ethyl ester as yellow crystals, mp 169.0–171.0° C. with a phase change at 153–155° C.

$^1$H NMR (300 MHz, CDCl$_3$) δ 8.23 (d, J=8.8, 2H), 7.95 (d, J=8.6, 2H), 4.83 (br s, 2H), 4.48–4.37 (m, 4H), 3.14 (dd, J=7.3, 7.3, 2H), 2.75 (dd, J=7.7, 7.7, 2H), 2.41 (s, 3H), 2.35 (s, 3H), 2.24–2.13 (m, 2H), 1.91–1.77 (m, 2H), 1.43 (t, J=7.1), 1.05 (t, J=7.3, 3H); MS (APCI) m/z 459 (M+H)$^+$; Anal. Calcd for C$_{23}$H$_{30}$N$_4$O$_4$S: C, 60.24; H, 6.59; N, 12.22; Found: C, 60.22; H, 6.80; N 12.20.

EXAMPLE 100

4-[3-(4-Amino-6,7-dimethyl-2-propyl-1H-imidazo[4,5-c]pyridin-1-yl)propane-1-sulfonyl]benzoic acid hydrochloride

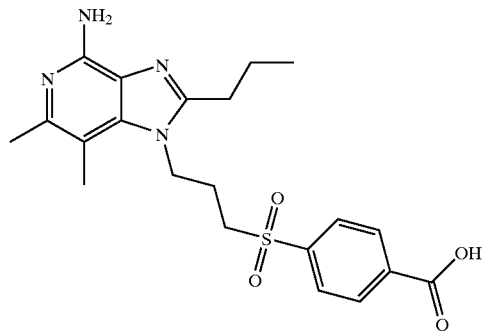

Under a nitrogen atmosphere, aqueous sodium hydroxide (1.5 mL of 1 M) was added to a solution of 4-[3-(4-amino-6,7-dimethyl-2-propyl-1H-imidazo[4,5-c]pyridin-1-yl)propane-1-sulfonyl]benzoic acid ethyl ester (558 mg, 1.22 mmol), prepared as described in Example 99, in methanol (5.5 mL) and THF (5.5 mL), and the reaction was stirred for two hours at room temperature. The solvents were removed under reduced pressure, and the residual solid was dissolved in water (60 mL). The solution was washed with dichloromethane (2×20 mL) and ethyl acetate (20 mL) and then treated with concentrated hydrochloric acid to adjust to pH 5. A precipitate formed, which was isolated by filtration and dried overnight in a vacuum oven at 60° C. The material was treated with 1 M hydrochloric acid in diethyl ether, and then the solvent was removed under reduced pressure. The resulting white solid was recrystallized from ethanol, and the crystals were dissolved in a mixture of 1 N hydrochloric acid and methanol with gentle heating. The solution was concentrated under reduced pressure, and the resulting solid was dried at 80° C. under high vacuum to provide 240 mg of 4-[3-(4-amino-6,7-dimethyl-2-propyl-1H-imidazo[4,5-c]pyridin-1-yl)propane-1-sulfonyl]benzoic acid hydrochloride as a white powder, mp >250° C.

$^1$H NMR (300 MHz, DMSO-d$_6$) δ 8.18 (d, J=8.6, 2H), 8.03 (d, J=8.6, 2H), 7.79 (br s, 2H), 4.41(dd, J=7.7, 7.7, 2H), 3.65 (dd, J=7.3, 7.3, 2H), 2.79 (dd, J=7.7, 7.7, 2H), 2.41 (s, 3H), 2.29 (s, 3H), 2.03–1.91 (m, 2H), 1.81–1.69 (m, 2H), 0.96 (t, J=7.5, 3H); MS (APCI) m/z 431 (M+H–HCl)$^+$; Anal. Calcd for C$_{21}$H$_{27}$ClN$_4$O$_4$S: C, 52.01; H, 5.92; N, 11.56; Found: C, 51.62; H, 5.86; N, 11.41.

EXAMPLE 101

{4-[3-(4-Amino-6,7-dimethyl-2-propyl-1H-imidazo[4,5-c]pyridin-1-yl)propane-1-sulfonyl]phenyl}morpholin-4-ylmethanone

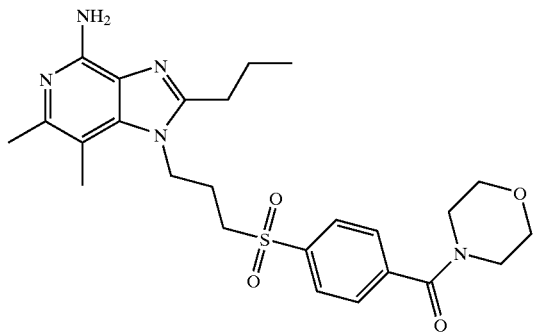

Part A

4-[3-(5,6-Dimethyl-8-propyl-7H-imidazo[4,5-c]tetrazolo[1,5-a]pyridin-7-yl)propane-1-sulfonyl]benzoic acid ethyl ester (2.50 g, 5.16 mmol), prepared as described in Parts A–E of Example 92 using the modification of Example 99, was treated with aqueous sodium hydroxide (10 mL of 1 N) in ethanol (26 mL), and the reaction stirred for two hours and became homogeneous. The solvents were removed under reduced pressure, and the residual white solid was dissolved in water (50 mL). The solution was washed with ethyl acetate (3×10 mL) and then adjusted to pH 4 with the addition of concentrated hydrochloric acid. A white solid precipitated, which was isolated by filtration, washed with water, and dried for three hours in a vacuum oven at 60° C. to provide 2.26 g of 4-[3-(5,6-dimethyl-8-propyl-7H-imidazo[4,5-c]tetrazolo[1,5-a]pyridin-7-yl)propane-1-sulfonyl]benzoic acid as a white solid.

Part B

Under a nitrogen atmosphere, a mixture of 4-[3-(5,6-dimethyl-8-propyl-7H-imidazo[4,5-c]tetrazolo[1,5-a]

pyridin-7-yl)propane-1-sulfonyl]benzoic acid (2.26 g, 4.95 mmol) and dichloromethane (50 mL) was cooled to 0° C. Oxalyl chloride (0.95 mL, 10.9 mmol) was added dropwise, and the reaction was stirred for two hours at room temperature. To one-third of the solution was added morpholine (0.43 mL, 4.9 mmol), and the reaction was stirred under nitrogen overnight. Additional morpholine (1.0 mL, 11 mmol) was added, and the reaction was stirred for two hours. A white precipitate formed, which was isolated by filtration, washed with ethyl acetate and water, and then dried for two hours in a vacuum oven at 80° C. to provide 0.75 g of {4-[3-(5,6-dimethyl-8-propyl-7H-imidazo[4,5-c]tetrazolo[1,5-a]pyridin-7-yl)propane-1-sulfonyl]phenyl}morpholin-4-ylmethanone as a white solid.

Part C

{4-[3-(5,6-Dimethyl-8-propyl-7H-imidazo[4,5-c]tetrazolo[1,5-a]pyridin-7-yl)propane-1-sulfonyl]phenyl}morpholin-4-ylmethanone (0.75 g, 1.4 mmol) was converted to {4-[3-(4-amino-6,7-dimethyl-2-propyl-1H-imidazo[4,5-c]pyridin-1-yl)propane-1-sulfonyl]phenyl}morpholin-4-ylmethanone using the general method of Part F of Example 92. The crude product was triturated with ethyl acetate, isolated by filtration, and dried overnight under high vacuum at 90° C. to provide 0.52 g of the desired product as a white powder, mp 224.0–226.0° C.

$^1$H NMR (300 MHz, DMSO-$d_6$) δ 7.92 (d, J=8.4, 2H), 7.63 (d, J=8.4, 2H), 5.55 (br s, 2H), 4.25 (dd, J=7.8, 7.8, 2H), 3.60 (br s, 4H), 3.52 (dd, J=7.6, 7.6, 2H), 3.23 (br s, 2H), 2.66 (dd, J=7.5, 7.5, 2H), 2.22 (s, 3H), 2.17 (s, 3H), 1.91–1.79 (m, 2H), 1.73–1.61 (m, 2H), 0.90 (t, J=7.3, 3H); MS (APCI) m/z 500 (M+H)$^+$; Anal. Calcd for $C_{25}H_{33}N_5O_4S$: C, 60.10; H, 6.657; N, 14.02; Found: C, 59.96; H, 6.70; N, 13.81.

EXAMPLE 102

N-{2-[2-(4-Amino-2-ethyl-6,7-dimethyl-1H-imidazo[4,5-c]pyridin-1-yl)ethoxy]ethyl}methanesulfonamide

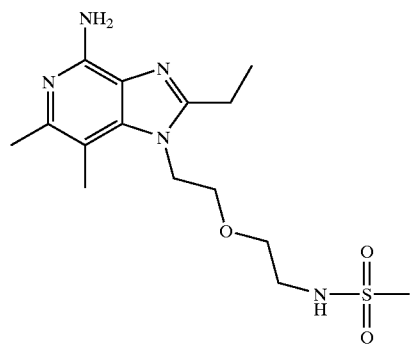

Part A

The general method described in Part A of Example 80 was followed using 2-(2-aminoethoxy)ethanol (46.0 mL, 458 mmol) in lieu of ethanolamine to prepare 90.0 g of tert-butyl 2-(2-hydroxyethoxy)ethylcarbamate as a colorless oil.

Part B

Under a nitrogen atmosphere, a solution of tert-butyl 2-(2-hydroxyethoxy)ethylcarbamate (89.0 g, 434 mmol) in dichloromethane (1.5 L) was cooled to 0° C.; triethylamine (90.7 mL, 650 mmol) was added dropwise. Methanesulfonyl chloride (36.9 mL, 477 mmol) was then added over a period of 45 minutes. A precipitate formed, and the reaction became yellow. The reaction was allowed to warm to room temperature and stirred overnight. Saturated aqueous sodium bicarbonate (750 mL) was added. The organic layer was then sequentially washed with water (3×500 mL) and brine (250 mL), dried over magnesium sulfate, filtered, and concentrated under reduced pressure to provide 119.2 g of 2-{2-[(tert-butoxycarbonyl)amino]ethoxy}ethyl methanesulfonate as a light orange oil.

Part C

Under a nitrogen atmosphere, sodium azide (29.8 g, 458 mmol) was added to a solution of 2-{2-[(tert-butoxycarbonyl)amino]ethoxy}ethyl methanesulfonate (118 g, 416 mmol) in DMF, and the reaction was heated at 90° C. for six hours. The reaction was allowed to cool to room temperature overnight, and then the solvent was removed under reduced pressure. Water (1 L) was added, and the resulting solution was extracted with diethyl ether (4×500 mL). The combined extracts were washed with water (1×250 mL), dried over magnesium sulfate, filtered, and concentrated under reduced pressure to yield 93.0 g of tert-butyl 2-(2-azidoethoxy)ethylcarbamate as a colorless oil.

Part D

Under a nitrogen purge, 10% palladium on carbon (9.2 g) was added to a solution of tert-butyl 2-(2-azidoethoxy)ethylcarbamate (92.0 g, 399 mmol) in toluene (900 mL) in a pressure vessel. The vessel was placed under hydrogen pressure (30 psi, 2.0×10$^5$ Pa), and for the first 20 minutes, the hydrogen was replaced every five minutes and brought to a pressure of (20 psi, 1.4×10$^5$ Pa). The reaction was maintained under hydrogen pressure (20 psi, 1.4×10$^5$ Pa) overnight. The reaction mixture was filtered through a layer of CELITE filter aid, and the filter cake was washed with ethanol. The filtrate was concentrated under reduced pressure to yield 77.4 g of tert-butyl 2-(2-aminoethoxy)ethylcarbamate as a light green oil.

Part E

The general method described in Part B of Example 82 was used with tert-butyl 2-(2-aminoethoxy)ethylcarbamate in lieu of 2-[3-(1,3-thiazol-2-yl)propoxy]ethylamine. The reaction was heated at 60° C. overnight. The crude product, an orange oil, was recrystallized from 40:60 ethyl acetate:hexane (100 mL) using seed crystals from a previous run. The crystals were isolated by filtration and washed with cold 90:10 hexane:ethyl acetate. The mother liquor was concentrated under reduced pressure to provide a solid which was purified by column chromatography on silica gel (1200 mL, eluting with 70:30 hexane:ethyl acetate). The products purified by each method were combined to provide 59.5 g of tert-butyl 2-{2-[(2-chloro-5,6-dimethyl-3-nitropyridin-4-yl)amino]ethoxy}ethylcarbamate as a light orange solid, m.p. 70–73° C.

Part F

The general method described in Part A of Example 92 was used to convert tert-butyl 2-{2-[(2-chloro-5,6-dimethyl-3-nitropyridin-4-yl)amino]ethoxy}ethylcarbamate (57.0 g, 147 mmol) to 51.6 g of tert-butyl 2-{2-[(5,6-dimethyl-8-nitrotetrazolo[1,5-a]pyridin-7-yl)amino]ethoxy}ethylcarbamate, obtained as a yellow solid, m.p. 109–111° C.

Part G

Under a nitrogen purge, 5% platinum on carbon (2.5 g) was added to a Parr vessel containing a solution of tert-butyl 2-{2-[(2-chloro-5,6-dimethyl-8-nitrotetrazolo[1,5-a]pyridin-7-yl)amino]ethoxy}ethylcarbamate (25.0 g, 63.2 mmol) in toluene (500 mL). The vessel was placed under hydrogen pressure (30 psi, 2.0×10$^5$ Pa) for four hours, and then 2-propanol (50 mL) was added. The reaction mixture was filtered through a layer of CELITE filter aid, and the filter cake was washed with 2-propanol (500 mL) and ethanol (500 mL). The filtrate was concentrated under reduced pressure to yield 22.9 g of tert-butyl 2-{2-[(8-amino-5,6-dimethyltetrazolo[1,5-a]pyridin-7-yl)amino]ethoxy}ethylcarbamate as a brown oil.

Part H

The general method described in Part E of Example 85 was used to convert tert-butyl 2-{2-[(8-amino-5,6-dimethyltetrazolo[1,5-a]pyridin-7-yl)amino]ethoxy}ethylcarbamate (22.8 g, 62.4 mmol) to tert-butyl 2-{2-[(8-ethyl-5,6-dimethyl-7H-imidazo[4,5-c]tetraazolo[1,5-a]pyridin-7-yl)]ethoxy}ethylcarbamate. Triethylorthopropionate (13.2 mL, 65.5 mmol) was used in lieu of trimethylorthobutyrate. The crude product was obtained as a light brown solid (20.2 g), which was stirred with water (500 mL) for 15 minutes, isolated by filtration, and dried overnight in a vacuum oven at 80° C., to provide the desired product, mp 186–188° C., which was used without further purification.

Part I

A solution of trifluoroacetic acid (188 mL, 2.44 mol) in dichloromethane (300 mL) was cooled to 0° C. A solution of tert-butyl 2-{2-[(8-ethyl-5,6-dimethyl-7H-imidazo[4,5-c]tetrazolo[1,5-a]pyridin-7-yl)]ethoxy}ethylcarbamate (19.7 g, 48.8 mmol) in dichloromethane (300 mL) was then slowly added over a period of 30 minutes, and the reaction was stirred overnight. The volatiles were removed under reduced pressure, and the residual brown oil was stirred with 2-propanol (300 mL) to form a white salt, which was isolated by filtration and dried in a vacuum at 80° C. The salt was dissolved in water (200 mL), and solid sodium carbonate was added to adjust to pH 12. The solution was extracted with chloroform overnight with a continuous extractor. The extracts were dried over magnesium sulfate, filtered, and concentrated under reduced pressure to provide 11.5 g of 2-[2-(8-ethyl-5,6-dimethyl-7H-imidazo[4,5-c]tetrazolo[1,5-a]pyridin-7-yl)ethoxy]ethylamine as a white solid, m.p. 181–183° C.

Part J

The general method described in Part B of this example was used with the following modifications. 2-[2-(8-Ethyl-5,6-dimethyl-7H-imidazo[4,5-c]tetrazolo[1,5-a]pyridin-7-yl)ethoxy]ethylamine (2.25 g, 7.42 mmol) was used in lieu of tert-butyl 2-(2-hydroxyethoxy)ethylcarbamate. The reaction was stirred for 2 hours, and 2.8 g of crude product were obtained after the work-up. The crude product was purified by column chromatography on silica gel (200 mL, eluting with 90:10 dichloromethane:methanol) to provide 2.30 g of N-{2-[2-(8-ethyl-5,6-dimethyl-7H-imidazo[4,5-c]tetrazolo[1,5-a]pyridin-7-yl)ethoxy]ethyl}methanesulfonamide as a white solid, m.p. 216–218° C.

Part K

The general method described in Part F of Example 92 was used to convert N-{2-[2-(8-ethyl-5,6-dimethyl-7H-imidazo[4,5-c]tetrazolo[1,5-a]pyridin-7-yl)ethoxy]ethyl}methanesulfonamide (2.25 g, 5.90 mmol) to N-{2-[2-(4-amino-2-ethyl-6,7-dimethyl-1H-imidazo[4,5-c]pyridin-1-yl)ethoxy]ethyl}methanesulfonamide. The crude product was obtained as a colorless oil (2.03 g), which was recrystallized from 2-propanol (45 mL) and dried in a vacuum oven at 70° C. to provide 1.37 g of the desired product as a white powder, mp 145–147° C.

$^1$H NMR (300 MHz, DMSO) δ 6.99 (br t, 1H), 5.57 (s, 2H), 4.41 (t, J=5.6 Hz, 2H), 3.69 (t, J=5.6, 2H), 3.40 (t, J=5.8, 2H), 3.02 (q, J=5.6, 2H), 2.85 (q, J=7.5, 2H), 2.82 (s, 3H), 2.35 (s, 3H), 2.30 (s, 3H), 1.31 (t, J=7.5, 3H); MS (APCI) m/z 356 (M+H)$^+$; Anal. Calcd for $C_{15}H_{25}N_5O_3S$: C, 50.69; H, 7.09; N, 19.70. Found: C, 50.69; H, 7.17; N, 19.68.

EXAMPLES 103 AND 104

2-[2-(8-Ethyl-5,6-dimethyl-7H-imidazo[4,5-c]tetrazolo[1,5-a]pyridin-7-yl)ethoxy]ethylamine was obtained as described in Parts A through I of Example 102. Under a nitrogen atmosphere, a solution of 2-[2-(8-ethyl-5,6-dimethyl-7H-imidazo[4,5-c]tetraazolo[1,5-a]pyridin-7-yl)ethoxy]ethylamine (1 equivalent) and in dichloromethane was cooled to 0° C.; triethylamine (1.1 equivalents) was added. The acid chloride (1.1 equivalents) selected from the table below was then added dropwise, and the solution was allowed to warm to room temperature and stirred for several hours. The reaction was washed with 5% aqueous sodium hydroxide (200 mL), and the aqueous layer was extracted with dichloromethane (2×200 mL). The combined organic solutions were dried over magnesium sulfate, filtered, and concentrated under reduced pressure to provide a white solid, which was treated using the general method described in Part F of Example 92 and purified as described below.

| Example Number | Acid Chloride | R |
| --- | --- | --- |
| 103 | 4-morpholinecarbonyl chloride | —N(morpholine)O |
| 104 | cyclohexylcarbonyl chloride | —(cyclohexyl) |

EXAMPLE 103

N-{2-[2-(4-Amino-2-ethyl-6,7-dimethyl-1H-imidazo[4,5-c]pyridin-1-yl)ethoxy]ethyl}morpholine-4-carboxamide The crude product was obtained as a white solid, which was recrystallized from 2-propanol and dried overnight in a vacuum oven at 80° C. The crystals were dissolved in dichloromethane, and the solution was concentrated under reduced pressure to provide 1.46 g of N-{2-[2-(4-amino-2-ethyl-6,7-dimethyl-1H-imidazo[4,5-c]pyridin-1-yl)ethoxy]ethyl}morpholine-4-carboxamide as a white powder, mp 182–184° C.

$^1$H NMR (300 MHz, DMSO) δ 6.40 (t, J=5.4 Hz, 1H), 5.63 (s, 2H), 4.39 (t, J=5.4, 2H), 3.67 (t, J=5.4, 2H), 3.51 (m, 4H), 3.34 (t, J=6.1, 2H), 3.18 (m, 4H), 3.11 (q, J=5.8, 2H), 2.84 (q, J=7.5, 2H), 2.35 (s, 3H), 2.30 (s, 3H), 1.30 (t, J=7.5, 3H); MS (APCI) m/z 391 (M+H)$^+$; Anal. Calcd for $C_{19}H_{30}N_6O_3$: C, 58.44; H, 7.74; N, 21.52. Found: C, 58.22; H, 7.77; N, 21.73.

EXAMPLE 104

N-{2-[2-(4-Amino-2-ethyl-6,7-dimethyl-1H-imidazo[4,5-c]pyridin-1-yl)ethoxy]ethyl}cyclohexanecarboxamide The crude product was purified by column chromatography on silica gel (150 mL, eluting with 85:15 dichloromethane:methanol) and recrystallization from 2-propanol (20 mL). The purified crystals were dissolved in methanol, and the resulting solution was concentrated under reduced pressure to provide 0.88 g of N-{2-[2-(4-amino-2-ethyl-6,7-dimethyl-1H-imidazo[4,5-c]pyridin-1-yl)ethoxy]ethyl}cyclohexanecarboxamide as a white powder, mp 170–172° C.

$^1$H NMR (300 MHz, CDCl3) δ 5.36 (br t, 1H), 4.89 (s, 2H), 4.43 (t, J=5.4 Hz, 2H), 3.72 (t, J=5.5, 2H), 3.43–3.38 (m, 2H), 3.34–3.27 (m, 2H), 2.88 (q, J=7.5, 2H), 2.45 (s, 3H), 2.43 (s, 3H), 1.92–1.61 (m, 6H), 1.42 (t, J=7.5, 3H), 1.35–1.16 (m, 5H); MS (APCI) m/z 388 (M+H)$^+$; Anal. Calcd for $C_{21}H_{33}N_5O_2$: C, 65.09; H, 8.53; N, 18.07. Found: C, 64.85; H, 8.66; N, 17.86.

EXAMPLE 105

N-Cyclohexyl-N'-{2-[2-(2-ethyl-6,7-dimethyl-1H-imidazo[4,5-c]pyridin-2-yl)ethoxy]ethyl}urea

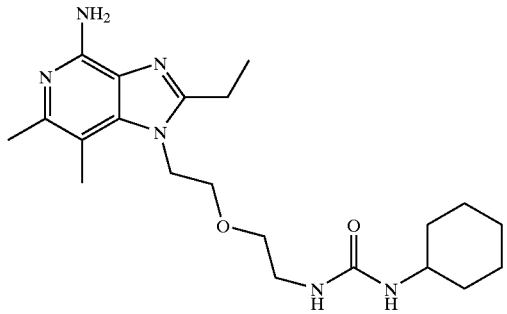

A modification of the methods described in Examples 103 and 104 was used to convert 2-[2-(8-ethyl-5,6-dimethyl-7H-imidazo[4,5-c]tetrazolo[1,5-a]pyridin-7-yl)ethoxy]ethylamine (2.00 g, 6.59 mmol) to N-cyclohexyl-N'-{2-[2-(2-ethyl-6,7-dimethyl-1H-imidazo[4,5-c]pyridin-2-yl)ethoxy]ethyl}urea. No triethylamine was used, and cyclohexyl isocyanate (0.93 mL, 7.25 mmol) was used in lieu of an acid chloride. The crude hydrogenation product was isolated as an off-white solid, which was recrystallized twice from 2-propanol (15–17 mL/g) to provide 1.29 g of the desired product as white crystals, mp 187–189° C.

$^1$H NMR (300 MHz, CDCl3) δ 4.94 (s, 2H), 4.42 (t, J=5.3 Hz, 2H), 4.23 (d, J=8.1, 1H), 3.89 (t,J=5.3, 1H), 3.67 (t,J=5.3, 2H), 3.51–3.37 (m, 1H), 3.36–3.31 (m, 2H), 3.19 (q, J=5.3, 2H), 2.86 (q, J=7.5, 2H), 2.45 (s,3H), 2.42 (s, 3H), 1.92–1.82 (m, 2H, 1.75–1.54 (m, 3H), 1.41 (t, J=7.5, 3H), 1.36–1.04 (m, 5H); MS (APCI) m/z 403 (M+H)$^+$; Anal. Calcd for $C_{21}H_{34}N_6O_2$: C, 62.66; H, 8.51; N, 20.88. Found: C, 62.39; H, 8.74; N, 20.85.

EXAMPLE 106

1-{2-[2-(1,1-Dioxidoisothiazolidin-2-yl)ethoxy]ethyl}-2-ethyl-6,7-dimethyl-1H-imidazo[4,5-c]pyridin-4-amine

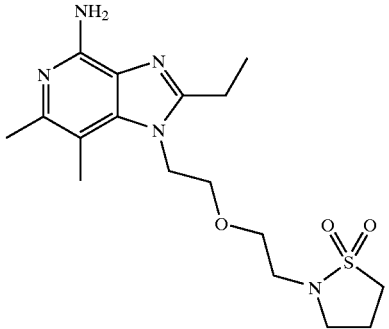

Part A

2-[2-(8-Ethyl-5,6-dimethyl-7H-imidazo[4,5-c]tetraazolo[1,5-a]pyridin-7-yl)ethoxy]ethylamine (2.00 g, 6.59 mmol) was obtained as described in Parts A through I of Example 102 and treated using the method of Part J of Example 102 with 3-chloropropanesulfonyl chloride (0.88 mL, 7.25 mmol) used in lieu of methanesulfonyl chloride. The crude product was purified by column chromatography on silica gel (100 mL, eluting with 95:5 dichloromethane:methanol) to provide an amber oil, which was triturated with diethyl ether. The product was isolated by filtration to provide 2.62 g of 3-chloro-N-{2-[2-(8-ethyl-5,6-dimethyl-7H-imidazo[4,5-c]tetrazolo[1,5-a]pyridin-7-yl)ethoxy]ethyl}propane-1-sulfonamide as a white solid, m.p. 126–129° C.

Part B

Under a nitrogen atmosphere, 1,8-diazabicyclo[5.4.0]undecene-7 (4.2 mL, 28 mmol) was added to a solution of 3-chloro-N-{2-[2-(8-ethyl-5,6-dimethyl-7H-imidazo[4,5-c]tetrazolo[1,5-a]pyridin-7-yl)ethoxylethyl}propane-1-sulfonamide (2.50 g, 5.63 mmol) in DMF (50 mL), and the reaction was stirred overnight at room temperature. The solution was concentrated to about 25 mL under reduced pressure, and water (300 mL) was added. A white precipitate formed, which was isolated by filtration and recrystallized from acetonitrile (20 mL) to provide 1.95 g of 7-{2-[2-(1,1-dioxidoisothiazolidin-2-yl)ethoxy]ethyl}-8-ethyl-5,6-dimethyl-7H-imidazo[4,5-c]tetraazolo[1,5-a]pyridine as white crystals, m.p. 176–178° C.

Part C

7-{2-[2-(1,1-Dioxidoisothiazolidin-2-yl)ethoxy]ethyl}-8-ethyl-5,6-dimethyl-7H-imidazo[4,5-c]tetrazolo[1,5-a]pyridine (1.60 g, 3.93 mmol) was treated using the procedure described in Part F of Example 92. The crude product was purifed by column chromatography on silica gel (75 mL, eluting with 80:20 dichloromethane:methanol) and recrystallized from 2-propanol to provide 0.38 g of white crystals. The crystals were dissolved in 2-propanol (10 mL) and treated with a 1 M solution of hydrochloric acid in diethyl ether (1 mL). The solution was stirred for 30 minutes, and the resulting salt was isolated by filtration and washed with diethyl ether. The salt was dissolved in water (25 mL), and solid sodium carbonate was added to adjust to pH 12. The solution was seeded with material made in a previous run, and the resulting solid was isolated by filtration and washed with water to provide 0.18 g of 1-{2-[2-(1,1-dioxidoisothiazolidin-2-yl)ethoxy]ethyl}-2-ethyl-6,7-dimethyl-1H-imidazo[4,5-c]pyridin-4-amine as a white solid, mp 157–159° C.

¹H NMR (300 MHz, CDCl3) δ 4.86 (s, 2H), 4.44 (t, J=5.4 Hz, 2H), 3.74 (t, J=5.4, 2H), 3.57–3.51 (m, 2H), 3.13–3.08 (m, 2H), 3.04–2.97 (m, 2H), 2.89 (q, J=7.5, 2H), 2.87 (t, J=6.8, 2H), 2.44 (s, 3H), 2.42 (s, 3H), 2.19–2.08 (m, 2H), 1.41 (t, J=7.5, 3H); MS (APCI) m/z 382 (M+H)⁺; Anal. Calcd for $C_{17}H_{27}N_5O_3S \cdot 0.50\ H_2O$: C, 52.29; H, 7.23; N, 17.93. Found: C, 52.54; H, 7.49; N, 18.02.

EXAMPLE 107

N-{2-[2-(4-Amino-2-ethyl-6,7-dimethyl-1H-imidazo[4,5-c]pyridin-1-yl)ethoxy]ethyl}-N'-benzoylurea

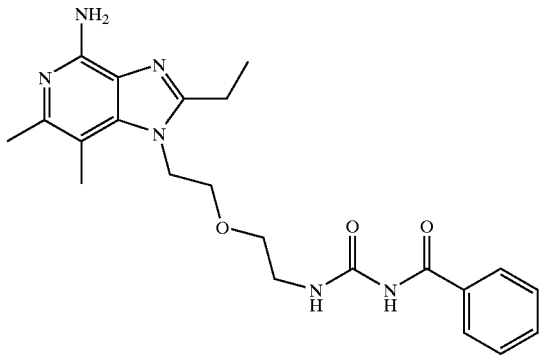

Part A

2-[2-(8-Ethyl-5,6-dimethyl-7H-imidazo[4,5-c]tetrazolo[1,5-a]pyridin-7-yl)ethoxy]ethylamine (2.00 g, 6.59 mmol) was obtained as described in Parts A through I of Example 102 and treated using the method of Part F of Example 92. The crude product was recrystallized from toluene (57 mL/g) to provide 3.19 g of 1-[2-(2-aminoethoxy)ethyl]-2-ethyl-6,7-dimethyl-1H-imidazo[4,5-c]pyridin-4-amine as white crystals, m.p. 152–154° C.

Part B

A solution of 1-[2-(2-aminoethoxy)ethyl]-2-ethyl-6,7-dimethyl-1H-imidazo[4,5-c]pyridin-4-amine (1.60 g, 5.77 mmol) was treated with benzoyl isocyanate (0.98 g, 6.6 mmol) using the method described in Example 105. The crude product was purified by column chromatography on silica gel (150 mL, eluting with 90:10 dichloromethane:methanol) and recrystallized from acetonitrile (75 mL/g). The crystals were subsequently recrystallized twice from 2-propanol (40–44 mL/g) and then stirred in water for 30 minutes and isolated by filtration. The solid was dried for three days under high vacuum to provide 0.54 g of N-{2-[2-(4-amino-2-ethyl-6,7-dimethyl-1H-imidazo[4,5-c]pyridin-1-yl)ethoxy]ethyl}-N'-benzoylurea as a white solid, mp 185–187° C. ¹H NMR (300 MHz, CDCl3) δ 8.98 (br s, 1H), 8.87 (br t, 1H), 7.93–7.87 (m, 2H), 7.63–7.56 (m, 1H), 7.52–7.44 (m, 2H), 4.84 (s, 2H), 4.45 (t, J=5.8 Hz, 2H), 3.76 (t, J=5.8, 2H), 3.57–3.46 (m, 4H), 2.91 (q, J=7.5, 2H), 2.42 (s, 6H), 1.41 (t, J=7.5, 3H); MS (APCI) m/z 425 (M+H)⁺; Anal. Calcd for $C_{22}H_{28}N_6O_3 \cdot 0.25\ H_2O$: C, 61.59; H, 6.70; N, 19.59. Found: C, 61.25; H, 6.90; N, 19.72.

EXAMPLE 108

N-[({2-[2-(4-Amino-2-ethyl-6,7-dimethyl-1H-imidazo[4,5-c]pyridin-1-yl)ethoxy]ethyl}amino)carbonyl]benzenesulfonamide

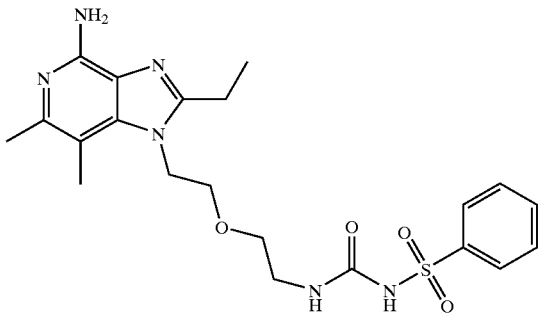

A solution of 1-[2-(2-aminoethoxy)ethyl]-2-ethyl-6,7-dimethyl-1H-imidazo[4,5-c]pyridin-4-amine (1.45 g, 5.23 mmol), obtained as described in Part A of Example 107, was treated with benzenesulfonyl isocyanate (0.70 mL, 5.2 mmol) using a modification of the method described in Example 105. The crude reaction mixture was concentrated under reduced pressure, and the residue was purified by column chromatography on silica gel (eluting with 79.5:19.5:1 dichloromethane:methanol:triethylamine) to provide a white solid. The solid (1.05 g) was stirred with 90:10 dichloromethane:methanol (40 mL), isolated by filtration, and recrystallized from DMF (10 mL) to provide 0.41 g of N-[({2-[2-(4-amino-2-ethyl-6,7-dimethyl-1H-imidazo[4,5-c]pyridin-1-yl)ethoxy]ethyl}amino)carbonyl]benzenesulfonamide as a white solid, mp 201–203° C. MS (ESI) m/z 461 (M+H)⁺.

EXAMPLE 109

2-(Ethoxymethyl)-6,7-dimethyl-1-[2-(pyridin-4-ylmethoxy)ethyl]-1H-imidazo[4,5-c]pyridin-4-amine

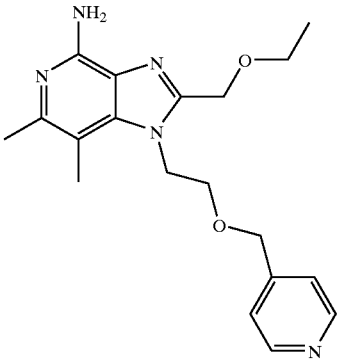

Part A (2-Chloro-5,6-dimethyl-3-nitropyridin-4-yl)-[2-(pyridin-4-ylmethoxy)ethyl]amine (19.6 g, 58.2 mmol), which was prepared as described in Parts A through C of Example 84, was treated with sodium azide (7.57 g, 116 mmol) using the general method described in Part A of Example 92. The crude solid was recrystallized from acetonitrile to provide 16.2 g of (5,6-dimethyl-8-nitrotetrazolo[1,5-a]pyridin-7-yl)-[2-(pyridin-4-ylmethoxy)ethyl]amine as an orange solid.

Part B (5,6-Dimethyl-8-nitrotetraazolo[1,5-a]pyridin-7-yl)-[2-(pyridin-4-ylmethoxy)ethyl]amine (16.2 g, 46.9 mmol) was hydrogenated using the conditions described in Part G of Example 80 with the following modification. The filter cake was washed with hot toluene and 50:50 dichloromethane:methanol, the filtrate was concentrated under reduced pressure to provide the crude product, which was triturated with diethyl ether and isolated by filtration to afford 5,6-dimethyl-$N^7$-[2-(pyridin-4-ylmethoxy)ethyl]tetrazolo[1,5-a]pyridine-7,8-diamine as a white solid.

Part C

The general method described in Part E of Example 82 was used to convert 5,6-dimethyl-$N^7$-[2-(pyridin-4-ylmethoxy)ethyl]tetrazolo[1,5-a]pyridine-7,8-diamine (6.0 g, 19 mmol) to 8-ethoxy-5,6-dimethyl-7-[2-(pyridin-4-ylmethoxy)ethyl]-7H-imidazo[4,5-c]tetrazolo[1,5-a]pyridine. The crude product was triturated with diethyl ether, isolated by filtration, and recrystallized from acetonitrile (1.8 mL/g) to provide 4.53 g of the desired product as off-white crystals.

Part D

Under a nitrogen atmosphere, a solution of 8-ethoxy-5,6-dimethyl-7-[2-(pyridin-4-ylmethoxy)ethyl]-7H-imidazo[4,5-c]tetrazolo[1,5-a]pyridine (4.04 g, 10.5 mmol) and triphenyl phosphine (3.04 g, 11.6 mmol) in xylene (50 mL) was heated at reflux for 18 hours. The solution was allowed to cool to room temperature, and the volatiles were removed under reduced pressure. The residual oil was treated with aqueous hydrochloric acid (50 mL of 1 M) and stirred for 30 minutes; a white precipitate formed. The solution was then washed with dichloromethane (3×2 mL), treated with 1 N aqueous potassium hydroxide to adjust to pH 14, and cooled to near 0° C. The product precipitated and was isolated by filtration, washed with diethyl ether, and dried under reduced pressure. The resulting solid was washed with water, isolated by filtration, washed with diethyl ether, and recrystallized from toluene. The solid was dissolved in methanol, and the solution was concentrated under reduced pressure. This was repeated three times before the solid was finally triturated with diethyl ether and isolated by filtration to provide 2.17 g of 2-(ethoxymethyl)-6,7-dimethyl-1-[2-(pyridin-4-ylmethoxy)ethyl]-1H-imidazo[4,5-c]pyridin-4-amine as small tan crystals, mp 143–145° C.

$^1$H NMR (300 MHz, DMSO) δ 8.45 (d, J=6.2 Hz, 2H), 7.11 (d, J=5.6 Hz, 2H), 5.80 (s, 2H), 4.69 (s, 2H), 4.61 (t, J=5.6 Hz, 2H), 4.48 (s, 2H), 3.80 (t, J=5.6 Hz, 3.48 (q, J=6.9 Hz, 2H), 2.37 (s, 3H), 2.31 (s, 3H), 1.10 (t, J=6.9 Hz, 3H); MS (APCI) m/z 356 (M+H)$^+$; Anal. Calcd for $C_{19}H_{25}N_5O_2$: C, 64.20; H, 7.09; N, 19.70; Found: C, 63.93; H, 7.43; N, 19.76.

EXAMPLE 110

2,6,7-Trimethyl-1-[2-(pyridin-4-ylmethoxy)ethyl]-1H-imidazo[4,5-c]pyridin-4-amine

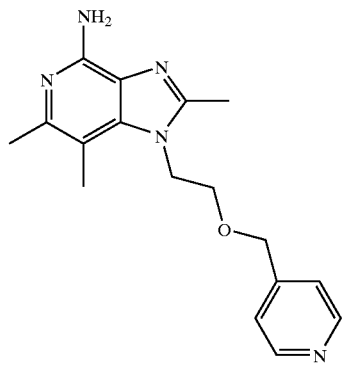

Using the general method described in Part E of Example 85, 5,6-dimethyl-$N^7$-[2-(pyridin-4-ylmethoxy)ethyl]tetrazolo[1,5-a]pyridine-7,8-diamine (6.0 g, 19 mmol), prepared as described in Parts A and B of Example 109, was treated with triethylorthoacetate (3.7 mL, 20 mmol) in lieu of trimethylorthobutyrate. The crude product was triturated with diethyl ether and isolated by filtration to provide 6.07 g of 5,6,8-trimethyl-7-[2-(pyridin-4-ylmethoxy)ethyl]-7H-imidazo[4,5-c]tetrazolo[1,5-c]pyridine as a brown solid.

Part B

The general method of Part D of Example 109 was used to convert 5,6,8-trimethyl-7-[2-(pyridin-4-ylmethoxy)ethyl]-7H-imidazo[4,5-c]tetrazolo[1,5-c]pyridine (4.44 g, 13.0 mmol) to 2.18 g of 2,6,7-trimethyl-1-[2-(pyridin-4-ylmethoxy)ethyl]-1H-imidazo[4,5-c]pyridin-4-amine, which was obtained as a white solid, mp 208–210° C.

$^1$H NMR (300 MHz, DMSO) δ 8.45 (m, 2H), 7.11 (d, J=6.2 Hz, 2H), 5.64 (s, 2H), 4.50 (t, J=5.6 Hz, 2H), 4.48 (s, 2H), 3.77 (t, J=5.3 Hz, 2H), 2.50 (s, 3H), 2.33 (s,3H), 2.29 (s, 3H); MS (APCI) m/z 312 (M+H)$^+$; Anal. Calcd for $C_{17}H_{21}N_5O$: C, 65.57; H, 6.80; N, 22.49; Found: C, 65.60; H, 6.84; N, 22.57.

EXAMPLE 111

2-(Ethoxymethyl)-6,7-dimethyl-1-{2-[(3-pyrimidin-5-ylprop-2-ynyl)oxy]ethyl}-1H-imidazo[4,5-c]pyridin-4-amine

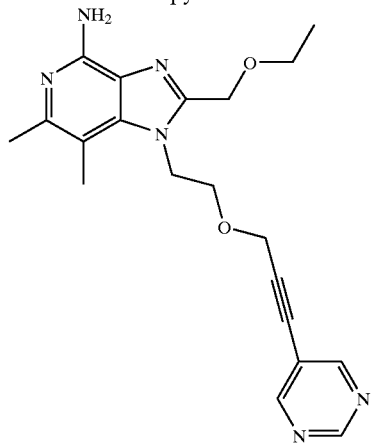

Part A

Using a modification of the method described in Part A of Example 85, 2-(2-chloro-5,6-dimethyl-3-nitropyridin-4-ylamino)ethanol was prepared. Ethanolamine was used in lieu of 5-amino-1-pentanol, and the reaction was heated at 60° C. for six hours.

Part B

Pyridine (1.0 mL, 12 mmol) and 4-dimethylaminopyridine (DMAP) (0.005 g, 0.04 mmol) was added to a solution of 2-(2-chloro-5,6-dimethyl-3-nitropyridin-4-ylamino)ethanol (0.50 g, 2.0 mmol) in anhydrous dichloromethane (4.5 mL). Under a nitrogen atmosphere, acetic anhydride (0.8 mL, 8 mmol) was added, and the yellow solution was stirred at room temperature for 1.3 hours. The volatiles were removed under reduced pressure, and the residual yellow oil was dissolved in dichloromethane. The solution was washed with aqueous sodium bicarbonate, water, and brine, and then dried over sodium sulfate, filtered, and concentrated under reduced pressure to provide 0.55 g of acetic acid 2-(2-chloro-5,6-dimethyl-3-nitropyridin-4-ylamino)ethyl ester as a yellow solid.

Part C

A modification of the method of Part A of Example 92 was used to convert acetic acid 2-(2-chloro-5,6-dimethyl-3-nitropyridin-4-ylamino)ethyl ester (8.02 g, 27.9 mmol) to acetic acid 2-(5,6-dimethyl-8-nitrotetrazolo[1,5-a]pyridin-7-ylamino)ethyl ester. A 3:1 acetonitrile:water mixture was used as the solvent, and the reaction was heated at reflux for 21 hours. The crude product was obtained as an oil, which was triturated with diethyl ether, isolated by filtration, and washed with water and diethyl ether to provide 7.3 g of the desired product.

Part D

The procedure described in Part F of Example 80 was used to convert acetic acid 2-(5,6-dimethyl-8-nitrotetraazolo[1,5-a]pyridin-7-ylamino)ethyl ester (6.18 g, 21.0 mmol) to 5.20 g of acetic acid 2-(8-amino-5,6-dimethyltetrazolo[1,5-a]pyridin-7-ylamino)ethyl ester, which was obtained as a tan solid.

Part E

The method described in Part E of Example 82 was used to convert acetic acid 2-(8-amino-5,6-dimethyltetrazolo[1,5-a]pyridin-7-ylamino)ethyl ester (5.20 g, 19.7 mmol) to 6.10 g of acetic acid 2-(8-ethoxymethyl-5,6-dimethyl-7H-imidazo[4,5-c]tetrazolo[1,5-a]pyridin-7-yl)ethyl ester, which was obtained as a tan solid.

Part F

A mixture of 2-(8-ethoxymethyl-5,6-dimethyl-7H-imidazo[4,5-c]tetrazolo[1,5-a]pyridin-7-yl)ethyl ester (6.10 g, 18.4 mmol) and methanol (60 mL) was stirred and heated to 70° C. Potassium carbonate (1.90 g, 13.8 mmol) was added to the resulting solution, and the reaction was stirred at 70° C. for 15 minutes then allowed to cool to room temperature. The volatiles were removed under reduced pressure, and the residue was dissolved in 9:1 dichloromethane:methanol and filtered through a layer of silica gel (53 g). The volatiles were removed under reduced pressure to provide 4.98 g of 2-(8-ethoxymethyl-5,6-dimethyl-7H-imidazo[4,5-c]tetrazolo[1,5-a]pyridin-7-yl)ethanol as a solid containing some minor impurities.

Part G

The method described in Part A of Example 81 was followed. 2-(8-Ethoxymethyl-5,6-dimethyl-7H-imidazo[4,5-c]tetrazolo[1,5-a]pyridin-7-yl)ethanol (4.98 g, 16.8 mmol) was used in lieu tert-butyl 2-hydroxyethylcarbamate. 8-Ethoxymethyl-5,6-dimethyl-7-(2-prop-2-ynyloxyethyl)-7H-imidazo[4,5-c]tetrazolo[1,5-a]pyridine (5.5 g), containing some minor impurities, was obtained as a white solid.

Part H

The method described in Part B of Example 81 was followed. 8-Ethoxymethyl-5,6-dimethyl-7-(2-prop-2-ynyloxyethyl)-7H-imidazo[4,5-c]tetrazolo[1,5-a]pyridine (5.5 g, 17 mmol) was used as the starting material in lieu of tert-butyl 2-(prop-2-ynyloxy)ethylcarbamate, and 5-bromopyrimidine was used in lieu of 3-bromopyridine. The crude product was purified by column chromatography on silica gel (620 g, eluting with 98:2 dichloromethane:methanol), and the resulting solid was mixed with 2-propanol (150 mL). Insoluble impurities were removed by filtration, and the solution was concentrated to a volume of 20 mL. The product crystallized and was isolated by filtration and washed with 2-propanol and diethyl ether to provide 6.10 g of 8-ethoxymethyl-5,6-dimethyl-7-[2-(3-pyrimidin-5-ylprop-2-ynyloxy)ethyl]-7H-imidazo[4,5-c]tetrazolo[1,5-a]pyridine as white crystals.

Part I

The method described in Part D of Example 109 was used with the following modification. The reaction was carried out in refluxing toluene, and 8-ethoxymethyl-5,6-dimethyl-7-[2-(3-pyrimidin-5-ylprop-2-ynyloxy)ethyl]-7H-imidazo[4,5-c]tetrazolo[1,5-a]pyridine (6.20 g, 15.3 mmol) was used in lieu of 8-ethoxy-5,6-dimethyl-7-[2-(pyridin-4-ylmethoxy)ethyl]-7H-imidazo[4,5-c]tetrazolo[1,5-a]pyridine. The crude product was purified by column chromatography on silica gel (200 g, eluting with 95:5 dichloromethane:methanol) to provide 0.852 g of 2-(ethoxymethyl)-6,7-dimethyl-1-{2-[(3-pyrimidin-5-ylprop-2-ynyl)oxy]ethyl}-1H-imidazo[4,5-c]pyridin-4-amine as a white powder, mp 122–124° C.

$^1$H NMR (300 MHz, DMSO) δ 9.18 (s, 1H), 8.83 (s, 2H), 6.05 (s, 2H), 4.70 (s, 2H), 4.61 (t, J=5.6 Hz, 2H), 4.44 (s, 2H), 3.90 (t, J=5.6 Hz, 2H), 3.50 (q, J=6.9 Hz, 2H), 2.40 (s, 3H), 2.30 (s, 3H), 1.12 (t, J=7.2 Hz, 3H); MS (APCI) m/z 381 (M+H)$^+$; Anal. Calcd for $C_{20}H_{24}N_6O_2$: C, 63.14; H, 6.36; N, 22.09; Found: C, 62.84; H, 6.37; N, 22.12.

EXAMPLE 112

2-(Ethoxymethyl)-6,7-dimethyl-1-[2-(3-pyrimidin-5-ylpropoxy)ethyl]-1H-imidazo[4,5-c]pyridin-4-amine

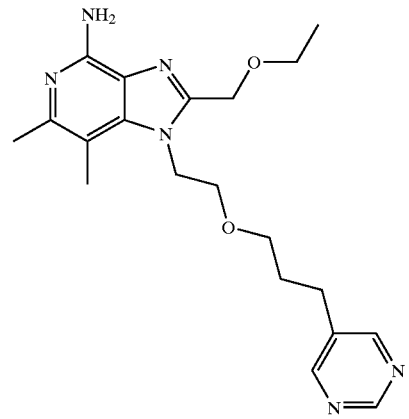

Under a nitrogen purge, 2-(ethoxymethyl)-6,7-dimethyl-1-{2-[(3-pyrimidin-5-ylprop-2-ynyl)oxy]ethyl}-1H-imidazo[4,5-c]pyridin-4-amine (0.69 g, 1.8 mmmol), prepared as described in Example 111, 10% palladium on carbon (0.1 g), and methanol (10 mL) were added to a Parr vessel. The vessel was placed under hydrogen pressure (50 psi, 3.4×10⁵ Pa) for 2.5 hours. The reaction mixture was filtered through a layer of CELITE filter aid, and the filter cake was rinsed with methanol (200 mL). The filtrate was concentrated under reduced pressure to yield an oil, which was triturated with diethyl ether then recrystallized from toluene (3 mL). The crystals were dried for 24 hours at 94° C. and then dissolved in methanol. The solution was concentrated to provide an oil that was triturated with diethyl ether and dried under reduced pressure to provide 0.202 g of 2-(ethoxymethyl)-6,7-dimethyl-1-[2-(3-pyrimidin-5-ylpropoxy)ethyl]-1H-imidazo[4,5-c]pyridin-4-amine as a white powder, mp 127–129° C.

$^1$H NMR (300 MHz, DMSO) δ 9.00 (s, 1H), 8.54 (s, 2H), 5.79 (s, 2H), 4.69 (s, 2H), 4.54 (t, J=5.6 Hz, 2H), 3.70 (t, J=5.6 Hz, 2H), 3.5 (q, J=7.1 Hz, 2H), 3.33 (t, J=6.2 Hz, 2H), 2.47 (t, J=8.1 Hz, 2H), 2.39 (s, 3H), 2.31 (s, 3H), 1.74 (p, J=7.5, 6.2 Hz, 2H), 1.31 (t, J=6.9 Hz, 3H); MS (APCI) m/z 385 (M+H)⁺; Anal. Calcd for $C_{20}H_{28}N_6O_2$: C, 62.48; H, 7.34; N, 21.86; Found: C, 62.20; H, 7.34; N, 21.58.

EXAMPLE 113

N-{2-[2-(4-Amino-7-bromo-2-propyl-1H-imidazo[4,5-c]pyridin-1-yl)ethoxy]ethyl}methanesulfonamide

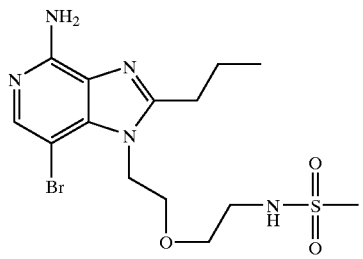

Solid potassium acetate (0.62 g, 6.32 mmol) was added to a solution of N-{2-[2-(4-amino-2-propyl-1H-imidazo[4,5-c]pyridin-1-yl)ethoxy]ethyl}methanesulfonamide (1.8 g, 5.27 mmol) in acetic acid (32 mL). After the potassium acetate had dissolved bromine (1.26 g, 7.91 mmol) was added dropwise. The reaction was stirred at ambient temperature for 40 minutes at which time analysis by thin layer chromatography indicated that the reaction was complete. Excess bromine was quenched by the addition of saturated aqueous sodium bisulfite (~1 mL). The pH of the reaction mixture was adjusted to pH 7 by the addition of saturated aqueous sodium bicarbonate (100 mL) followed by the addition of solid sodium bicarbonate. The reaction mixture was extracted with dichloromethane (2×100 mL). The combined extracts were washed sequentially with water, saturated aqueous sodium bicarbonate (100 mL) and brine (100 mL), dried over sodium sulfate, filtered and then concentrated under reduced pressure to provide a brown gooey solid. This material was purified by chromatography (silica gel eluting with 95:5 dichloromethane:methanol) to provide 1.7 g of N-{2-[2-(4-amino-7-bromo-2-propyl-1H-imidazo[4,5-c]pyridin-1-yl)ethoxy]ethyl}methanesulfonamide as a white waxy solid, mp 129–131° C.

$^1$H NMR (300 MHz, DMSO-d₆) δ 7.68 (s, 1H), 7.00 (t, J=6.0 Hz, 1H), 6.21 (bs, 2H), 4.55 (t, J=5.7 Hz, 2H), 3.75 (t, J=5.7 Hz, 2H), 3.42 (t, J=5.7 Hz, 2H), 3.03 (q, J=5.9 Hz, 2H), 2.86 (t, J=7.5 Hz, 2H), 2.84 (s, 3H), 1.81 (sextet, J=7.5 Hz, 2H), 1.01 (t, J=7.5 Hz, 3H); MS (APCI) m/z 420/422 (M+H)⁺; Anal. Calcd for $C_{14}H_{22}BrN_5O_3S$: C, 40.01; H, 5.28: N, 16.66. Found: C, 39.66; H, 4.95; N, 16.29.

EXAMPLE 114

1-[2-(2-Aminoethoxy)ethyl]-7-bromo-2-propyl-1H-imidazo[4,5-c]pyridin-4-amine

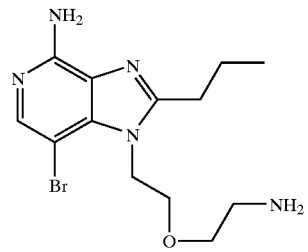

Part A

Using the general method of Example 113, tert-butyl 2-[2-(4-amino-2-propyl-1H-imidazo[4,5-c]pyridin-1-yl)ethoxy]ethylcarbamate (0.9 g, 2.48 mmol) was brominated to provide 0.85 g of tert-butyl 2-[2-(4-amino-7-bromo-2-propyl-1H-imidazo[4,5-c]pyridin-1-yl)ethoxy]ethylcarbamate as a brown foam.

Part B

Hydrochloric acid (1.8 mL of 4.25 M in ethanol) was added to a solution of the material from Part A in ethanol (10 mL). The reaction was heated at reflux for 1 hour and then concentrated under reduced pressure to provide a brown foam. The foam was recrystallized from ethyl acetate (13 mL) to provide 0.4 g of 1-[2-(2-aminoethoxy)ethyl]-7-bromo-2-propyl-1H-imidazo[4,5-c]pyridin-4-amine as brown rock-needles, mp 114–117° C. Anal. Calcd for $C_{13}H_{20}BrN_5O$: C, 45.62; H, 5.89; N, 20.46. Found: C, 45.90; H, 5.58; N, 20.15.

EXAMPLE 115

N-{2-[2-(4-Amino-7-bromo-2-propyl-1H-imidazo[4,5-c]pyridin-1-yl)ethoxy]ethyl}-4-chlorobenzamide

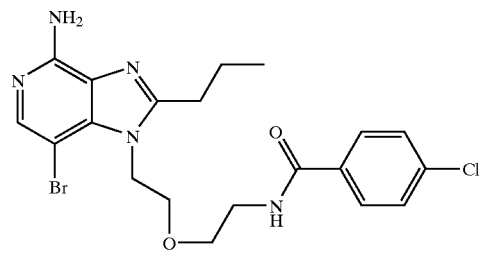

Triethylamine (0.07 g, 0.66 mmol) was added to a solution of 1-[2-(2-aminoethoxy)ethyl]-7-bromo-2-propyl-1H-imidazo[4,5-c]pyridin-4-amine (0.15 g, 0.44 mmol) in dichloromethane (2 mL). 4-Chlorobenzoyl chloride (0.09 g, 0.53 mmol) was added dropwise to the reaction mixture. The reaction mixture was stirred at ambient temperature for 10 minutes at which time analysis by thin layer chromatography indicated that the reaction was complete. The reaction mixture was partitioned between dichloromethane (30 mL) and saturated aqueous sodium bicarbonate (20 mL). The layers were separated. The organic layer was washed sequentially with saturated aqueous ammonium chloride (20 mL) and brine (20 mL), dried over sodium sulfate, filtered and then concentrated under reduced pressure to provide 0.23 g of a clear, glassy solid. The crude material was purified by chromatography (silica gel eluting with 95:5 dichloromethane:methanol) to provide 0.05 g of N-{2-[2-(4-amino-7-bromo-2-propyl-1H-imidazo[4,5-c]pyridin-1-yl)ethoxy]ethyl}-4-chlorobenzamide as a white amorphous solid.

$^1$H NMR (300 MHz, DMSO-d$_6$) δ 8.46 (t, J=5.6 Hz, 1H), 7.80 (d, J=8.7 Hz, 2H), 7.66 (s, 1H) 7.53 (d, J=8.7 Hz, 2H) 6.21 (bs, 2H), 4.55 (t, J=5.7 Hz, 2H), 3.75 (t, J=5.7 Hz, 2H), 3.42 (t, J=5.7 Hz, 2H), 3.03 (q, J=5.9 Hz, 2H), 2.86 (t, J=7.5 Hz, 2H), 2.84 (s, 3H), 1.81 (sextet, J=7.5 Hz, 2H), 1.01 (t, J=7.5 Hz, 3H); MS (APCI) m/z 480/482 (M+H)$^+$; Anal. Calcd for C$_{20}$H$_{23}$BrClN$_5$O$_2$·0.25 H$_2$O: C, 49.50; H, 4.88: N, 14.43. Found: C, 49.43; H, 4.81; N, 14.13.

EXAMPLE 116

N-{2-[2-(4-Amino-7-bromo-2-propyl-1H-imidazo[4,5-c]pyridin-1-yl)ethoxy]ethyl}-N'-cyclohexylurea

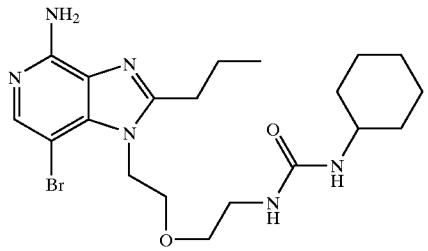

Cyclohexyl isocyanate (0.09 g, 0.69 mmol) was added dropwise to a suspension of 1-[2-(2-aminoethoxy)ethyl]-7-bromo-2-propyl-1H-imidazo[4,5-c]pyridin-4-amine (0.215 g, 0.63 mmol) in dichloromethane (3.5 mL). The reaction mixture became homogeneous for a short time and then a precipitate formed. The precipitate was isolated by filtration and washed with dichloromethane to provide 0.23 g of a beige powder, which was recrystallized from ethanol (1.5 mL) to provide 0.06 g of N-{2-[2-(4-amino-7-bromo-2-propyl-1H-imidazo[4,5-c]pyridin-1-yl)ethoxy]ethyl}-N'-cyclohexylurea as white needles, mp 185–186° C.

$^1$H NMR (300 MHz, DMSO-d$_6$) δ 7.67 (s, 1H), 6.20 (bs, 2H), 5.78 (d, J=7.5 Hz, 1H) 5.65 (t, J=5.3 Hz, 1H) 4.53 (t, J=5.7 Hz, 2H), 3.73 (t, J=5.7 Hz, 2H), 3.33 (t, J=5.9 Hz, 2H), 3.07 (q, J=5.9 Hz, 2H), 2.85 (t, J=7.5 Hz, 2H), 1.81 (sextet, J=7.5 Hz, 2H), 1.73–1.69 (m, 2H), 1.64–1.60 (m, 2H), 1.53–1.49 (m, 2H), 1.26–1.06 (m, 4H) 1.00 (t, J=7.5 Hz, 3H); MS (APCI) m/z 467/469 (M+H)$^+$. Anal. Calcd for C$_{20}$H$_{31}$BrN$_6$O$_2$: C, 51.39; H, 6.68: N, 17.98. Found: C, 51.35; H, 6.73; N, 18.05.

EXAMPLE 117

N-{2-[2-(4-Amino-7-hex-1-ynyl-2-propyl-1H-imidazo[4,5-c]pyridin-1-yl)ethoxy]ethyl}methanesulfonamide

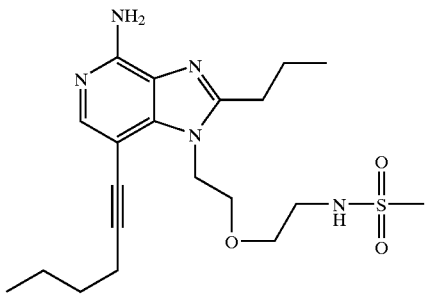

Dichlorobis(triphenylphosphine)palladium(II) (0.25 g, 0.36 mmol) and copper (I) iodide (0.14 g, 0.71 mmol) were added to a suspension containing N-{2-[2-(4-amino-7-bromo-2-propyl-1H-imidazo[4,5-c]pyridin-1-yl)ethoxy]ethyl}methanesulfonamide (1.5 g, 3.57 mmol), triethylamine (2 mL, 14 mmol), hexyne (1.23 mL, 10.7 mmol) and acetonitrile (18 mL). The reaction was heated to reflux and the progress was monitored by high performance liquid chromatography. After 2.5 hours hexyne (1 eq.), dichlorobis(triphenylphosphine)palladium(II) (0.1 eq) and copper (I) iodide (0.2 eq) were added. After an additional hour dichlorobis(triphenylphosphine)palladium(II) (0.1 eq) and copper (I) iodide (0.2 eq) were added. After a total reaction time of 5.5 hr the reaction mixture was allowed to cool to ambient temperature and then it was concentrated under reduced pressure to provide a dark oil. The oil was partitioned between dichloromethane (200 mL) and saturated aqueous ammonium chloride (100 mL). The organic layer was separated, washed with brine (100 mL), dried over sodium sulfate, filtered and then concentrated under reduced pressure to provide a dark sludge. This material was purified by chromatography (silica gel eluting with 95:5 dichloromethane:methanol) to provide 1.0 g of a brown oil which was found to be a 85:15 mixture of product and starting material. The oil was combined with triethylamine (1.5 eq), hexyne (1 eq.), acetonitrile (5 mL), dichlorobis(triphenylphosphine)palladium(II) (0.1 eq), and copper (I) iodide (0.2 eq) and then heated at reflux for 2 hr. The reaction mixture was allowed to cool to ambient temperature and then stirred for 20 hr. The reaction mixture was concentrated under reduced pressure to provide a dark oil. The oil was purified by chromatography (silica gel eluting with 95:5 dichloromethane:methanol) to provide N-{2-[2-(4-amino-7-hex-1-ynyl-2-propyl-1H-imidazo[4,5-c]pyridin-1-yl)ethoxy]ethyl}methanesulfonamide as a colorless oil.

$^1$H NMR (300 MHz, DMSO-d$_6$) δ 7.68 (bs, 1H), 6.99 (t, J=6.0 Hz, 1H), 6.30 (bs, 2H), 4.55 (t, J=5.7 Hz, 2H), 3.74 (t, J=5.7 Hz, 2H), 3.41 (t, J=5.7 Hz, 2H), 3.03 (q, J=5.9 Hz, 2H), 2.86–2.81 (m, 5H), 2.46 (m, 2H), 1.83 (sextet, J=7.5 Hz, 2H), 1.59–1.40 (m, 4H), 1.00 (t, J=7.5 Hz, 3H), 0.93 (t, J=7.2 Hz, 3H); MS (APCI) m/z 422 (M+H)$^+$.

EXAMPLE 118

N-{2-[2-(4-Amino-7-hexyl-2-propyl-1H-imidazo[4,5-c]pyridin-1-yl)ethoxy]ethyl}methanesulfonamide

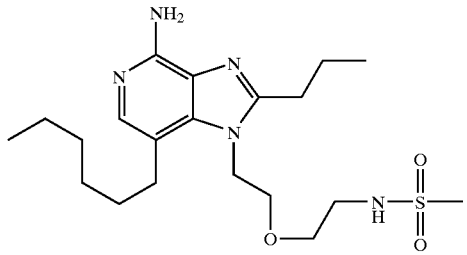

Solid palladium on carbon (0.5 g of 10%) was added to a Parr vessel and then wetted with isopropanol (1 mL). N-{2-[2-(4-Amino-7-hex-1-ynyl-2-propyl-1H-imidazo[4,5-c]pyridin-1-yl)ethoxy]ethyl}methanesulfonamide (~0.5 g) was added to the vessel followed by the addition of methanol (~10 mL). The vessel was placed on a shaker and placed under hydrogen pressure (50 psi, $3.4 \times 10^5$ Pa). After 20 hours the reaction mixture was filtered through a layer of CELITE filter agent to remove the catalyst and the filter cake was washed with methanol (~100 mL). The filtrate was concentrated under reduced pressure. The residue was purified by chromatography (silica gel eluting with 95:5 dichloromethane:methanol) to provide N-{2-[2-(4-amino-7-hexyl-2-propyl-1H-imidazo[4,5-c]pyridin-1-yl)ethoxy]ethyl}methanesulfonamide as a clear oil.

$^1$H NMR (300 MHz, DMSO-d$_6$) δ 7.38 (s, 1H), 6.97 (t, J=6.0 Hz, 1H), 6.00 (bs, 2H), 4.35 (t, J=5.7 Hz, 2H), 3.68 (t, J=5.7 Hz, 2H), 3.37 (m, 2H), 3.00 (q, J=5.9 Hz, 2H), 2.84 (t, J=7.5 Hz, 2H), 2.82 (s, 3H), 2.72 (t, J=7.5 Hz, 2H), 1.81 (sextet, J=7.5 Hz, 2H), 1.55–1.50 (m, 2H), 1.37–1.28 (m, 2H), 1.01 (t, J=7.5 Hz, 3H), 0.89–0.84 (m, 3H); MS (APCI) m/z 426 (M+H)$^+$.

EXAMPLE 119

4-[3-(4-Amino-6,7-dimethyl-2-propyl-1H-imidazo[4,5-c]pyridin-1-yl)propane-1-sulfonyl]-N-butylbenzamide

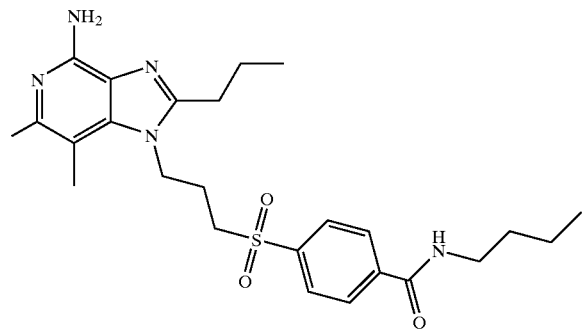

The general methods described in Example 101 were followed with the following modifications. To one-third of the crude solution of 4-[3-(5,6-dimethyl-8-propyl-7H-imidazo[4,5-c]tetrazolo[1,5-a]pyridin-7-yl)propane-1-sulfonyl]benzoyl chloride in dichloromethane, described in Part B of Example 101, was added butylamine (0.49 mL, 4.9 mmol) in lieu of morpholine, and the reaction was stirred overnight. Additional butylamine (0.5 mL) was added, and the reaction was stirred for two hours. Dichloromethane (100 mL) was added to the reaction mixture, and the resulting solution was washed with saturated aqueous sodium carbonate (3×25 mL), water (3×25 mL), 10% by volume acetic acid in water (3×30 mL), and water (30 mL), dried over sodium sulfate, filtered, and concentrated under reduced pressure. The crude product was dried for three hours in a vacuum oven at 100° C. and then triturated with ethyl acetate to provide a solid that was isolated by filtration and dried for three hours in a vacuum oven at 90° C. N-Butyl-4-[3-(5,6-dimethyl-8-propyl-7H-imidazo[4,5-c]tetrazolo[1,5-a]pyridin-7-yl)propane-1-sulfonyl]benzamide (830 mg, 1.62 mmol) was treated as described in Part C of Example 101. The crude product was purified by column chromatography on silica gel (eluting sequentially with chloroform and 90:10 chloroform:methanol) to provide the product as an oil, which was recrystallized from ethyl acetate:hexane with a few drops of methanol to yield crystals. The crystals were isolated by filtration, washed with hexanes, and dried in a vacuum oven at 80° C. to provide 0.18 g of 4-[3-(4-amino-6,7-dimethyl-2-propyl-1H-imidazo[4,5-c]pyridin-1-yl)propane-1-sulfonyl]-N-butylbenzamide as a white powder, mp 147.0–149.0° C.

$^1$H NMR (300 MHz, CDCl$_3$) δ 7.83–7.75 (m, 4H), 6.71–6.63 (m, 1H), 4.83 (br s, 2H), 4.35 (dd, J=7.2, 7.2, 2H), 3.50 (quart, J=7.2, 2H), 3.05 (dd, J=7.5, 7.5, 2H), 2.74 (dd, J=7.7, 7.7, 2H), 2.35 (s, 3H), 2.28 (s, 3H), 2.13 (quint, J=7.4, 2H), 1.84 (sextet, J=7.6, 2H), 1.73–1.62 (m, 2H), 1.46 (sextet, J=7.3, 2H), 1.05 (t, J=7.3, 3H), 0.99 (t, J=7.3, 3H); MS (APCI) m/z 486 (M+H)$^+$; Anal. Calcd for C$_{25}$H$_{35}$N$_5$O$_3$S: C, 61.83; H, 7.264; N, 14.42; Found: C, 61.50; H, 7.2; N, 14.06.

EXAMPLE 120

4-[3-(4-Amino-6,7-dimethyl-2-propyl-1H-imidazo[4,5-c]pyridin-1-yl)propane-1-sulfonyl]-N-butyl-N-methylbenzamide

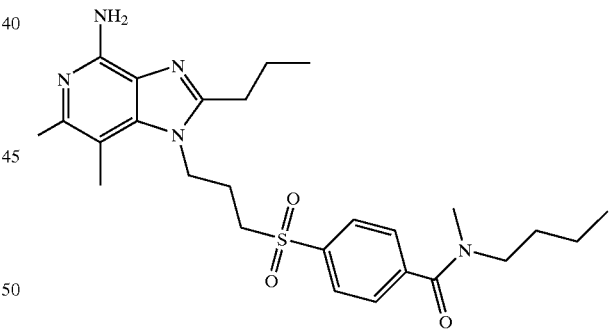

The general methods described in Example 101 were used with the following modifications. To one-third of the crude solution of 4-[3-(5,6-dimethyl-8-propyl-7H-imidazo[4,5-c]tetrazolo[1,5-a]pyridin-7-yl)propane-1-sulfonyl]benzoyl chloride in dichloromethane, described in Part B of Example 101, was added N-methyl butylamine (0.583 mL, 4.92 mmol) in lieu of morpholine, and the reaction was stirred overnight. Additional N-methyl butylamine (0.5 mL) was added, and the reaction was stirred for two hours. The crude product was recrystallized from ethyl acetate:hexane, and the crystals were dried for three hours in a vacuum oven at 90° C. N-Butyl-4-[3-(5,6-dimethyl-8-propyl-7H-imidazo[4,5-c]tetrazolo[1,5-a]pyridin-7-yl)propane-1-sulfonyl]N-methyl benzamide (770 mg, 1.46 mmol) was treated as described in Part C of Example 101. The crude product was recrystallized from ethyl acetate:hexane with a couple drops of methanol to provide crystals, which were isolated by filtration, washed with hexane, and dried for four hours under high vacuum at 50° C. to provide 0.56 g of 4-[3-(4-amino-6,7-dimethyl-2-propyl-1H-imidazo[4,5-c]pyridin-1-yl)propane-1-sulfonyl]-N-butyl-N-methylbenzamide as a white powder, mp 127.0–129.0° C. $^1$H NMR (300 MHz, CDCl$_3$) δ 7.95 (d, J=8.4, 2H), 7.58 (d, J=8.4, 2H), 4.92 (br s, 2H), 4.42 (dd, J=7.8, 7.8, 2H), 3.55 (dd, J=7.8, 7.8, 1H), 3.21–3.05 (m, 4.5 H), 2.90 (s, 1.5 H), 2.77 (dd, J=7.7, 7.7, 2H), 2.43 (s, 3H), 2.39 (s, 3H), 2.23 (quint, J=7.6, 2H), 1.93–1.36 (m, 5H), 1.15 (quart, J=7.5, 1H), 1.07 (t, J=7.4, 3H), 0.99 (t, J=7.0, 1.5H), 0.81 (t, J=7.4, 1.5H); MS (APCI) m/z 500 (M+H)$^+$; Anal. Calcd for C$_{26}$H$_{37}$N$_5$O$_3$S: C, 62.50; H, 7.464; N, 14.02; Found: C, 62.26; H, 7.78; N, 13.87.

EXAMPLE 121

1-[2-(2-Aminoethoxy)ethyl]-6-chloro-7-methyl-2-propyl-1H-imidazo[4,5-c]pyridin-4-amine

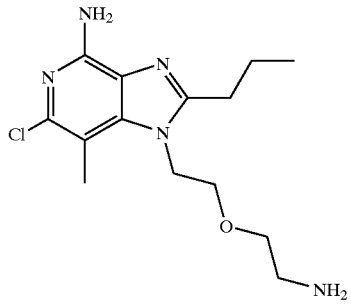

Part A

Under a nitrogen atmosphere, propanenitrile (120 mL, 1.7 mmol) was added dropwise to malonyl dichloride (100 g, 0.709 mmol), and the reaction was stirred for 24 hours at room temperature during which time a precipitate formed. Dioxane (300 mL) was added to the reaction mixture, and the precipitate was isolated by filtration and washed with dioxane (100 mL) to provide a tan solid. The solid was dissolved in a mixture of dioxane (75 mL) and methanol (30 mL) with heating. The methanol was removed under reduced pressure, and a white precipitate formed, which was isolated by filtration and washed with dioxane. The solid was dried overnight in a vacuum oven at 80° C. to provide 13.0 g of 6-chloro-4-hydroxy-5-methylpyridin-2(1H)-one hydrochloride hydrate as a white solid.

Part B

A solution of 6-chloro-4-hydroxy-5-methylpyridin-2(1H)-one hydrochloride hydrate (67.0 g, 0.313 mmol) in concentrated sulfuric acid (335 mL) was cooled to ~0° C.; nitric acid (19.6 mL of 16 M) was added dropwise over a period of ten minutes. The reaction was stirred for 20 minutes and then poured slowly into 2.5 L of ice water. A yellow precipitate formed, which was isolated by filtration and dried overnight in a vacuum oven at 60° C. to provide 39.7 g of 6-chloro-4-hydroxy-5-methyl-3-nitropyridin-2(1H)-one as a yellow solid.

Part C

A solution of 6-chloro-4-hydroxy-5-methyl-3-nitropyridin-2(1H)-one (10.9 g, 53.4 mmol) in dichloromethane (380 mL) was cooled to 0° C. Triethylamine (22.3 mL, 160 mmol) was added, and the solution was stirred for ten minutes. Trifluoromethanesulfonic anhydride (18.0 mL, 107 mmol) was then added dropwise over a period of five minutes, and the solution was stirred for 1.5 hours at 0° C. A solution of tert-butyl 2-(2-aminoethoxy) ethylcarbamate (12.0 g, 58.8 mmol), prepared as described in Parts A through D of Example 102, in a small amount of dichloromethane was then added over a period of five minutes, and the reaction was allowed to warm to room temperature slowly and stirred overnight. The solution was then washed with water (2×150 mL) and brine (150 mL), dried over magnesium sulfate, filtered, and concentrated under reduced pressure. The residue was purified by column chromatography on silica gel (eluting sequentially with 80:20 hexanes:ethyl acetate and 50:50 hexanes:ethyl acetate) to provide a yellow oil, which was dissolved in diethyl ether and concentrated under reduced pressure to provide 16.5 g of trifluoromethanesulfonic acid 4-[(2-{2-[(tert-butoxycarbonyl)amino]ethoxy}ethyl)amino]-6-chloro-5-methyl-3-nitropyridin-2-yl ester as a solid.

Part D

A solution of trifluoromethanesulfonic acid 4-[(2-{2-[(tert-butoxycarbonyl)amino]ethoxy}ethyl)amino]-6-chloro-5-methyl-3-nitropyridin-2-yl ester (14.3 g, 27.4 mmol), bis(4-methoxybenzyl)amine (7.00 g, 27.4 mmol), and triethylamine (3.82 mL, 27.4 mmol) in toluene (250 mL) was heated at 90° C. for two hours and then allowed to cool to room temperature overnight. Diethyl ether (300 mL) was added, and the solution was washed with water (200 mL) and brine (200 mL), dried over magnesium sulfate, filtered, and concentrated under reduced pressure. The residue was purified twice by column chromatography on silica gel (eluting sequentially with 80:20 hexanes:ethyl acetate and 70:30 hexanes:ethyl acetate) to provide 8.73 g of {2-[2-(2-[bis{4-methoxybenzyl}amino]-6-chloro-5-methyl-3-nitropyridin-4-ylamino)ethoxy]ethyl}carbamic acid tert-butyl ester.

Part E

Under a nitrogen atmosphere, sodium borohydride (0.76 g, 20.0 mmol) was added in two portions to a solution of nickel (II) chloride hydrate (1.57 g, 6.62 mmol) in methanol (160 mL), and the mixture was stirred at room temperature for 15 minutes. A solution of {2-[2-(2-[bis{4-methoxybenzyl}amino]-6-chloro-5-methyl-3-nitropyridin-4-ylamino)ethoxy]ethyl}carbamic acid tert-butyl ester (8.37 g, 13.3 mmol) in methanol (10 mL) and dichloromethane (10 mL) was then added, and the addition funnel was rinsed with a mixture of methanol (10 mL) and dichloromethane (10 mL). The reaction was stirred for two hours, during which time additional sodium borohydride was added three times (0.5 g, 0.5, g and 1.0 g). Water (200 mL) was then added, and the methanol was removed under reduced pressure. The remaining solution was extracted with diethyl ether (700 mL, 300 mL), and the combined extracts were washed with water (200 mL) and brine (200 mL), dried over magnesium sulfate, filtered, and concentrated under reduced pressure to product the crude product contaminated with water. Toluene (300 mL) was added and then removed by distillation to provide [2-(2-{3-amino-2-[bis-(4-methoxybenzyl)amino]-6-chloro-5-methylpyridin-4-ylamino}ethoxy)ethyl]carbamic acid tert-butyl ester, which was used in Part F without further purification.

Part F

The material from Part E was treated using the general method described in Part E of Example 85 with the following modification. Pyridinium p-toluenesulfonate (0.1 equivalent) was used in lieu of pyridine hydrochloride. The crude product was purified by column chromatography on silica gel (eluting sequentially with 80:20 hexanes:ethyl acetate and 70:30 hexanes:ethyl acetate) to provide 5 g of

[2-(2-{4-[bis-(4-methoxybenzyl)amino]-6-chloro-7-methyl-2-propyl-1H-imidazo[4,5-c]pyridin-1-yl}ethoxy)ethyl] carbamic acid tert-butyl ester, which was dissolved in dichloromethane and concentrated under reduced pressure several times.

Part G

Trifluoroacetic acid (40 mL) was added to [2-(2-{4-[bis-(4-methoxybenzyl)amino]-6-chloro-7-methyl-2-propyl-1H-imidazo[4,5-c]pyridin-1-yl}ethoxy)ethyl]carbamic acid tert-butyl ester (1 g, 1.5 mmol). The reaction was swirled until it became homogeneous and was allowed to stand at room temperature overnight. The reaction was concentrated under reduced pressure, and dichloromethane was added and removed under reduced pressure (5×40 mL) to provide a white solid. The solid was triturated in chloroform, isolated by filtration, and dried under reduced pressure with heating. The solid was dissolved in concentrated hydrochloric acid (5 mL) and stirred for three hours. Aqueous sodium hydroxide was then added. A white solid formed, which was isolated by filtration, washed with water and diethyl ether, and dried for five hours under high vacuum at 70° C. to provide 0.144 g of 1-[2-(2-aminoethoxy)ethyl]-6-chloro-7-methyl-2-propyl-1H-imidazo[4,5-c]pyridin-4-amine as a white solid, mp 158.0–161.0° C.

$^1$H NMR (300 MHz, DMSO-$d_6$) δ 6.15 (br s, 2H), 4.43 (t, J=5.4, 2H), 3.67 (t, J=5.3, 2H), 3.27 (t, J=5.7, 2H), 2.84–2.79 (m, 2H), 2.54 (t, J=5.7, 2H), 2.47 (s, 3H) 1.86 –1.74 (m, 2H), 1.19 (br s, 2H), 1.00 (t, J=7.3, 3H); MS (APCI) m/z 312 (M+H)$^+$;

HRMS (ESI) calcd for $C_{14}H_{22}N_5OCl+H$ 312.1591, found 312.1588; Anal. calcd for $C_{14}H_{22}N_5OCl.0.2H_2O$: C, 53.31; H, 7.16; N, 22.20. Found: C, 53.34; H, 7.23; N, 22.02.

EXAMPLE 122

2-Ethoxymethyl-6,7-dimethyl-1-{2-[(3-phenylprop-2-ynyl)oxy]ethyl}-1H-imidazo[4,5c]pyridin-4-amine

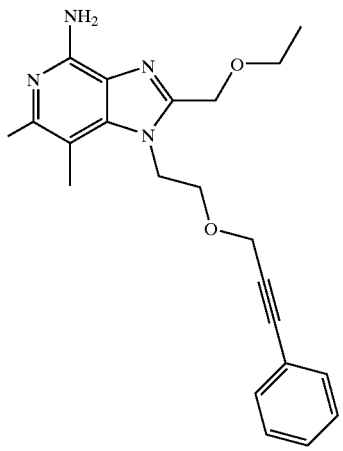

Part A

The general methods described in Parts A and B of Example 111 were used to prepare acetic acid 2-[(2-chloro-5,6-dimethyl-3-nitropyridin-4-yl)amino]ethyl ester. Using the general method described in Part A of Example 92, acetic acid 2-[(2-chloro-5,6-dimethyl-3-nitropyridin-4-yl)amino]ethyl ester (64.0 g, 0.222 mmol) was converted to acetic acid 2-[(5,6-dimethyl-8-nitrotetrazolo[1,5-a]pyridin-7-yl)amino]ethyl ester. The crude product was triturated with diethyl ether and isolated by filtration to provide 60.0 g of the desired product as a yellow solid.

Part B

A Parr vessel was charged with acetic acid 2-[(5,6-dimethyl-8-nitrotetrazolo[1,5-a]pyridin-7-yl)amino]ethyl ester (50.0 g, 170 mmol), 5% platinum on carbon (5.00 g), toluene (600 mL), and 2-propanol (50 mL) and purged with nitrogen. The vessel was then placed under hydrogen pressure (20 psi, ) for 20 hours at room temperature. The reaction mixture was filtered through a layer of CELITE filter aid, and the filter cake was washed with 90:10 dichloromethane:methanol. The filtrate was concentrated under reduced pressure to provide a dark gray solid, which was triturated with diethyl ether, isolated by filtration, and dried to provide 41.0 g of acetic acid 2-[(8-amino-5,6-dimethyltetrazolo[1,5-a]pyridin-7-yl)amino]ethyl ester as a light gray solid.

Part C

The general methods described in Parts G and H of Example 80 were used to convert acetic acid 2-[(8-amino-5,6-dimethyltetrazolo[1,5-a]pyridin-7-yl)amino]ethyl ester (48.8 g, 185 mmol) to 56.5 g of acetic acid 2-(8-ethoxymethyl-5,6-dimethyl-7H-imidazo[4,5-c]tetrazolo[1,5-a]pyridin-7-yl)ethyl ester with the following modifications. In Part H, one portion of pyridine hydrochloride (6.3 g, 54 mmol) was added, and the reaction was heated at reflux for 20 hours. After the work-up, the desired product was obtained as a tan solid, which was used without purification.

Part D

The general method described in Part F of Example 111 was used to convert acetic acid 2-(8-ethoxymethyl-5,6-dimethyl-7H-imidazo[4,5-c]tetrazolo[1,5-a]pyridin-7-yl) ethyl ester (56.5 g, 170 mmol) to 2-(8-ethoxymethyl-5,6-dimethyl-7H-imidazo[4,5-c]tetrazolo[1,5-a]pyridin-7-yl) ethanol. The crude product was purified by column chromatography on silica gel,(1.2 kg, eluting with 90:10 dichloromethane:methanol) to provide 48.25 g of the desired product.

Part E

The general method described in Part A of Example 81 was followed, using 2-(8-ethoxymethyl-5,6-dimethyl-7H-imidazo[4,5-c]tetrazolo[1,5-a]pyridin-7-yl)ethanol (4.51 g, 15.5 mmol) in lieu of tert-butyl 2-hydroxyethylcarbamate and 3-bromo-1-phenylpropyne, prepared as described in Part A of Example 7, in lieu of propargyl bromide. The crude product was triturated with diethyl ether, isolated by filtration, and dried under reduced pressure to provide 5.93 g of 8-ethoxymethyl-5,6-dimethyl-7-{2-[(3-phenylprop-2-ynyl)oxy]ethyl}-7H-imidazo[4,5-c]tetrazolo[1,5-a]pyridine as a yellow solid.

Part F

The general method described in Part D of Example 109 was followed using 8-ethoxymethyl-5,6-dimethyl-7-{2-[(3-phenylprop-2-ynyl)oxy]ethyl}-7H-imidazo[4,5-c]tetrazolo[1,5-a]pyridine (6.47 g, 16.0 mmol) as the starting material. The reaction with triphenyl phosphine (4.61 g, 17.6 mmol) required 41 hours, and the hydrolysis of the intermediate required 18 hours. The crude product (11.6 g) was dissolved in dichloromethane and treated with a 1 M solution of hydrochloric acid in diethyl ether (80 mL). The volatiles were removed under reduced pressure, and the resulting solid was recrystallized from acetonitrile. The crystals were dissolved in water (20 mL), and the solution was adjusted to pH 14 with the addition of 50% aqueous sodium hydroxide to provide a solid that was isolated by filtration. The solid was stirred with 1 M aqueous potassium hydroxide for one hour, isolated by filtration, dried for three days under reduced pressure at 70° C. to provide 0.828 g of 2-ethoxymethyl-6,7-dimethyl-1-{2-[(3-phenylprop-2-ynyl)

oxy]ethyl}-1H-imidazo[4,5-c]pyridin-4-amine as a white powder, mp 129–130° C.

$^1$H NMR (300 MHz, DMSO) δ 7.34–7.39 (m, 5H), 5.80 (s, 2H), 4.69 (s, 2H), 4.58 (t, J=5.6 Hz, 2H), 4.37(s, 2H), 3.89 (t, J=5.6 Hz, 2H), 3.51 (q, J=6.9 Hz, 2H), 2.39 (s, 3H), 2.32 (s, 3H), 1.13 (t, J=7.2, 3H); MS (APCI) m/z 379 (M+H)$^+$; Anal. Calcd for $C_{22}H_{26}N_4O_2 \cdot 0.1H_2O$: C, 69.49; H, 6.94; N, 14.73; Found: C, 69.25; H, 7.00; N, 14.65.

EXAMPLE 123

2-Ethoxymethyl-6,7-dimethyl-1-[2-(3-phenylpropoxy)ethyl]-1H-imidazo[4,5-c]pyridin-4-amine hydrochloride

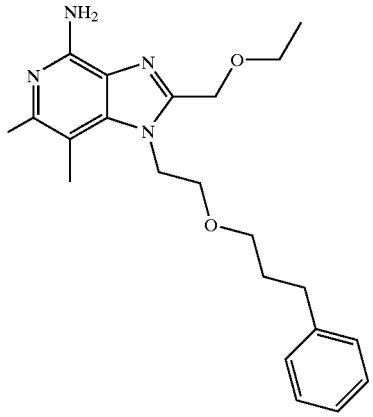

The general method described in Example 112 was used to hydrogenate 2-ethoxymethyl-6,7-dimethyl-1-{2-[(3-phenylprop-2-ynyl)oxy]ethyl}-1H-imidazo[4,5-c]pyridin-4-amine (1.17 g, 3.09 mmol), prepared as described in Example 122. The reaction was complete after 18 hours. The crude product, isolated as an oil, was dissolved with diethyl ether (20 mL) and treated with a 1 M solution of hydrochloric acid in diethyl ether. The resulting salt was isolated by filtration, dried under reduced pressure, and recrystallized from ethyl acetate. The crystals, obtained in two crops, were dried for three hours under high vacuum at 60° C. to provide 0.777 g of 2-ethoxymethyl-6,7-dimethyl-1-[2-(3-phenylpropoxy)ethyl]-1H-imidazo[4,5-c]pyridin-4-amine hydrochloride as a white powder, mp 128–130° C.

$^1$H NMR (300 MHz, DMSO) δ 13.85 (s, 1 H), 8.13 (s, 2 H), 7.10–7.24 (m, 3 H), 6.93–6.97 (m, 2 H), 4.79 (s, 2 H), 4.67 (t, J=5.0 Hz, 2 H), 3.73 (t, J=5.3 Hz, 2 H), 3.55 (q, J=7.1 Hz, 2 H), 3.27 (t, J=5.9Hz, 2 H), 2.45 (s, 6H), 2.38 (t, J=7.8Hz, 2 H), 1.65 (p, J=7.5, 6.2Hz, 2 H), 1.15 (t, J=6.9, 3 H); MS (APCI) m/z 383 (M+H)$^+$; Anal. Calcd for $C_{22}H_{30}N_4O_2 \cdot 1HCl$: C, 63.07; H, 7.46; N, 13.37; Found: C, 63.01; H, 7.48; N, 13.29.

EXAMPLE 124

1-{2-[2-(4-Amino-2-ethyl-6,7-dimethyl-1H-imidazo[4,5-c]pyridin-1-yl)ethoxy]ethyl}pyrrolindin-2-one

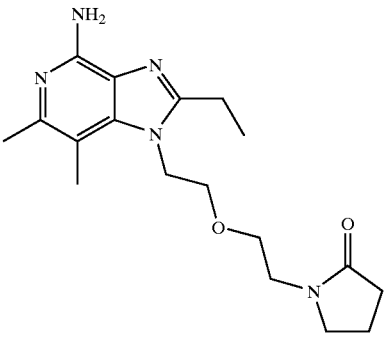

Part A

2-[2-(8-Ethyl-5,6-dimethyl-7H-imidazo[4,5-c]tetrazolo[1,5-a]pyridin-7-yl)ethoxy]ethylamine (2.0 g, 6.6 mmol), obtained as described in Parts A through I of Example 102 was treated as described in Part J of Example 102 with 4-chlorobutyryl chloride (0.78 mL, 6.9 mmol) in lieu of methanesulfonyl chloride. The crude product was purified by column chromatography on silica gel (125 mL, eluting with 90:10 dichloromethane:methanol) to provide 2.30 g of 4-chloro-N-{2-[2-(8-ethyl-5,6-dimethyl-7H-imidazo[4,5-c]tetrazolo[1,5-a]pyridin-7-yl)ethoxy]ethyl}butanamide as a white solid, mp 149–151° C.

Part B

Under a nitrogen atmosphere, a mixture of sodium hydride (0.24 g, 6.1 mmol), 60% in mineral oil, and anhydrous DMF (10 mL) was cooled to ~0° C. A solution of 4-chloro-N-{2-[2-(8-ethyl-5,6-dimethyl-7H-imidazo[4,5-c]tetrazolo[1,5-a]pyridin-7-yl)ethoxy]ethyl}butanamide (2.25 g, 5.52 mmol) in DMF (35 mL) was slowly added to the mixture, and the reaction was stirred for one hour. The volatiles were then removed under reduced pressure, and the residue was partitioned between water (100 mL) and dichloromethane (100 mL). The aqueous layer was extracted with dichloromethane (2×100 mL), and the combined organic solutions were dried, filtered, and concentrated under reduced pressure to provide 1.94 g of a light orange solid. The solid was combined with crude product from a previous run (1.45 g) and purified by column chromatography on silica gel (150 mL, eluting with 95:5 dichloromethane:methanol) to provide 2.96 g of 1-{2-[2-(8-ethyl-5,6-dimethyl-7H-imidazo[4,5-c]tetrazolo[1,5-a]pyridin-7-yl)ethoxy]ethyl}pyrrolidin-2-one as a white solid, mp 141–143° C.

Part C

1-{2-[2-(8-Ethyl-5,6-dimethyl-7H-imidazo[4,5-c]tetrazolo[1,5-a]pyridin-7-yl)ethoxy]ethyl}pyrrolidin-2-one (2.86 g, 7.70 mmol) was treated using a modification of the general method described in Part D of Example 109. 1,2-Dichlorobenzene was used as the solvent, and the reaction was heated at 130° C. for two days. The crude product was purified by column chromatography on silica gel (150 mL, eluting with 80:20 dichloromethane:methanol) to provide 2.03 g of a light brown oil, which solidified overnight. The solid was recrystallized from acetonitrile (4.9 mL/g) twice and dried for two days in a vacuum oven at 50° C. to provide 0.97 g of 1-{2-[2-(4-amino-2-ethyl-6,7-dimethyl-1H-imidazo[4,5-c]pyridin-1-yl)ethoxy]ethyl}pyrrolindin-2-one as a white solid, mp 128–130° C. $^1$H NMR (300 MHz, CDCl3) δ 4.84 (s, 2H), 4.42 (t, J=5.5 Hz, 2H), 3.71 (t, J=5.5, 2H), 3.50–3.44 (m, 2H), 3.40–3.34 (m, 2H), 3.14–3.08 (m, 2H), 2.87 (q, J=7.5, 2H), 2.44 (s, 3H), 2.42 (s, 3H), 2.32–2.22 (m, 2H), 1.91–1.79 (m, 2H), 1.40 (t, J=7.5, 3H); MS (APCI) m/z 346 (M+H)$^+$; Anal. Calcd for $C_{18}H_{27}N_5O_2$: C, 62.59; H, 7.88; N, 20.27. Found: C, 62.58; H, 8.16; N, 20.51.

EXAMPLE 125

N-{2-[2-(4-Amino-6-chloro-7-methyl-2-propyl-1H-imidazo[4,5-c]pyridin-4-yl)ethoxy]ethyl}benzamide

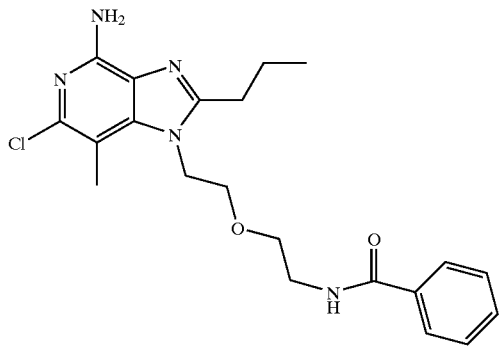

Under a nitrogen atmosphere, triethylamine (3.0 mL, 12 mmol) was added to a mixture of 1-[2-(2-aminoethoxy)ethyl]-6-chloro-7-methyl-2-propyl-1H-imidazo[4,5-c]pyridin-4-amine bistrifluoroacetate (0.95 g, 1.76 mmol), the salt made from Part G of Example 121, in tetrahydrofuran (20 mL). Benzoyl chloride (0.3 mL) was added dropwise to the resulting solution, and the reaction was stirred at room temperature. A solution of 2% aqueous sodium carbonate (40 mL) was added, and the resulting mixture was stirred for 20 minutes and then extracted with diethyl ether (120 mL). A white solid precipitated from the diethyl ether and was isolated by filtration and washed with water (5 mL) and diethyl ether (30 mL). The solid was recrystallized from 2-propanol, isolated by filtration, and dried for 4.5 hours under high vacuum at 40° C. to provide 265 mg of N-{2-[2-(4-amino-6-chloro-7-methyl-2-propyl-1H-imidazo[4,5-c]pyridin-4-yl)ethoxy]ethyl}benzamide as a white solid, mp 188.0–189.0° C.

$^1$H NMR (300 MHz, CDCl$_3$) δ 7.63–7.59 (m, 2H), 7.53–7.41 (m, 3H), 6.15 (br s, 1H), 5.01 (br s, 2H), 4.45 (t, J=5.5, 2H), 3.76 (t, J=5.5, 2H), 3.59–3.53 (m, 4H), 2.83–2.78 (m, 2H), 2.55 (s, 3H), 1.91–1.79 (m, 2H), 1.03 (t, J=7.3, 3H); MS (APCI) m/z 416 (M+H)$^+$; HRMS (ESI) calcd for $C_{21}H_{26}N_5O_2Cl+H$ 416.1853, found 416.1856; Anal. calcd for $C_{21}H_{26}N_5O_2Cl$: C, 60.64; H, 6.34; N, 16.84. Found: C, 60.61; H, 6.34; N, 16.74.

Compounds of the invention have been found to induce cytokine biosynthesis when tested using the method described below.

Cytokine Induction in Human Cells

An in vitro human blood cell system is used to assess cytokine induction. Activity is based on the measurement of interferon-α and tumor necrosis factor-α (IFN-α and TNF-α, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using Histopaque®-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at 4×10$^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30–0.014 μM.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (30–0.014 μM). The final concentration of PBMC suspension is 2×10$^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (~200×g) at 4° C. The cell-free culture supernatant is removed with a sterile polypropylene pipet and transferred to sterile polypropylene tubes. Samples are maintained at −30° C. to −70° C. until analysis. The samples are analyzed for IFN-α by ELISA and for TNF-α by ELISA or IGEN Assay.

IFN-α and TFN-α Analysis by ELISA

IFN-α concentration is determined by ELISA using a Human Multi-Species kit from PBL Biomedical Laboratories, New Brunswick, N.J. Results are expressed in pg/mL.

TNF-α concentration is determined using ELISA kits available from Biosource International, Camarillo, Calif. Alternately, the TNF-α concentration can be determined by Origen® M-Series Immunoassay and read on an IGEN M-8 analyzer from IGEN International, Gaithersburg, Md. The immunoassay uses a human TNF-α capture and detection antibody pair from Biosource International, Camarillo, Calif. Results are expressed in pg/mL.

The complete disclosures of the patents, patent documents, and publications cited herein are incorporated by reference in their entirety as if each were individually incorporated. The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. A compound of the Formula (Ia):

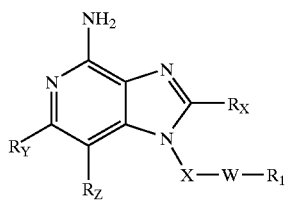
(Ia)

wherein:

X is —CH(R$_5$)—, —CH(R$_5$)-alkylene-, —CH(R$_5$)-alkenylene-, or —CH(R$_5$)-alkylene-Y-alkylene-;

Y is —O—, or —S(O)$_{0-2}$—;

—W—R$_1$ is —O—R$_{1-1-5}$;

R$_{1-1-5}$ is selected from
- —R$_6$—C(R$_7$)—Z—R$_8$-alkyl;
- —R$_6$—C(R$_7$)—Z—R$_8$-alkenyl;
- —R$_6$—C(R$_7$)—Z—R$_8$-aryl;
- —R$_6$—C(R$_7$)—Z—R$_8$-heteroaryl;
- —R$_6$—C(R$_7$)—Z—R$_8$-heterocyclyl;
- —R$_6$—C(R$_7$)—Z—H;
- —R$_6$—N(R$_9$)—C(R$_7$)—R$_8$-alkyl;
- —R$_6$—N(R$_9$)—C(R$_7$)—R$_8$-alkenyl;
- —R$_6$—N(R$_9$)—C(R$_7$)—R$_8$-aryl;
- —R$_6$—N(R$_9$)—C(R$_7$)—R$_8$-heteroaryl;
- —R$_6$—N(R$_9$)—C(R$_7$)—$_8$-heterocyclyl; and
- —R$_6$—N(R$_9$)—C(R$_7$)—R$_{10}$;

Z is —N(R$_5$)—, —O—, or —S—;

wherein heteroaryl is an aromatic ring or ring system that contains at least one ring heteroatom selected from the group consisting of O, S, and N; and heterocyclyl is a non-aromatic ring or ring system that contains at least one ring heteroatom selected from the group consisting of O, S, and N;

each R$_5$ is independently hydrogen, C$_{1-10}$ alkyl, or C$_{2-10}$ alkenyl;

R$_6$ is alkylene, alkenylene, or alkynylene, which may be interrupted by one or more —O— groups;

R$_7$ is =O or =S;

R$_8$ is a bond, alkylene, alkenylene, or alkynylene, which may be interrupted by one or more —O— groups;

R$_9$ is hydrogen, C$_{1-10}$ alkyl, or arylalkyl; or R$_9$ can join together with any carbon atom of R$_6$ to form a ring of the formula

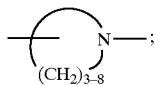

R$_{10}$ is hydrogen or C$_{1-10}$ alkyl; or R$_9$ and R$_{10}$ can join together to form a ring selected from

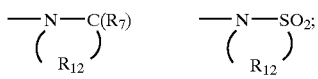

R$_{12}$ is C$_{2-7}$ alkylene which is straight chain or branched, wherein the branching does not prevent formation of the ring; and R$_X$, R$_Y$ and R$_Z$ are independently selected from hydrogen and non-interfering substitutents;

or a pharmaceutically acceptable salt thereof, wherein the compound or salt of Formula Ia induces the biosynthesis of one or more cytokines.

2. A compound of the Formula (I-1):

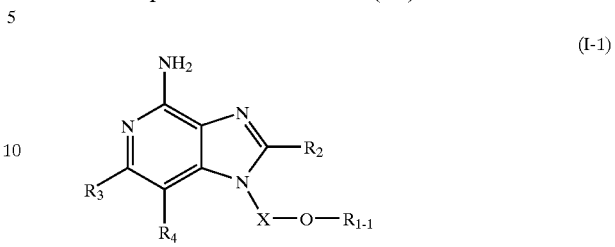
(I-1)

wherein:

X is —CH(R$_5$)—, —CH(R$_5$)-alkylene-, —CH(R$_5$)-alkenylene-, or —CH(R$_5$)-alkylene-Y-alkylene-;

R$_{1-1}$ is selected from the group consisting of:
- —R$_6$—C(R$_7$)—Z—R$_8$-alkyl;
- —R$_6$—C(R$_7$)—Z—R$_8$-alkenyl;
- —R$_6$—C(R$_7$)—Z—R$_8$-aryl;
- —R$_6$—C(R$_7$)—Z—R$_8$-heteroaryl;
- —R$_6$—C(R$_7$)—Z—H;
- —R$_6$—C(R$_7$)—Z—R$_8$-heterocyclyl;
- —R$_6$—N(R$_9$)—C(R$_7$)—R$_8$-alkyl;
- —R$_6$—N(R$_9$)—C(R$_7$)—R$_8$-alkenyl;
- —R$_6$—N(R$_9$)—C(R$_7$)—R$_8$-aryl;
- —R$_6$—N(R$_9$)—C(R$_7$)—R$_8$-heteroaryl;
- —R$_6$—N(R$_9$)—C(R$_7$)—R$_8$-heterocyclyl; and
- —R$_6$—N(R$_9$)—C(R$_7$)—R$_{10}$;

Z is —N(R$_5$)—, —O—, or —S—;

R$_2$ is selected from the group consisting of:
- -hydrogen;
- -alkyl;
- -alkenyl;
- -aryl;
- -heteroaryl;
- -heterocyclyl;
- -alkylene-Y-alkyl;
- -alkylene-Y-alkenyl;
- -alkylene-Y-aryl; and
- -alkyl or alkenyl substituted by one or more substituents selected from the group consisting of:
  - —OH;
  - -halogen;
  - —N(R$_5$)$_2$;
  - —C(O)—C$_{1-10}$ alkyl;
  - —C(O)—O—C$_{1-10}$ alkyl;
  - —N$_3$;
  - -aryl;
  - -heteroaryl;
  - -heterocyclyl;
  - —C(O)-aryl; and
  - —C(O)-heteroaryl;

wherein heteroaryl is an aromatic ring or ring system that contains at least one ring heteroatom selected from the group consisting of O, S, and N; and heterocyclyl is a non-aromatic ring or ring system that contains at least one ring heteroatom selected from the group consisting of O, S, and N;

Y is —O— or —S(O)$_{0-2}$—;

R$_3$ and R$_4$ are independently selected from the group consisting of hydrogen, C$_{1-10}$ alkyl, C$_{2-10}$ alkenyl, C$_{2-10}$ alkynyl, C$_{1-10}$ alkoxy, C$_{1-10}$ alkylthio, amino, alkylamino, dialkylamino, halogen, and nitro;

each $R_5$ is independently hydrogen, $C_{1-10}$ alkyl, or $C_{2-10}$ alkenyl;

$R_6$ is alkylene, alkenylene, or alkynylene, which may be interrupted by one or more —O— groups;

$R_7$ is =O or =S;

$R_8$ is a bond, alkylene, alkenylene, or alkynylene which may be interrupted by one or more —O— groups;

$R_9$ is hydrogen, $C_{1-10}$ alkyl, or arylalkyl; or $R_9$ can join together with any carbon atom of $R_6$ to form a ring of the formula

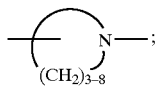

$R_{10}$ is hydrogen or $C_{1-10}$ alkyl; or $R_9$ and $R_{10}$ can join together to form a ring selected from

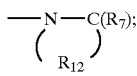

$R_{12}$ is $C_{2-7}$ alkylene which is straight chain or branched, wherein the branching does not prevent formation of the ring;

or a pharmaceutically acceptable salt thereof.

3. A compound or salt of claim 2 wherein $R_3$ and $R_4$ are independently hydrogen, alkyl, halogen, or nitro.

4. A compound or salt of claim 2 wherein $R_3$ and $R_4$ are both methyl.

5. A compound or salt of claim 2 wherein X is —CH($R_5$)—$C_{1-5}$ alkylene-.

6. A compound or salt of claim 2 wherein $R_7$ is =O and $R_8$ is a bond.

7. A compound or salt of claim 2 wherein $R_2$ is hydrogen.

8. A compound or salt of claim 2 wherein $R_2$ is alkyl.

9. A compound or salt of claim 2 wherein $R_2$ is -alkylene-O-alkyl.

10. A compound or salt of claim 2 wherein $R_9$ is $C_{1-10}$ alkyl.

11. A compound or salt of claim 2 wherein $R_{1-1}$ is —$R_6$—N($R_9$)—C($R_7$)—$R_8$-alkyl.

12. A compound or salt of claim 2 wherein $R_{1-1}$ is —$R_6$—N($R_9$)—C($R_7$)—$R_8$-aryl or —$R_6$—N($R_9$)—C($R_7$)—$R_8$-heteroaryl.

13. A compound or salt of claim 2 wherein $R_{1-1}$ is —$R_6$—N($R_9$)—C($R_7$)—$R_{10}$, and $R_9$ and $R_{10}$ join to form the ring.

14. A pharmaceutical composition comprising a pharmaceutically effective amount of a compound of claim 1 in combination with a pharmaceutically acceptable carrier.

15. A pharmaceutical composition comprising a pharmaceutically effective amount of a compound of claim 2 in combination with a pharmaceutically acceptable carrier.

16. A method of inducing cytokine biosynthesis in an animal comprising administering an effective amount of a compound of claim 1 to the animal.

17. A method of claim 16 wherein the cytokine is interferon-α.

18. A method of inducing cytokine biosynthesis in an animal comprising administering an effective amount of a compound of claim 2 to the animal.

19. A method of treating a neoplastic disease in an animal comprising administering an effective amount of a compound of claim 1 to the animal.

20. A method of treating a neoplastic disease in an animal comprising administering an effective amount of a compound of claim 2 to the animal.

21. A method of treating a viral disease in an animal comprising administering an effective amount of a compound of claim 1 to the animal.

22. A method of treating a viral disease in an animal comprising administering an effective amount of a compound of claim 2 to the animal.

* * * * *

UNITED STATES PATENT AND TRADEMARK OFFICE
CERTIFICATE OF CORRECTION

PATENT NO.    : 6,797,718 B2
DATED         : September 28, 2004
INVENTOR(S)   : Dellaria, Jr., Joseph F It is certified that error appears in the above-identified patent and that said Letters Patent is hereby corrected as shown below:

Column 1,
Line 3, delete "Chem.," and insert -- Chem., --, therefor.

Column 2,
Line 49, delete "repesented" and insert -- represented --, therefor.
Line 64, before "CH($R_5$)" insert -- — --.
Line 66, delete "R," and insert -- $R_1$ --, therefor.

Column 4,
Line 45, delete "substitutents" and insert -- substituents --, therefor.
Line 66, before "CH($R_5$)" insert -- — --.

Column 7,
Line 28, before "CH($R_5$)" insert -- — --.

Column 8,
Line 51, before "CH($R_5$)" insert -- — --.

Column 10,
Line 14, before "CH($R_5$)" insert -- — --.

Column 11,
Line 45, before "CH($R_5$)" insert -- — --.

Column 12,
Line 35, before "CH($R_5$)" insert -- — --.

Column 13,
Line 24, before "CH($R_5$)" insert -- — --.

Column 14,
Line 29, before "CH($R_5$)" and after "Y-alkylene" insert -- — --.

Column 15,
Line 25, before "CH($R_5$)" insert -- — --.
Line 46, delete "alkyene" and insert -- alkylene --, therefor.

Column 16,
Line 21, before "CH($R_5$)" insert -- — --.

Column 17,
Line 21, before "CH($R_5$)" insert -- — --.

UNITED STATES PATENT AND TRADEMARK OFFICE
CERTIFICATE OF CORRECTION

PATENT NO. : 6,797,718 B2
DATED : September 28, 2004
INVENTOR(S) : Dellaria, Jr., Joseph F It is certified that error appears in the above-identified patent and that said Letters Patent is hereby corrected as shown below:

Column 18,
Line 16, before "CH($R_5$)" insert -- — --.

Column 20,
Line 28, before "CH($R_5$)" insert -- — --.

Column 21,
Lines 26 and 64, before "CH($R_5$)" insert -- — --.

Column 22,
Line 26, before "CH($R_5$)" insert -- — --.

Column 32,
Line 59, delete "1-4" and insert -- I-4 --, therefor.

Column 37,
Line 37-53, delete " 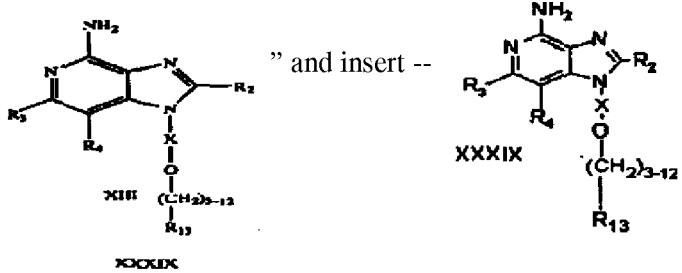 " and insert -- -- , therefor.

Column 39,
Line 38, after "X" insert -- are as --.

Column 40,
Line 37, delete "la" and insert -- Ila --, therefor.
Line 46, after "an" delete ",".

Column 44,
Line 20, delete "1-6" and insert -- I-6 --, therefor.

Column 46,
Line 30, delete "Llla" and insert -- Lllla --, therefor.

Column 51,
Line 60, delete "10" before "In".

UNITED STATES PATENT AND TRADEMARK OFFICE
CERTIFICATE OF CORRECTION

PATENT NO. : 6,797,718 B2
DATED : September 28, 2004
INVENTOR(S) : Dellaria, Jr., Joseph F It is certified that error appears in the above-identified patent and that said Letters Patent is hereby corrected as shown below:

Column 53,
Line 25, delete "TV" and insert -- IV --, therefor.

Column 55,
Line 13, delete "a" before "suitable".

Column 63,
Line 36, delete "N-pyridin-3" and insert -- N'-pyridin-3 --, therefor.

Column 64,
Line 10, delete "ethoxy}ethyl-N" and insert -- ethoxy}ethyl)-N' --, therefor.
Line 30, delete "ethoxy}ethyl" and insert -- ethoxy}ethyl) --, therefor.

Column 65,
Line 36, delete "ethoxy}ethoxy)" and insert -- ethoxy}ethyl) --, therefore.
Line 39, delete "yl]ethoxy}ethyxy" and insert -- yl]ethyxy}ethyl) --, therefore.

Column 75,
Line 42, delete "propy-1H-imidazo" and insert -- propyl-1H-imidazo --, therefor.
Line 64, delete "thiolpropyl}-7-methyl" and insert -- thio]propyl}-7-methyl --, therefor.

Column 82,
Line 41, after "amine" insert -- ; --.

Column 84,
Line 62, delete "buyl" and insert -- butyl --, therefor.

Column 88,
Lines 43 and 46, delete "[c]" and insert -- [4, 5-c] --, therefor.

Column 91,
Line 43, after "pyridin" insert -- – --, therefor.

Column 92,
Line 11, delete "bpenyl" and insert -- pentyl --, therefor.

Column 94,
Line 27, delete "ethoxy]ethyl}" and insert -- ethoxy]ethyl}-4 --, therefor.
Line 36, delete "5" before "N".
Line 48, delete "sulfonyl}-butyl" and insert -- sulfonyl}-N-butyl --, therefor.

UNITED STATES PATENT AND TRADEMARK OFFICE
CERTIFICATE OF CORRECTION

PATENT NO. : 6,797,718 B2
DATED : September 28, 2004
INVENTOR(S) : Dellaria, Jr., Joseph F It is certified that error appears in the above-identified patent and that said Letters Patent is hereby corrected as shown below:

Column 101,
Line 52, delete "C. for 48hours" and insert -- C for 48 hours --, therefor.

Column 102,
Line 1, delete "EXAMPLES" and insert -- EXAMPLE --, therefor.
Line 48, delete "recrytallized" and insert -- recrystallized --, therefor.

Column 103,
Line 31, delete "wased" and insert -- washed --, therefor.

Column 104,
Line 31, delete "mm01" and insert -- mmol --, therefor.

Column 106,
Line 33, delete "phenoxypryridine" and insert -- phenoxypyridine --, therefor.

Column 109,
Line 32, delete "11 g" and insert -- 11.1 g --, therefor.

Column 110,
Line 65, delete "67" and insert -- $\delta$ --, therefor.

Column 115,
Line 12, delete "IN" and insert -- 1N --, therefor.

Column 118,
Line 4, after "mL)", delete ")".

Column 120,
Line 42, after "mmol)", delete ")".
Line 54, delete "2-t2" and insert -- 2-{2 --, therefor.

Column 122,
Line 2, delete "of" before "tert".

Column 123,
Line 9, after "(M+H)" insert -- • -- and move "MS(CI) m/e 264 (M+H)" to line 7.
Line 67, after "(M+H" insert -- • -- .

Column 126,
Line 38, insert -- ~ -- before "18".

UNITED STATES PATENT AND TRADEMARK OFFICE
CERTIFICATE OF CORRECTION

PATENT NO. : 6,797,718 B2
DATED : September 28, 2004
INVENTOR(S) : Dellaria, Jr., Joseph F It is certified that error appears in the above-identified patent and that said Letters Patent is hereby corrected as shown below:

Column 141,
Line 45, after "ethyl", delete ")".

Column 143,
Line 16, delete "c," and insert -- C, --, therefor.

Column 147,
Line 53, delete "scaled" and insert -- sealed --, therefor.

Column 149,
Line 28, after "(br s, 2H)" insert -- , --.
Line 67, delete "N 16.76" and insert -- N, 16.76 --, therefor.

Column 150,
Line 29, delete "N 13.55" and insert -- N, 13.55 --, therefor.

Column 153,
Line 62, delete "of" before "potassium".

Column 154,
Line 15, after "mmol)", delete ")".
Line 34, delete "67" and insert -- $\delta$ --, therefor.
Line 35, after "2.45" insert -- (s, 6H), 2.35 --.
Line 40, delete "H 7.44" and insert -- H, 7.44 --, therefor.

Column 158,
Line 49, insert -- $\delta$ -- before "8.01".

Column 161,
Line 45, delete "N 12.20" and insert -- N, 12.20 --, therefor.

Column 167,
Line 64, delete "(m, 2H," and insert -- (m, 2H) --, therefor.

Column 168,
Line 38, delete "ethoxylethyl" and insert -- ethoxy]ethyl --, therefor.

Column 168,
Line 53, delete "purifed" and insert -- purified --, therefor.

Column 169,
Line 52, delete "cluting" and insert -- eluting --, therefor.

UNITED STATES PATENT AND TRADEMARK OFFICE
CERTIFICATE OF CORRECTION

PATENT NO. : 6,797,718 B2
DATED : September 28, 2004
INVENTOR(S) : Dellaria, Jr., Joseph F It is certified that error appears in the above-identified patent and that said Letters Patent is hereby corrected as shown below:

Column 171,
Line 63, delete "Hz, 3.48" and insert -- Hz, 2H), 3.48 --, therefor.

Column 174,
Line 65, delete "mmmol" and insert -- mmol --, therefor.

Column 189,
Line 30, delete "$-_8$" and insert -- $-R_8$ --, therefor.

Line 60, delete " $\begin{pmatrix} -N-SO_2 \\ R_{12} \end{pmatrix}$ "

Line 67, delete "substitutents" and insert -- substituents --, therefor.

Column 191,
Lines 19-23, after " $\begin{pmatrix} -N-C(R_7) \\ R_{12} \end{pmatrix}$ " insert -- and --.

Signed and Sealed this

First Day of February, 2005

JON W. DUDAS
*Director of the United States Patent and Trademark Office*